US010046068B2

(12) United States Patent
Hecht et al.

(10) Patent No.: US 10,046,068 B2
(45) Date of Patent: Aug. 14, 2018

(54) SACCHARIDE CONJUGATES

(71) Applicant: Arizona Board of Regents, for and on behalf of, Arizona State University, Scottsdale, AZ (US)

(72) Inventors: Sidney Hecht, Phoenix, AZ (US); Manikandadas Mathilakathu Madathil, Tempe, AZ (US); Chandrabali Bhattacharya, Tempe, AZ (US); Trevor Bozeman, Tempe, AZ (US); Rakesh Paul, Baltimore, MD (US); Zhiqiang Yu, Tempe, AZ (US); Michael J. Rishel, Saratoga Springs, NY (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 14/776,578

(22) PCT Filed: Mar. 14, 2014

(86) PCT No.: PCT/US2014/027656
§ 371 (c)(1),
(2) Date: Sep. 14, 2015

(87) PCT Pub. No.: WO2014/152718
PCT Pub. Date: Sep. 25, 2014

(65) Prior Publication Data
US 2016/0038615 A1 Feb. 11, 2016

Related U.S. Application Data

(60) Provisional application No. 61/800,635, filed on Mar. 15, 2013.

(51) Int. Cl.
| | | |
|---|---|---|
| *A61K 9/14* | (2006.01) | |
| *A61K 49/00* | (2006.01) | |
| *A61K 49/22* | (2006.01) | |
| *A61K 51/04* | (2006.01) | |
| *A61K 51/06* | (2006.01) | |
| *A61B 5/00* | (2006.01) | |
| *A61K 47/54* | (2017.01) | |
| *A61K 47/69* | (2017.01) | |

(52) U.S. Cl.
CPC ........ *A61K 49/0052* (2013.01); *A61B 5/0071* (2013.01); *A61K 47/545* (2017.08); *A61K 47/6925* (2017.08); *A61K 49/0002* (2013.01); *A61K 49/0032* (2013.01); *A61K 49/0054* (2013.01); *A61K 49/223* (2013.01); *A61K 51/0497* (2013.01); *A61K 51/065* (2013.01)

(58) Field of Classification Search
None
See application file for complete search history.

(56) References Cited

U.S. PATENT DOCUMENTS

| | | | |
|---|---|---|---|
| 6,506,734 B1 | 1/2003 | Lerchen et al. | |
| 9,624,255 B2 | 4/2017 | Hecht | |
| 2007/0269380 A1 | 11/2007 | Zhang et al. | |
| 2010/0150843 A1* | 6/2010 | Johannesen | A61K 49/0032 424/9.6 |
| 2011/0293530 A1 | 12/2011 | Hecht et al. | |
| 2012/0094946 A1 | 4/2012 | Thorson et al. | |
| 2012/0148502 A1 | 6/2012 | Hecht et al. | |
| 2013/0266518 A1 | 10/2013 | Hecht et al. | |
| 2016/0045611 A1 | 2/2016 | Hecht et al. | |

FOREIGN PATENT DOCUMENTS

| | | |
|---|---|---|
| CN | 102260875 | 11/2011 |
| DE | 19909979 A1 | 9/2000 |
| EP | 1219634 A1 | 7/2002 |
| EP | 2594575 A1 | 5/2013 |
| WO | WO 1996/039197 | 12/1996 |
| WO | WO 1998/051703 | 11/1998 |
| WO | WO 2011/019419 | 2/2011 |
| WO | WO 2012/142141 | 10/2012 |
| WO | WO 2014/145109 | 9/2014 |

OTHER PUBLICATIONS https://en.wikibooks.org/w/index.php?title=Principles_of_Biochemistry/The_Carbohydrates:_Monosaccharides,_Disaccharides_and_Polysaccharides&oldid=2072628, published on the web Mar. 22, 2011.*
Abraham, A.T. et al., "RNA Cleavage and Inhibition of Protein Synthesis by Bleomycin", In Chemistry & Biology, vol. 10, No. 1, Jan. 2003, pp. 45-52.
Bekerman, C. et al., "Scintigraphic Evaluation of Lymphoma: A Comparative Study of 67 Ga-Citrate and 111 In-Bleomycin", In Radiology, vol. 123, No. 3, Jun. 1977, pp. 687-694.
Boger, D.L. et al., "Total Synthesis of Bleomycin A2 and Related Agents. 4. Synthesis of the Disaccharide Subunit 2-O-(3-O-Carbamoyl-.alpha.-D-mannopyranosyl)-L-gulopyranose and Completion of the Total Synthesis of Bleomycin A2", In the Journal of the Am. Cancer Soc., vol. 116, No. 13, Jun. 1994, pp. 5647-5656.
Burton, I.E. et al., "Static and Dynamic Imaging with Indium-111 Labelled Bleomycin in the Localization of Squamous Cell Neoplasia", In the British Journal of Radiology, vol. 50, No. 595, Jul. 1977, pp. 508-512.
Chen, J. and Stubbe, J., "Bleomycins: Towards Better Therapeutics", In Nature Reviews Cancer, vol. 5, No. 2, Feb. 2005, pp. 102-112.

(Continued)

*Primary Examiner* — James W Rogers
(74) *Attorney, Agent, or Firm* — Byrne Poh LLP; Nina R. Horan

(57) ABSTRACT

This invention relates to compounds comprising a saccharide conjugated to an imaging agent or a reporter group, compositions comprising them and methods of using them. Specifically BLM-disaccharide and BLM-monosaccharide conjugates containing different linker groups and an imaging agent or a reporter group are provided for the targeting and imaging of tumors.

12 Claims, 12 Drawing Sheets

(56) References Cited

OTHER PUBLICATIONS

Choudhury, A.K. et al. "Synthesis and DNA Cleavage Activity of a Novel Bleomycin A5 Glycoconjugate", In Organic Letters, vol. 3, No. 9, Apr. 2001, pp. 1291-1294.
Christiansen, J.P. et al., "Noninvasive Imaging of Myocardial Reperfusion Injury using Leukocyte-Targeted Contrast Echocardiography", In Circulation, vol. 105, No. 15, Apr. 2002, pp. 1764-1767.
Claussen, C.A. and Long, E.C., "Nucleic Acid Recognition by Metal Complexes of Bleomycin", In Chemical Reviews, vol. 99, No. 9, Sep. 1999, pp. 2797-2816.
Dondoni, A. et al., "Carbohydrate Homologation by the Use of 2-(Trimethylsilyl)thiazole. Preparative Scale Synthesis of Rare Sugars:? I-Gulose, I-Idose, and the Disaccharide Subunit of Bleomycin A2", In the Journal of Organic Chemistry, vol. 62, No. 18, Sep. 1997, pp. 6261-6267.
Goodwin, D.A. et al., "Clinical Studies with In-111 BLEDTA, a Tumor-Imaging Conjugate of Bleomycin with a Bifunctional Chelating Agent", In the Journal of Nuclear Medicine, vol. 22, No. 9, Sep. 1981, pp. 787-792.
Grote, J. et al., "Methodology for the Regiospecific Synthesis and Characterization of Methotrexate Conjuagets", In Tetrahedron Letters, vol. 53, No. 39, Sep. 2012, pp. 5331-5334.
Hamilton, A.J. et al., "Intravascular Ultrasound Molecular Imaging of Alheroma Components in Vivo", In the Journal of the American College of Cardiology, vol. 43, No. 3, Feb. 4, 2004, pp. 453-460.
Hecht, S.M., "Bleomycin: New Perspectives on the Mechanism of Action", In the Journal of Natural Products, vol. 63, No. 1, Dec. 1999, pp. 158-168.
Holmes, C.E. et al., "Characterization of Iron(II).cntdot.bleomycin-mediated RNA Strand Scission", In Biochemistry, vol. 32, No. 16, Apr. 1993. pp. 4293-4307.
International Preliminary Report on Patentability dated Jul. 21, 2014 in International Patent Application No. PCT/US2014/027656.
International Preliminary Report on Patentability dated Aug. 1, 2014 in International Patent Application No. PCT/US2014/029793.
International Search Report and Written Opinion dated Jul. 21, 2014 in International Patent Application No. PCT/US2014/027656.
International Search Report and Written Opinion dated Aug. 1, 2014 in International Patent Application No. PCT/US2014/029793.
Jones, S.E. et al., "Indium-111 Bleomycin Tumor Scanning in Lymphoma", In Medical and Pediatric Oncology, vol. 1, No. 1, Feb. 1975. p. 11-21.
Kane, S.A. and Hecht, S.M., "Polynucleotide Recognition and Degradation by Bleomycin", In Progress in Nucleic Acid Research and Molecular Biology, vol. 49, 1994, pp. 313-352.
Klibanov, A.L., "Ligand-Carrying Gas-Filled Microbubbles: Ultrasound Contrast Agents for Targeted Molecular Imaging", In Bioconjugate Chemistry, vol. 16, No. 1, Jan.-Feb. 2005, pp. 9-17.
Kralovec, J. et al., "Synthesis of Methotrexate-antibody Conjugates by Regiospecific Coupling and Assessment of Drug and Antitumor Activities", In the Journal of Medicinal Chemistry, vol. 32, No. 11, Nov. 1989, pp. 2426-2431.
Levi, J.A. et al., "The Importance of Bleomycin in Combination Chemotherapy for Good-Prognosis Germ Cell Carcinoma", In the Journal of Clinical Oncology, vol. 11, No. 7, Jul. 1993, pp. 1300-1305.
Lindner, J.R., "Microbubbles in Medical Imaging: Current Applications and Future Directions", In Nature Reviews Drug Discovery, vol. 3, Jun. 2004, pp. 527-533.
Nagy, A. et al., "Selective Coupling of Methotrexate to Peptide Hormone Carriers through a Gamma Carboxamide Linkage of its Glutamic Acid Moiety", In Proceedings of the National Academy of Sciences, vol. 90, No. 13, Jul. 1993, pp. 6373-6376.
Rychak, J.J. et al., "Deformable Gas-Filled Microbubbles Targeted to P-Selectin", in Journal of Controlled Release, vol. 114, Jun. 2006, pp. 288-299.

Silverstein, M.J. et al., "Indium-Bleomycin Breast and Axilla Imaging", In Cancer, vol. 37, No. 1, Jan. 1976, pp. 36-42.
Stern, P.H. et al., "Cytotoxic Activity, Tumor Accumulation, and Tissue Distribution of Ruthenium-103-labeled Bleomycin", In the Journal of the National Cancer Institute, vol. 66, No. 5, May 1981, pp. 807-811.
Tao, Z.F. et al., "An Efficient Mammalian Transfer RNA Target for Bleomycin", In the Journal of the American Chemical Society, vol. 128, No. 46, Nov. 2006, pp. 14806-14807.
U.S. Food and Drug Administration, "List of Approved Oncology Drugs with Approved Indications", Jan. 17, 2009, pp. 1-48, available at: http://web.archive.org/web/20090117201233/http://www.fda.gov/cder/cancer/druglistframe.htm.
Yu, Z. et al. "Selective Tumor Cell Targeting by the Disaccharide Moiety of Bleomycin", In the Journal of American Chemistry Society, vol. 135, No. 8, Feb. 27, 2013, pp. 2833-2886.
Chen, E.X. et al., "Phase I and Pharmacokinetic Study of Bay 38/3441, a Camptothecin Glycoconjugate, Administrated as a 30-minute Infusion Daily for Five Days every 3 Weeks in Patients with Advanced Solid Malignancies", In the Journal of New Anti-cancer Agents, vol. 23, No. 5, Oct. 2005, pp. 455-465.
Dehuyser, L. et al., "Synthesis of Novel Mannoside Glycolipid Conjugates for Inhibition of HIV-1 Trans-Infection", In Bioconjugate Chemistry, vol. 23, No. 9, Sep. 19, 2012, pp. 1731-1739.
Dongbang, S. et al., "Camptothecin Delivery into Hepatoma Cell Line by Galactose-Appended Fluorescent Drug Deliver System", In RSC Advances, vol. 4, No. 36, Jan. 2014, pp. 18744.
Extended European Search Report dated Oct. 31, 2016 in European Patent Application No. 14764855.4.
Iglesias-Guerra, F. et al., "Alkylating Agents from Sugars: Synthesis of Chlorambucil Derivatives Carried by Chiral Glycosyl Glycerols Derived from D-Glucosamine", In Chirality, vol. 14, No. 2-3, Jan. 2002, pp. 199-203.
Office Action dated Mar. 12, 2013 in U.S. Appl. No. 13/128,142.
Office Action dated Mar. 22, 2016 in U.S. Appl. No. 13/382,581.
Office Action dated Mar. 23, 2016 in U.S. Appl. No. 13/910,565.
Office Action dated Mar. 23, 2017 in U.S. Appl. No. 14/776,396.
Office Action dated Sep. 8, 2016 in U.S. Appl. No. 13/382,581.
Office Action dated Sep. 21, 2016 in U.S. Appl. No. 13/910,565.
Pignatello, R. et al., "Lipophilic Conjugates of Methotrexate with Glucosyl-Lipoamino Acids: Calorimetric Study of the Interaction with a Biomembrane Model", In Thermochimica Acta, Elsevier Science Publishers, Amsterdam, NL, vol. 426, No. 102, Feb. 2005, pp. 163-171.
Pignatello, R. et al., "Lipophilic Methotrexate Conjugates with Glucose-Lipoamino Acid Moieties: Synthesis and In Vitro Antitumor Activity", In Drug Development Research, vol. 52, No. 3, Mar. 2001, pp. 454-461.
Totani, K. et al., "Tight Binding Ligand Approach to Oligosaccharide-Grafted Protein", In Bioorganic & Medicinal Chemistry Letters, vol. 14, No. 9, May 2004, pp. 2285-2289.
Yu, Z. et al., "Selective Tumor Cell Targeting by the Disaccharide Moiety of Bleomycin", In the Journal of hte American Chemical Society, vol. 135, No. 8, Feb. 2013, pp. 2883-2886.
Zhang, Z. et al., "Bioreduction Activated Prodrugs of Camptothecin: Molecular Design, Synthesis, Activation Mechanism and Hypoxia Selective Cytotoxicity", In Organic & Biomolecular Chemistry, Royal Society of Chemistry, GB, vol. 3, No. 10, May 21, 2005, pp. 1905-1910.
Office Action dated Jul. 19, 2017 in U.S. Appl. No. 14/776,396.
Office Action dated Dec. 5, 2017 in Australian Patent Application No. 2014233404.
Zhouen, Z. et al., "Bioreduction Activated Prodrugs of Camptothecin: MOlecular Design, Syntehsis, Activation Mechanism and Hypoxia Selective Cytotoxicity", In Organic & Biomolecular Cehmistry, Royal Society of Chemistry, GB, vol. 3, No. 10, May 21, 2005, pp. 1905-1910.

* cited by examiner

Comparison of modified disaccharide-Cy5** conjugates (45, 46, 53, 64, 65, 76, 77) binding/uptake in human cells.

Lung cells

Brain cells

Colon cells

Skin cells

Comparison of BLM-disaccharide trimer-Cy5** conjugate (96) binding/uptake in human prostate cancer cells (DU-145).

Effect of temperature on the binding/uptake of BLM-disaccharide-Cy5 conjugate (98) in human cells Comparison of BLM disaccharide-Cy5 (98) and BLM monosaccharide-Cy5** (117) conjugates binding/uptake in human cells.

Comparison of modified monosaccharide-Cy5** conjugates (140, 141, 142, 143) binding/uptake in human cells.

Comparison of BLM-monosaccharide trimer-Cy5 conjugate (127) and BLM-monosaccharide-Cy5 (117) conjugate binding/uptake in human cells.

Comparison of BLM-monosaccharide-Cy5 conjugate (117) and decarbamoyl monosaccharide-Cy5 (123) conjugate binding/uptake in human cells.

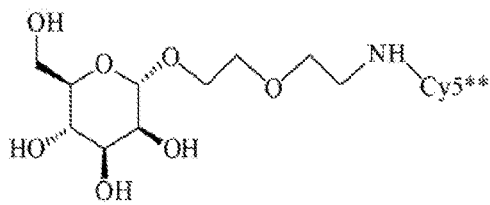
decarbamoyl BLM monosaccharide (123)
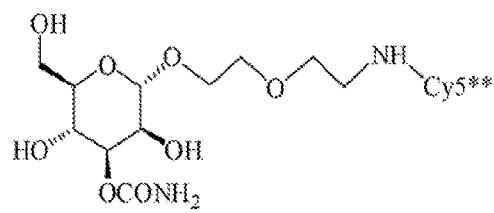
BLM monosaccharide (117)
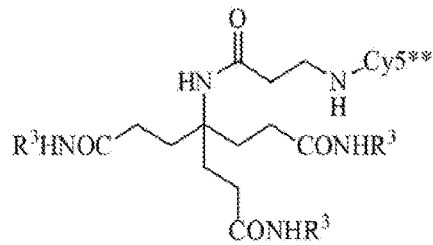
BLM monosaccharide trimer (127)
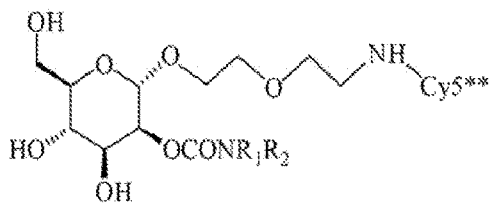
140 $R_1 = H, R_2 = CH_3$
141 $R_1 = CH_3, R_2 = CH_3$
142 $R_1 = H, R_2 = n\text{-Bu}$
143 $R_1, R_2$ = pyrrolidine
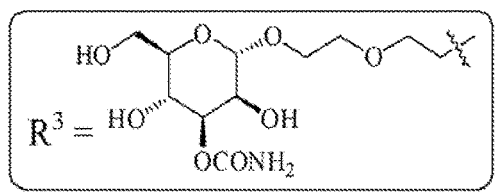
FIG. 14-2

SACCHARIDE CONJUGATES

CROSS REFERENCE TO RELATED APPLICATION

This application is a national stage application under 35 U.S.C. § 371 of the International Application No. PCT/US2014/027656, filed Mar. 14, 2014, claims the benefit U.S. Provisional Application No. 61/800,635, filed Mar. 15, 2013, which is incorporated by reference herein in its entirety.

FEDERALLY SPONSORED RESEARCH OR DEVELOPMENT

This invention was made with government support under R01 CA140471 awarded by the National Institutes of Health. The government has certain rights in the invention.

FIELD OF THE INVENTION

This invention relates to compounds comprising a saccharide conjugated to an imaging agent or a reporter group, compositions comprising them and methods of using them.

BACKGROUND OF THE INVENTION

The bleomycins (BLMs) are a family of glycopeptide-derived antitumor antibiotics used clinically for the treatment of squamous cell carcinomas and malignant lymphomas. [Levi, J. A. et al., J. Clin. Oncol. 1993, 11, 1300; Bleomycin Chemotherapy; Sikic, B. I., Rozencweig, M., Carter, S. K., Eds.; Academic Press: Orlando, Fla., 1985.] Their antitumor activity is thought to result from selective oxidative cleavage of 5'-GC-3' and 5'-GT-3' sequences in DNA and possibly also from oxidative degradation of RNA. [Holmes, C. E. et al., Biochemistry 1993, 32, 4293; Kane, S. A.; Hecht, S. M. Prog. Nucleic Acid Res. Mol. Biol. 1994, 49, 313; Claussen, C. A.; Long, E. C. Chem. Rev. 1999, 99, 2797; Hecht, S. M. J. Nat. Prod. 2000, 63, 158; Abraham, A. T. et al., Chem. Biol. 2003, 10, 45; Chen, J.; Stubbe, J. Nat. Rev. Cancer 2005, 5, 102; Tao, Z. F.; Konishi, K. et al., J. Am. Chem. Soc. 2006, 128, 14806]. In addition to its antitumor activity, BLM has been recognized for its ability to target tumors and shown to act as a tumor-imaging agent. [Jones, S. E.; Lilien, D. L.; O'Mara, R. E.; Durie, B. G.; Salmon, S. E. Med. Pediatr. Oncol. 1975, 1, 11; Silverstein, M. J.; Verma, R. C.; Greenfield, L.; Morton, D. L. Cancer 1976, 37, 36; Bekerman, C.; Moran, E. M.; Hoffer, P. B.; Hendrix, R. W.; Gottschalk, A. Radiology 1977, 123, 687; Burton, I. E.; Todd, J. H.; Turner, R. L. Br. J. Radiol. 1977, 50, 508; Goodwin, D. A.; Meares, C. F.; DeRiemer, L. H.; Diamanti, C. I.; Goode, R. L.; Baumert, J. E., Jr.; Sartoris, D. J.; Lantieri, R. L.; Fawcett, H. D. J. Nucl. Med. 1981, 22, 787; Stern, P. H.; Helpern, S. E.; Hagan, P. L.; Howell, S. B.; Dabbs, J. E.; Gordon, R. M. J, Natl. Cancer Inst. 1981, 66, 807].

SUMMARY OF THE INVENTION

The present disclosure provides a compound of formula (I):

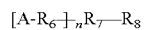
(I)

or a pharmaceutically acceptable salt thereof, wherein A is:

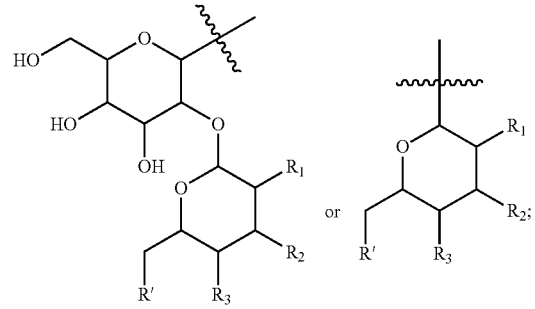

$R_1$ is selected from the group consisting of H, OH, SH, $NH_2$, $OR_4$, $OC(O)R_4$, $OC(O)NHR_4$, $OC(O)NR_4R_5$, $OC(O)SR_4$, $OC(S)NHR_4$, $OC(S)NR_4R_5$, $OC(S)SR_4$, $OC(S)NR_4R_5$, $SC(O)NHR_4$, $SC(O)NR_4R_5$, $NHC(O)NHR_4$, $NHC(O)NR_4R_5$, $NHC(S)NHR_4$, $NHC(S)NR_4R_5$, $NHC(N)NHR_4$, $NHC(N)NR_4R_5$, $OCH_2C(O)NHR_4$, $OCH_2C(O)NR_4R_5$, $OCH_2C(S)NHR_4$, $OCH_2C(S)NR_4R_5$, $SCH_2C(O)NHR_4$, $SCH_2C(O)NR_4R_5$, $NHCH_2C(O)NHR_4$, $NHCH_2C(O)NR_4R_5$, $NHCH_2C(S)NHR_4$ and $NHCH_2C(S)NR_4R_5$;

each $R_4$ is selected from the group consisting of H, $C_1$-$C_6$ alkyl, $C_2$-$C_6$ alkenyl and $C_2$-$C_6$ alkynyl;

each $R_5$ is selected from the group consisting of $C_1$-$C_6$ alkyl, $C_2$-$C_6$ alkenyl and $C_2$-$C_6$ alkynyl;

or $R_4$ and $R_5$ are taken together to form a 5-6 member heterocyclic ring;

$R_2$ is selected from the group consisting of H, OH, SH, $NH_2$, $OR_4$, $OC(O)R_4$, $OC(O)NHR_4$, $OC(O)NR_4R_5$, $OC(O)SR_4$, $OC(S)NHR_4$, $OC(S)NR_4R_5$, $OC(S)SR_4$, $SC(O)NHR_4$, $SC(O)NR_4R_5$, $NHC(O)NHR_4$, $NHC(O)NR_4R_5$, $NHC(S)NHR_4$, $NHC(S)NR_4R_5$, $NHC(N)NHR_4$, $NHC(N)NR_4R_5$, $OCH_2C(O)NHR_4$, $OCH_2C(O)NR_4R_5$, $OCH_2C(S)NHR_4$, $OCH_2C(S)NR_4R_5$, $SCH_2C(O)NHR_4$, $SCH_2C(O)NR_4R_5$, $NHCH_2C(O)NHR_4$, $NHCH_2C(O)NR_4R_5$, $NHCH_2C(S)NHR_4$ and $NHCH_2C(S)NR_4R_5$;

$R_3$ is selected from the group consisting of H, OH, SH, $NH_2$, $OR_4$, $OC(O)R_4$, $OC(O)NHR_4$, $OC(O)NR_4R_5$, $OC(O)SR_4$, $OC(S)NHR_4$, $OC(S)NR_4R_5$, $OC(S)SR_4$, $SC(O)NHR_4$, $SC(O)NR_4R_5$, $NHC(O)NHR_4$, $NHC(O)NR_4R_5$, $NHC(S)NHR_4$, $NHC(S)NR_4R_5$, $NHC(N)NHR_4$, $NHC(N)NR_4R_5OCH_2C(O)NHR_4$, $OCH_2C(O)NR_4R_5$, $OCH_2C(S)NHR_4$, $OCH_2C(S)NR_4R_5$, $SCH_2C(O)NHR_4$, $SCH_2C(O)NR_4R_5$, $NHCH_2C(O)NHR_4$, $NHCH_2C(O)NR_4R_5$, $NHCH_2C(S)NHR_4$ and $NHCH_2C(S)NR_4R_5$;

R' is selected from the group consisting of H, OH and $NHR_4$;

$R_6$ is a first linker;

n is an integer selected from 1 to 3;

$R_7$ is absent or a second linker, provided that when n is 1, $R_7$ is absent; and $R_8$ is selected from the group consisting of absent, an imaging agent and a reporting group.

In some embodiments, A is selected from the group consisting of:

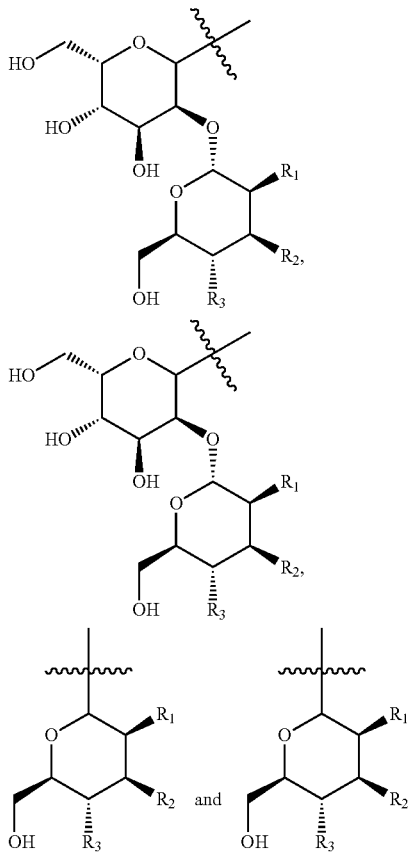

In some embodiments, the first linker is selected from the group consisting of a bond, $C_1$-$C_{20}$ alkyl, $C_1$-$C_{20}$ alkenyl, $C_1$-$C_{20}$ alkynyl, aryl, heteroaryl, heterocyclyl, $C_3$-$C_5$ cycloalkyl, an oligoalkylene glycol, an oligopeptide or a dendrimer.

In alternate embodiments, the first linker is X-$(L^1$-$Y)_m$-$L^2$-Z, wherein X is $CH_2$ or O;

$L^1$ is $C_2$-$C_6$ alkyl;

Y is O, S, or $NR^y$, wherein $R^y$ is hydrogen or $C_1$-$C_6$ alkyl;

m is an integer selected from 1 to 10;

$L^2$ is $C_1$-$C_{20}$ alkyl, $C_2$-$C_{20}$ alkenyl, $C_2$-$C_{20}$ alkynyl, aryl, heteroaryl, heterocyclyl, $C_3$-$C_5$ cycloalkyl; and Z is absent, O, $NR^x$, S, C(O), S(O), $S(O)_2$, OC(O), $N(R^x)C(O)$, $N(R^x)S(O)$, $N(R^x)S(O)_2$, C(O)O, C(O)N$(R^x)$, $S(O)N(R^x)$, $S(O)_2N(R^x)$, OC(O)O, OC(O)N$(R^x)$, $N(R^x)C(O)O$, $N(R^x)C(O)N(R^x)$, or $N(R^x)S(O)_2N(R^x)$, wherein each $R^x$ is independently hydrogen or $C_1$-$C_6$ alkyl.

In some aspects of this embodiment, X is O, $L^1$ is $C_2$-$C_4$ alkyl; $L^2$ is $C_1$-$C_6$ alkyl; and Z is a bond, O, $NR^x$, S, C(O), S(O), or $S(O)_2$.

In some aspects of this embodiment, the first linker is O—$(CH_2CH_2$—$O)_m$—$CH_2CH_2$—Z, wherein Z is O, N(H), or S and m is an integer selected from 1 to 20.

In some aspects of this embodiment, the first linker is O—$(CH_2CH_2$—$O)_m$—$CH_2CH_2$—Z, wherein Z is C(O) or $S(O)_2$ and m is an integer selected from 1 to 20.

In some embodiments, $R_7$ is absent. In alternate embodiments, $R_7$ is a second linker.

In some embodiments, the second linker is $(B$-$L^3)_p$-D-E-$L^4$-F, wherein B is bond, O, $NR^x$, S, C(O), S(O), $S(O)_2$, OC(O), $N(R^x)C(O)$, $N(R^x)S(O)$, $N(R^x)S(O)_2$, C(O)O, C(O)N$(R^x)$, $S(O)N(R^x)$, $S(O)_2N(R^x)$, OC(O)O, OC(O)N$(R^x)$, $N(R^x)C(O)O$, $N(R^x)C(O)N(R^x)$, or $N(R^x)S(O)_2N(R^x)$;

$L^3$ is $C_2$-$C_6$ alkyl;

p is 2 or 3;

D is CH when p is 2 and D is C when p is 3;

E is a bond, O, $NR^x$, S, C(O), S(O), $S(O)_2$, OC(O), $N(R^x)C(O)$, $N(R^x)S(O)$, $N(R^x)S(O)_2$, C(O)O, C(O)N$(R^x)$, $S(O)N(R^x)$, $S(O)^2N(R^x)$, OC(O)O, OC(O)N$(R^x)$, $N(R^x)C(O)O$, $N(R^x)C(O)N(R^x)$, or $N(R^x)S(O)_2N(R^x)$;

$L^4$ is $C_2$-$C_6$ alkyl; and

F is a bond, O, $NR^x$, S, C(O), S(O), $S(O)_2$, OC(O), $N(R^x)C(O)$, $N(R^x)S(O)$, $N(R^x)S(O)_2$, C(O)O, C(O)N$(R^x)$, $S(O)N(R^x)$, $S(O)_2N(R^x)$, OC(O)O, $OC(O)N(R^X)$, $N(R^x)C(O)O$, $N(R^x)C(O)N(R^x)$, or $N(R^x)S(O)_2N(R^x)$, wherein each $R^x$ is independently hydrogen or $C_1$-$C_6$ alkyl.

In some aspects of this embodiment, B is $NR^x$ or C(O);

$L^3$ is $C_2$-$C_4$ alkyl;

$L^4$ is $C_2$-$C_4$ alkyl;

E is $NR^x$, $N(R^x)C(O)$, C(O)O or C(O)N$(R^x)$; and

F is O, S, C(O), $NR^x$ or $NR^xC(O)$.

In some aspects of this embodiment, the second linker is [C(O)—$CH_2CH_2]_p$-D-$NR^xC(O)$—$CH_2CH_2$-E.

In some embodiments, A is

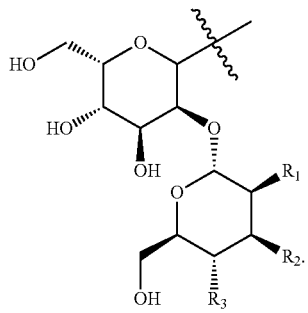

In alternative embodiments, A is

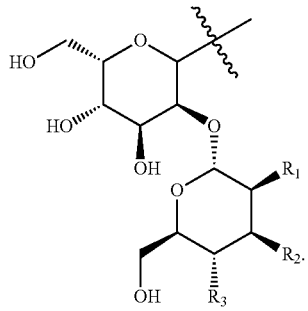

In alternative embodiments, A is

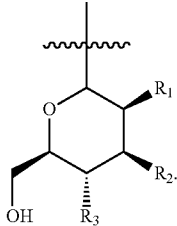

In alternative embodiments, A is

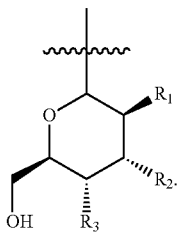

In some embodiments, n is 1. In other embodiments, n is 2. In yet other embodiments, n is 3.

In some embodiments, $R_1$ is selected from the group consisting of H, OH, $OR_4$, $OC(O)R_4$, $OCONHR_4$, $NHC(N)NHR_4$, $NHC(N)NR_4R_5$, $OCONR_4R_5$, $OCOSR_4$ and $OCSSR_4$.

In some embodiments, $R_2$ is selected from the group consisting of H, OH, $OR_4$, $OC(O)R_4$, $OC(O)SR_4$, $NHC(N)NHR_4$, $NHC(N)NR_4R_5$, $OCONHR_4$, $OCONR_4R_5$, $OCSNHR_4$, $OCSNR_4R_5$, $NHCONHR_4$, $NHCONR_4R_5$, $OCH_2CONHR_4$, and $OCH_2CONR_4R_5$.

In some embodiments, $R_3$ is selected from the group consisting of OH, $OR_4$, $OC(O)R_4$, $NHC(N)NHR_4$, $NHC(N)NR_4R_5$, $OCONHR_4$ and $OCONR_4R_5$.

In some embodiments, R' is OH. In other embodiments, R' is H.

In some embodiments, each $R_4$ is selected from the group consisting of H, methyl, ethyl, butyl, isobutyl and hexyl.

In some embodiments, each $R_5$ is selected from the group consisting of methyl, ethyl, butyl, isobutyl and hexyl.

In some embodiments, $R_4$ and $R_5$ are taken together to form a 5-6 member heterocyclic ring. In some aspects of this embodiment, $R_4$ and $R_5$ form a pyrrolidine ring.

In some embodiments, A is selected from the group consisting of:

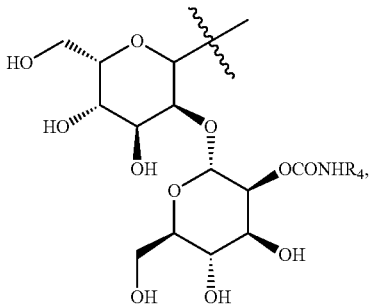

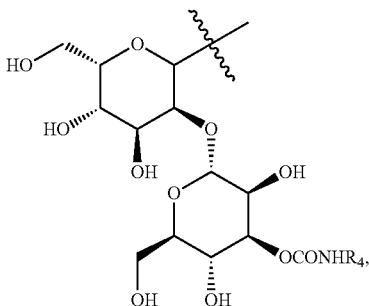

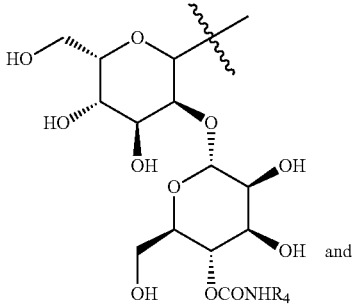

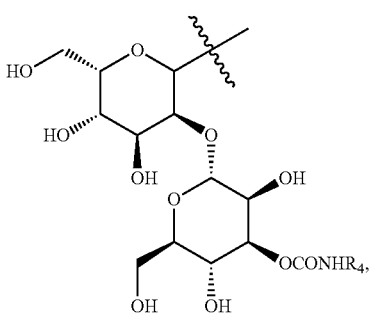

wherein $R_4$ is H or $C_1$-$C_6$ alkyl. In some aspects of this embodiment, $R_4$ is H or methyl.

In some embodiments, A is:

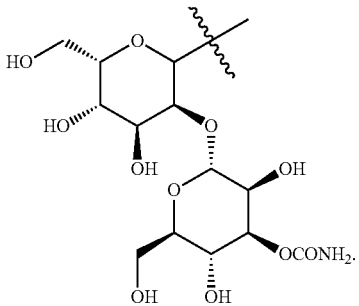

In some embodiments, A is selected from the group consisting of:

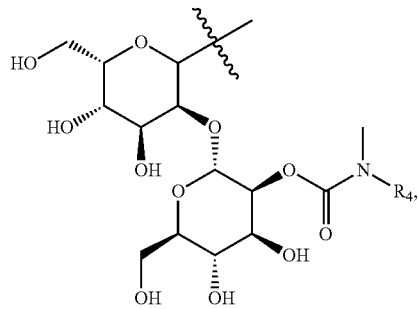
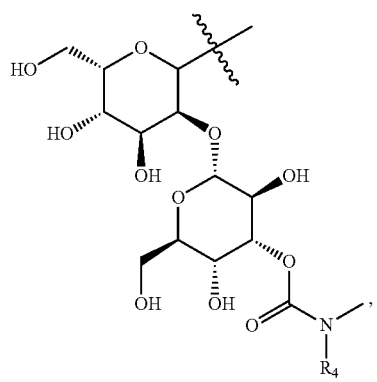
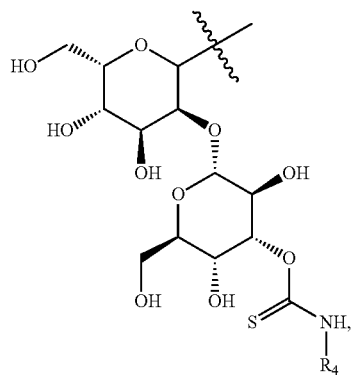
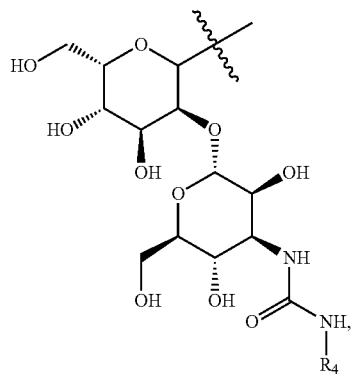
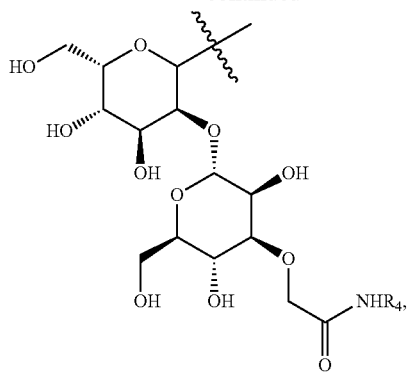
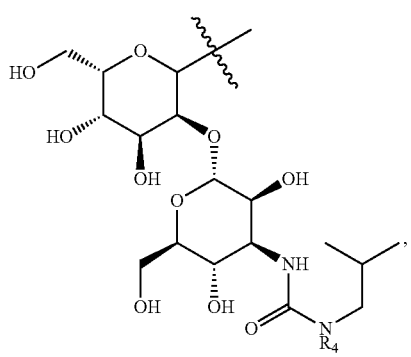
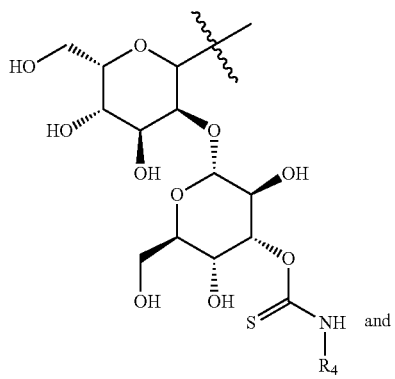
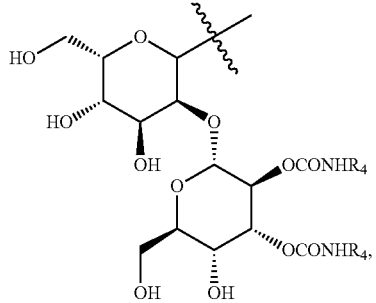
wherein $R_4$ is H or $C_1$-$C_6$ alkyl. In some aspects of this embodiment, $R_4$ is H, methyl or ethyl.

In some embodiments, A is:

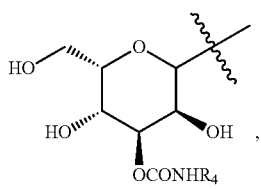

wherein $R_4$ is H or $C_1$-$C_6$ alkyl. In some aspects of this embodiment, $R_4$ is H.

In some embodiments, A is:

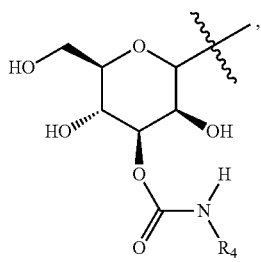

wherein $R_4$ is H or $C_1$-$C_6$ alkyl. In some aspects of this embodiment, $R_4$ is H or methyl.

In some embodiments, A is:

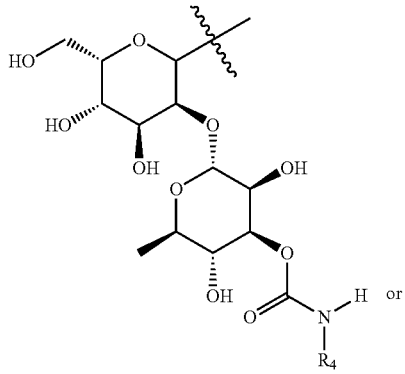

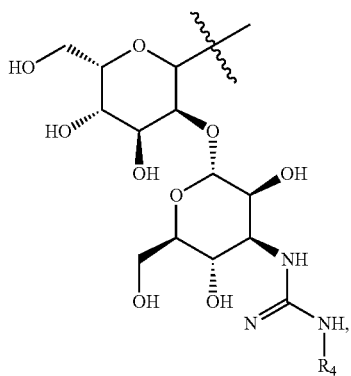

wherein $R_4$ is H or $C_1$-$C_6$ alkyl. In some aspects of this embodiment, $R_4$ is H or methyl.

In some embodiments, A is:

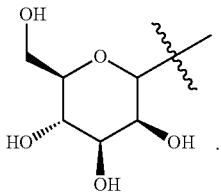

In some embodiments, A is:

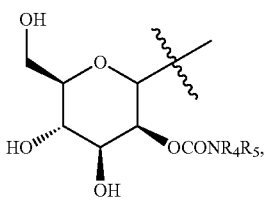

wherein $R_4$ is H or $C_1$-$C_6$ alkyl and $R_5$ is $C_1$-$C_6$ alkyl, or $R_4$ and $R_5$ are taken together to form a 5-6 membered heterocyclic ring. In some aspects of this embodiment, $R_4$ is H, methyl, ethyl, butyl, isobutyl or hexyl. In some aspects, $R_5$ is methyl, butyl isobutyl or hexyl. In other aspects, $R_4$ and $R_5$ are taken together to form a pyrrolidine ring.

In some embodiments, A is:

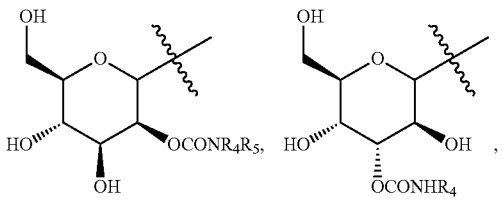

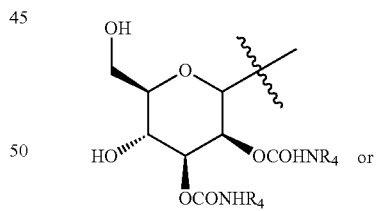

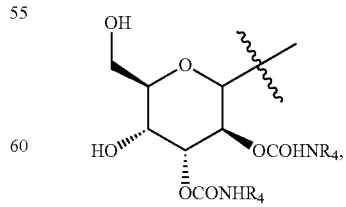

wherein each $R_4$ is H or $C_1$-$C_6$ alkyl. In some aspects of this embodiment, each $R_4$ is selected from the group consisting of H, methyl and hexyl.

In some embodiments, A is:

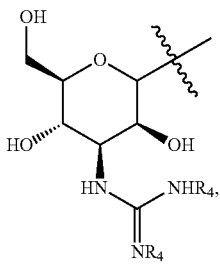

wherein $R_4$ is H or $C_1$-$C_6$ alkyl. In some aspects of this embodiment, $R_4$ is H or methyl.

In some embodiments, A is selected from the group consisting of:

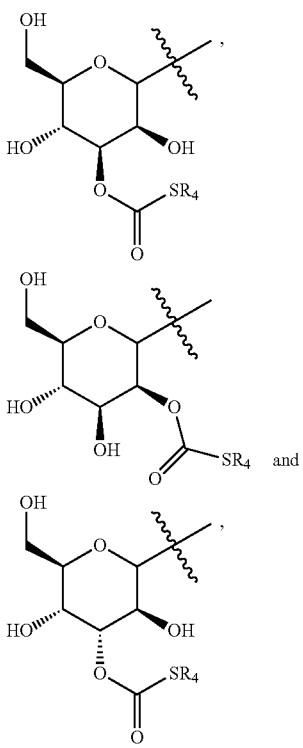

wherein $R_4$ is H or $C_1$-$C_6$ alkyl. In some aspects of this embodiment, $R_4$ is H or methyl.

In some embodiments, A is:

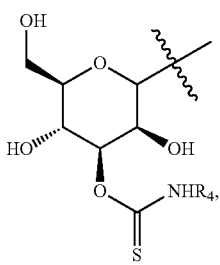

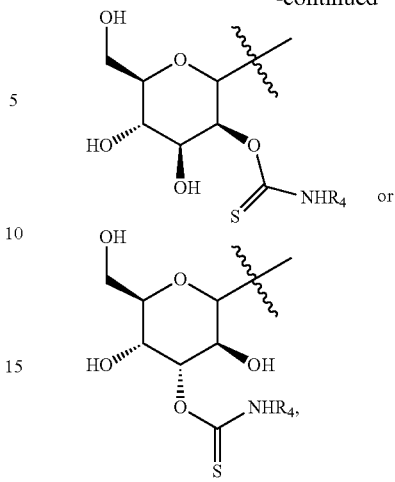

wherein $R_4$ is H or $C_1$-$C_6$ alkyl. In some aspects of this embodiment, $R_4$ is H or methyl.

In some embodiments, A is:

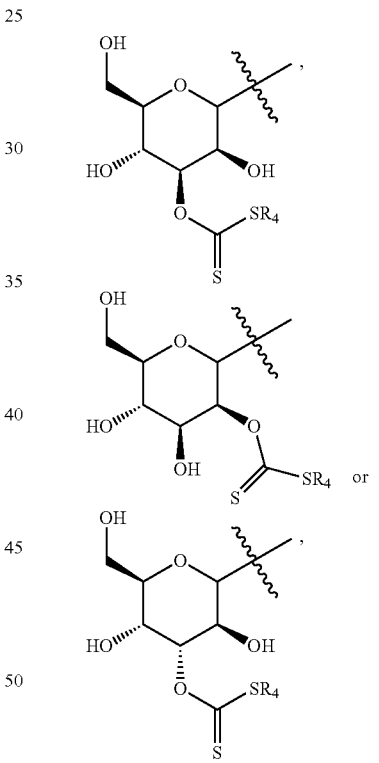

wherein $R_4$ is H or $C_1$-$C_6$ alkyl. In some aspects of this embodiment, $R_4$ is H or methyl.

In some embodiments, $R^8$ is an imaging agent or a reporter group.

In some embodiments, the imaging agent or reporter group comprises a radiolabel, an enzyme, a fluorescent label, a luminescent label, a bioluminescent label, a magnetic label, or biotin.

In some embodiments, $R^8$ is a fluorescent imaging agent. In some aspects of this embodiment, $R^8$ is selected from the group consisting of Alexa Fluor 647, Sulfo Cy5, Cy5, Cy7 and Cy5. In some aspects, $R^8$ is Cy5. Cy5** can be protonated or a salt thereof.

In some embodiments, $R^8$ comprises a chelating group coordinated to a radioactive imaging moiety.

In some embodiments in which the imaging agent or reporter group comprises a radiolabel, the radiolabel is selected from the group consisting of: $^3H$, $^{11}C$, $^{14}C$, $^{18}F$, $^{32}P$, $^{35}S$, $^{57}Co$, $^{64}Cu$, $^{68}Ga$, $^{90}Y$, $^{99m}Tc$, $^{111}In$, $^{125}I$, $^{131}I$ $^{177}Lu$, $^{166}Ho$ and $^{153}Sm$.

In some embodiments in which the imaging agent or reporter group comprises an enzyme, the enzyme is selected from the group consisting of luciferase, alkaline phosphatase, beta-galactosidase and horseradish peroxidase.

In some embodiments, the reporter group is biotin.

In some embodiments, the compound of formula (I) is selected from the group consisting of:

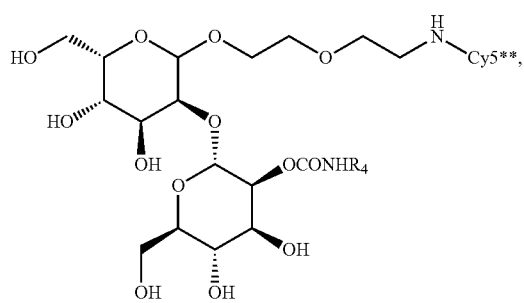

45 $R_4$ = H
46 $R_4$ = $CH_3$

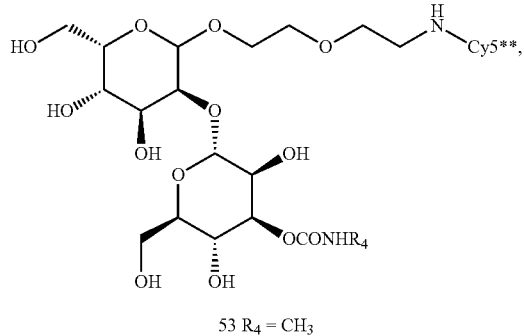

53 $R_4$ = $CH_3$

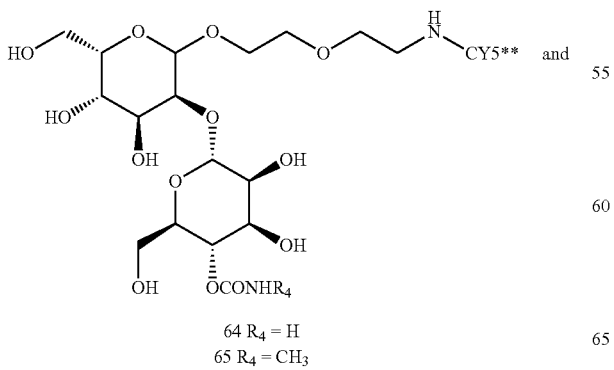

64 $R_4$ = H
65 $R_4$ = $CH_3$

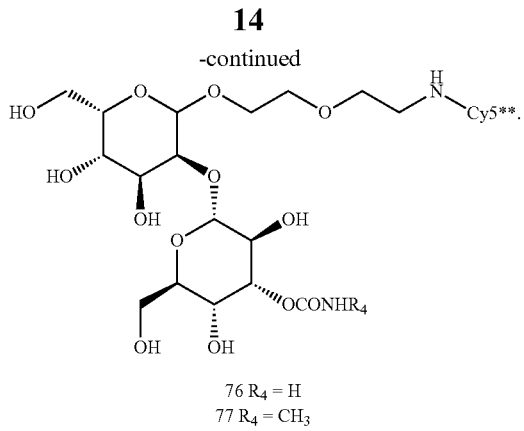

76 $R_4$ = H
77 $R_4$ = $CH_3$

In some embodiments, the compound of formula (I) is:

98

[structure with OCONH$_2$ and Cy5**]

In some embodiments, the compound of formula (I) is selected from the group consisting of:

[structure]

99 $R_4$ = $CH_3$
100 $R_4$ = $C_2H_5$

[structure]

101 $R_4$ = $CH_3$
102 $R_4$ = $C_2H_5$

-continued
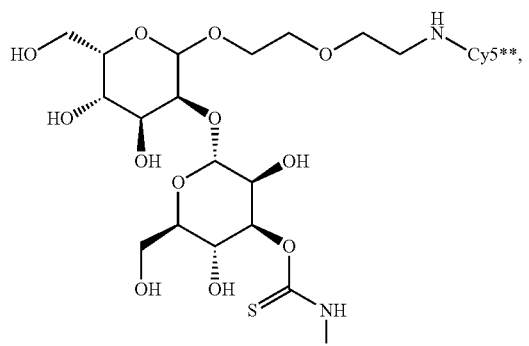
103 R₄ = H
104 R₄ = CH₃
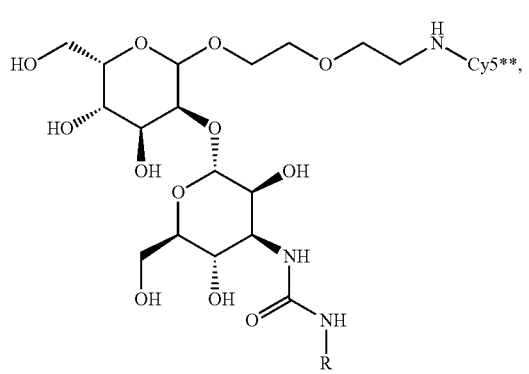
107 R₄ = H
108 R₄ = CH₃
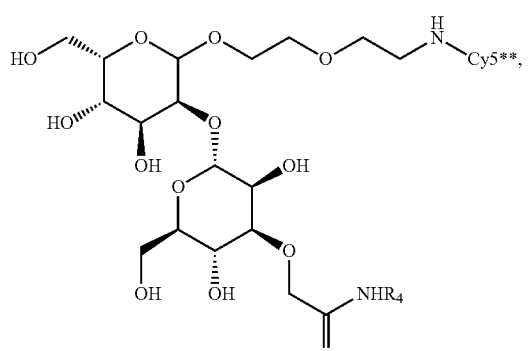
109 R₄ = H
110 R₄ = CH₃
-continued
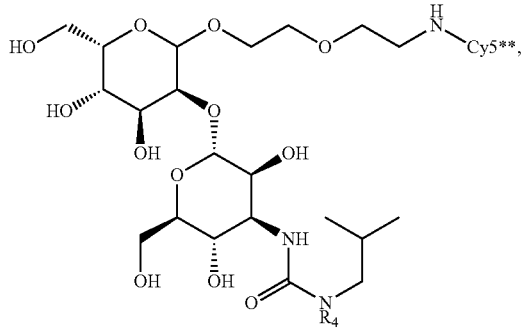
111 R₄ = H
112 R₄ = CH₃
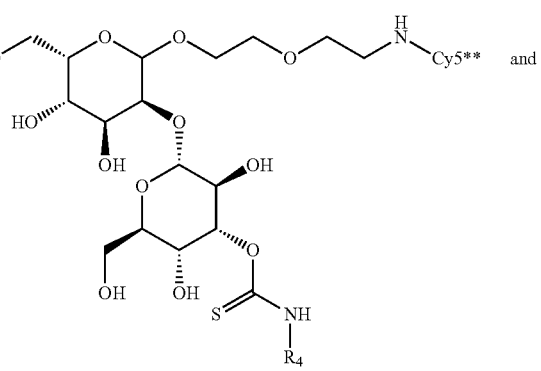
105 R₄ = H
106 R₄ = CH₃
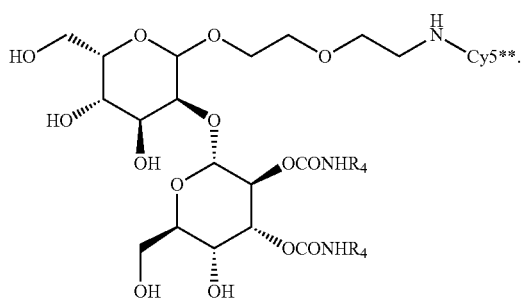
113 R₄ = H
114 R₄ = CH₃
In some embodiments, the compound of formula (I) is:
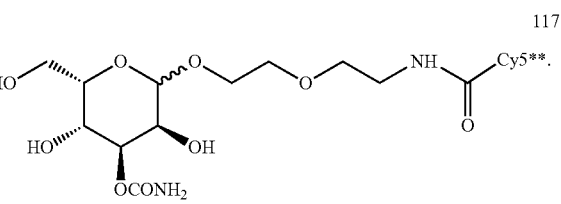
117

In some embodiments, the compound of formula (I) is:
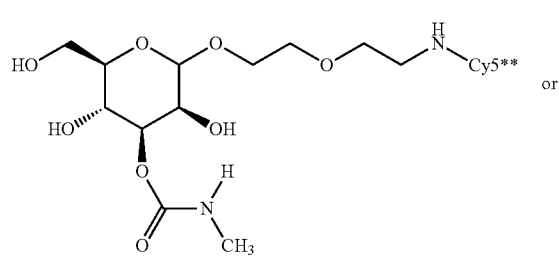
182
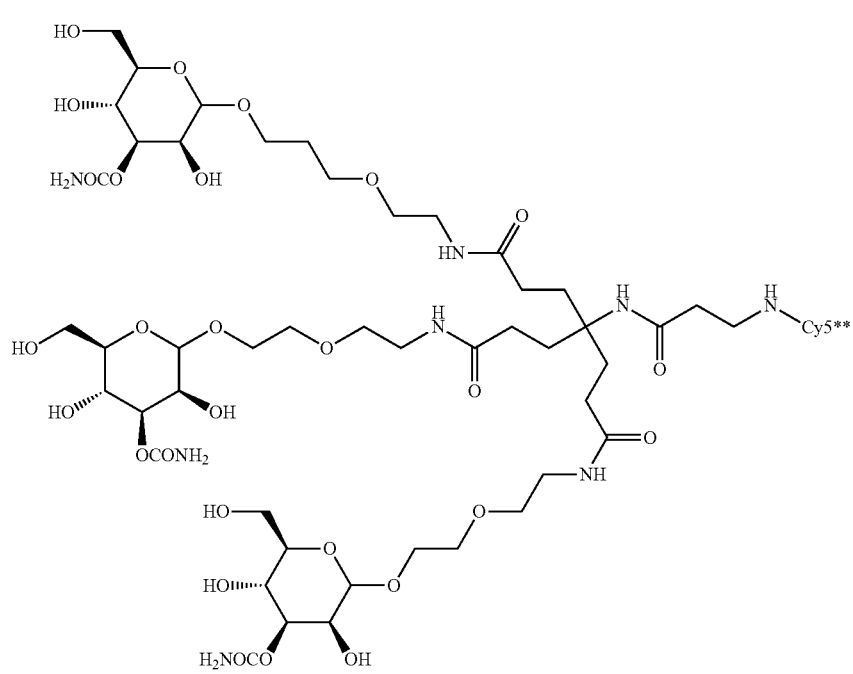
127
In some embodiments, the compound of formula (I) is:
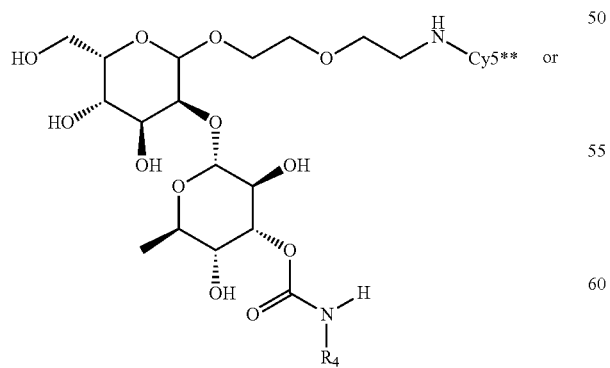
178 R$_4$ = H
179 R$_4$ = CH$_3$
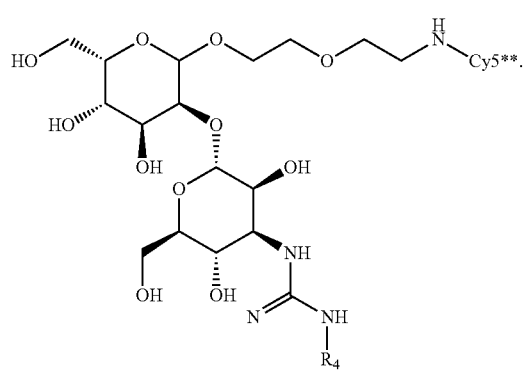
180 R$_4$ = H
181 R$_4$ = CH$_3$ In some embodiments, the compound of formula (I) is:
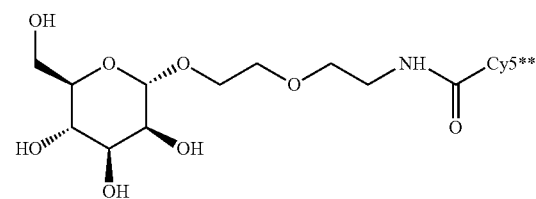
decarbamoyl BLM monosaccharide (123)
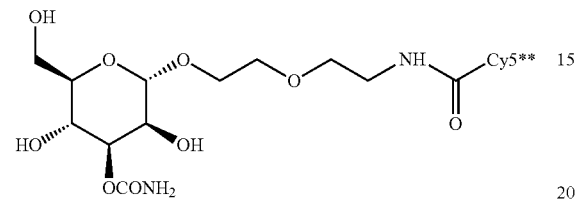
BLM monosaccharide (117)
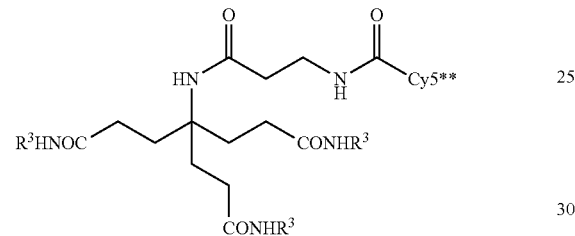
BLM monosaccharide trimer (127)
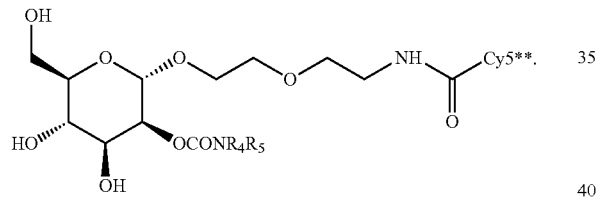
140 $R_4$ = H, $R_5$ = $CH_3$
141 $R_4$ = $CH_3$, $R_5$ = $CH_3$
142 $R_4$ = H, $R_5$ = n-Bu
143 $R_4$, $R_5$ = pyrrolidine
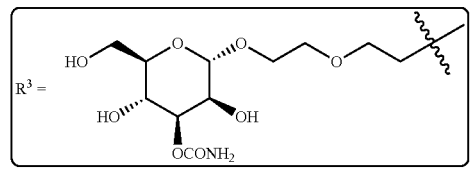
In some embodiments, the compound of formula (I) is:
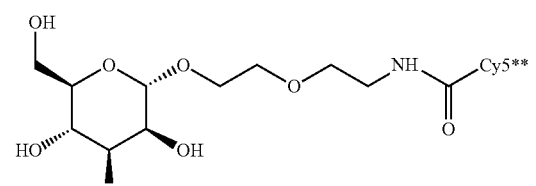
144 $R_4$ = $CH_3$
-continued
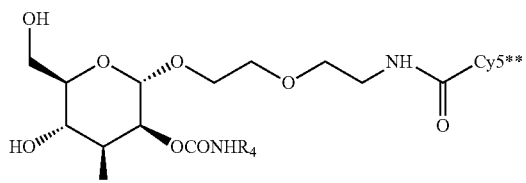
145 $R_4$ = Hex
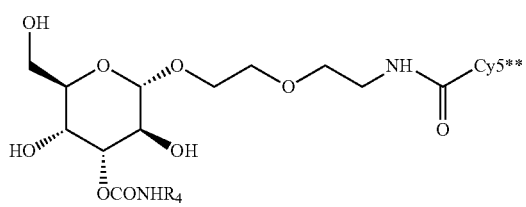
146 $R_4$ = H
147 $R_4$ = $CH_3$
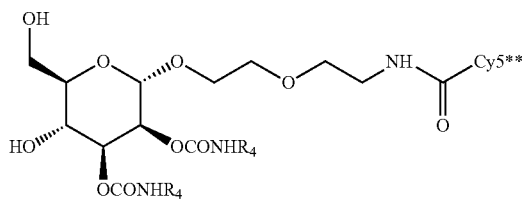
148 $R_4$ = H
149 $R_4$ = $CH_3$
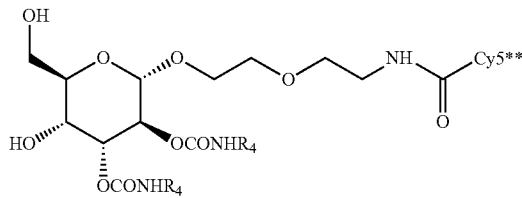
150 $R_4$ = H
151 $R_4$ = $CH_3$
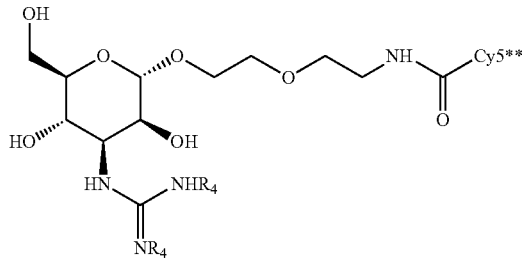
152 $R_4$ = H
153 $R_4$ = $CH_3$
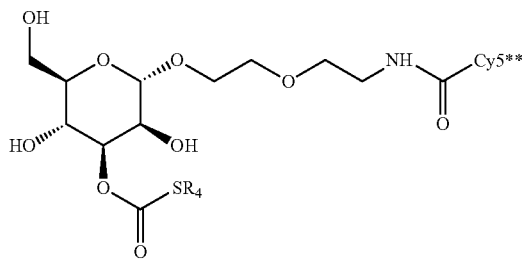
154 $R_4$ = H
155 $R_4$ = $CH_3$

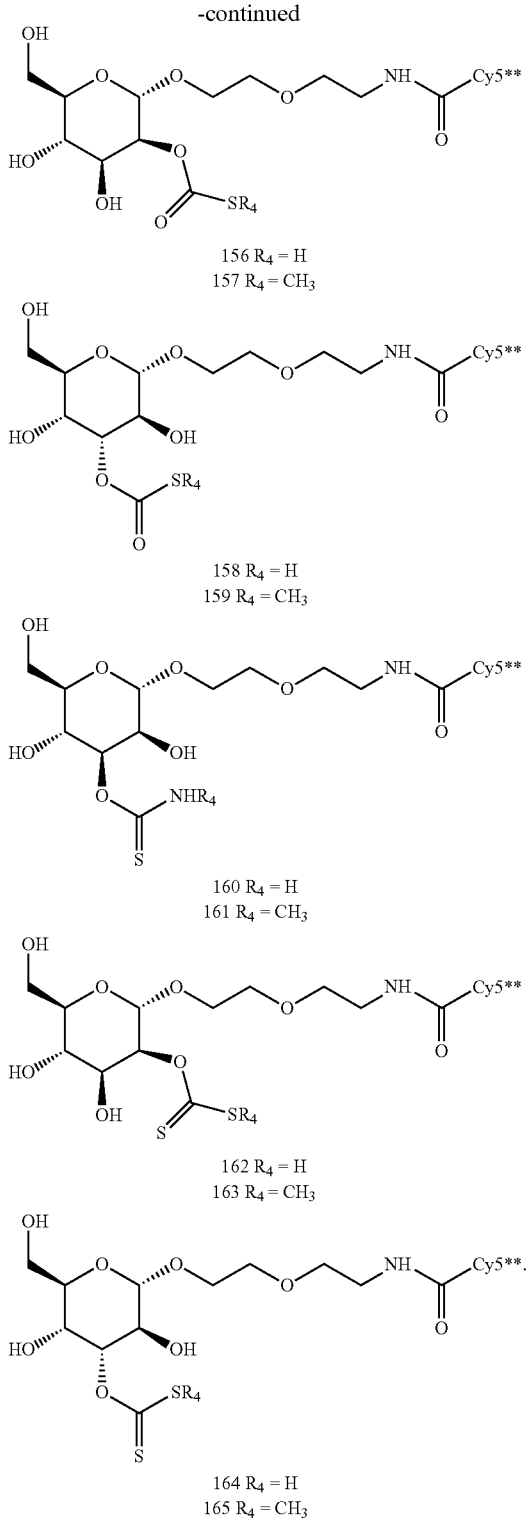

156 R₄ = H
157 R₄ = CH₃

158 R₄ = H
159 R₄ = CH₃

160 R₄ = H
161 R₄ = CH₃

162 R₄ = H
163 R₄ = CH₃

164 R₄ = H
165 R₄ = CH₃

The present disclosure also provides compositions comprising a compound of formula (I) and a pharmaceutically acceptable carrier.

The present disclosure also provides a microbubble conjugate comprising (a) a microbubble comprising an outer shell, wherein the outer shell is derivatized with streptavidin; and (b) a compound of formula (I), wherein $R^8$ is biotin.

The present disclosure also provides a composition comprising a microbubble conjugate and a pharmaceutically acceptable carrier.

The present disclosure provides a method of imaging a tumor in a patient. The method comprises (a) administering to a patient in need of imaging a compound of formula (I), or a composition comprising the compound of formula (I) and a pharmaceutically acceptable carrier; and (b) subjecting the patient to a technique that produces images of the tumor.

In some embodiments, the technique is selected from the group consisting of ultrasound, radioimaging, magnetic resonance imaging and fluorescent imaging.

The present disclosure also provides a method of detecting a tumor in a patient. The method comprises (a) administering to a patient suspected of having a tumor a compound of formula (I), or a composition thereof; and (b) illuminating the patient with light of a wavelength absorbable by the fluorescent imaging agent; and (c) detecting an optical signal emitted by the fluorescent imaging agent, wherein the detectable optical signal indicates the presence of a tumor. In the compound of formula (I) used in this method, $R^8$ is a fluorescent imaging agent. In some embodiments, $R^8$ is selected from the group consisting of Alexa Fluor 647, Sulfo Cy5, Cy5, Cy7 and Cy5. In some aspects, $R^8$ is Cy5.

The present disclosure also provides a method of imaging a cell or an in vitro biopsy sample. The method comprises (a) contacting the cell or the in vitro biopsy sample with a compound of formula (I), a microbubble, or compositions thereof; and (b) imaging the cell or in vitro biopsy sample.

DETAILED DESCRIPTION OF THE INVENTION

Figure 1:
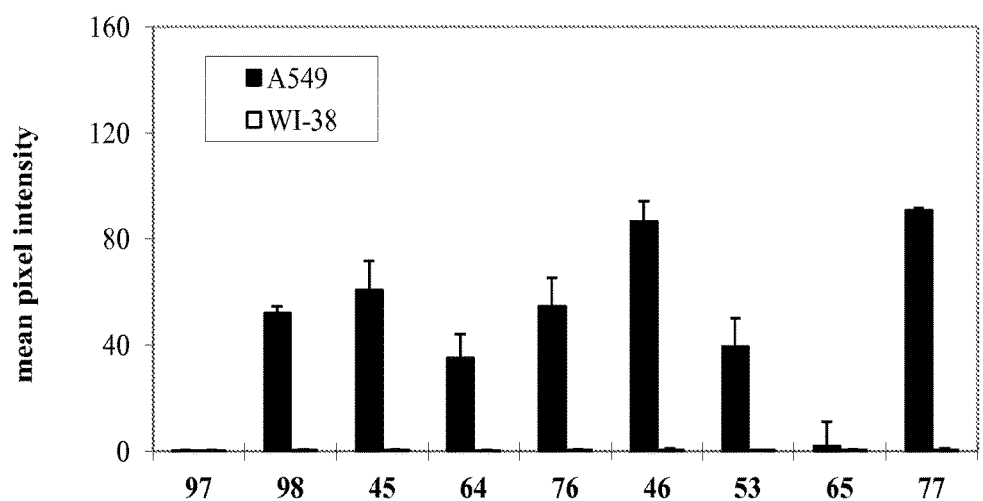
FIG. 1 shows a comparison of modified disaccharide-Cy5** conjugates of the present disclosure binding/uptake in human lung cancer and normal cells.
Figure 2:
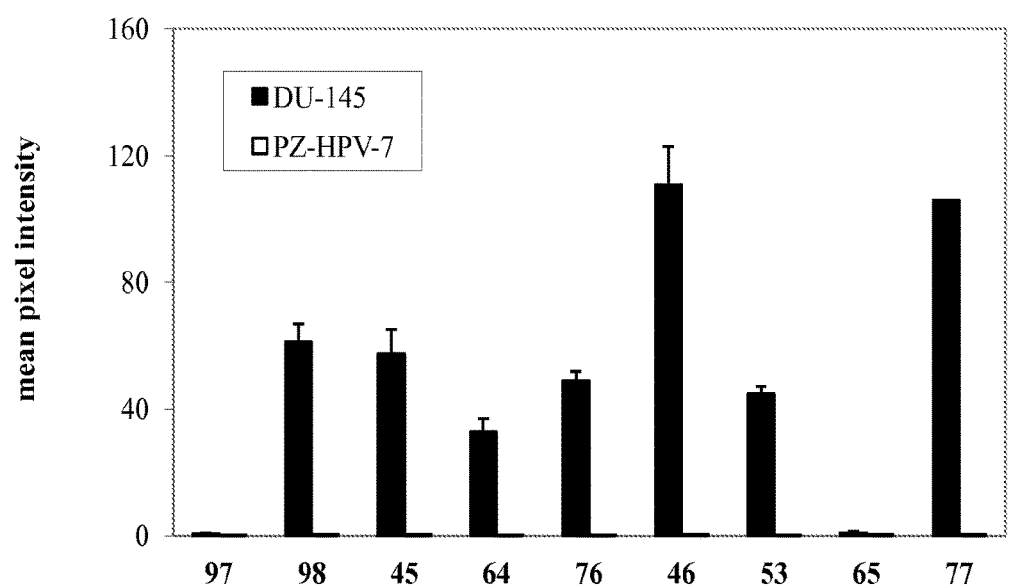
FIG. 2 shows a comparison of modified disaccharide-Cy5** conjugates of the present disclosure binding/uptake in human prostate cancer and normal cells.
Figure 3:
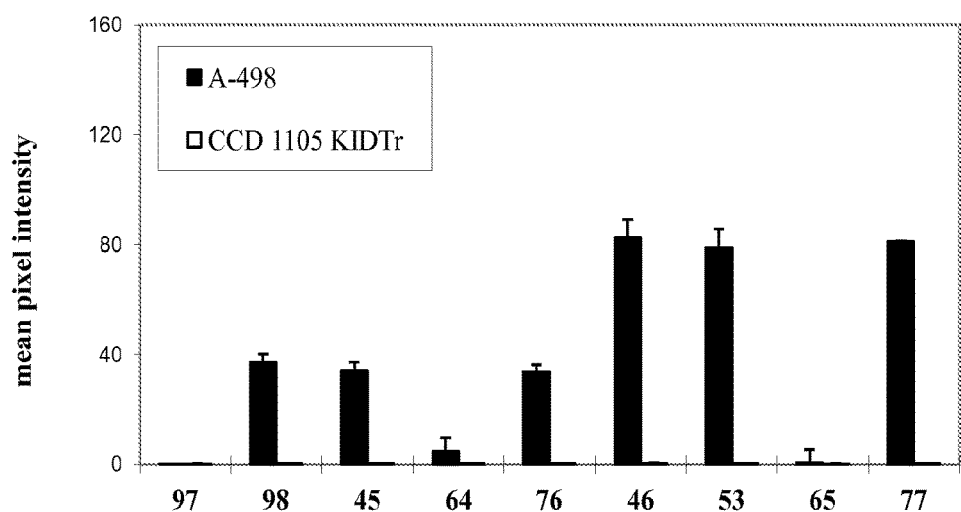
FIG. 3 shows a comparison of modified disaccharide-Cy5** conjugates of the present disclosure binding/uptake in human kidney cancer and normal cells.
Figure 4:
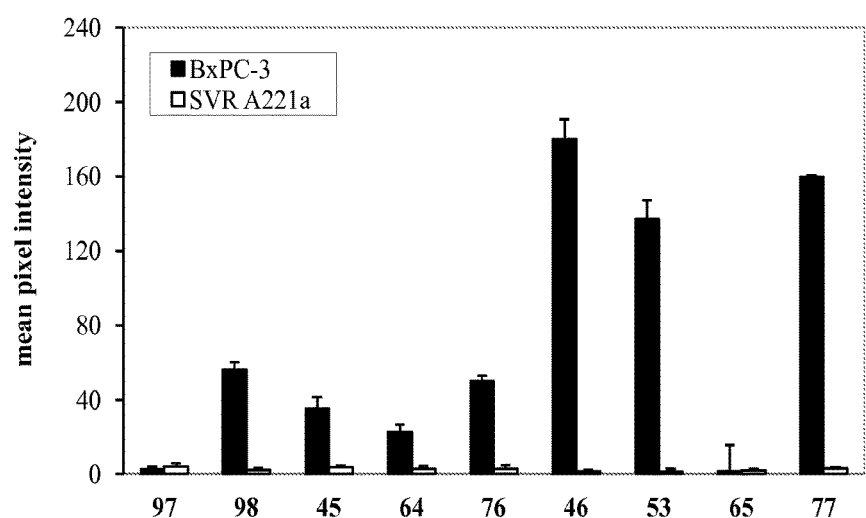
FIG. 4 shows a comparison of modified disaccharide-Cy5** conjugates of the present disclosure binding/uptake in human pancreatic cancer and normal cells.
Figure 5:
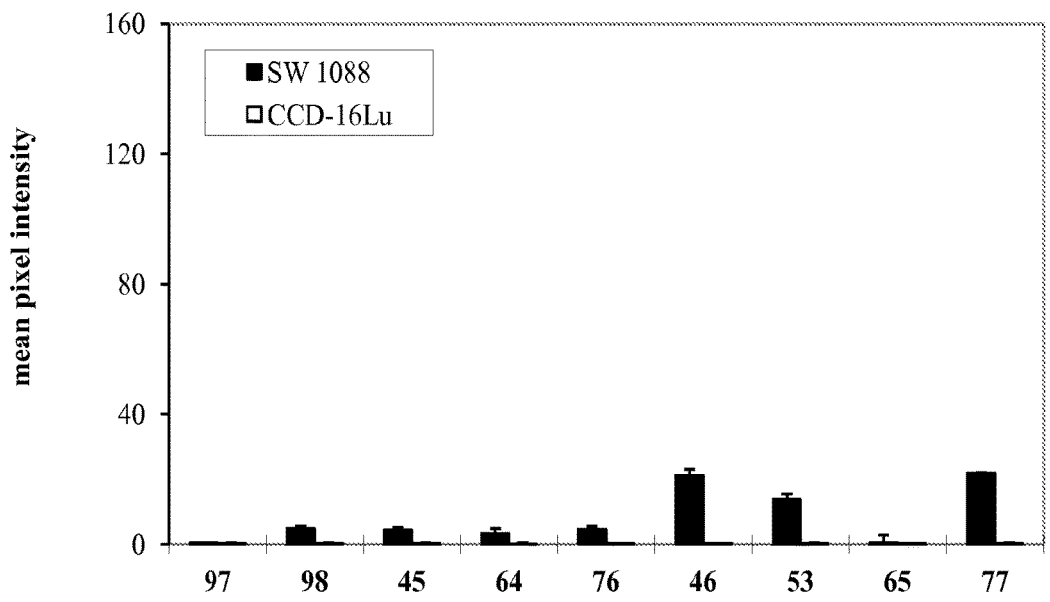
FIG. 5 shows a comparison of modified disaccharide-Cy5** conjugates of the present disclosure binding/uptake in human brain cancer and normal cells.
Figure 6:
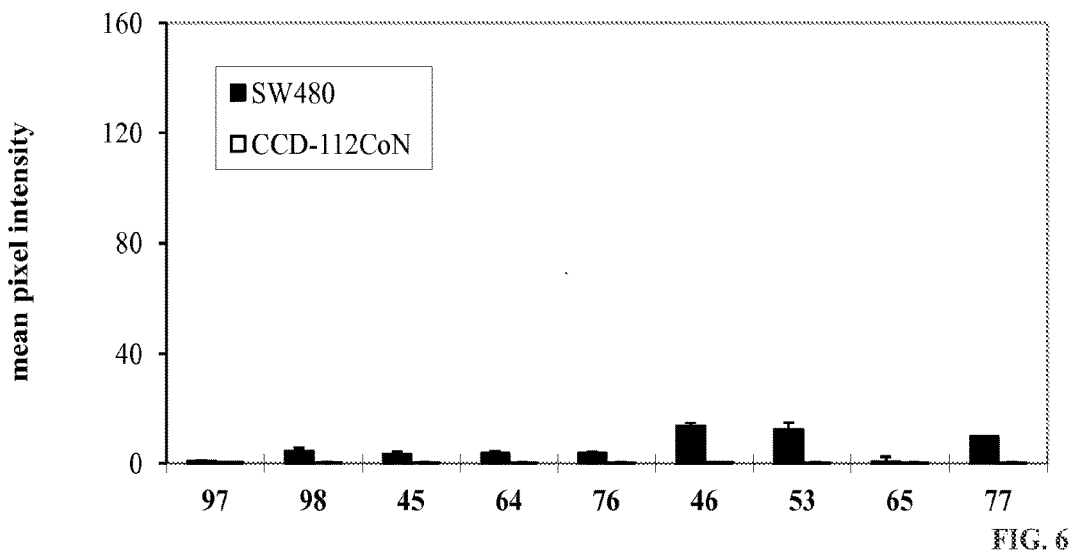
FIG. 6 shows a comparison of modified disaccharide-Cy5** conjugates of the present disclosure binding/uptake in human colon cancer and normal cells.
Figure 7:
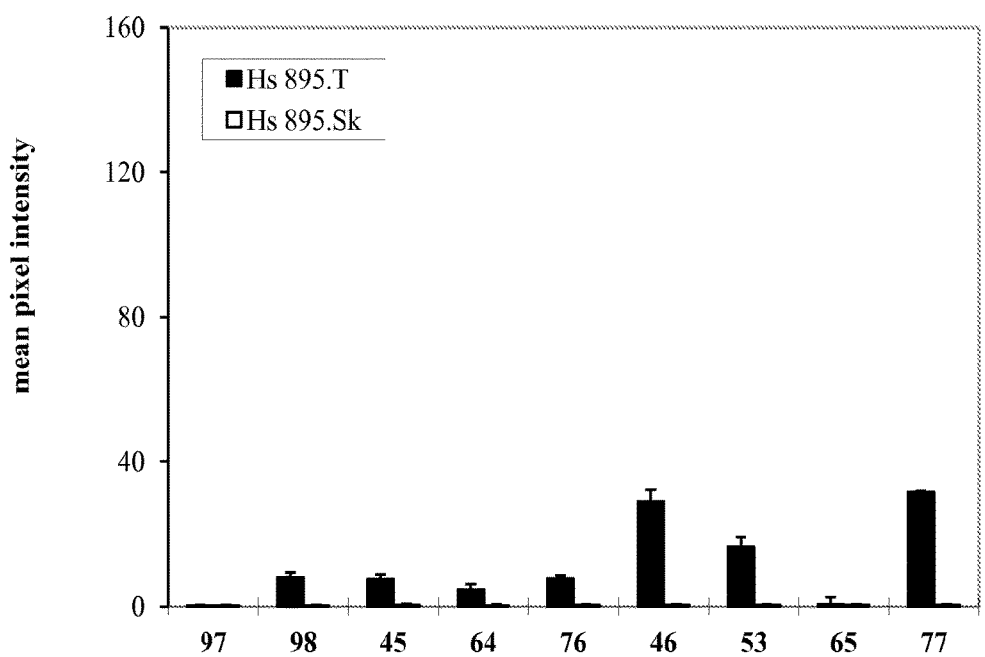
FIG. 7 shows a comparison of modified disaccharide-Cy5** conjugates of the present disclosure binding/uptake in human skin cancer and normal cells.
Figure 8:
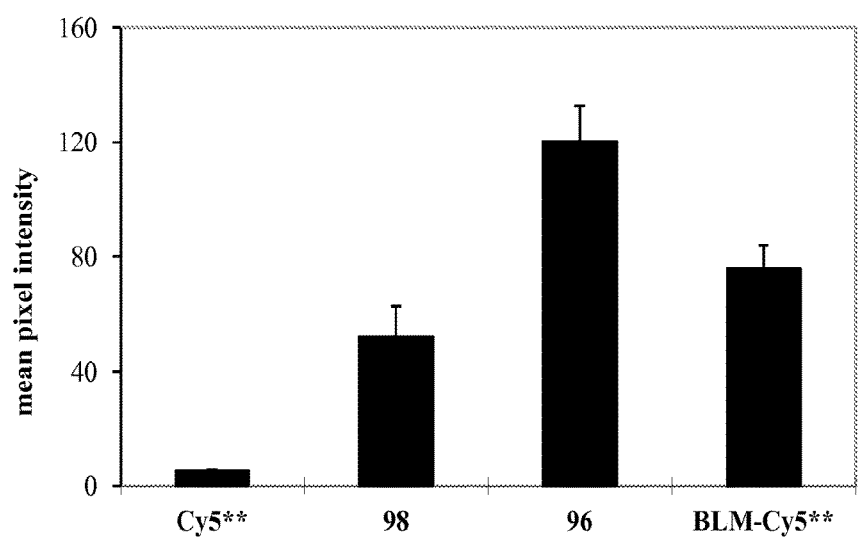
FIG. 8 shows a comparison of BLM disaccharide trimer-Cy5 conjugate (96) binding/uptake in human prostate cancer cells (DU-145). The BLM-disaccharide-Cy5 conjugate (98) is shown for comparison.
Figure 9:
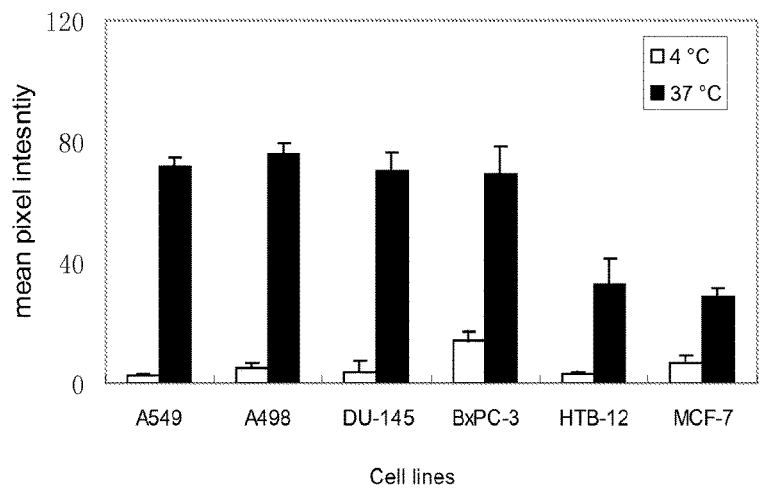
FIG. 9 shows the effects of temperature on the uptake of BLM-disaccharide-Cy5conjugates in different cancer cells. The cells were treated with 25 µM disaccharide-Cy5 at 4° C. or 37° C. for 1 h. Quantification of the uptake of disaccharide-Cy5** conjugates in six cancer cells. Fluorescence imaging was carried out with a 3 s exposure time.
Figure 10:
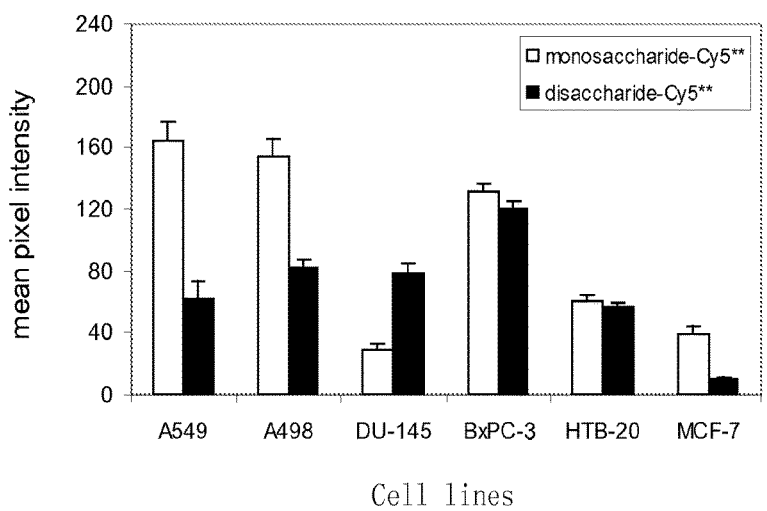
FIG. 10 shows a comparison of the uptake of BLM-monosaccharide-Cy5 and BLM-disaccharide-Cy5 in the different cancer cell lines. The cells were treated with 25 µM disaccharide-Cy5 or disaccharide-Cy5 at 37° C. for 1 h. Quantification of the uptake of monosaccharide-Cy5** conjugates in six cancer cells. Fluorescence imaging was carried out with a 3 s exposure time.
Figure 11:
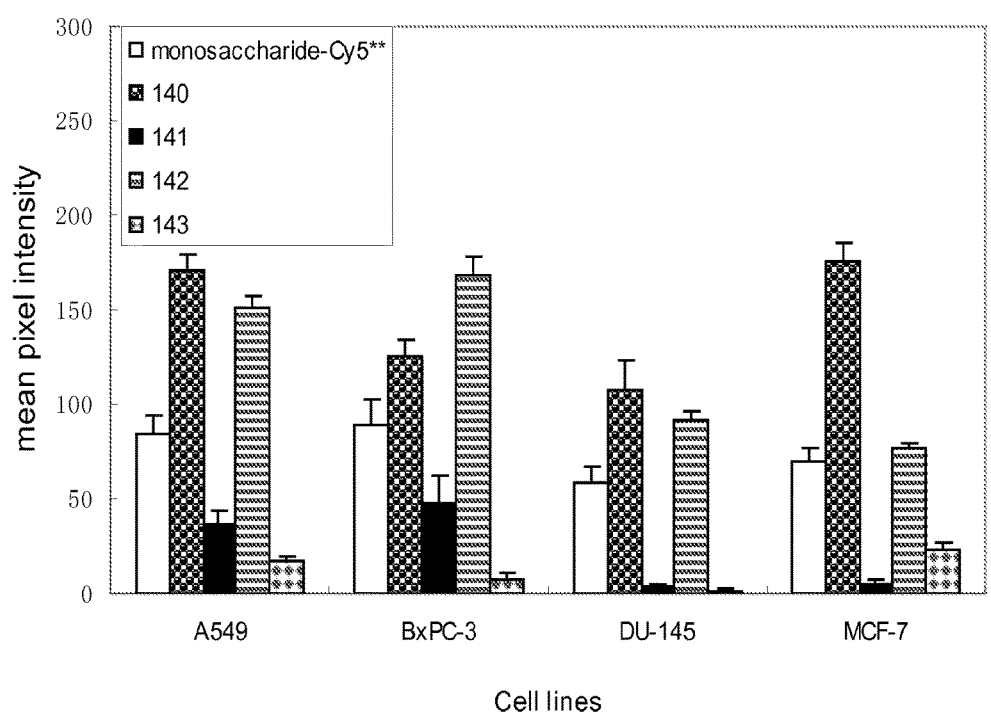
FIG. 11 shows a comparison of the uptake of modified monosaccharide-Cy5 library conjugates in the different cancer cell lines. The cells were treated with 25 µM of monosaccharide-Cy5 conjugates at 37° C. for 1 h. After washing with PBS, the cells were fixed with 4% paraformaldehyde. The cell nuclei were stained with DAPI. Quantification of the uptake of modified monosaccharide-Cy5** conjugates in four cancer cells. Fluorescence imaging was carried out after a 3-sec irradiation.
Figure 12:
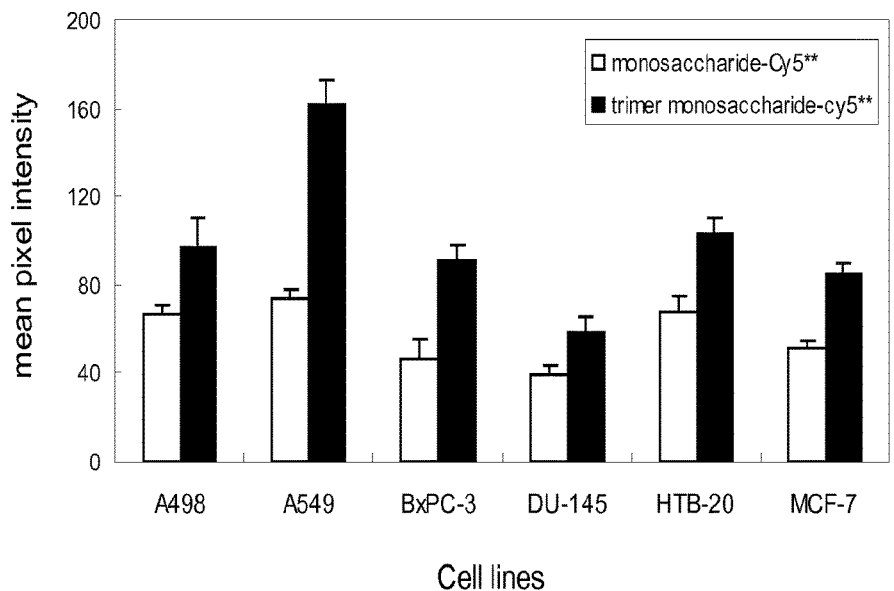
FIG. 12 shows a comparison of BLM-monosaccharide trimer-Cy5 conjugate (127) and BLM-monosaccharide-Cy5 (117) conjugate binding/uptake in six human cancer cells.
Figure 13:
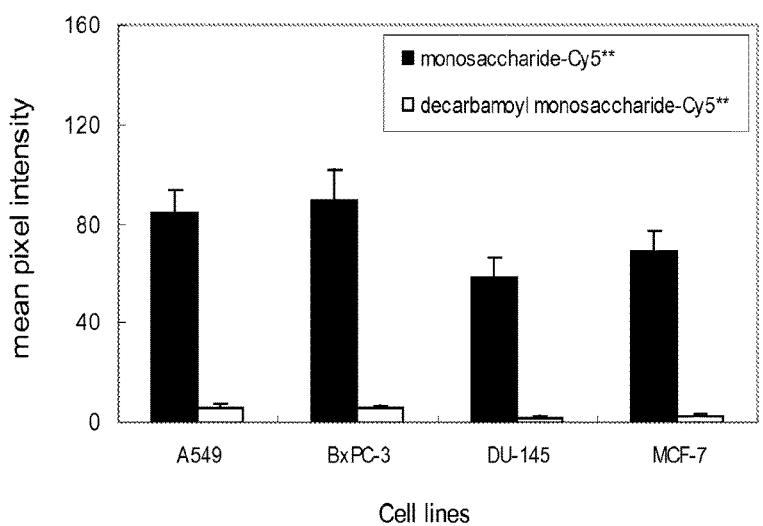
FIG. 13 shows a comparison of BLM-monosaccharide-Cy5 conjugate (117) and decarbamoyl monosaccharide-Cy5 (123) conjugate binding/uptake in four human cancer cells.
Figures 1, 14:
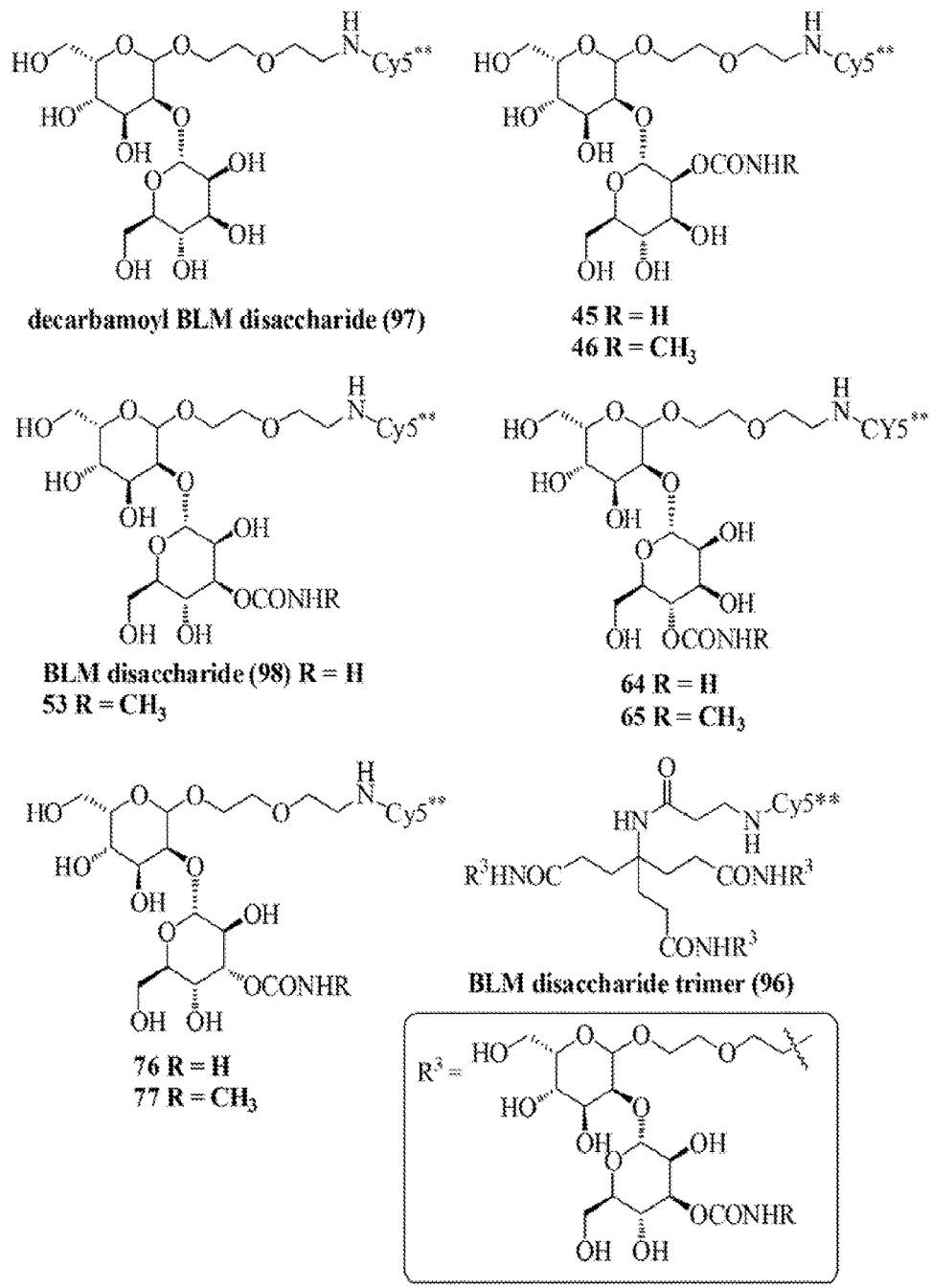
FIG. 14 shows the chemical structures of the Cy5** conjugates tested in FIGS. 1-13.

In order that the invention herein described may be fully understood, the following detailed description is set forth.

Unless defined otherwise, all technical and scientific terms used herein have the same meaning as those commonly understood by one of ordinary skill in the art to which this invention belongs. Although methods and materials similar or equivalent to those described herein can be used in the practice or testing of the present invention, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110.

The term "alkenyl" as used herein, refers to a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" refers to an alkyl group, as defined herein, appended to a parent moiety via an oxygen atom. Representative examples of alkoxy include, but are not limited to, methoxy, ethoxy, n-propoxy, iso-propoxy, n-butoxy, sec-butoxy, iso-butoxy, tert-butoxy, n-pentoxy, isopentoxy, neopentyloxy, n-hexyloxy, 3-methylhexyloxy, 2,2-dimethylpentoxy, 2,3-dimethylpentoxy, n-heptyloxy, n-octyloxy, n-nonyloxy, and n-decyloxy.

The term "alkoxyalkyl" as used herein, means an alkoxy group, as defined herein, appended to a parent moiety via an alkyl group, as defined herein. Representative examples of alkoxyalkyl include, but are not limited to, methoxymethyl, methoxyethyl, ethoxymethyl, ethoxyethyl, n-propoxymethyl, iso-propoxymethyl, n-butoxymethyl, sec-butoxymethyl, iso-butoxymethyl, and tert-butoxymethyl.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, —CH$_2$CH(CH$_2$CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "aryl," as used herein, means a phenyl (i.e., monocyclic aryl), a bicyclic ring system containing at least one phenyl ring or an aromatic bicyclic ring containing only carbon atoms in the aromatic bicyclic ring system. The bicyclic aryl can be azulenyl, naphthyl, or a phenyl (base ring) fused to a monocyclic cycloalkyl, a monocyclic cycloalkenyl, or a monocyclic heterocyclyl. The bicyclic aryl is attached to the parent molecular moiety through any carbon atom contained within the base ring, or any carbon atom with the napthyl or azulenyl ring. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2,3-dihydrobenzo[b][1,4]dioxan-5-yl, and 2,3-dihydrobenzo[b][1,4]dioxan-6-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl.

The term "cycloalkyl" as used herein, means a monocyclic or bicyclic ring system. Monocyclic ring systems are cyclic hydrocarbon groups containing from 3 to 8 carbon atoms, where such groups can be saturated (i.e., cycloalkanyl) or unsaturated (i.e., cycloalkenyl), but not aromatic. Examples of monocyclic cycloalkyls include cyclopropyl, cyclobutyl, cyclopentyl, cyclopentenyl, cyclohexyl, cyclohexenyl, cycloheptyl, and cyclooctyl. In certain embodiments, monocyclic cycloalkyl groups are fully saturated. Bicyclic cycloalkyl groups are a monocyclic cycloalkyl ring (base ring) fused to one ring selected from the group consisting of a phenyl ring, a monocyclic cycloalkyl, a monocyclic cycloalkenyl, a monocyclic heterocyclyl, and a monocyclic heteroaryl. The bicyclic cycloalkyl is attached to the parent molecular moiety through any carbon atom contained within the base ring. In certain embodiments, bicyclic cycloalkyl groups are a monocyclic cycloalkyl ring (base ring) fused to one ring selected from the group consisting of a phenyl ring, a 5 or 6 membered monocyclic cycloalkyl, a 5 or 6 membered monocyclic cycloalkenyl, a 5 or 6 membered monocyclic heterocyclyl, and a 5 or 6 membered monocyclic heteroaryl.

The term "heteroaryl," as used herein, means a monocyclic or bicyclic heteroaryl ring system. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl ring (base ring) fused to a phenyl, a monocyclic cycloalkyl, a monocyclic cycloalkenyl, a monocyclic heterocyclyl, or a monocyclic heteroaryl. When the bicyclic heteroaryl contains a fused cycloalkyl, cycloalkenyl, or heterocyclyl ring, then the bicyclic heteroaryl group is connected to the parent molecular moiety through any carbon atom or nitrogen atom contained within the base ring. When the bicyclic heteroaryl is a monocyclic heteroaryl fused to a phenyl ring or a monocyclic heteroaryl, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, and thienopyridinyl. In certain embodiments, the bicyclic heteroaryl is a 5 or 6 membered monocyclic heteroaryl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl.

The term "heterocyclyl" as used herein, means a monocyclic or bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is a monocyclic heterocycle ring (base ring) fused to a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the base ring. In certain embodiments, bicyclic heterocycles are a monocyclic heterocycle ring (base ring) fused to a phenyl, a 5 or 6 membered monocyclic cycloalkyl, a 5 or 6 membered monocyclic cycloalkenyl, a 5 or 6 membered monocyclic heterocycle, or a 5 or 6 membered monocyclic heteroaryl. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl.

The term "nitro" as used herein, means a —NO$_2$ group.

The term "saturated" as used herein means the referenced chemical structure does not contain any multiple carbon-carbon bonds. For example, a saturated cycloalkyl group as defined herein includes cyclohexyl, cyclopropyl, and the like. The term "unsaturated" as used herein means the referenced chemical structure contains at least one multiple carbon-carbon bond, but is not aromatic. For example, an unsaturated cycloalkyl group as defined herein includes cyclohexenyl, cyclopentenyl, cyclohexadienyl, and the like.

The term "imaging agent" refers to a chemical moiety that can provide a detectable signal. Such detectable signals include, but are not limited to, an optical signal generated upon interrogation of the imaging agent with light (e.g., via light absorption, fluorescence, or light scattering) or upon a reaction of the imaging agent with a second chemical moiety (e.g., a chemiluminescent signal), and radioactive decay signal. Examples of imaging agents include, but are not limited to visible dyes, fluorescent dyes, semiconductor nanoparticles, and radioisotopes.

The term "oligoalkylene glycol" refers to a linear oligoalkylene glycol, a branched oligoalkylene glycol, and a comb-oligoalkylene glycol, each comprising from about 1 to 1000 repeat units. In certain embodiments, an oligoalkylene glycol is a linear oligoalkylene glycol.

The term "oligopeptide" refers to a peptide with fewer than about 20 amino acid residues.

The term "dendrimer" refers to a highly branched polymer or oligomer having a well-defined chemical structure comprising a core and a given number of generations of branches, or spindles, and end groups. The generations of spindles consist of structural units that are identical for the same generation of spindles and that may be identical or different for different generations of spindles. The generations of spindles extend radially in a geometrical progression from the core. The end groups of a dendrimer from the Nth generation are the end functional groups of the spindles of the Nth generation or end generation.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the disclosure.

Compounds

The present disclosure provides a compound of formula (I):

or a pharmaceutically acceptable salt thereof, wherein A is:

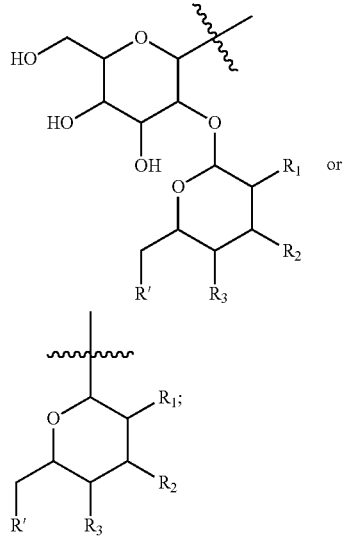

$R_1$ is selected from the group consisting of H, OH, SH, $NH_2$, $OR_4$, $OC(O)R_4$, $OC(O)NHR_4$, $OC(O)NR_4R_5$, $OC(O)SR_4$, $OC(S)NHR_4$, $OC(S)NR_4R_5$, $OC(S)SR_4$, $OC(S)NR_4R_5$, $SC(O)NHR_4$, $SC(O)NR_4R_5$, $NHC(O)NHR_4$, $NHC(O)NR_4R_5$, $NHC(S)NHR_4$, $NHC(S)NR_4R_5$, $NHC(N)NHR_4$, $NHC(N)NR_4R_5$, $OCH_2C(O)NHR_4$, $OCH_2C(O)NR_4R_5$, $OCH_2C(S)NHR_4$, $OCH_2C(S)NR_4R_5$, $SCH_2C(O)NHR_4$, $SCH_2C(O)NR_4R_5$, $NHCH_2C(O)NHR_4$, $NHCH_2C(O)NR_4R_5$, $NHCH_2C(S)NHR_4$ and $NHCH_2C(S)NR_4R_5$;

each $R_4$ is selected from the group consisting of H, $C_1$-$C_6$ alkyl, $C_2$-$C_6$ alkenyl and $C_2$-$C_6$ alkynyl;

each $R_5$ is selected from the group consisting of $C_1$-$C_6$ alkyl, $C_2$-$C_6$ alkenyl and $C_2$-$C_6$ alkynyl;

or $R_4$ and $R_5$ are taken together to form a 5-6 membered heterocyclic ring;

$R_2$ is selected from the group consisting of H, OH, SH, $NH_2$, $OR_4$, $OC(O)R_4$, $OC(O)NHR_4$, $OC(O)NR_4R_5$, $OC(O)SR_4$, $OC(S)NHR_4$, $OC(S)NR_4R_5$, $OC(S)SR_4$, $SC(O)NHR_4$, $SC(O)NR_4R_5$, $NHC(O)NHR_4$, $NHC(O)NR_4R_5$, $NHC(S)NHR_4$, $NHC(S)NR_4R_5$, $NHC(N)NHR_4$, $NHC(N)NR_4R_5$, $OCH_2C(O)NHR_4$, $OCH_2C(O)NR_4R_5$, $OCH_2C(S)NHR_4$, $OCH_2C(S)NR_4R_5$, $SCH_2C(O)NHR_4$, $SCH_2C(O)NR_4R_5$, $NHCH_2C(O)NHR_4$, $NHCH_2C(O)NR_4R_5$, $NHCH_2C(S)NHR_4$ and $NHCH_2C(S)NR_4R_5$;

$R_3$ is selected from the group consisting of H, OH, SH, $NH_2$, $OR_4$, $OC(O)R_4$, $OC(O)NHR_4$, $OC(O)NR_4R_5$, $OC(O)SR_4$, $OC(S)NHR_4$, $OC(S)NR_4R_5$, $OC(S)SR_4$, $SC(O)NHR_4$, $SC(O)NR_4R_5$, $NHC(O)NHR_4$, $NHC(O)NR_4R_5$, $NHC(S)NHR_4$, $NHC(S)NR_4R_5$, $NHC(N)NHR_4$, $NHC(N)NR_4R_5$, $OCH_2C(O)NHR_4$, $OCH_2C(O)NR_4R_5$, $OCH_2C(S)NHR_4$, $OCH_2C(S)NR_4R_5$, $SCH_2C(O)NHR_4$, $SCH_2C(O)NR_4R_5$, $NHCH_2C(O)NHR_4$, $NHCH_2C(O)NR_4R_5$, $NHCH_2C(S)NHR_4$ and $NHCH_2C(S)NR_4R_5$;

R' is selected from the group consisting of H, OH and $NHR_4$;

$R_6$ is a first linker;

n is an integer selected from 1 to 3;

$R_7$ is absent or a second linker, provided that when n is 1, $R_7$ is absent; and $R_8$ is selected from the group consisting of absent, an imaging agent and a reporting group.

In some embodiments, A is selected from the group consisting of:

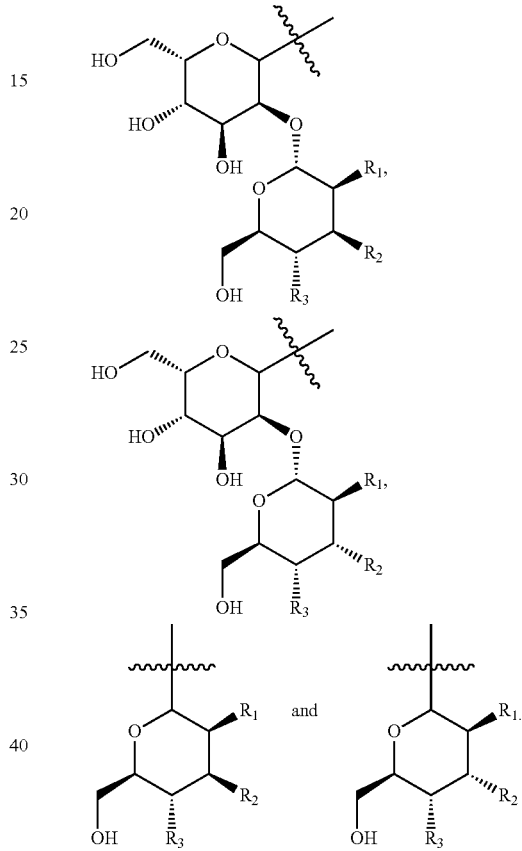

In some embodiments, the first linker is selected from the group consisting of a bond, $C_1$-$C_{20}$ alkyl, $C_1$-$C_{20}$ alkenyl, $C_1$-$C_{20}$ alkynyl, aryl, heteroaryl, heterocyclyl, $C_3$-$C_5$ cycloalkyl, an oligoalkylene glycol, an oligopeptide or a dendrimer.

In alternate embodiments, the first linker is X-($L^1$)-Y$_m$-$L^2$-Z, wherein X is $CH_2$ or O;

$L^1$ is $C_2$-$C_6$ alkyl;

Y is O, S, or $NR^y$, wherein $R^y$ is hydrogen or $C_1$-$C_6$ alkyl;

m is an integer selected from 1 to 10;

$L^2$ is $C_1$-$C_{20}$ alkyl, $C_2$-$C_{20}$ alkenyl, $C_2$-$C_{20}$ alkynyl, aryl, heteroaryl, heterocyclyl, $C_3$-$C_5$ cycloalkyl; and Z is absent, O, $NR^x$, S, C(O), S(O), $S(O)_2$, OC(O), $N(R^x)C(O)$, $N(R^x)S(O)$, $N(R^x)S(O)_2$, C(O)O, C(O)N($R^x$), S(O)N($R^x$), $S(O)_2N(R^x)$, OC(O)O, OC(O)N($R^x$), $N(R^x)C(O)O$, $N(R^x)C(O)N(R^x)$, or $N(R^x)S(O)_2N(R^x)$, wherein each $R^x$ is independently hydrogen or $C_1$-$C_6$ alkyl.

In some aspects of this embodiment, X is O, $L^1$ is $C_2$-$C_4$ alkyl; $L^2$ is $C_1$-$C_6$ alkyl; and Z is a bond, O, $NR^x$, S, C(O), S(O), or $S(O)_2$.

In some aspects of this embodiment, the first linker is O—(CH$_2$CH$_2$—O)$_m$—CH$_2$CH$_2$—Z, wherein Z is O, N(H), or S and m is an integer selected from 1 to 20.

In some aspects of this embodiment, the first linker is O—(CH$_2$CH$_2$—O)$_m$—CH$_2$CH$_2$—Z, wherein Z is C(O) or S(O)$_2$ and m is an integer selected from 1 to 20.

In some embodiments, R$_7$ is absent. In alternate embodiments, R$_7$ is a second linker.

In some embodiments, the second linker is (B-L$^3$)$_p$-D-E-L$^4$-F, wherein B is bond, O, NR$^x$, S, C(O), S(O), S(O)$_2$, OC(O), N(R$^x$)C(O), N(R$^x$)S(O), N(R$^x$)S(O)$_2$, C(O)O, C(O)N(R$^x$), S(O)N(R$^x$), S(O)$_2$N(R$^x$), OC(O)O, OC(O)N(R$^x$), N(R$^x$)C(O)O, N(R$^x$)C(O)N(R$^x$), or N(R$^x$)S(O)$_2$N(R$^x$);

L$^3$ is C$_2$-C$_6$ alkyl;

p is 2 or 3;

D is CH when p is 2 and D is C when p is 3;

E is a bond, O, NR$^x$, S, C(O), S(O), S(O)$_2$, OC(O), N(R$^x$)C(O), N(R$^x$)S(O), N(R$^x$)S(O)$_2$, C(O)O, C(O)N(R$^x$), S(O)N(R$^x$), S(O)$_2$N(R$^x$), OC(O)O, OC(O)N(R$^x$), N(R$^x$)C(O)O, N(R$^x$)C(O)N(R$^x$), or N(R$^x$)S(O)$_2$N(R$^x$);

L$^4$ is C$_2$-C$_6$ alkyl; and

F is a bond, O, NR$^x$, S, C(O), S(O), S(O)$_2$, OC(O), N(R$^x$)C(O), N(R$^x$)S(O), N(R$^x$)S(O)$_2$, C(O)O, C(O)N(R$^x$), S(O)N(R$^x$), S(O)$_2$N(R$^x$), OC(O)O, OC(O)N(R$^X$), N(R$^X$)C(O)O, N(R$^x$)C(O)N(R$^x$), or N(R$^x$)S(O)$_2$N(R$^x$), wherein each R$^x$ is independently hydrogen or C$_1$-C$_6$ alkyl.

In some aspects of this embodiment, B is NR$^x$ or C(O); L$^3$ is C$_2$-C$_4$ alkyl; L$^4$ is C$_2$-C$_4$ alkyl; E is NR$^x$, N(R$^x$)C(O), C(O)O or C(O)N(R$^x$); and F is O, S, C(O), NR$^x$ or NR$^x$C(O).

In some aspects of this embodiment, the second linker is [C(O)—CH$_2$CH$_2$]$_p$-D-NR$^x$C(O)—CH$_2$CH$_2$-E.

In some embodiments, A is

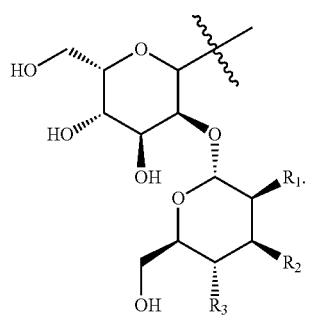

In alternative embodiments, A is

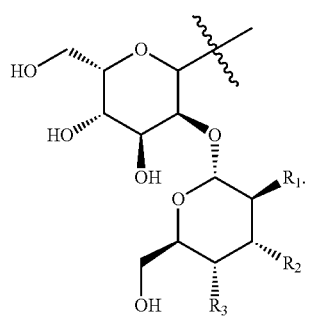

In alternative embodiments, A is

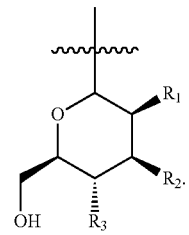

In alternative embodiments, A is

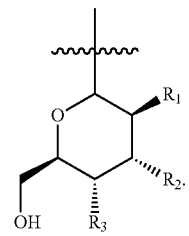

In some embodiments, n is 1. In other embodiments, n is 2. In yet other embodiments, n is 3.

In some embodiments, R$_1$ is selected from the group consisting of H, OH, OR$_4$, OC(O)R$_4$, NHC(N)NHR$_4$, NHC(N)NR$_4$R$_5$, OCONHR$_4$, OCONR$_4$R$_5$, OCOSR$_4$ and OCSSR$_4$.

In some embodiments, R$_2$ is selected from the group consisting of H, OH, OR$_4$, OC(O)R$_4$, OC(O)SR$_4$, NHC(N)NHR$_4$, NHC(N)NR$_4$R$_5$, OCONHR$_4$, OCONR$_4$R$_5$, OCSNHR$_4$, OCSNR$_4$R$_5$, NHCONHR$_4$, NHCONR$_4$R$_5$, OCH$_2$CONHR$_4$, and OCH$_2$CONR$_4$R$_5$.

In some embodiments, R$_3$ is selected from the group consisting of OH, OR$_4$, OC(O)R$_4$, NHC(N)NHR$_4$, NHC(N)NR$_4$R$_5$, OCONHR$_4$ and OCONR$_4$R$_5$.

In some embodiments, R' is OH. In other embodiments, R' is H.

In some embodiments, each R$_4$ is selected from the group consisting of H, methyl, ethyl, butyl, isobutyl and hexyl.

In some embodiments, each R$_5$ is selected from the group consisting of methyl, ethyl, butyl, isobutyl and hexyl.

In some embodiments, R$_4$ and R$_5$ are taken together to form a 5-6 membered heterocyclic ring. In some aspects of this embodiment, they form a pyrrolidine ring.

In some embodiments, A is selected from the group consisting of:

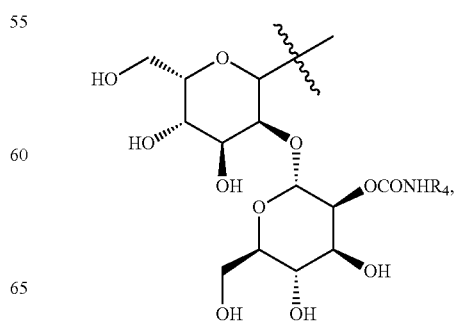

-continued
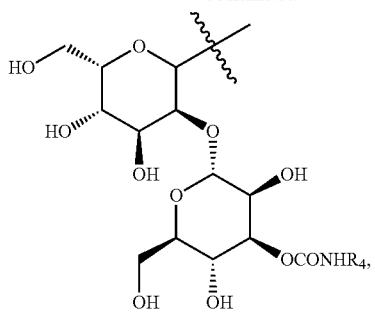
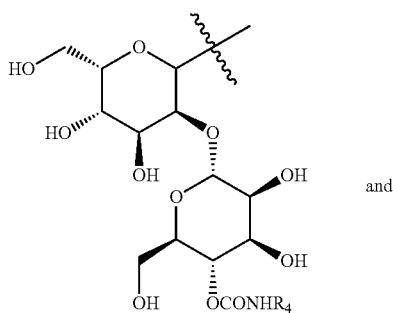
and
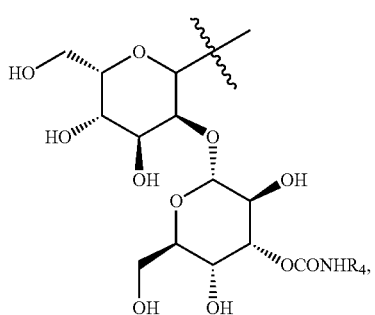
wherein $R_4$ is H or $C_1$-$C_6$ alkyl. In some aspects of this embodiment, $R_4$ is H or methyl.
In some embodiments, A is:
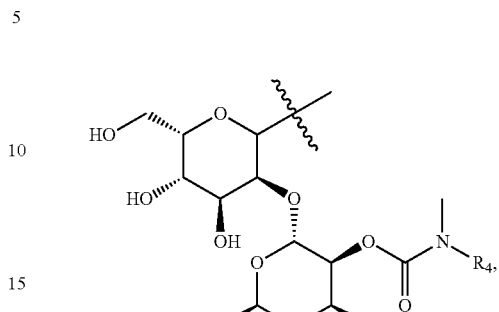
In some embodiments, A is selected from the group consisting of:
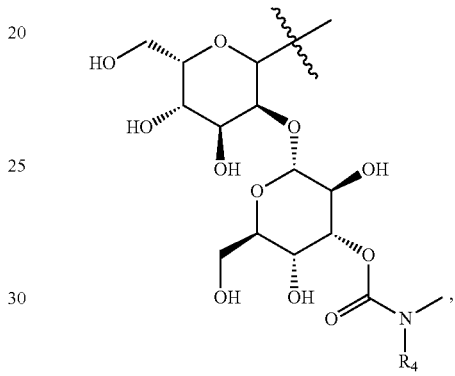

-continued

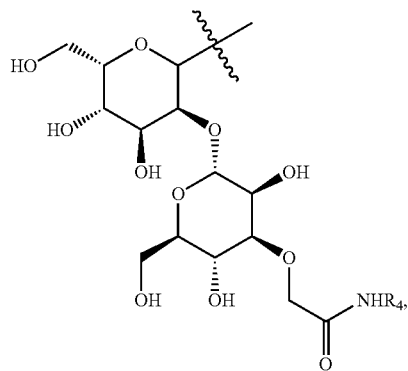

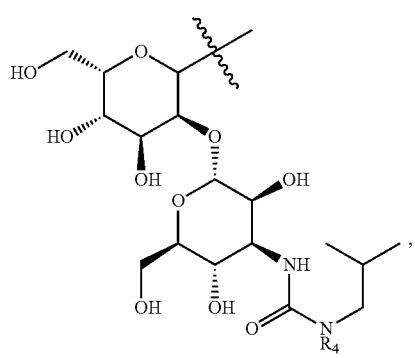

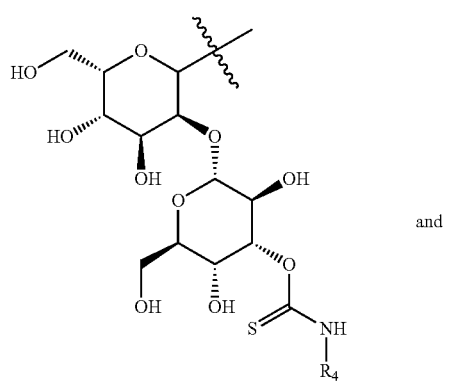

and

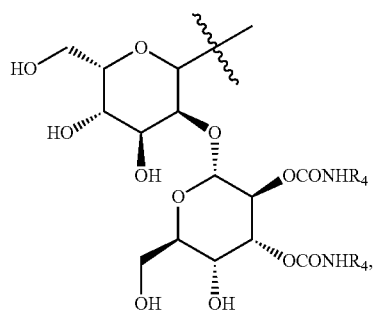

wherein $R_4$ is H or $C_1$-$C_6$ alkyl. In some aspects of this embodiment, $R_4$ is H, methyl or ethyl.

In some embodiments, A is:

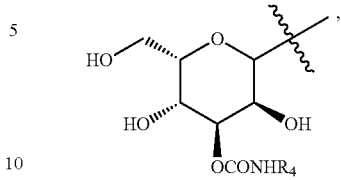

wherein $R_4$ is H or $C_1$-$C_6$ alkyl. In some aspects of this embodiment, $R_4$ is H.

In some embodiments, A is:

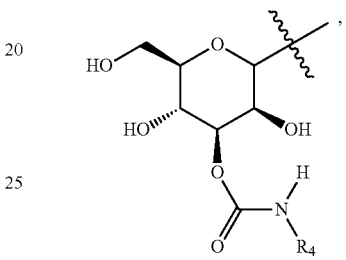

wherein $R_4$ is H or $C_1$-$C_6$ alkyl. In some aspects of this embodiment, $R_4$ is H or methyl.

In some embodiments, A is:

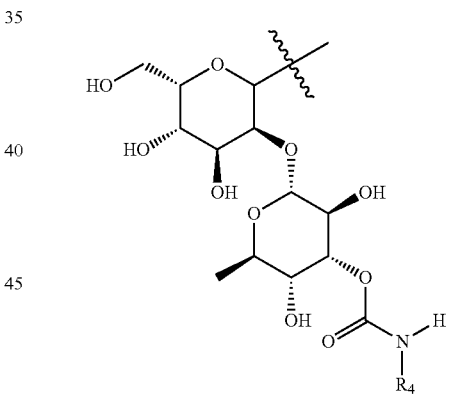

or

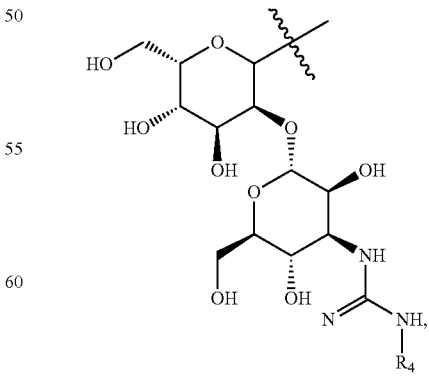

wherein $R_4$ is H or $C_1$-$C_6$ alkyl. In some aspects of this embodiment, $R_4$ is H or methyl.

In some embodiments, A is:

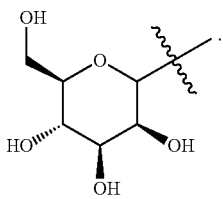 [SMILES: *C1O[C@H](CO)[C@@H](O)[C@H](O)[C@@H]1O]

In some embodiments, A is:

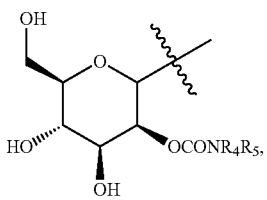

wherein $R_4$ is H or $C_1$-$C_6$ alkyl and $R_5$ is $C_1$-$C_6$ alkyl, or $R_4$ and $R_5$ are taken together to form a 5-6 membered heterocyclic ring. In some aspects of this embodiment, $R_4$ is H, methyl, ethyl, butyl, isobutyl or hexyl. In some aspects, $R_5$ is methyl, ethyl, butyl, isobutyl or hexyl. In other aspects, $R_4$ and $R_5$ are taken together to form a pyrrolidine ring.

In some embodiments, A is:

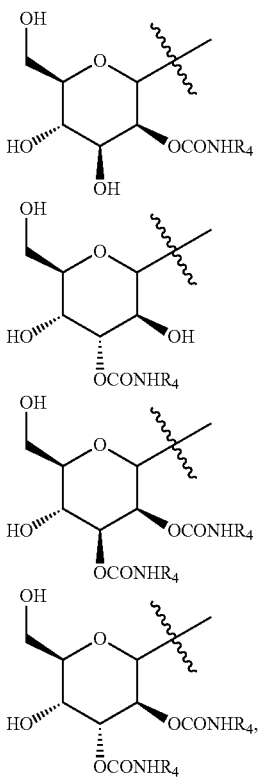

wherein each $R_4$ is H or $C_1$-$C_6$ alkyl. In some aspects of this embodiment, each $R_4$ is selected from the group consisting of H, methyl and hexyl.

In some embodiments, A is:

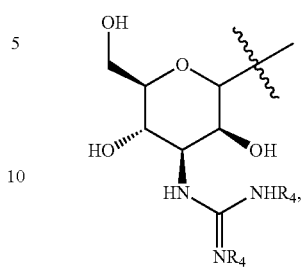

wherein $R_4$ is H or $C_1$-$C_6$ alkyl. In some aspects of this embodiment, $R_4$ is H or methyl.

In some embodiments, A is selected from the group consisting of:

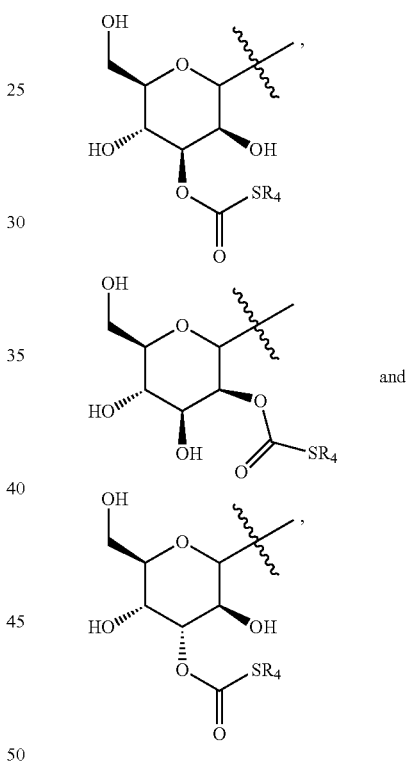

wherein $R_4$ is H or $C_1$-$C_6$ alkyl. In some aspects of this embodiment, $R_4$ is H or methyl.

In some embodiments, A is:

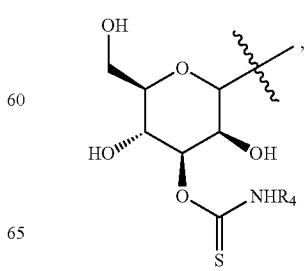

-continued

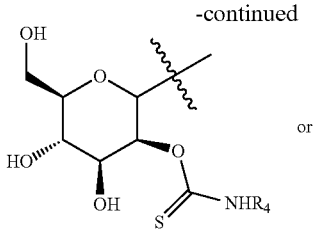

or

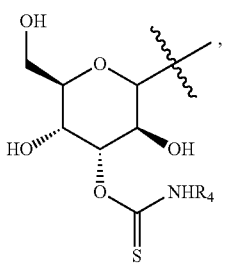

wherein $R_4$ is H or $C_1$-$C_6$ alkyl. In some aspects of this embodiment, $R_4$ is H or methyl.

In some embodiments, A is:

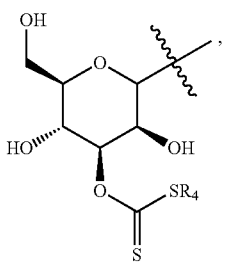

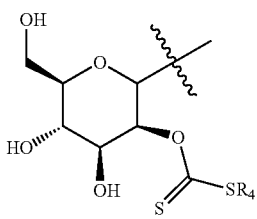

or

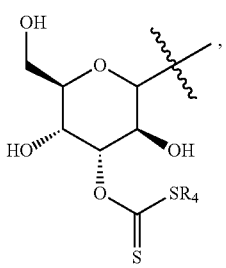

wherein $R_4$ is H or $C_1$-$C_6$ alkyl. In some aspects of this embodiment, $R_4$ is H or methyl.

In some embodiments, $R^8$ is an imaging agent or a reporter group.

In some embodiments, the imaging agent or reporter group comprises a radiolabel, an enzyme, a fluorescent label, a luminescent label, a bioluminescent label, a magnetic label, or biotin.

In some embodiments, $R^8$ is a fluorescent imaging agent. In some aspects of this embodiment, $R^8$ is selected from the group consisting of Alexa Fluor 647, Sulfo Cy5, Cy5, Cy7 and Cy5. In some aspects, $R^8$ is Cy5. Cy5** can be protonated or a salt thereof.

In some embodiments, $R^8$ comprises a chelating group coordinated to a radioactive imaging moiety.

In some embodiments in which the imaging agent or reporter group comprises a radiolabel, the radiolabel is selected from the group consisting of: $^3$H, $^{11}$C, $^{14}$C, $^{18}$F, $^{32}$P, $^{35}$S, $^{57}$Co, $^{64}$Cu, $^{68}$Ga, $^{90}$Y, $^{99m}$Tc, $^{111}$In, $^{125}$I, $^{131}$I, $^{177}$Lu, $^{166}$Ho, and $^{153}$Sm.

In some embodiments in which the imaging agent or reporter group comprises an enzyme, the enzyme is selected from the group consisting of luciferase, alkaline phosphatase, beta-galactosidase and horseradish peroxidase.

In some embodiments, the reporter group is biotin.

In some embodiments, the compound of formula (I) is selected from the group consisting of:

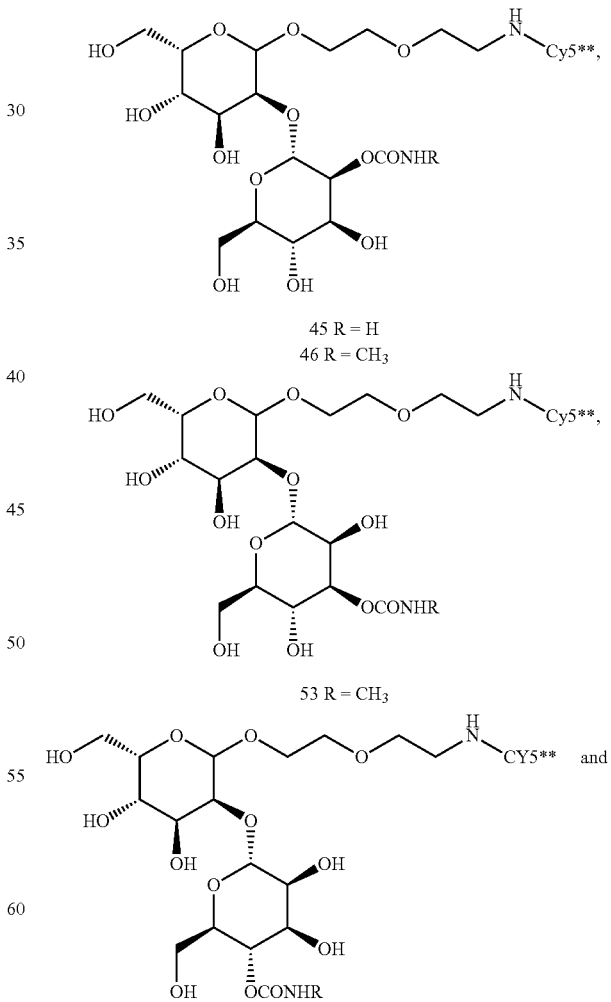

45 R = H
46 R = CH$_3$

53 R = CH$_3$ and

64 R = H
65 R = CH$_3$

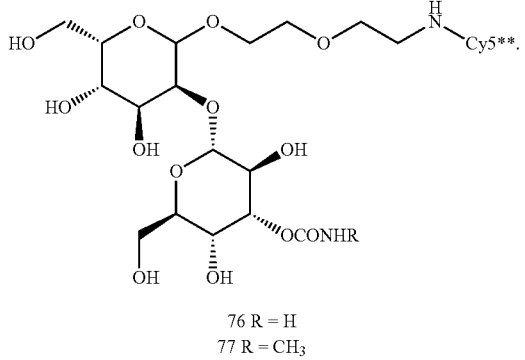
76 R = H
77 R = CH₃
In some embodiments, the compound of formula (I) is:
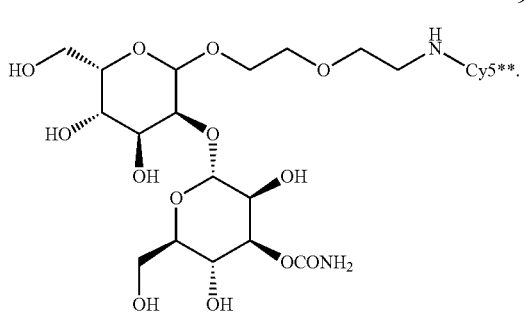
98
In some embodiments, the compound of formula (I) is selected from the group consisting of:
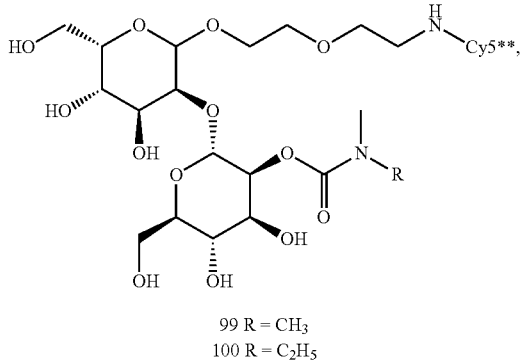
99 R = CH₃
100 R = C₂H₅
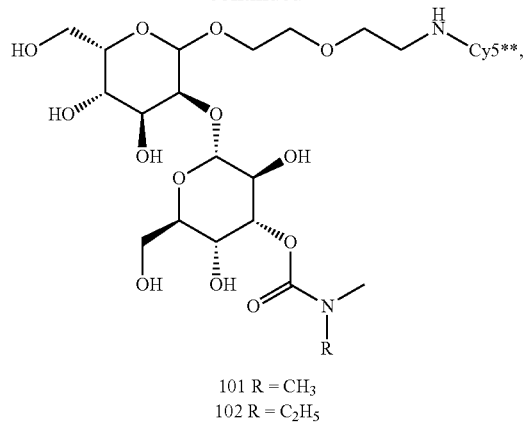
101 R = CH₃
102 R = C₂H₅
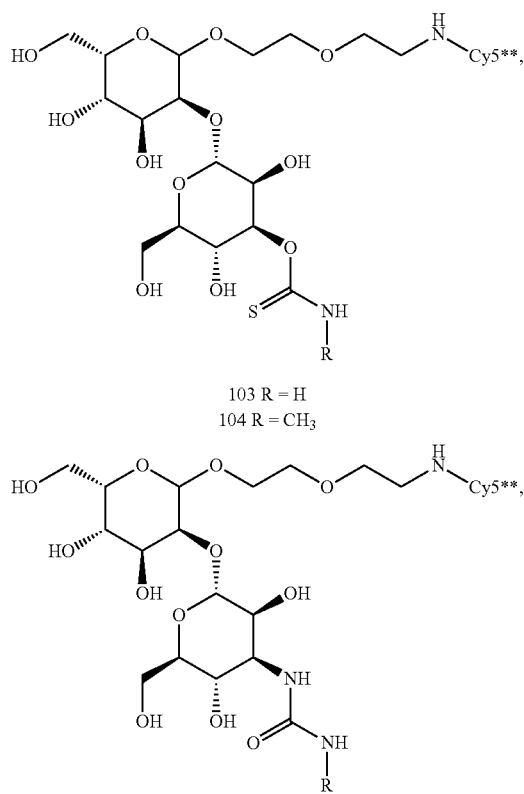
103 R = H
104 R = CH₃
107 R = H
108 R = CH₃
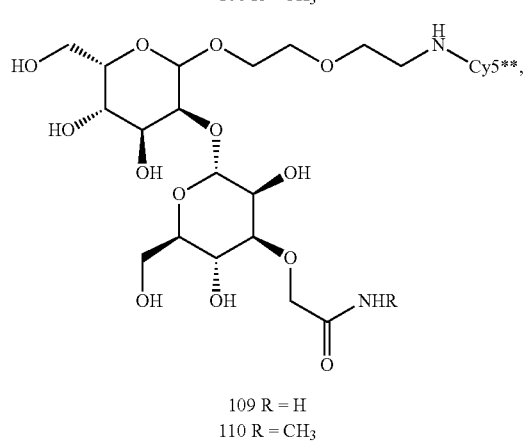
109 R = H
110 R = CH₃

-continued
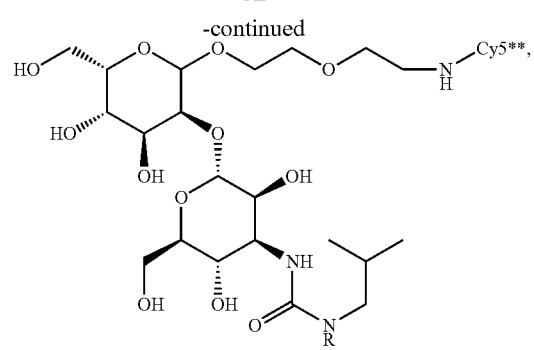
111 R = H
112 R = CH₃
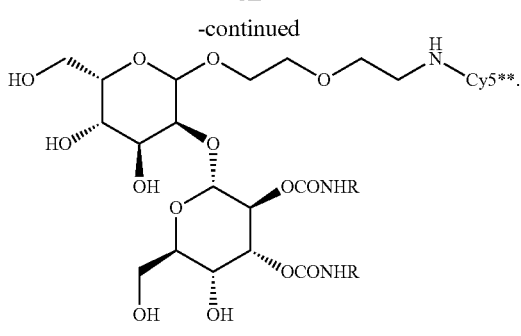
113 R = H
114 R = CH₃
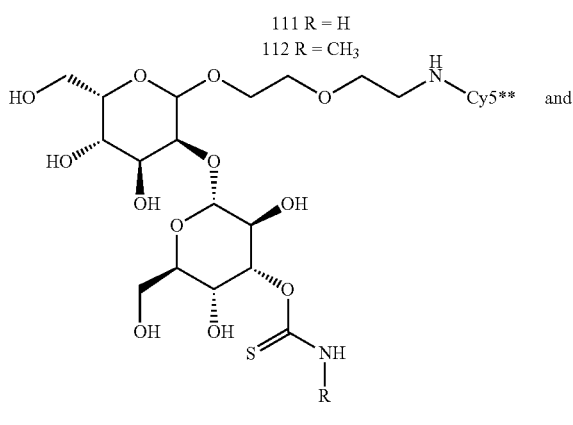
105 R = H
106 R = CH₃
In some embodiments, the compound of formula (I) is:
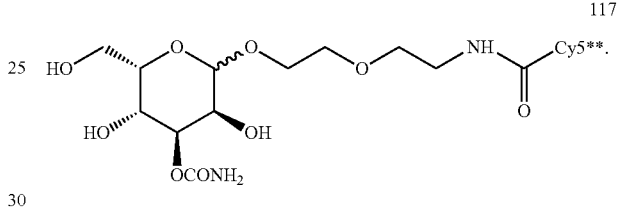
117
In some embodiments, the compound of formula (I) is:
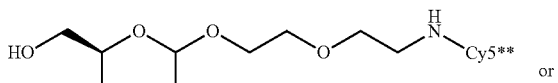
182
or
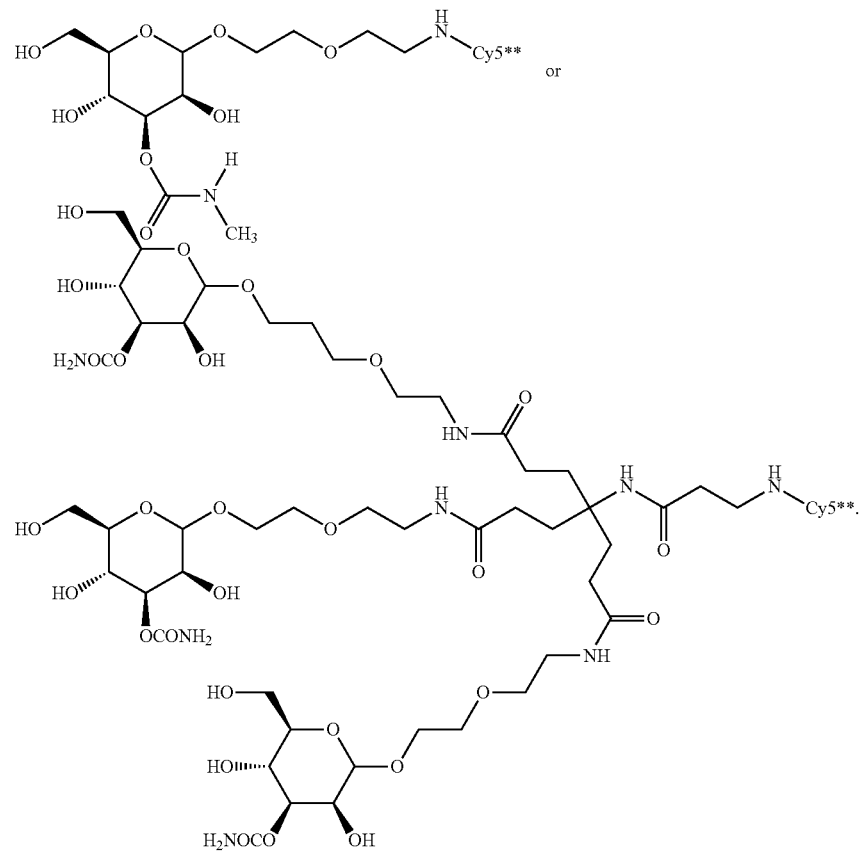
127

In some embodiments, the compound of formula (I) is:

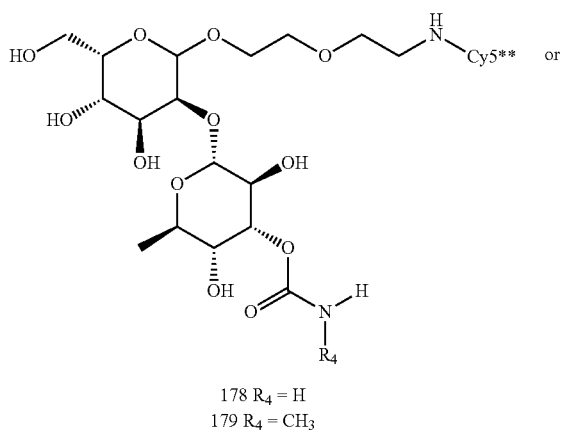

178 R$_4$ = H
179 R$_4$ = CH$_3$

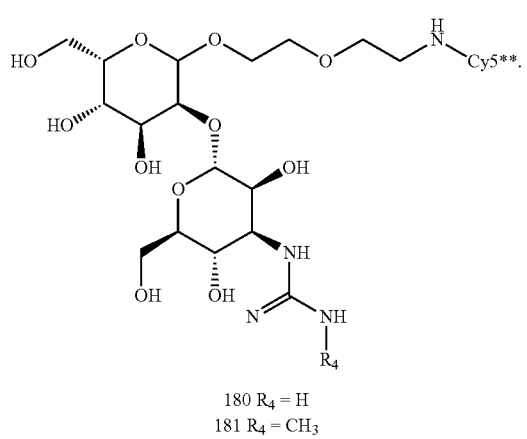

180 R$_4$ = H
181 R$_4$ = CH$_3$

In some embodiments, the compound of formula (I) is:

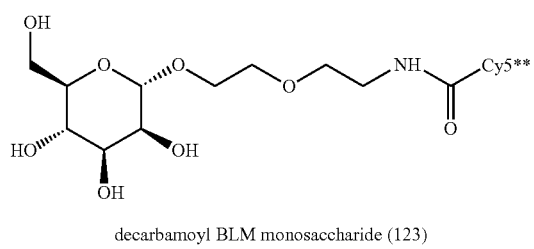

decarbamoyl BLM monosaccharide (123)

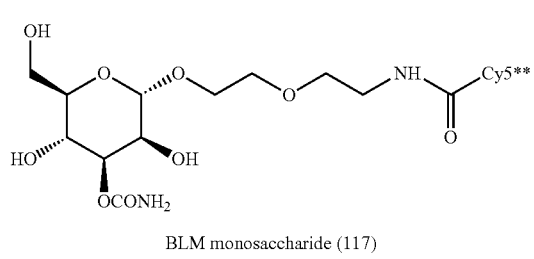

BLM monosaccharide (117)

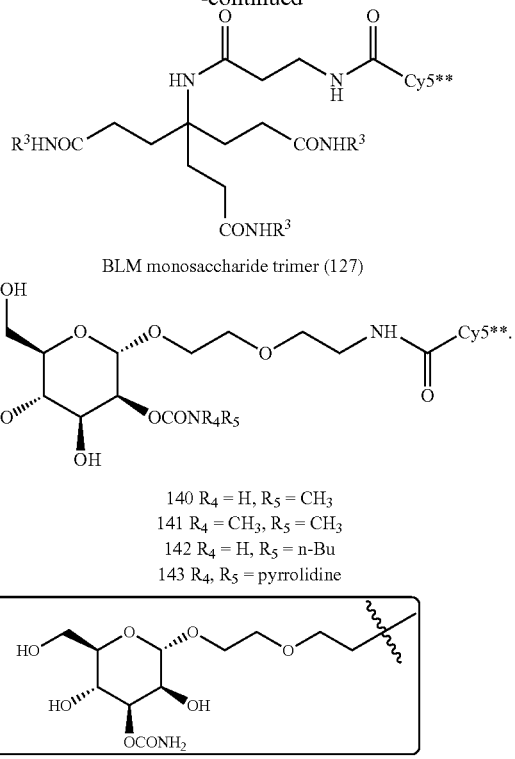

BLM monosaccharide trimer (127)

140 R$_4$ = H, R$_5$ = CH$_3$
141 R$_4$ = CH$_3$, R$_5$ = CH$_3$
142 R$_4$ = H, R$_5$ = n-Bu
143 R$_4$, R$_5$ = pyrrolidine In some embodiments, the compound of formula (I) is:

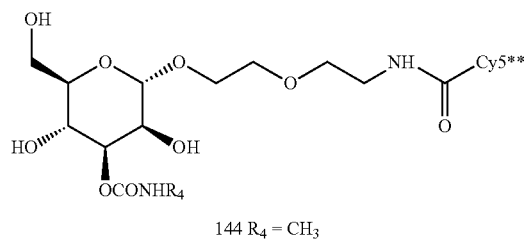

144 R$_4$ = CH$_3$

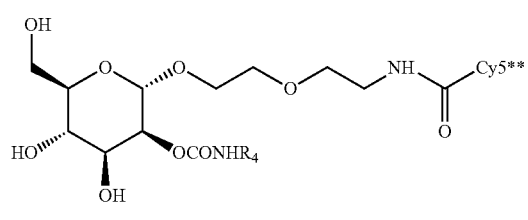

145 R$_4$ = Hex

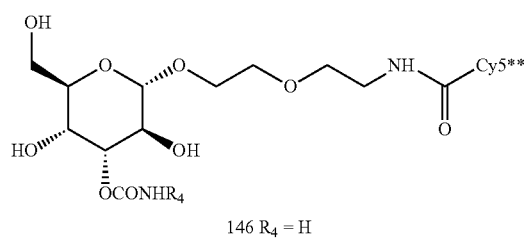

146 R$_4$ = H
147 R$_4$ = CH$_3$

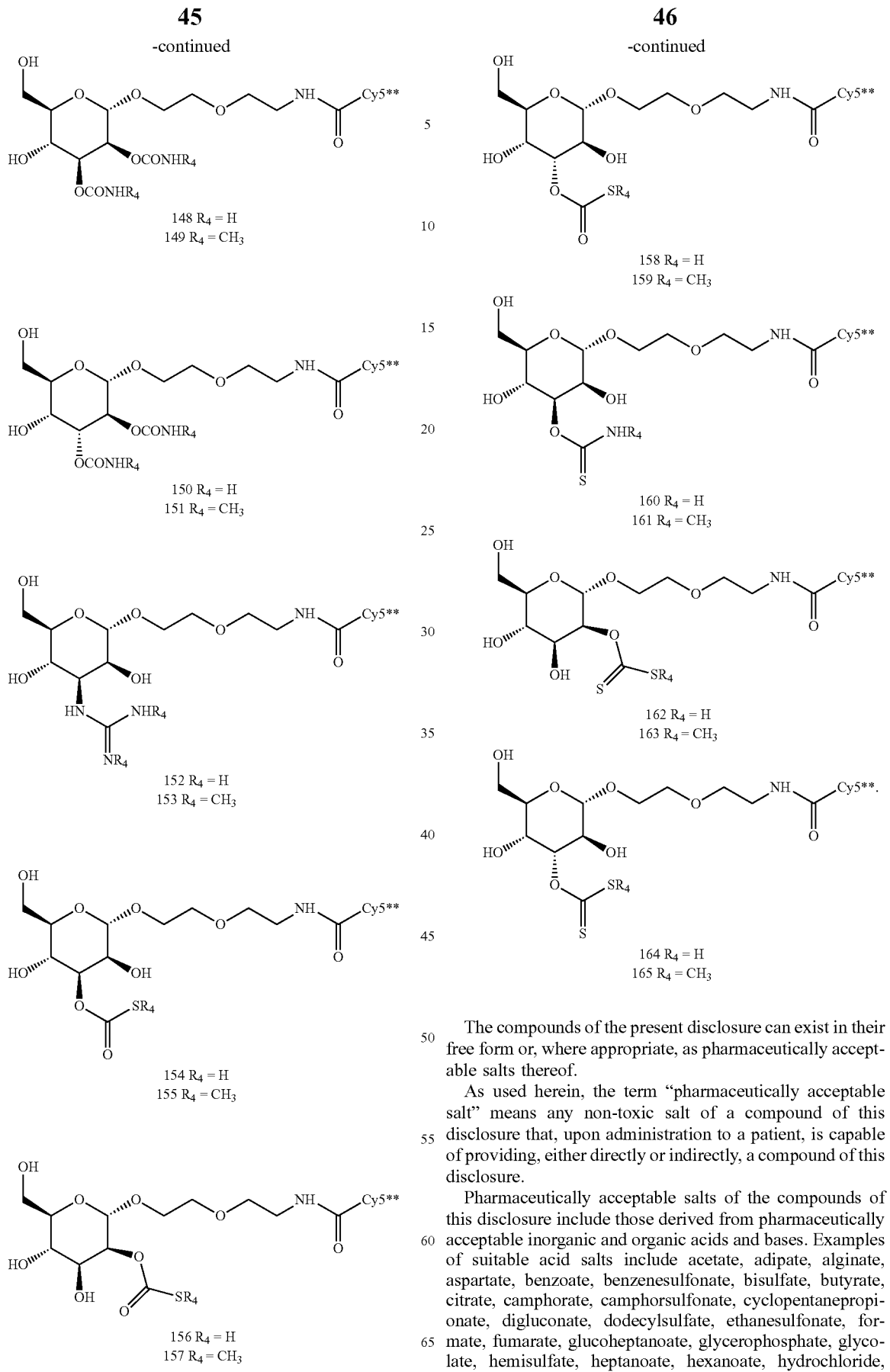

The compounds of the present disclosure can exist in their free form or, where appropriate, as pharmaceutically acceptable salts thereof.

As used herein, the term "pharmaceutically acceptable salt" means any non-toxic salt of a compound of this disclosure that, upon administration to a patient, is capable of providing, either directly or indirectly, a compound of this disclosure.

Pharmaceutically acceptable salts of the compounds of this disclosure include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the disclosure and their pharmaceutically acceptable acid addition salts.

Salts derived from appropriate bases include alkali metal (e.g., sodium and potassium), alkaline earth metal (e.g., magnesium), ammonium and $N^+(C_{1-4}$ alkyl$)_4$ salts. This disclosure also envisions the quaternization of any basic nitrogen-containing groups of the compounds disclosed herein. Water or oil-soluble or dispersible products may be obtained by such quaternization.

Compositions

The present disclosure provides a pharmaceutical composition comprising a compound of formula (I) as described above and a pharmaceutically acceptable carrier.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the present compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present disclosure may be administered orally, parenterally, by inhalation spray, topically, rectally, nasally, buccally, intraocularly, vaginally or via an implanted reservoir. The term "parenteral", as used herein, includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers that are commonly used in the manufacture of pharmaceutically acceptable solid, liquid, or other dosage forms may also be used for the purposes of formulation.

The pharmaceutically acceptable compositions of this disclosure may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this disclosure are formulated for oral administration.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in as imaging agents.

Typically, the pharmaceutical compositions of this disclosure will be administered from about 1 to 5 times per day or alternatively, as a continuous infusion. Or, alternatively, the compositions of the present disclosure may be administered in a pulsatile formulation. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

One skilled in the art would recognize that a variety of compounds of the present disclosure may be prepared according to methods known in the art, and the synthetic Examples set forth below.

Microbubble Conjugates

The present disclosure provides a microbubble conjugate comprising (a) a microbubble comprising an outer shell, wherein the outer shell is derivatized with streptavidin; and (b) a compound as described above, wherein $R_8$ is biotin. The biotin and streptavidin are bound to each other.

Microbubbles are ultrasound contrast agents made of a shell enclosing a gas core. The shell is usually composed of albumin, galactose or lipids. The make-up of the gas core defines the ability of the microbubbles to strongly reflect ultrasound waves. Air or heavy insoluble gases such as perfluorocarbons or nitrogen (Lindner, J. R. Nature Rev., 3, 527-532, 2004) are typically used. When microbubbles are administrated intravenously to the systemic circulation, their echogenocity allows contrast-enhanced ultrasound and improved medical sonography. In medical imaging, these agents have applications in radiology and cardiology. See Hamilton, A. J., et al., J. Am. Coll. Cardiol., 43, 453-60, (2004); Christensen, J. P., et al., Circulation, 96, 473-82 (2002). Currently, two FDA-approved microbubbles are available. Optison, made by GE Healthcare has an albumin shell and an octofluoropropane gas core, Levovist, made by Schering, has a lipid-galactose shell and air core (Lindner, J. R. supra).

In some embodiments, the microbubbles have a diameter of about 0.1 to 10 microns. In some aspects, the microbubbles have a diameter between 1 and 4 um, which allows the microbubbles to flow freely through the circulation and microcirculation. Circulation time can be greatly improved by the use of lipid-based membranes coated with longer chain fully saturated lipid molecules, such as distearoylphosphatidylcholine. See Rychak, J. J., et al., J. Con. Rel., 114, 288-99, (2006). Microbubbles designed with low solubility gases such as decafluorobutane slow the rate at which gas diffused into the bloodstream, thus allowing the microbubble to retain its structure longer. See Klibanov, A. L., Bioconjugate Chem., 16, 9-17, (2005). With these characteristics, contrast agents can be regarded as pure intravascular tracers that behave similarly to red blood cells within the microcirculation and entry into the bloodstream is made possible by simple intravenous insertion via a catheter. See Lindner, J. R., supra.

The microbubbles are formed by entrapping the gas into a liquid. The microbubbles may be made of various insoluble gases such as fluorocarbon or sulfur hexafluoride gas. The liquid includes any liquid which can form microbubbles. Generally any insoluble gas can be used. It must be gaseous at body temperature and be nontoxic. The gas must also form stable microbubbles of average size of between about 0.1 and 10 microns in diameter when the pharmaceutical composition is sonicated to form microbubbles. Generally perfluorocarbon gases such as perfluoromethane, perfluoroethane, perfluoropropane, perfluorobutane, perfluoropentane are preferred. Other inert gases such as sulfur hexafluoride are also useful in forming microbubbles.

Once the microbubbles are formed they may be stabilized by coating with a suitable lipid of protein, such as albumin, human gamma, globulin, human apotransferrin, Beta lactose or urease.

Microbubbles may be formed by sonication, typically with a sonicating horn. Sonication by ultrasonic energy causes cavitation within the dextrose albumin solution at sites of gas in the fluid. These cavitation sites eventually resonate and produce small microbubbles (about 7 microns in size) which are non-collapsing and stable. In general, sonication conditions which produce concentrations of greater than about $4 \times 10^{-8}$ M of between about 5 and about 6 micron microbubbles are preferred. Generally the mixture will be sonicated for about 80 seconds, while being perfused with an insoluble gas. A variety of other methods used to make microbubbles are described in published PCT application WO 96/39197. This same application also describes many of the gases which may be included within the microbubbles. Any such methods can be used to prepare microbubbles to be conjugated to a saccharide containing compound as described herein.

Moreover, there are various sources of commercially available microbubbles that can be derivatized with the saccharides of the present disclosure in analogy to what is described herein. For example, Optison® (GE HealthCare) and Levovist (Schering). In exemplary embodiments described herein the microbubbles used are Targestar$^B$ Ultrasound Contrast Agent. To create biotinylated microbubbles, a biotin-labeled conjugate is conjugated to Targestar$^B$ Targeted Ultrasound Contrast Agent (Targeson). Coupling Reagent (Targeson) is added to conjugated Targestar$^B$ microbubbles and incubated at room temperature with gentle agitation. The product is divided into two syringes, rinsed with Infusion Buffer, and then centrifuged. The infranatant is drained to 1 mL. A biotinylated-compound of the present disclosure, as described herein, is added to one of the vials and both can be incubated at room temperature with gentle agitation. To each sample is added Infusion Buffer before centrifugation. This solution is drained to 1.0 mL before recovery of the supernatant and repetition of the previous step. Finally, the supernatant is resuspended in Infusion Buffer.

Any suitable specific binding pair can be used for binding the saccharides of the present disclosure to the microbubble. Preferably, the binding pair is one with a dissociation constant of $10^{-3}$ M or less; in other embodiments, a dissociation constant of $10^{-4}$ M or less; $10^{-5}$ M or less; or $10^{-6}$ M or less. In one embodiment, the binding pair comprises biotin-streptavidin or biotin-avidin. Other non-limiting embodiments include metal/chelators binding pairs; protein/protein binding pairs; protein-cofactors binding pairs; (modified) nucleic acid-nucleic acid binding pairs; and protein/nucleic acid binding pairs. Any suitable method can be used to derivatize the microbubble and the disaccharide to incorporate the binding pair member into their structure.

Once prepared, the conjugated microbubbles are transferred to a sterile syringe and injected parenterally into a subject (for example, a mammal), preferably near the target site of activity of the agent. The microbubbles of the present disclosure can be used to attach specifically to tumor cells in a patient. The compositions are administered using conventional methods for delivering such compositions, i.e., using parenteral administration of microbubbles, preferably at or near the site of the tumor. The imaging of the tumor site is then achieved through conventional methods that involve imaging of diagnostic contrast agents.

Methods of Use

The present disclosure also provides a method of imaging a tumor in a patient. According to this method, a compound of formula (I) or a composition comprising a compound of formula (I) and a pharmaceutically acceptable carrier are administered to a patient in need of such imaging. The compound or composition may be any of those described above.

Next, the patient is subjected to a technique that produces images of the tumor. In some embodiments, the technique is selected from the group consisting of ultrasound, radioimaging, magnetic resonance imaging and fluorescent imaging.

The term "patient", as used herein, means an animal, preferably a mammal, and most preferably, a mouse, rat, other rodent, rabbit, dog, cat, swine, cattle, sheep, horse, or primate, and even more preferably a human.

The term "a patient in need of such imaging" as used herein refers to a patient who has a tumor, is suspected of having a tumor or previously had a tumor.

The term "tumor" as used herein includes, but is not limited to, tumors derived from lung cells, prostate cells, kidney cells, pancreatic cells, brain cells, colon cells, skin cells, testicular cells, breast cells, bladder cells, liver cells and white blood cells In alternative embodiments, the present disclosure provides a method of detecting a tumor in a patient. According to this method, a compound of formula (I) or a composition comprising a compound of formula (I) and a pharmaceutically acceptable carrier are administered to a patient suspected of having a tumor. The compound of formula (I) may be any of those described above wherein $R^8$ is a fluorescent imaging agent. In some embodiments, $R^8$ is selected from the group consisting of Alexa Fluor 647, Sulfo Cy5, Cy5, Cy7 and Cy5. In some aspects, $R^8$ is Cy5. $R^8$ is Cy5**.

Next, the patient is illuminated with light of a wavelength absorbable by the fluorescent imaging agent.

Then, an optical signal emitted by the fluorescent imaging agent is detected. The optical signal, if detected, indicates the presence of a tumor.

In further embodiments, the present disclosure provides a method of imaging a cell or an in vitro biopsy sample. According to this method, a cell or an in vitro biopsy sample is contacted with a compound of formula (I), a microbubble, or compositions thereof. The compound of formula (I), the microbubble and compositions thereof may be any described above.

Next, the cell or the in vitro biopsy sample is imaged.

In order that this disclosure be more fully understood, the following examples are set forth. These examples are for the purpose of illustration only and are not to be construed as limiting the scope of the disclosure in any way.

EXAMPLES

The compounds and methods of the disclosure are illustrated further by the following examples, which are provided for illustrative purposes and not intended to be construed as limiting the disclosure in scope or spirit to the specific compounds and methods described in them.

The chemicals were all ACS reagent grade and were used without further purification. The reactions were carried out under an argon atmosphere unless specified. Flash column chromatography was carried out using silica gel (Silicycle R10030B, 60 particle size, 230-400 mesh), applying a low pressure stream of nitrogen. Analytical thin layer chromatographic separations were carried out on glass plates coated with silica gel (60 particle size F254, SiliCycle TLG-R10011B-323). The TLC chromatograms were developed by immersing the plates in 2.5% potassium permanganate in ethanol or 2% anisaldehyde+5% sulfuric acid+1.5% glacial acetic acid in ethanol, followed by heating, or else visualized by UV irradiation (254 nm). Melting points were recorded on a MelTemp apparatus and are uncorrected. Tetrahydrofuran was distilled from sodium/benzophenone ketyl and dichloromethane from calcium hydride. $^1$H and $^{13}$C NMR spectra were recorded on a Gemini 300 or Varian Inova 400, or on a Varian Inova 500 spectrometer, using $CDCl_3$ as solvent and internal standard, unless otherwise indicated. $^1$H NMR chemical shifts were reported relative to residual $CHCl_3$ at 7.26 ppm, or to residual DMSO-$d_5$ at 2.50 ppm; $^{13}$C NMR shifts were reported relative to the central line of $CDCl_3$ at 77.16 ppm, or to $^{13}$C DMSO-$d_6$ at 39.51 ppm. Splitting patterns are designated as s, singlet; br s, broad singlet; d, doublet; dd, doublet of doublets; dt, doublet of triplets; m, multiplet; q, quartet; quin, quintet. Cyanine dyes were obtained from our collaborators at General Electric. High resolution mass spectrometric data was obtained at the Michigan State Mass Spectrometry Facility or at the Arizona State University CLAS High Resolution Mass Spectrometry Facility.

Example 1: Synthesis of Gulose Acceptor 8

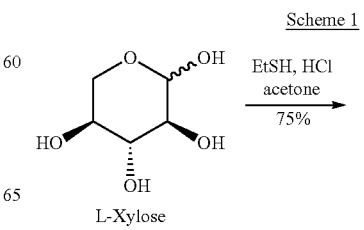

Scheme 1

L-Xylose

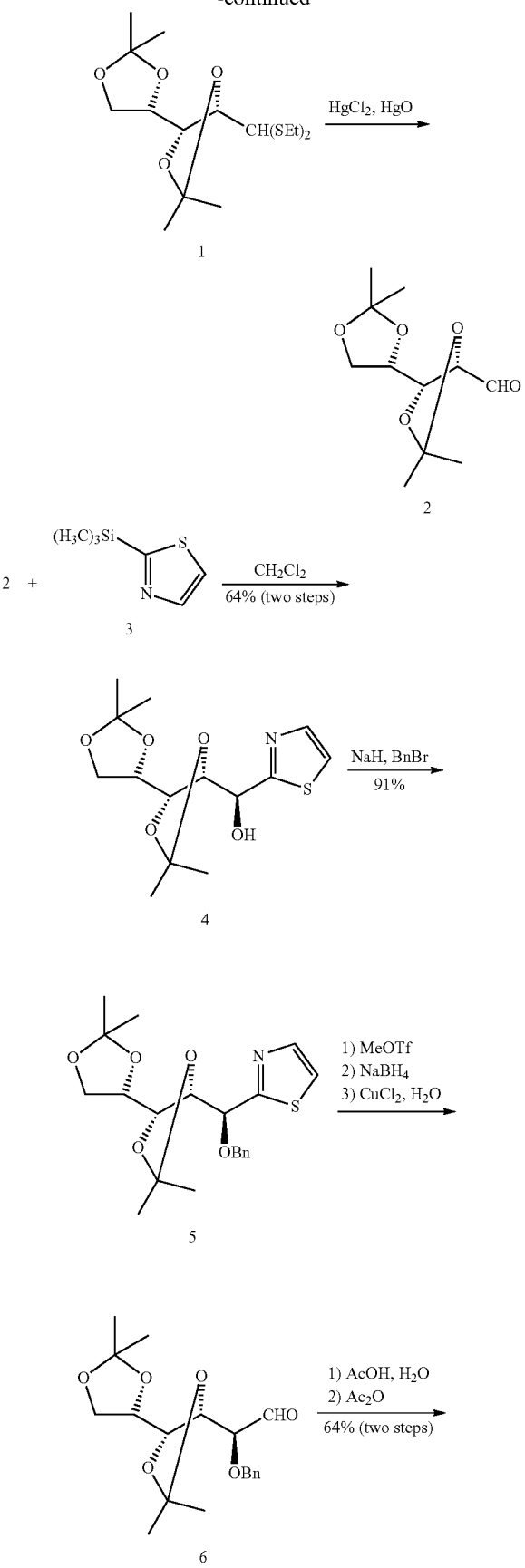

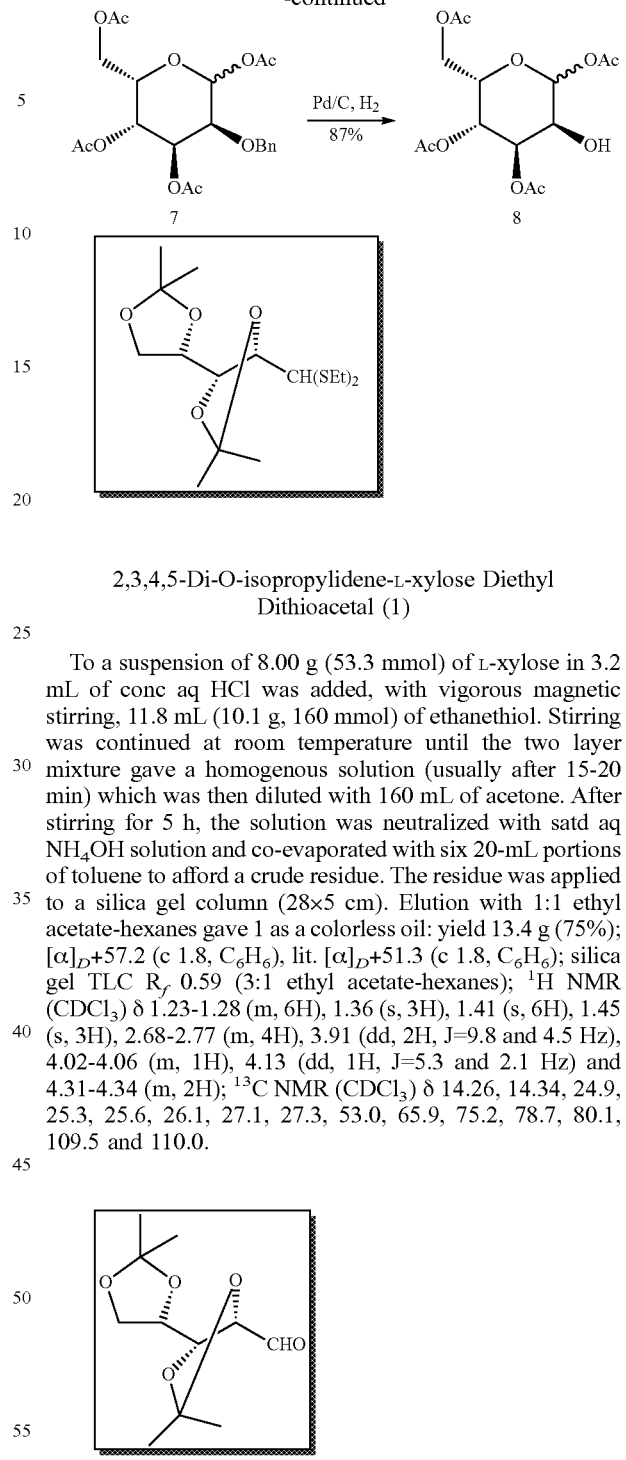

2,3,4,5-Di-O-isopropylidene-L-xylose Diethyl Dithioacetal (1)

To a suspension of 8.00 g (53.3 mmol) of L-xylose in 3.2 mL of conc aq HCl was added, with vigorous magnetic stirring, 11.8 mL (10.1 g, 160 mmol) of ethanethiol. Stirring was continued at room temperature until the two layer mixture gave a homogenous solution (usually after 15-20 min) which was then diluted with 160 mL of acetone. After stirring for 5 h, the solution was neutralized with satd aq NH$_4$OH solution and co-evaporated with six 20-mL portions of toluene to afford a crude residue. The residue was applied to a silica gel column (28×5 cm). Elution with 1:1 ethyl acetate-hexanes gave 1 as a colorless oil: yield 13.4 g (75%); $[\alpha]_D$+57.2 (c 1.8, C$_6$H$_6$), lit. $[\alpha]_D$+51.3 (c 1.8, C$_6$H$_6$); silica gel TLC R$_f$ 0.59 (3:1 ethyl acetate-hexanes); $^1$H NMR (CDCl$_3$) δ 1.23-1.28 (m, 6H), 1.36 (s, 3H), 1.41 (s, 6H), 1.45 (s, 3H), 2.68-2.77 (m, 4H), 3.91 (dd, 2H, J=9.8 and 4.5 Hz), 4.02-4.06 (m, 1H), 4.13 (dd, 1H, J=5.3 and 2.1 Hz) and 4.31-4.34 (m, 2H); $^{13}$C NMR (CDCl$_3$) δ 14.26, 14.34, 24.9, 25.3, 25.6, 26.1, 27.1, 27.3, 53.0, 65.9, 75.2, 78.7, 80.1, 109.5 and 110.0.

2,3,4,5-Di-O-isopropylidene-aldehydo-L-xylose (2)

To a stirred solution containing 2.60 g (7.70 mmol) of thioacetal 1 in 26 mL of acetone diluted with 2.6 mL of water was added 3.80 g (17.7 mmol) of yellow mercury(II) oxide and 3.80 g (13.9 mmol) of mercuric(II) chloride. The reaction mixture was stirred at 55° C. for 2 h and then allowed to cool to room temperature. The solvent was filtered through a pad of Celite 545® and concentrated under diminished pressure to afford a crude residue. The residue was suspended in three 30-mL portions of dichloromethane and filtered through a pad of Celite 545®. The organic layer was washed with 40 mL of 1 M aq KI, dried (MgSO$_4$) and then concentrated under diminished pressure to afford the crude aldehyde 2. The aldehyde was used for the next reaction immediately.

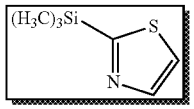

2-(Trimethylsilyl)thiazole (3)

A 500-mL, four-necked, round-bottomed flask, containing a magnetic stirring bar, was equipped with two 100-mL, pressure-equalizing dropping funnels and a low-temperature thermometer. The anh apparatus was filled with argon and kept under a slightly positive pressure during the entire reaction. The flask was charged with 80 mL of freshly distilled Et$_2$O and 42 mL (67 mmol) of a 1.6 M solution of n-BuLi in hexane. One of the two dropping funnels was charged with 5.5 mL (10 g, 61 mmol) of 2-bromothiazole in 20 mL of Et$_2$O and the other with 7.7 mL (6.6 g, 61 mmol) of chlorotrimethylsilane in 20 mL of Et$_2$O. The reaction flask was cooled to −78° C. in an acetone bath. While the solution in the flask was stirred, 2-bromothiazole was added dropwise over a period of 1 h. After 20 min of additional stirring, chlorotrimethylsilane was added dropwise over 30 min and the stirring was continued for a period of 1 h at −78° C. The resulting mixture was then allowed to warm up to room temperature. A satd aq NaHCO$_3$ was added and the mixture was transferred into a 1 L separatory funnel. The organic layer was recovered and the aqueous layer was extracted with two 200-mL portions of Et$_2$O. The combined organic layer was dried (Na$_2$SO$_4$), filtered, and concentrated under diminished pressure with the external bath temperature not exceeding 40° C. The residue was distilled from a 100-mL flask at diminished pressure in a Claisen apparatus. The distillation was carried out under diminished pressure at 45° C. after a forerun at 25° C. consisting mainly of bromobutane was collected. The pure product 3 was isolated as a colorless oil: yield 7.3 g (76%); $^1$H NMR (CDCl$_3$) δ 0.39 (s, 12H), 7.50 (1H, d, J=3.0 Hz) and 8.09 (1H, d, J=2.9 Hz); $^{13}$C NMR (CDCl$_3$) δ 1.03, 127.3, 145.6 and 174.2.

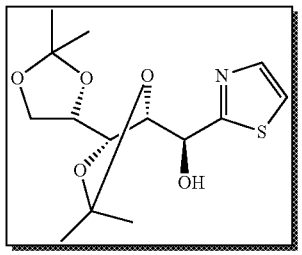

1,2,3,4-bis-O-(1-Methylethylidene)-5-C-2-thiazolyl-(5S)-D-xylitol (4)

To a stirred solution containing 2.22 g (9.65 mmol) of crude aldehyde 2 in 38 mL of anh dichloromethane cooled to −20° C. was added 2.00 mL (1.97 g, 12.5 mmol) of 2-(trimethylsilyl)thiazole (3) dropwise over a period of 15 min. The solution was stirred at 0° C. for 1 h and then concentrated under diminished pressure to afford a crude residue. The residue was dissolved in 38 mL of anh THF and treated with 3.00 g (9.65 mmol) of n-Bu$_4$NF.3H$_2$O at 20° C. for 30 min and then concentrated under diminished pressure. The residue was diluted by the addition of 250 ml, of dichloromethane. The organic layer was washed with three 50-mL portions of water, dried (Na$_2$SO$_4$) and then concentrated under diminished pressure to yield compound 4 as a crude residue. Recrystallization of the residue from cyclohexane afforded alcohol 4 as a colorless crystalline solid: yield 1.94 g (64% over two steps); [α]$_D$+18.2 (c 1.1, CHCl$_3$), lit. [α]$_D$+18.5 (c 1.1, CHCl$_3$); silica gel TLC R$_f$ 0.49 (1:1 ethyl acetate-hexanes); $^1$H NMR (CDCl$_3$) δ 1.28 (s, 3H), 1.36 (s, 6H), 1.40 (s, 3H), 3.67 (t, 1H, J=6.6 Hz), 3.79-3.84 (m, 2H), 4.12 (dd, 1H, J=7.2 and 3.6 Hz), 4.31-4.34 (m, 1H), 4.56 (br s, 1H), 5.10 (d, 1H, J=5.5 Hz), 7.30 (d, 1H, J=3.2 Hz) and 7.71 (d, 1H, J=3.2 Hz); $^{13}$C NMR (CDCl$_3$) δ 25.6, 26.1, 27.07, 27.13, 65.7, 71.7, 75.5, 77.4, 79.8, 109.5, 110.2, 119.7, 142.1 and 170.9.

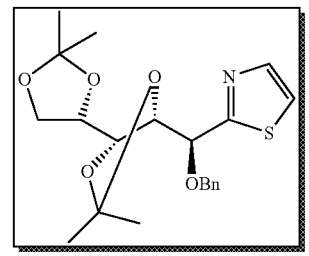

1,2,3,4-bis-O-(1-Methylethylidene)-5-O-(phenylmethyl)-5-C-2-thiazolyl-(5S)-D-xylitol (5)

To a solution containing 1.94 g (6.15 mmol) of alcohol 4 in anh DMF cooled to 0° C. was added 0.49 g (60% dispersion in oil, 12.3 mmol) of NaH portionwise and the reaction mixture was stirred at 0° C. for 0.5 h. To this solution was then added 1.10 mL (1.58 g, 9.20 mmol) of benzyl bromide and the reaction mixture was stirred at room temperature for 0.5 h. The reaction mixture was quenched by the addition of 1.2 mL of methanol, stirred for 10 min and then diluted with 40 mL of distilled water. The aqueous layer was extracted with three 100-mL portions of ether. The combined organic layer was dried (MgSO$_4$) and concentrated under diminished pressure to afford a crude residue. The residue was applied to a silica gel column (25×4 cm). Elution with 6:1 ethyl acetate-hexanes gave ether 5 as a colorless solid: yield 2.26 g (91%); [α]$_D$ −32.2 (c 1.1, CHCl$_3$), lit. [α]$_D$ −32.3 (c 1.1, CHCl$_3$); silica gel TLC R$_f$ 0.36 (9:1 toluene-methanol); $^1$H NMR (CDCl$_3$) δ 1.20 (s, 3H), 1.25 (s, 3H), 1.29 (s, 3H), 1.33 (s, 3H), 3.62-3.68 (m, 1H), 3.75-3.80 (m, 1H), 3.89-3.93 (m, 1H), 3.96-3.99 (m, 1H), 4.35 (dd, 1H, J=7.3 and 2.5 Hz), 4.44 (d, 1H, J=12.1 Hz), 4.63 (d, 1H, J=12.1 Hz), 4.80 (d, 1H, J=4.8 Hz), 7.21-7.28 (m, 5H), 7.32 (d, 1H, J=3.2 Hz) and 7.78 (d, 1H, J=3.2 Hz); $^{13}$C NMR (CDCl$_3$) δ 14.0, 25.5, 26.03, 26.05, 26.7, 27.0, 65.5, 72.2, 75.5, 77.7, 78.5, 79.4, 109.4, 110.3, 120.1, 127.9, 128.1, 128.3, 136.8, 142.4 and 168.9.

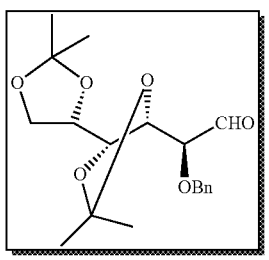

2-O-Benzyl-3,4,5,6-di-O-isopropylidene-aldehydo-L-gulose (6)

A solution containing 0.61 g (1.50 mmol) of O-benzyl ether 5 and 2.80 g of activated 4 Å molecular sieves dissolved in 15 mL of anh acetonitrile was stirred at 20° C. for 10 min and then 0.22 mL (329 mg, 1.95 mmol) of methyl triflate was added dropwise. The suspension was stirred at room temperature for 15 min and then concentrated under diminished pressure to afford the crude N-methylthiazolium salt. To a stirred solution of the crude N-methylthiazolium salt in 15 mL of methanol cooled to 0° C. was added 0.12 g (3.30 mmol) of sodium borohydride. The reaction mixture was stirred at room temperature for 5 min and diluted with 5 mL of acetone. The solvent was filtered through a pad of Celite 545® and concentrated under diminished pressure to afford a crude mixture of thiazolidines. This was dissolved in 14 mL of acetonitrile and 1.4 mL of water and treated under vigorous stirring with 0.96 g (12.0 mmol) of CuO and 0.26 g (1.50 mmol) of $CuCl_2 \cdot 2H_2O$. The reaction mixture was stirred at 20° C. for 15 min, filtered through a pad of Celite 545® and then concentrated under diminished pressure to remove acetonitrile and most of the water (bath temperature not exceeding 40° C.) to afford a crude residue. The brown residue was triturated with four 50-mL portions of ether and the liquid phase was pipetted and filtered through a pad of Florisil® (60-100 mesh) to afford a colorless solution. After a further washing of Florisil® with 50 mL of ethyl acetate, the combined organic layer was concentrated under diminished pressure to yield the crude aldehyde 6 as a brown syrup, which was used immediately for the next reaction.

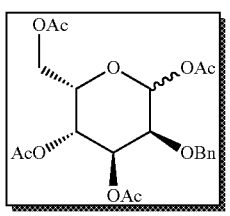

1,3,4,6-Tetra-O-acetyl-2-O-benzyl-L-gulopyranose (7)

A solution containing 470 mg (1.34 mmol) of the crude aldehyde 6 was dissolved in 7.4 mL of glacial acetic acid and 1.9 mL of distilled water and stirred at 100° C. for 40 min. The reaction mixture was then concentrated by co-evaporation three times with toluene to afford the crude 2-O-benzyl-L-gulose as a mixture of β-pyranose, α-pyranose and furanose forms. A solution of the crude residue and 0.16 g (1.34 mmol) of DMAP in 3.4 mL of pyridine and 3.4 mL of acetic anhydride was stirred at 20° C. for 12 h and concentrated under diminished pressure to yield a brown syrup. The crude residue was applied to a silica gel column (38×3 cm). Elution with 3:1 ethyl acetate-hexanes gave 7 as a yellow oil: yield 1.56 g (64% over two steps); silica gel TLC $R_f$ 0.44 (1:1 ethyl acetate-hexanes); $^1$H NMR ($CDCl_3$) δ 2.01 (s, 3H), 2.05 (s, 3H), 2.08 (s, 3H), 2.11 (s, 3H), 3.64 (dd, 1H, J=8.3 and 4.9 Hz), 3.98-4.13 (m, 2H), 4.24-4.32 (m, 1H), 4.49 (d, 1H, J=11.9 Hz), 4.63 (d, 1H, J=11.9 Hz), 4.95 (dd, 1H, J=3.9 and 2.5 Hz), 5.43-5.45 (m, 1H), 5.89 (d, 1H, J=8.3 Hz) and 7.23-7.34 (m, 5H).

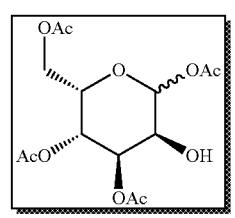

1,3,4,6-Tetra-O-acetyl-L-gulopyranose (8)

To a solution containing 1.47 g (3.35 mmol) of 7 in 23 mL of ethyl acetate was added 0.73 g of 10% Pd/C and the reaction mixture was stirred overnight under 1 atm of $H_2$. The solvent was filtered through a pad of Celite 545® and concentrated under diminished pressure to afford a crude residue. The residue was applied to a silica gel column (15×4 cm). Elution with 1:1 ethyl acetate-hexanes afforded 8 as a 77:20:3 mixture of α-pyranose, β-pyranose and furanose forms as determined by $^1$H NMR: yield 1.02 g (87%); silica gel TLC $R_f$ 0.52 (ethyl acetate); $^1$H NMR ($CDCl_3$) δ 1.91 (s, 3H), 2.00 (s, 3H), 2.03 (s, 6H), 3.22-3.52 (br s, 1H), 3.80 (dd, 1H, J=8.4 and 3.5 Hz), 3.91-3.97 (m, 1H), 3.99-4.04 (m, 1H), 4.14-4.19 (m, 1H), 4.82-4.88 (m, 1H), 5.19 (t, 1H, J=3.6 Hz) and 5.70 (d, 1H, J=8.4 Hz); $^{13}$C NMR ($CDCl_3$) δ 20.4, 20.5, 20.6, 20.8, 61.6, 66.2, 67.5, 69.5, 70.9, 92.1, 169.4, 169.6, 169.7 and 170.5.

Example 2: Synthesis of Mannose Donor 12

Scheme 2

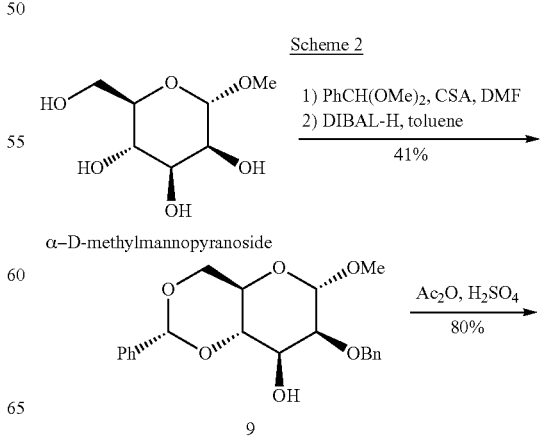

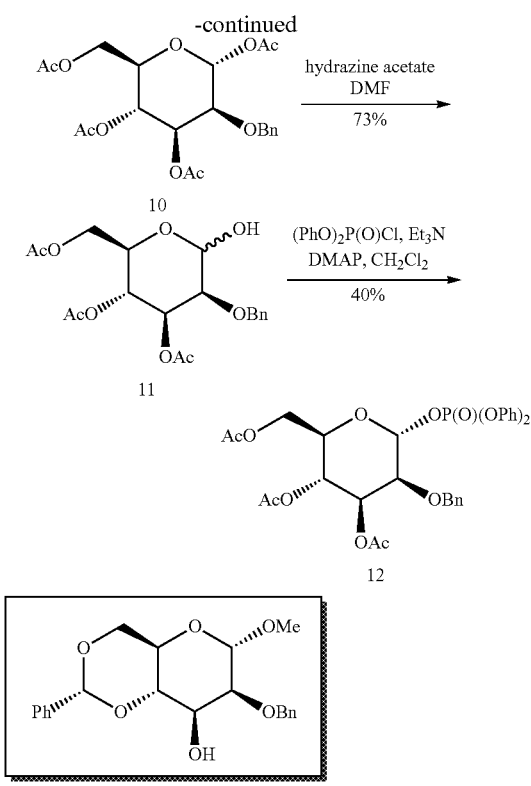

Methyl 4,6-O-Benzylidene-2-O-benzyl-α-D-mannopyranoside (9)

To a solution containing 5.00 g (26.0 mmol) of methyl α-D-mannopyranoside and 60.0 mg (0.26 mmol) of camphorsulfonic acid in 75 mL of DMF was added dropwise 9.7 mL (9.8 g, 65 mmol) of benzaldehyde dimethyl acetal. The resulting solution was heated to 60° C. on a rotary evaporator under a pressure of 250 mbar. After 3 h, analysis by silica gel TLC (1:3 ethyl acetate-hexanes) indicated complete conversion of starting material ($R_f$ 0.0) to two products ($R_f$ 0.50 and 0.80). To the reaction mixture was then added 4.90 mL (4.90 g, 32.4 mmol) of benzaldehyde dimethyl acetal and 30.0 mg (0.13 mmol) of camphorsulfonic acid. The reaction mixture was stirred under diminished pressure. After 2 h, silica gel TLC (1:3 ethyl acetate-hexanes) indicated the formation of a single product ($R_f$ 0.80). The solvent was concentrated under diminished pressure, the residue was co-evaporated with 50 mL of toluene and then dissolved in 100 mL of dichloromethane. The organic layer was washed with 50 mL of satd aq NaHCO$_3$ and brine. The organic phase was then dried (MgSO$_4$), filtered and concentrated under diminished pressure. The resulting crude mixture of endo and exo dibenzylidene derivatives was dissolved in 150 mL of freshly distilled toluene and cooled to −40° C. under an argon atmosphere. Then 65 mL of DIBAL (1 M solution in toluene, 64.9 mmol) was added slowly to the reaction mixture. The reaction mixture was allowed to warm to room temperature slowly. After 2 h, silica gel TLC analysis (1:3 ethyl acetate-hexanes) indicated complete consumption of starting material ($R_f$ 0.80) and formation of two products ($R_f$ 0.40 and $R_f$ 0.30). The reaction mixture was quenched by the dropwise addition of 50 mL of methanol and the mixture was diluted with 250 mL of dichloromethane. The organic layer was washed with 200 mL of 10% solution of Rochelle's salt and brine and then dried (MgSO$_4$). The organic layer was filtered and the filtrate was concentrated under diminished pressure. The resulting residue was purified by flash column chromatography (1:3 ethyl acetate-hexanes) to afford the undesired compound methyl 4,6-O-benzylidene-3-O-benzyl-α-D-mannopyranoside (14) ($R_f$ 0.30) and the desired methyl 4,6-O-benzylidene-2-O-benzyl-α-D-mannopyranoside (9) as a colorless crystalline solid: yield 3.0 g (41%); silica gel TLC $R_f$ 0.40 (1:3 ethyl acetate-hexanes); $^1$H NMR (CDCl$_3$) δ 3.34 (s, 3H), 3.79-3.82 (m, 3H), 3.96 (t, 1H, J=8.0 Hz), 4.10-4.12 (m, 1H), 4.26-4.27 (m, 1H), 4.72-4.75 (m, 3H), 5.53 (s, 1H), 7.33-7.41 (m, 8H) and 7.42-7.55 (m, 2H).

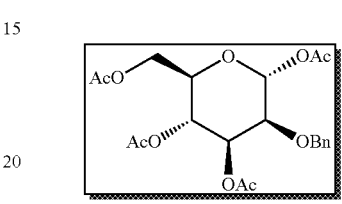

1,3,4,6-Tetra-O-acetyl-2-O-benzyl-α-D-mannopyranoside (10)

To a solution containing 3.57 g (9.59 mmol) of acetal 9 in 70 mL of Ac$_2$O was added a catalytic amount of H$_2$SO$_4$ and the reaction mixture was stirred at 25° C. for 40 min. The reaction mixture was poured into a stirring mixture of 100 mL of ethyl acetate and 80 mL of satd aq NaHCO$_3$. The organic and aqueous layers were separated and the organic layer was washed with 60 mL of brine and dried (MgSO$_4$). The organic layer was filtered and concentrated under diminished pressure to afford a crude residue. The residue was applied to a silica gel column (17×5 cm). Elution with 2:1 ethyl acetate-hexanes afforded 10 as a yellow oil: yield 3.35 g (80%); silica gel TLC $R_f$ 0.66 (1:1 ethyl acetate-hexanes); $^1$H NMR (CDCl$_3$) δ 1.98 (s, 3H), 2.04 (s, 3H), 2.08 (s, 3H), 2.12 (s, 3H), 3.82 (dd, 1H, J=3.2 and 2.2 Hz), 4.01 (ddd, 1H, J=10.0, 4.8 and 2.3 Hz), 4.08-4.15 (m, 1H), 4.23-4.28 (m, 1H), 4.56-4.76 (m, 2H), 5.19 (dd, 1H, J=10.0 and 3.3 Hz), 5.43-5.52 (m, 1H), 6.18 (d, 1H, J=1.9 Hz) and 7.27-7.38 (m, 5H); $^{13}$C NMR (CDCl$_3$) δ 20.8, 20.90, 20.93, 21.1, 62.4, 66.0, 70.7, 71.1, 73.0, 74.0, 91.3, 128.1, 128.2, 128.6, 137.3, 168.8, 169.6, 170.4 and 170.9.

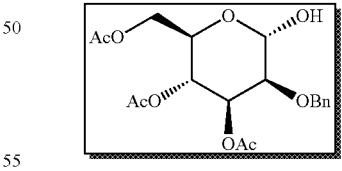

3,4,6-Tri-O-acetyl-2-O-benzyl-α-D-mannopyranoside (11)

To a solution containing 1.13 g (2.58 mmol) of compound 10 in 21 mL of anh DMF was added 286 mg (3.10 mmol) of hydrazine acetate. The reaction mixture was stirred at room temperature for 1.5 h and quenched by the addition of 100 mL of ethyl acetate. The organic layer was washed with three 50-mL portions of brine and dried (MgSO$_4$). The solvent was concentrated under diminished pressure to afford a crude residue. The residue was applied to a silica gel column (20×3 cm). Elution with 1:2 ethyl acetate-hexanes afforded pyranoside 11 as a colorless oil: yield 793 mg (73%); silica gel TLC $R_f$ 0.23 (1:1 ethyl acetate-hexanes); $^1$H NMR (CDCl$_3$) δ 1.97 (s, 3H), 2.00 (s, 3H), 2.02 (s, 3H), 3.81-3.87 (m, 1H), 4.05-4.17 (m, 2H), 4.20 (dt, 1H, J=9.3 and 4.7 Hz), 4.56-4.63 (m, 3H), 5.21-5.33 (m, 2H), 5.40 (t, 1H, J=9.9 Hz) and 7.21-7.36 (m, 5H); $^{13}$C NMR (CDCl$_3$) δ 20.57, 20.58, 20.7, 62.7, 66.6, 68.2, 70.9, 72.8, 75.6, 92.2, 127.70, 127.72, 128.2, 137.6, 169.8, 170.2 and 171.1; mass spectrum (APCI), m/z 397.1498 (M+H)$^+$ (C$_{19}$H$_{25}$O$_9$ requires 397.1498).

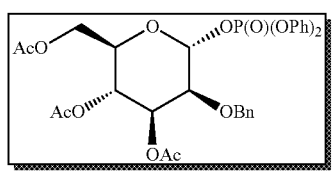

3,4,6-Tri-O-acetyl-2-O-benzyl-α-D-mannopyranosyl Diphenyl Phosphate (12)

To a stirred solution containing 793 mg (2.00 mmol) of 11 in 120 mL of anh dichloromethane was added 305 mg (2.50 mmol) of 4-dimethylaminopyridine (DMAP), 3.00 mL (2.17 g, 21.6 mmol) of Et$_3$N and 4.00 mL (5.20 g, 19.2 mmol) of diphenyl chlorophosphate. The reaction mixture was stirred at 0° C. for 2 h and poured into a stirring mixture of 300 mL of ethyl acetate and 150 mL of satd aq NaHCO$_3$. The aqueous and organic layers were separated and the organic layer was washed with three 50-mL portions of water and brine and then dried (MgSO$_4$). The solvent was concentrated under diminished pressure to afford a crude residue. The residue was applied to a silica gel column (20×3 cm). Elution with 1:2 ethyl acetate-hexanes afforded 12 as a colorless oil: yield 508 mg (40%); silica gel TLC $R_f$ 0.44 (1:1 ethyl acetate-hexanes); $^1$H NMR (CDCl$_3$) δ 2.17 (s, 3H), 2.20 (s, 3H), 2.23 (s, 3H), 4.10-4.25 (m, 3H), 4.42 (dd, 1H, J=12.2 and 3.9 Hz), 4.76-4.88 (m, 2H), 5.49 (d, 1H, J=8.0 Hz), 5.73 (t, 1H, J=10.1 Hz), 6.21 (d, 1H, J=5.7 Hz) and 7.33-7.62 (m, 15H); $^{13}$C NMR (CDCl$_3$) δ 20.39, 20.46, 20.53, 61.7, 65.3, 69.8, 70.8, 73.1, 74.4, 96.6, 119.9, 120.05, 120.09, 120.14, 124.59, 125.63, 127.8, 127.9, 128.3, 129.3, 129.8, 136.8, 149.9, 150.1, 150.8, 169.3, 169.8 and 170.53; mass spectrum (APCI), m/z 629.1788 (M+H)$^+$ (C$_{31}$H$_{34}$O$_{12}$P requires 629.1788).

Example 3: Synthesis of Mannose Donor 17

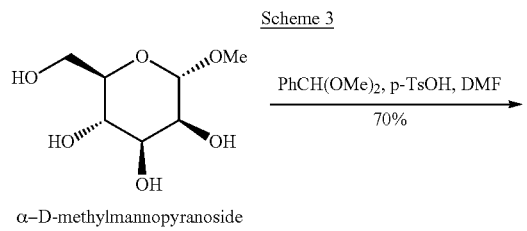

Scheme 3

α-D-methylmannopyranoside

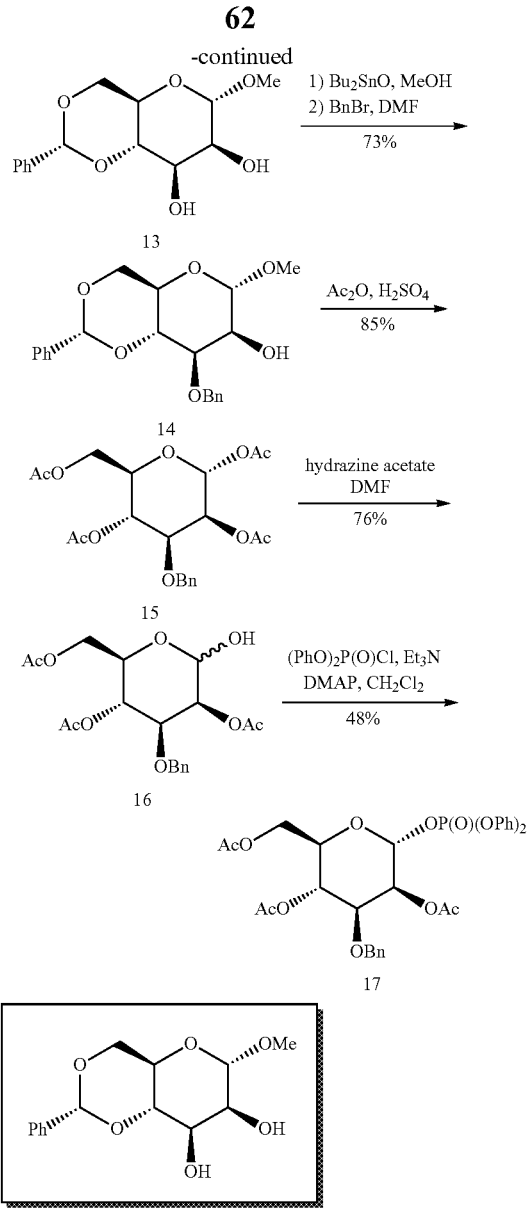

Methyl-4,6-O-benzylidene-α-D-mannopyranoside (13)

To a solution containing 7.00 g (36.0 mmol) of α-D-mannopyranoside in 85 mL of DMF was added 5.60 mL (5.68 g, 37.3 mmol) of benzaldehyde dimethyl acetal and a catalytic amount of p-TsOH. The reaction mixture was stirred at 60° C. under diminished pressure for 1 h, allowed to cool to room temperature and then poured into a stirring mixture of 120 mL of ethyl acetate and 100 mL satd aq NaHCO$_3$. The organic layer was washed with three 50-mL portions of brine and dried (MgSO$_4$). The solvent was concentrated under diminished pressure to afford a crude residue. The residue was applied to a silica gel column (30×5 cm). Elution with 4:1 ethyl acetate-hexanes afforded acetal 13 as a colorless solid: yield 7.13 g (70%); silica gel TLC $R_f$ 0.31 (1:1 ethyl acetate-hexanes); $^1$H NMR (CDCl$_3$) δ 3.38 (s, 3H), 3.78 (m, 2H), 3.87 (m, 1H), 3.98 (m, 2H), 4.25 (m, 1H), 4.72 (d, 1H), 5.55 (s, 1H), 7.36 (m, 3H) and 7.47 (m, 2H); $^{13}$C NMR (CDCl$_3$) δ 55.2, 63.3, 68.8, 69.0, 71.1, 79.0, 101.6, 102.4, 126.5, 128.6, 129.5 and 137.4.

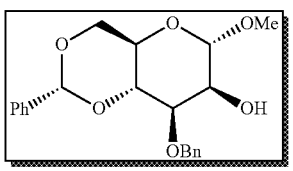

Methyl 4,6-O-Benzylidene-3-O-benzyl-α-D-mannopyranoside (14)

To a solution containing 2.00 g (7.10 mmol) of acetal 13 in 60 mL of methanol was added 1.94 g (7.79 mmol) of Bu$_2$SnO. The solution was heated to reflux for 1.5 h affording a clear solution. The solvent was concentrated under diminished pressure and the resulting solid was dried under vacuum overnight. The white residue was dissolved in 60 mL of DMF and treated with 1.69 mL (2.43 g, 14.2 mmol) of benzyl bromide and then warmed to 100° C. for 30 min. The cooled reaction mixture was poured into a stirred mixture of 90 mL of ethyl acetate and 60 mL of satd aq NaHCO$_3$. The organic layer was separated and washed with 60 mL of brine and dried (MgSO$_4$). The solvent was concentrated under diminished pressure to afford a crude residue. The residue was applied to a silica gel column (30×5 cm). Elution with 3:7 ethyl acetate-hexanes afforded acetal 14 as a colorless oil: yield 1.93 g (73%); silica gel TLC $R_f$ 0.30 (3:7 ethyl acetate-hexanes); $^1$H NMR (CDCl$_3$) δ 3.38 (s, 3H), 3.77 (m, 3H), 4.05 (m, 2H), 4.27 (m, 1H), 4.70 (m, 2H), 4.84 (m, 1H), 5.62 (s, 1H) and 7.28-7.52 (m, 10H); $^{13}$C NMR (CDCl$_3$) δ 55.2, 60.7, 63.5, 65.4, 69.1, 70.1, 73.2, 75.8, 79.0, 101.3, 101.8, 126.3, 127.2, 127.8, 128.11, 128.16, 128.5, 128.7, 129.2, 137.8 and 138.2.

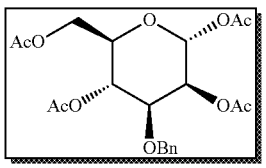

1,2,4,6-Tetra-O-acetyl-3-O-benzyl-α-D-mannopyranoside (15)

To a solution containing 1.93 g (4.40 mmol) of acetal 14 in 30 mL of Ac$_2$O was added a catalytic amount of H$_2$SO$_4$ and the solution was stirred at room temperature for 40 min. The reaction mixture was quenched by the addition of 120 mL of ethyl acetate and 80 mL of satd aq NaHCO$_3$. The organic and aqueous layers were separated and the organic layer was washed with brine and dried (MgSO$_4$). The solvent was concentrated under diminished pressure to afford a crude residue. The residue was applied to a silica gel column (30×5 cm). Elution with 2:1 ethyl acetate-hexanes afforded pyranoside 15 as a yellow oil: yield 1.94 g (85%); silica gel TLC $R_f$ 0.34 (3:7 ethyl acetate-hexanes); $^1$H NMR (CDCl$_3$) δ 2.02 (s, 3H), 2.07 (s, 3H), 2.11 (s, 3H), 2.15 (s, 3H), 3.83 (dd, 1H, J=9.7 and 3.4 Hz), 3.90 (m, 1H), 4.04 (m, 1H), 4.19 (m, 1H), 4.41 (m, 1H), 4.64 (m, 1H), 5.24 (m, 1H), 5.34 (dd, 1H, J=3.4 and 2.1 Hz), 6.09 (d, 1H, J=2.0 Hz) and 7.24-7.37 (m, 5H); $^{13}$C NMR (CDCl$_3$) δ 14.4, 20.98, 21.08, 21.13, 62.6, 67.0, 67.2, 71.0, 71.7, 74.3, 91.2, 128.0, 128.2, 128.6, 137.6, 168.3, 169.8, 170.2 and 171.0.

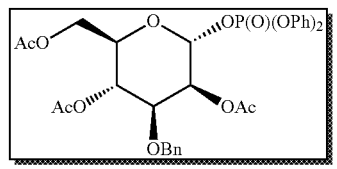

2,4,6-Tri-O-acetyl-3-O-benzyl-α-D-mannopyranosyl Diphenyl Phosphate (17)

To a solution containing 1.40 g (3.19 mmol) of acetate 15 in 25 mL of DMF was added 353 mg (3.83 mmol) of hydrazine acetate. The solution was stirred at room temperature for 1.5 h and quenched by the addition of 100 mL of ethyl acetate. The organic phase was washed with three 50-mL portions of brine and dried (MgSO$_4$). The solvent was concentrated under diminished pressure to afford a crude residue. The residue was applied to a silica gel column (20×4 cm). Elution with 1:2 ethyl acetate-hexanes afforded monosaccharide 16 as a colorless oil. This material was used for the next reaction immediately: yield 968 mg (76%); $^1$H NMR (CDCl$_3$) δ 1.95 (s, 3H), 2.02 (s, 3H), 2.10 (s, 3H), 3.90 (dd, 1H, J=9.7 and 3.3 Hz), 4.00-4.11 (m, 2H), 4.16 (ddd, 1H, J=12.3, 7.7 and 4.6 Hz), 4.33 (s, 1H), 4.38 (dd, 1H, J=12.3 and 4.3 Hz), 4.60 (d, 1H, J=12.2 Hz), 5.13-5.23 (m, 2H), 5.28-5.33 (m, 1H) and 7.18-7.31 (m, 5H); $^{13}$C NMR (CDCl$_3$) δ 14.2, 20.78, 20.85, 21.0, 60.6, 62.9, 67.5, 68.5, 68.8, 71.4, 74.0, 92.3, 127.78, 127.83, 128.4, 137.7, 169.9, 170.6 and 171.1.

To a stirred solution containing 968 mg (2.44 mmol) of pyranoside 16 in 144 mL of anh dichloromethane was added 372 mg (3.05 mmol) of DMAP, 3.67 mL (2.66 g, 26.3 mmol) of Et$_3$N and 4.83 mL (6.26 g, 23.4 mmol) of diphenyl chlorophosphate. The reaction mixture was stirred at 0° C. for 2 h and poured into a mixture of 300 mL of ethyl acetate and 150 mL of satd aq NaHCO$_3$. The organic layer was washed with three 50-mL portions of water and brine and then dried (MgSO$_4$). The solvent was concentrated under diminished pressure to afford a crude residue. The residue was applied to a silica gel column (20×4 cm). Elution with 1:2 ethyl acetate-hexanes afforded 17 as a colorless oil: yield 737 mg (48%); silica gel TLC $R_f$ 0.38 (1:1 ethyl acetate-hexanes); $^1$H NMR (CDCl$_3$) δ 1.93 (s, 3H), 1.97 (s, 3H), 2.10 (s, 3H), 3.84 (dd, 1H, J=9.7 and 3.3 Hz,), 3.89-4.03 (m, 2H), 4.10-4.20 (m, 1H), 4.33 (d, 1H, J=12.1 Hz), 4.57 (d, 1H, J=12.1 Hz), 5.27 (t, 1H, J=10.0 Hz), 5.38 (dd, 1H, J=8.6 and 6.2 Hz), 5.91 (dd, 1H, J=6.4 and 1.6 Hz) and 7.16-7.38 (m, 15H); $^{13}$C NMR (CDCl$_3$) δ 20.5, 20.62, 20.67, 61.8, 66.2, 67.2, 67.3, 70.9, 71.5, 73.4, 77.4, 96.5, 119.90, 119.95, 125.67, 125.71, 127.9, 128.3, 129.85, 137.2, 150.08, 150.15, 169.3, 169.6 and 170.4; mass spectrum (APCI), m/z 629.1770 (M+H)$^+$ (C$_{31}$H$_{34}$O$_{12}$P requires 629.1788).

Example 4: Synthesis of Mannose Donor 20

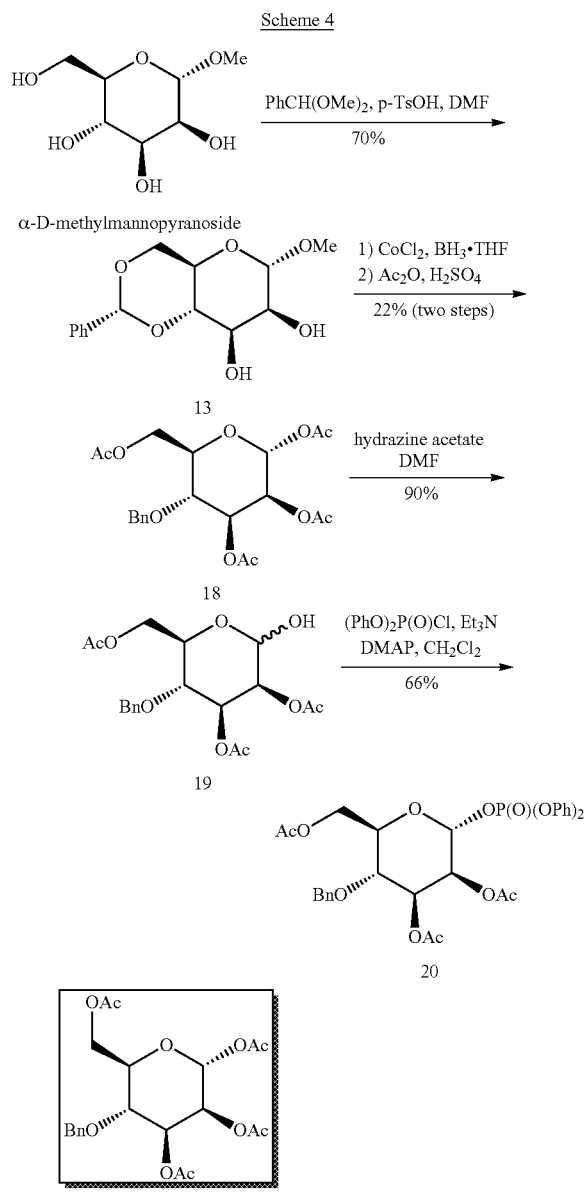

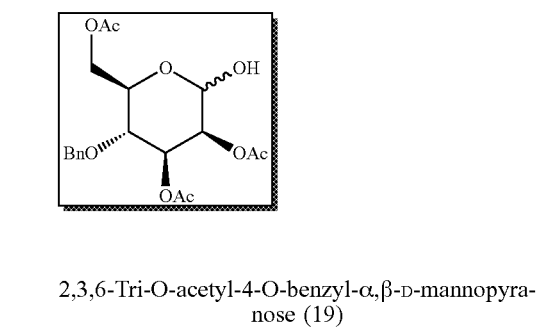

1,2,3,6-Tetra-O-acetyl-4-O-benzyl-α-D-mannopyranoside (18)

To a stirred solution containing 5.43 g (19.2 mmol) of acetal 13 in 50 mL of anh THF was added 58.0 mL (57.6 mmol) of a 1 M solution of $BH_3$ in THF and 7.48 g (57.6 mmol) of anh $CoCl_2$ at room temperature. The reaction mixture was stirred for 15 min at room temperature and quenched by the addition of 100 mL of ethyl acetate. The organic phase was filtered and the filtrate was treated with 20 mL of a 20% aq solution of $NaBH_4$. The solution was again filtered and washed successively with sat aq $NaHCO_3$ and water, and then dried ($MgSO_4$). The solution was concentrated under diminished pressure to afford a crude residue. To a solution containing 3.44 g (12.1 mmol) of the crude residue in 85 mL of $Ac_2O$ was added a catalytic amount of $H_2SO_4$. The solution was stirred at room temperature for 12 h. The reaction mixture was quenched by the addition of 120 mL of ethyl acetate and 80 mL of satd aq $NaHCO_3$. The organic and aqueous layers were separated and the organic layer was washed with brine and dried ($MgSO_4$). The solution was concentrated under diminished pressure to afford a crude residue. The residue was applied to a silica gel column (30×5 cm). Elution with 2:1 ethyl acetate-hexanes afforded pyranoside 18 as a yellow oil: yield 1.17 g (22% over two steps); silica gel TLC $R_f$ 0.26 (2:1 ethyl acetate-hexanes); $^1H$ NMR ($CDCl_3$) δ 2.00 (s, 3H), 2.08 (s, 3H), 2.13 (s, 3H), 2.15 (s, 3H), 3.87 (t, 1H, J=9.7), 3.99 (dt, 1H, J=9.9 and 3.4 Hz), 4.32 (d, 2H, J=3.5 Hz), 4.59 (d, 1H, J=11.2 Hz), 4.70 (d, 1H, J=10.8 Hz), 5.26 (dd, 1H, J=3.3 and 2.1 Hz), 5.37 (dd, 1H, J=9.5 and 3.4 Hz), 6.04 (t, 1H, J=6.1 Hz), and 7.24-7.38 (m, 5H); $^{13}C$ NMR ($CDCl_3$) δ 20.92, 20.97, 20.99, 21.04, 62.9, 68.9, 71.6, 71.8, 72.6, 75.2, 90.8, 127.9, 128.3, 128.7, 137.5, 168.4, 169.8, 169.9 and 170.8.

2,3,6-Tri-O-acetyl-4-O-benzyl-α,β-D-mannopyranose (19)

To a stirred solution containing 1.09 g (2.49 mmol) of acetate 18 in 20 mL of anh DMF was added 274 mg (2.98 mmol) of hydrazine acetate. The reaction mixture was stirred at room temperature for 1.5 h and quenched by the addition of 100 mL of ethyl acetate. The organic layer was washed with three 50-mL portions of brine and dried ($MgSO_4$). The solvent was concentrated under diminished pressure to afford a crude residue. The residue was applied to a silica gel column (20×3 cm). Elution with 1:2 ethyl acetate-hexanes afforded pyranoside 19 as a colorless oil: yield 884 mg (90%); silica gel TLC $R_f$ 0.36 (1:1 ethyl acetate-hexanes); $^1H$ NMR ($CDCl_3$) δ 1.92 (s, 3H), 2.01 (s, 3H), 2.08 (s, 3H), 3.77 (t, 1H, J=10.0 Hz), 4.11 (ddd, 1H, J=9.7, 4.1 and 2.1 Hz), 4.17-4.34 (m, 2H), 4.69-4.48 (m, 3H), 5.09 (s, 1H), 5.17-5.23 (m, 1H), 5.33-5.38 (m, 1H) and 7.18-7.32 (m, 5H); $^{13}C$ NMR ($CDCl_3$) δ 20.69, 20.73, 63.1, 69.2, 70.5, 71.5, 72.8, 74.6, 77.4, 91.8, 127.6, 127.8, 128.3, 137.5, 170.0, 170.2 and 171.0; HRMS (APCI), m/z 397.1483 (M+H)$^+$ ($C_{19}H_{25}O_9$ requires m/z 397.1498).

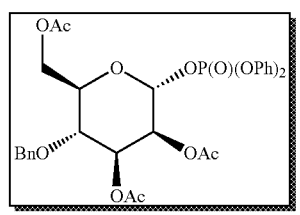

2,3,6-Tri-O-acetyl-4-O-benzyl-α-D-mannopyranosyl Diphenyl Phosphate (20)

To a stirred solution containing 812 mg (2.05 mmol) of 19 in 80 mL of anh dichloromethane was added 313 mg (2.56 mmol) of DMAP and 3.10 mL (2.25 g, 22.1 mmol) of Et$_3$N, 4.10 mL (5.33 g, 19.7 mmol) of diphenyl chlorophosphate. The reaction mixture was stirred at 0° C. for 2 h and then poured into a mixture of 300 mL of ethyl acetate and 150 mL of satd aq NaHCO$_3$. The aqueous and organic layers were separated and the organic layer was washed with three 50-mL portions of distilled water and brine and then dried (MgSO$_4$). The solvent was concentrated under diminished pressure to afford a crude residue. The residue was applied to a silica gel column (20×4 cm). Elution with 1:2 ethyl acetate-hexanes afforded 20 as a colorless oil: yield 857 mg (66%); silica gel TLC R$_f$ 0.29 (1:1 ethyl acetate-hexanes); $^1$H NMR (CDCl$_3$) δ 1.93 (s, 3H), 1.96 (s, 3H), 2.09 (s, 3H), 3.80 (t, 1H, J=9.6 Hz), 3.91-4.12 (m, 2H), 4.18 (dd, 1H, J=12.2 and 4.2 Hz), 4.50-4.68 (m, 2H), 5.27-5.38 (m, 2H), 5.80 (d, 1H, J=6.1 Hz) and 7.11-7.38 (m, 15H); $^{13}$C NMR (CDCl$_3$) δ 20.74, 20.9, 62.4, 69.1, 70.9, 71.8, 72.1, 75.0, 77.4, 96.3, 120.1, 120.4, 125.7, 125.9, 127.9, 128.2, 128.6, 129.9, 130.0, 137.3, 150.1, 150.3, 169.5, 169.6 and 170.5; HRMS (APCI), m/z 629.1794 (M+H)$^+$ (C$_{31}$H$_{34}$O$_{12}$P requires m/z 629.1788).

Example 5: Synthesis of Mannose Donor 25

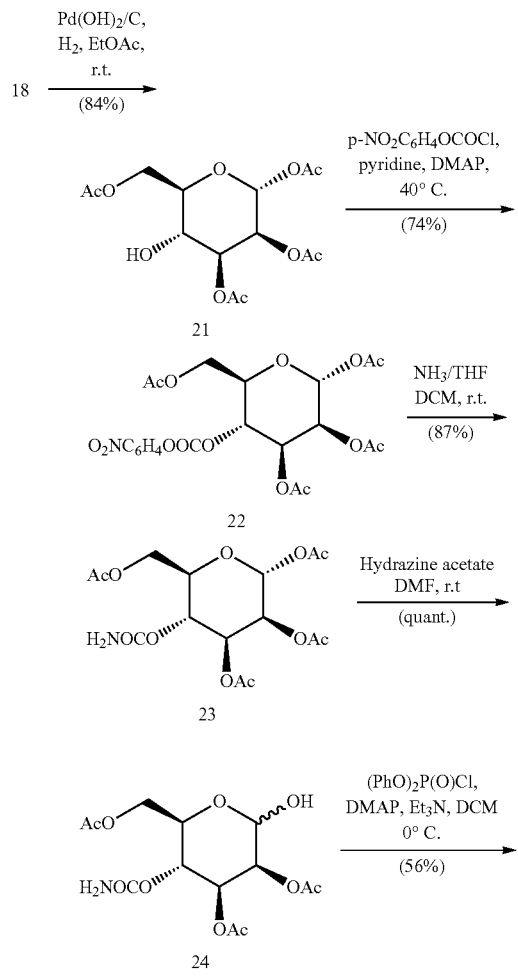

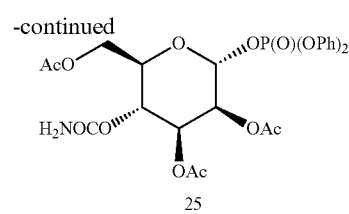

25

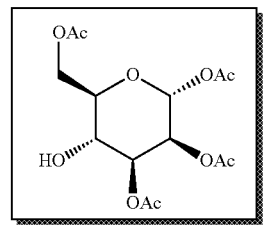

1,2,3,6-Tetra-O-acetyl-α-D-mannopyranoside (21)

To a solution of 1.63 g (3.72 mmol) of 18 in 33 mL of ethyl acetate was added a 308 mg of Pd(OH)$_2$/C and the reaction was placed under 1 atm of H$_2$ overnight. The catalyst was removed by filtration through a pad of Celite 545® and concentrated under diminished pressure. The residue was purified by flash chromatography on a silica gel column (5×20 cm). Elution with 2:1 hexanes-ethyl acetate afforded 21 as a colorless oil: yield 1.09 g (84%); silica gel TLC R$_f$ 0.25 (1:1 ethyl acetate-hexanes). $^1$H NMR (CDCl$_3$) δ 2.06 (s, 3H), 2.12 (s, 6H), 2.14 (s, 3H), 2.94 (br s, 1H), 3.83-3.92 (m, 2H), 4.24-4.27 (m, 1H), 4.50-4.54 (m, 1H), 5.18-5.23 (m, 2H), 6.04 (d, 1H, J=1.6 Hz).

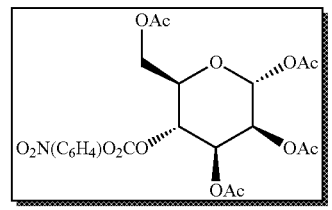

1,2,3,6-Tetra-O-acetyl-4-O-(p-nitrophenyl)carbamoyl-α-D-mannopyranoside (22)

To a solution of 1.74 g (5.00 mmol) of 21 in 17.8 mL of pyridine was added 2.44 g (20.0 mmol) of DMAP and 4.03 g (20.0 mmol) of p-nitrophenyl chloroformate. The reaction was stirred at 40° C. for 2.5 h at which time it was poured into a two-phase mixture of 50 mL ethyl acetate and 19 mL of water. The organic layer was washed with three 25-mL portions of 1N HCl, 25 mL of satd aq. NaHCO$_3$ and 25 mL of brine. The solution was dried (MgSO$_4$) and concentrated under diminished pressure to afford a crude residue. The residue was purified by flash chromatography on a silica gel column (5×28 cm). Elution with 1:2 ethyl acetate-hexanes afforded 22 as a white foam: yield 1.91 g (74%); silica gel TLC R$_f$ 0.21 (2:1 ethyl acetate-hexanes). $^1$H NMR (CDCl$_3$) δ 2.05 (s, 3H), 2.11 (s, 3H), 2.18 (s, 3H), 2.19 (s, 3H), 4.15-4.20 (m, 2H), 4.53-4.58 (m, 1H), 5.23 (t, 1H, J=9.9 Hz), 5.32-5.33 (m, 1H), 5.45 (dd, 1H, J=10.1, 3.5 Hz), 6.12 (d, 1H, J=1.9 Hz), 7.38 (d, 2H, J=9.2 Hz), 8.29 (d, 2H, J=8.8 Hz); $^{13}$C NMR (CDCl$_3$) δ 20.66, 20.69, 20.8, 61.6, 68.3, 68.6, 70.1 70.9, 90.4, 121.6, 125.4, 145.7, 151.7, 155.1, 167.9, 169.5, 169.8, 170.6.

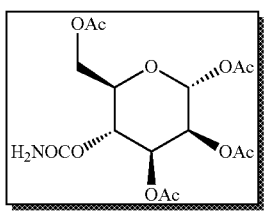

1,2,3,6-Tetra-O-acetyl-4-O-(carbamoyloxy)-α-D-mannopyranoside (23)

To a solution of 2.02 g (3.93 mmol) of 22 in 107 mL of dichloromethane was added a solution of 37 mL of anh THF satd with $NH_3$ at 0° C. The reaction mixture was allowed to warm to room temperature and stirred at room temperature overnight. The solution was concentrated under diminished pressure and the residue was purified by flash chromatography on a silica gel column (3×15 cm). Elution with 1:1 ethyl acetate-hexanes afforded 23 as a white foam: yield 1.22 g (87%); silica gel TLC $R_f$ 0.12 (1:1 hexanes-ethyl acetate). $^1$H NMR (CDCl$_3$) δ 2.03 (s, 3H), 2.09 (s, 3H), 2.16 (s, 3H), 2.17 (s, 3H), 4.00-4.05 (m, 1H), 4.15-4.19 (m, 1H), 4.26-4.31 (m, 1H), 4.73 (br s, 2H), 5.19 (t, 1H, J=10.1 Hz), 5.24-5.25 (m, 1H), 5.34-5.37 (m, 1H), 6.07 (d, 1H, J=1.9 Hz); $^{13}$C NMR (CDCl$_3$) δ 20.68, 20.72, 20.76, 20.85, 62.3, 66.7, 68.4, 68.6, 70.7, 90.6, 154.9, 168.0, 169.8, 170.1, 170.7; mass spectrum (APCI), m/z 392.1203 (M+H)$^+$ ($C_{15}H_{22}NO_{11}$ requires m/z 392.1193).

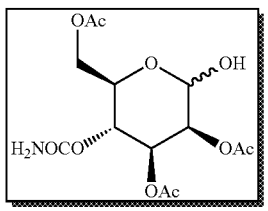

2,3,6-Tri-O-acetyl-4-O-(carbamoyloxy)-α-D-mannopyranoside (24)

To a solution containing 553 mg (1.41 mmol) of 23 in 9.20 mL of anh DMF was added 182 mg (1.98 mmol) of hydrazine acetate. The solution was stirred at 25° C. for 2 h and then treated with 120 mL of ethyl acetate. The organic solution was washed with 120 mL of water, 120 mL of satd aq. NaHCO$_3$, 120 mL of brine, and then dried (MgSO$_4$). The solvent was concentrated under diminished pressure to afford 24 as a white foam: yield 501 mg (quant.); silica gel TLC $R_f$ 0.28 (1:3 hexanes-ethyl acetate). $^1$H NMR (CDCl$_3$) δ 2.00 (s, 3H), 2.08 (s, 3H), 2.14 (s, 3H), 4.17-4.24 (m, 3H), 4.58-4.64 (br s, 1H), 5.10 (t, 1H, J=9.6 Hz), 5.07-5.15 (br s, 2H), 5.20-5.22 (m, 2H), 5.37-5.41 (m, 1H).

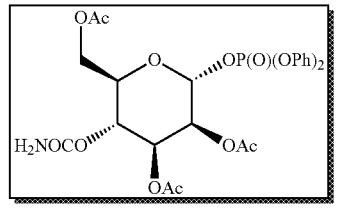

2,3,6-Tri-O-acetyl-4-O-(carbamoyloxy)-α-D-mannopyranosyl Diphenyl Phosphate (25)

To a solution of 496 mg (1.42 mmol) of 24 in 29 mL of dichloromethane at 0° C. was added 217 mg (1.78 mmol) of DMAP, 2.1 mL (15.0 mmol) of Et$_3$N, and 2.8 mL (13.6 mmol) of diphenyl phosphoryl chloride under an argon atmosphere. The reaction mixture was stirred for 1.5 h and the solution was poured into a two-phase mixture of 43 mL of ethyl acetate and 20 mL of satd aq NaHCO$_3$. The organic layer was washed with two 20-mL portions of brine, dried (MgSO$_4$) and concentrated under diminished pressure to afford a crude residue. The residue was purified by flash chromatography on a silica gel column (3×20 cm). Elution with 2:3 hexanes-ethyl acetate afforded 25 as a colorless oil: yield 460 mg (56%); silica gel TLC $R_f$ 0.33 (1:3 hexanes-ethyl acetate). $^1$H NMR (CDCl$_3$) δ 2.06 (s, 3H), 2.12 (s, 3H), 2.24 (s, 3H), 4.15-4.19 (m, 1H), 4.28-4.32 (m, 1H), 4.37-4.41 (m, 1H), 4.80 (s, 1H), 4.82-4.90 (br s, 2H), 5.21-5.30 (m, 1H), 5.41-5.50 (m, 1H), 5.95-5.97 (m, 1H), 7.24-7.36 (m, 6H), 7.44-7.48 (m, 4H); $^{13}$C NMR (400 MHz, CDCl$_3$) δ 20.56, 20.62, 20.7, 61.9, 66.3, 68.0, 68.7, 68.8, 70.8, 96.0, 120.01, 120.05, 120.16, 120.21, 125.7, 125.85, 125.86, 129.93, 129.99, 169.6, 169.9, 170.6; mass spectrum (APCI), m/z 582.1387 (M+H)$^+$ ($C_{25}H_{29}NO_{13}P$ requires m/z 582.1377).

Example 6: Synthesis of Altrose Donor 32

Scheme 6

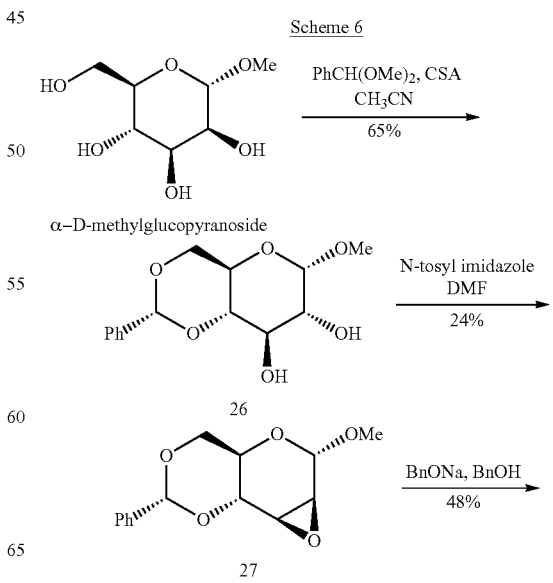

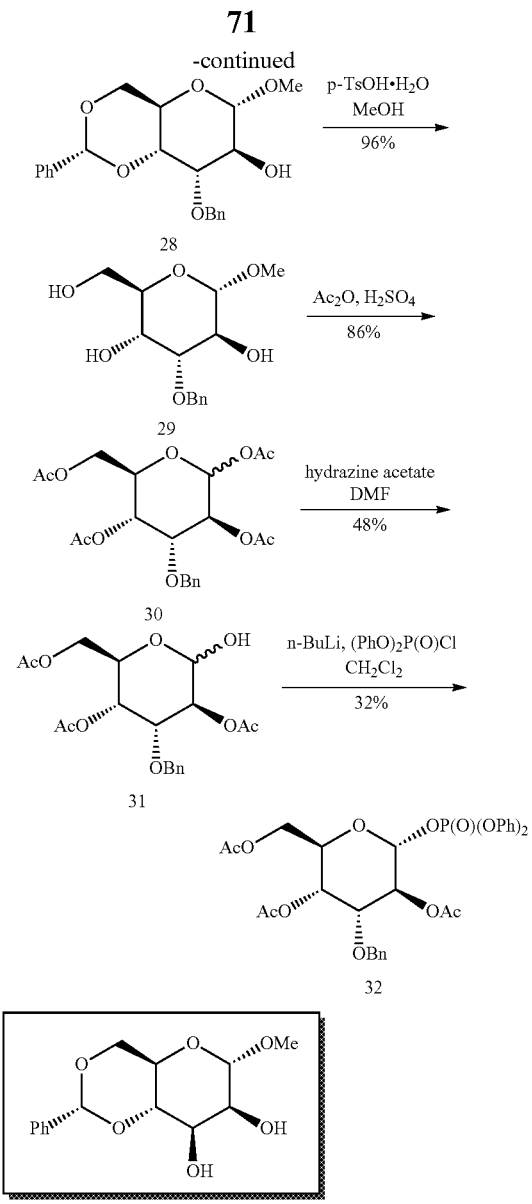

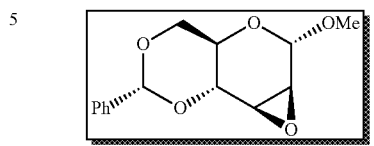

Methyl-4,6-O-benzylidene-α-D-glucopyranoside (26)

To a solution containing 10.0 g (51.5 mmol) of α-D-methyl glucopyranoside in 200 mL of acetonitrile was added 14.0 mL (14.2 g, 92.7 mmol) of benzaldehyde dimethyl acetal and 600 mg (2.57 mmol) of camphorsulfonic acid. The reaction mixture was heated to reflux for 20 min and then allowed to cool to room temperature and neutralized by the addition of 400 μL of triethylamine. The reaction mixture was diluted with 800 mL of ethyl acetate. The organic layer was washed with three 250-mL portions of water and dried (MgSO$_4$). The organic layer was concentrated under diminished pressure to afford a crude residue. The residue was crystallized from 1:7 dichloromethane-hexanes to afford acetal 26 as a colorless solid: yield 9.48 g (65%); silica gel TLC R$_f$ 0.17 (2:1 ethyl acetate-hexanes); $^1$H NMR (CDCl$_3$) δ 3.45-3.47 (m, 4H), 3.63 (dd, 1H, J=9.1 and 3.9 Hz), 3.71-3.85 (m, 2H), 3.93 (t, 1H, J=9.2 Hz), 4.29 (dd, 1H, J=9.7 and 4.3 Hz), 4.80 (d, 1H, J=3.9 Hz), 5.53 (s, 1H) and 7.33-7.53 (m, 5H); $^{13}$C NMR (CDCl$_3$) δ 55.7, 62.5, 69.1, 72.0, 73.0, 81.0, 99.9, 102.1, 126.4, 128.4, 129.4 and 137.2.

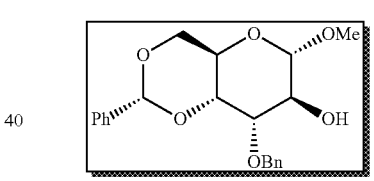

Methyl 2,3-Anhydro-4,6-O-benzyl-α-D-mannopyranoside (27)

To a solution containing 2.44 g (60% in oil dispersion, 60.9 mmol) of NaH in 290 mL of anh DMF at 0° C. was added 8.20 g (29.0 mmol) of acetal 26 under an argon atmosphere. The reaction mixture was stirred at room temperature for 0.5 h. To the above stirred solution at 0° C. was then added 7.10 g (31.9 mmol) of N-tosylimidazole. The suspension was stirred at room temperature for 1 h. The reaction mixture was poured with stirring into 2.5 L of ice-cold water and the resulting solid was filtered and washed with water to afford a crude residue. The residue so obtained was triturated with methanol to obtain the epoxide 27 as a colorless solid: yield 1.83 g (24%); silica gel TLC R$_f$ 0.68 (1:1 ethyl acetate-hexanes); $^1$H NMR (CDCl$_3$) δ 3.17 (d, 1H, J=3.6 Hz), 3.45-3.49 (m, 4H), 3.64-3.79 (m, 3H), 4.21-4.32 (m, 1H), 4.91 (s, 1H), 5.57 (s, 1H), 7.35-7.53 (m, 5H); $^{13}$C NMR (CDCl$_3$) δ 50.7, 54.0, 55.9, 61.8, 69.6, 75.0, 97.0, 102.6, 126.3, 128.5, 129.4 and 137.2.

Methyl 4,6-O-Benzylidene-3-O-benzyl-α-D-altropyranoside (28)

A solution containing 214 mg (9.32 mmol) of sodium metal in 2.9 mL of anh benzyl alcohol was heated (~100° C.) until all of the sodium metal had dissolved. The cooled solution was treated with 1.07 g (4.05 mmol) of anhydromannopyranoside 27. The reaction mixture was then heated to reflux for 15 min, cooled and diluted by the addition of 20 mL of ether. The solvent was concentrated under diminished pressure to afford a crude residue. The residue was applied to a silica gel column (20×5 cm). Elution with 1:4 ethyl acetate-hexanes afforded acetal 28 as a colorless solid: yield 723 mg (48%); silica gel TLC R$_f$ 0.55 (1:1 ethyl acetate-hexanes); $^1$H NMR (CDCl$_3$) δ 2.30 (s, 1H), 3.42 (s, 3H), 3.77 (t, 1H, J=10.3 Hz), 3.84 (t, 1H, J=2.8 Hz), 3.93 (d, 1H, J=2.8 Hz), 3.98 (dt, 1H, J=9.3 and 4.6 Hz), 4.28-4.45 (m, 2H), 4.55 (d, 1H, J=6.0 Hz), 4.70-4.90 (m, 2H), 5.56 (s, 1H) and 7.23-7.53 (m, 10H); $^{13}$C NMR (CDCl$_3$) δ 55.8, 58.7, 69.4, 70.2, 72.9, 74.9, 77.2, 102.0, 102.4, 126.3, 127.5, 127.7, 128.30, 128.36, 129.1, 137.7 and 138.7.

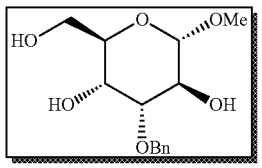

Methyl-3-O-benzyl-α-D-altropyranoside (29)

To a solution containing 1.67 g (4.48 mmol) of acetal 28 in 4.2 mL of methanol was added 43.0 mg (0.22 mmol) of p-toluenesulfonic acid monohydrate at 0° C. The reaction mixture was allowed to warm to room temperature and stirred for 4 h. The reaction mixture was quenched by the addition of 1.90 mL (1.38 g, 13.4 mmol) of triethylamine and concentrated under diminished pressure to afford a crude residue. The residue was applied to a silica gel column (10×3 cm). Elution with 5:1 ethyl acetate-hexanes afforded methyl pyranoside 29 as a colorless oil: yield 1.22 g (96%); silica gel TLC $R_f$ 0.17 (ethyl acetate); $^1$H NMR (CDCl$_3$) δ 3.01 (d, 1H, J=9.3 Hz), 3.33 (s, 3H), 3.53 (d, 1H, J=15.3 Hz), 3.70-3.77 (m, 2H), 3.80 (dt, 2H, J=8.8 and 4.3 Hz), 3.96 (s, 2H), 4.40-4.78 (m, 4H) and 7.21-7.35 (m, 5H); $^{13}$C NMR (CDCl$_3$) δ 55.5, 61.9, 63.4, 67.3, 69.2, 72.0, 77.4, 101.5, 127.9, 128.0, 128.5 and 138.0.

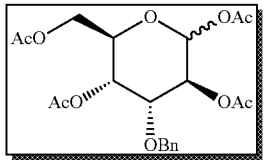

1,2,4,6-Tetra-O-acetyl-3-O-benzyl-α,β-D-altropyranoside (30)

To a solution containing 532 mg (1.87 mmol) of methyl pyranoside 29 in 13 mL of Ac$_2$O was added a catalytic amount of H$_2$SO$_4$. The solution was stirred overnight at room temperature. The reaction mixture was then poured into a stirred mixture of 120 mL of ethyl acetate and 80 mL of satd aq NaHCO$_3$. The organic and aqueous layers were separated and the organic layer was washed with brine and dried (MgSO$_4$). The solvent was concentrated under diminished pressure to afford a crude residue. The residue was applied to a silica gel column (30×3 cm). Elution with 1:2 ethyl acetate-hexanes afforded the product 30 as a 3:2 mixture of α and β anomers as determined by $^1$H NMR; yield 705 mg (86%); silica gel TLC $R_f$ 0.55 (1:1 ethyl acetate-hexanes); α anomer $^1$H NMR (CDCl$_3$) δ 2.01 (s, 3H), 2.06-2.09 (m, 6H), 2.14 (s, 3H), 3.96 (t, 1H, J=3.2 Hz), 4.11-4.16 (m, 1H), 4.24-4.37 (m, 2H), 4.55-4.75 (m, 2H), 5.03-5.09 (m, 1H), 5.29 (s, 1H), 5.99 (d, 1H, J=11.3 Hz) and 7.27-7.38 (m, 5H); $^{13}$C NMR (CDCl$_3$) δ 20.91, 20.92, 21.04, 21.05, 62.6, 66.3, 66.6, 68.0, 72.46, 72.49, 91.4, 127.8, 128.1, 128.5, 137.5, 169.0, 169.7, 169.8 and 170.9; HRMS (APCI), m/z 379.1387 (M–CH$_3$COO)$^+$ (C$_{19}$H$_{23}$O$_8$ requires m/z 379.1393).

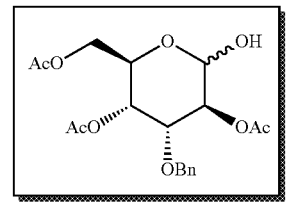

2,4,6-Tri-O-acetyl-3-O-benzyl-α,β-D-altropyranoside (31)

To a solution containing 1.93 g (4.40 mmol) of monosaccharide 30 in 35 mL of anh DMF was added 486 mg (5.28 mmol) of hydrazine acetate. The reaction mixture was stirred at room temperature for 1.5 h and quenched by the addition of 100 mL of ethyl acetate. The organic layer was then washed with three 50-mL portions of brine and dried (MgSO$_4$). The solvent was concentrated under diminished pressure to afford a crude residue. The residue was applied to a silica gel column (20×4 cm). Elution with 1:2 ethyl acetate-hexanes afforded 31 as a colorless oil. The product was isolated as a mixture of anomers as analyzed by $^1$H NMR: yield 837 mg (48%); silica gel TLC $R_f$ 0.31 (1:1 ethyl acetate-hexanes); $^1$H NMR (CDCl$_3$) δ 1.95 (s, 3H), 1.96 (s, 3H), 2.05 (s, 3H), 2.07 (s, 3H), 2.11 (s, 3H), 2.15 (s, 3H), 3.73-3.95 (br s, 1H), 3.98-4.05 (m, 1H), 4.09 (d, 1H, J=8.6 Hz), 4.12-4.27 (m, 4H), 4.32 (dt, 1H, J=14.2 and 7.1 Hz), 4.36-4.46 (m, 1H), 4.54-4.75 (m, 4H), 4.89-4.94 (m, 2H), 4.96-5.08 (m, 4H), 5.24 (t, 1H, J=12.1 Hz) and 7.41-7.27 (m, 10H); $^{13}$C NMR (CDCl$_3$) δ 20.80, 20.82, 20.86, 20.98, 21.02, 62.9, 63.2, 64.1, 66.2, 66.9, 68.3, 70.0, 70.3, 72.9, 73.3, 73.8, 74.2, 91.6, 92.8, 128.1, 128.2, 128.4, 128.5, 128.7, 128.8, 136.2, 137.3, 169.73, 169.78, 169.83, 170.4, 170.95 and 170.96; HRMS (APCI), m/z 379.1394 (M–OH)$^+$ (C$_{19}$H$_{23}$O$_8$ requires m/z 379.1393).

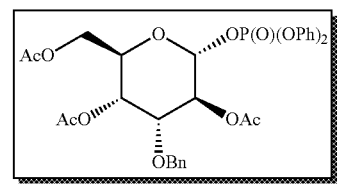

2,4,6-Tri-O-acetyl-3-O-benzyl-α-D-altropyranosyl Diphenyl Phosphate (32)

To a stirred solution containing 637 mg (1.61 mmol) of pyranoside 31 in 2.7 mL of anh dichloromethane was added 1.21 mL (1.6 M, 1.93 mmol) of n-BuLi solution at –78° C. The reaction mixture was stirred at this temperature for 10 min and 400 µL (520 mg, 1.93 mmol) of diphenyl chlorophosphate was added dropwise. The reaction mixture was stirred at –78° C. for an additional 10 min and then poured into a mixture of 20 mL of ethyl acetate and 10 mL of satd aq NaHCO$_3$. The organic and aqueous layers were separated and the organic layer was washed with three 10-mL portions of water and brine and then dried (MgSO$_4$). The solvent was concentrated under diminished pressure to afford a crude residue. The residue was applied to a silica gel column (20×3 cm). Elution with 1:2 ethyl acetate-hexanes afforded phosphate ester 32 as a colorless oil: yield 324 mg (32%); 121 mg of unreacted starting material was also recovered; silica gel TLC $R_f$ 0.40 (1:1 ethyl acetate-hexanes); $^1$H NMR (CDCl$_3$) δ 1.97 (s, 3H), 1.98 (s, 3H), 2.00 (d, 3H, J=2.1 Hz), 3.99 (dd, 1H, J=6.3 and 3.1 Hz), 4.05-4.28 (m, 3H), 4.50-4.62 (m, 2H), 5.13 (dd, 1H, J=7.0 and 3.2 Hz), 5.19 (dd, 1H, J=6.4 and 2.2 Hz), 5.96 (dd, 1H, J=7.1 and 2.2 Hz) and 7.12-7.36 (m, 15H); $^{13}$C NMR (CDCl$_3$) δ 20.74, 20.76, 20.9, 62.8, 66.9, 68.20, 68.28, 71.6, 72.94, 72.97, 95.5, 120.30, 120.35, 125.7, 128.0, 128.2, 128.5, 129.8, 129.9, 137.1, 150.2, 150.4, 169.9 and 170.6; HRMS (APCI), m/z 569.1598 (M–CH$_3$COO)$^+$ (C$_{29}$H$_{30}$O$_{10}$P requires m/z 569.1576).

Example 7: Synthesis of C2 Modified Mannose Disaccharide-Dye Conjugates 45 and 46

Scheme 7

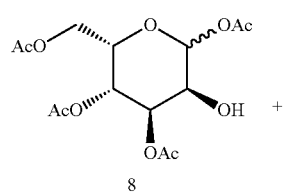

8

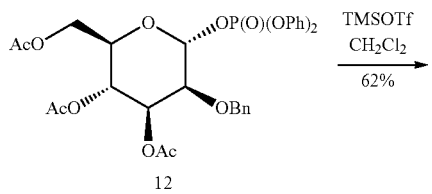

12

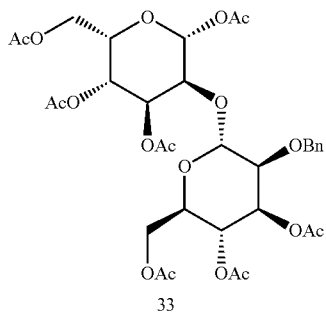

33

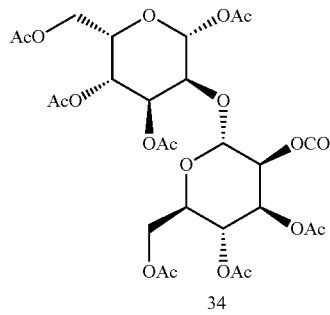

34

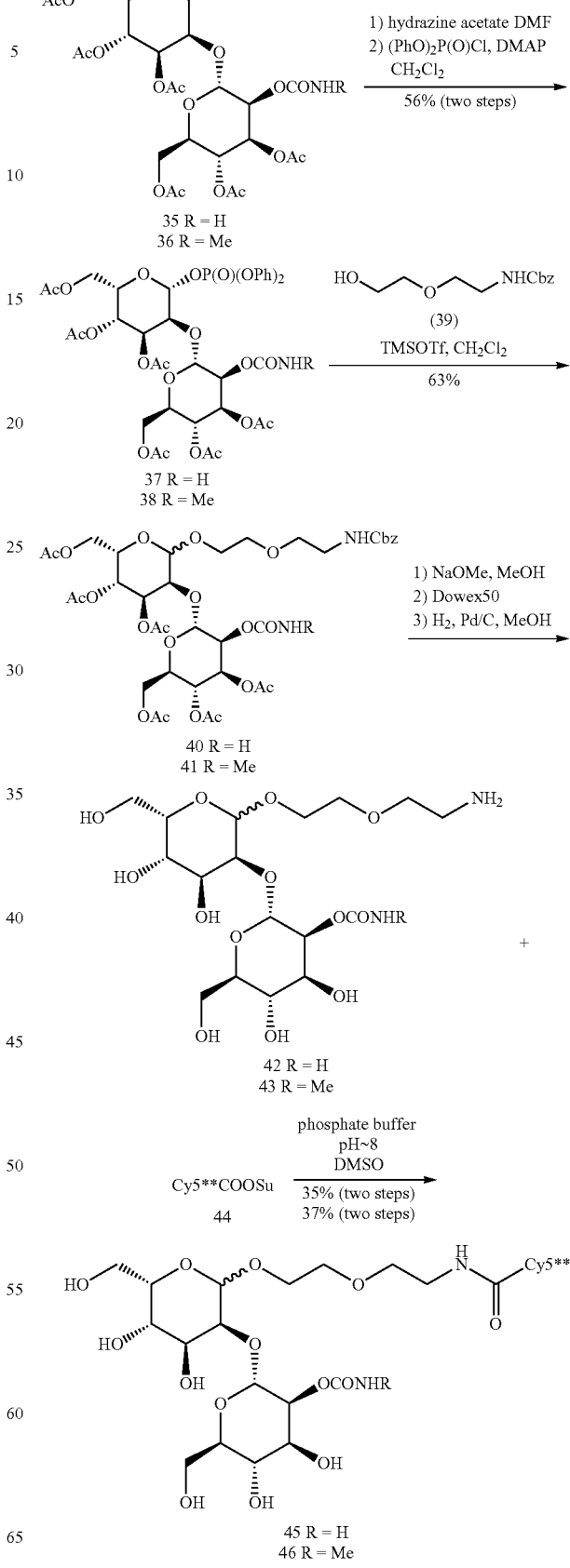

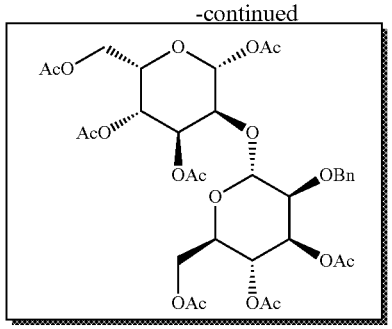

1,3,4,6-Tetra-O-acetyl-2-O-(3,4,6-tri-O-acetyl-2-O-benzyl-α-D-mannopyranosyl)-β-L-gulopyranose (33)

To a stirred solution containing 234 mg (0.67 mmol) of glycosyl acceptor 8 and 508 mg (1.17 mmol) of glycosyl donor 12 in 4.8 mL of anh dichloromethane at 0° C., was added 244 µL (300 mg, 1.35 mmol) of TMSOTf. The reaction mixture was stirred at 0° C. for 10 min at which time it was poured into a two phase mixture of 30 mL of ethyl acetate and 30 mL of satd aq NaHCO₃. The organic and aqueous layers were separated and the organic layer was washed with two 20-mL portions of brine and dried (MgSO₄). The solvent was concentrated under diminished pressure to afford a crude residue. The residue was applied to a silica gel column (30×3 cm). Elution with 2:1 ethyl acetate-hexanes afforded compound 33 as a colorless oil: yield 302 mg (62%); silica gel TLC R$_f$ 0.2 (1:1 ethyl acetate-hexanes); ¹H NMR (CDCl₃) δ 1.84 (s, 3H), 1.94 (s, 3H), 1.99 (s, 3H), 2.04 (s, 3H), 2.08 (s, 3H), 2.09 (m, 6H), 3.51-3.61 (m, 1H), 3.87-4.23 (m, 5H), 4.31 (t, 1H, J=6.3 Hz,), 4.44-4.47 (m, 1H), 4.56-4.69 (m, 1H), 4.80-4.97 (m, 2H), 5.02-5.07 (m, 2H), 5.27-5.47 (m, 2H), 5.78 (d, 1H, J=8.5 Hz,) and 7.16-7.36 (m, 5H); ¹³C NMR (CDCl₃) δ 20.61, 20.63, 20.66, 20.67, 20.69, 20.72, 61.3, 62.2, 65.3, 65.7, 66.0, 67.7, 68.8, 69.2, 70.4, 71.3, 72.2, 73.9, 90.6, 94.2, 127.7, 128.1, 128.2, 137.6, 168.7, 169.36, 169.37, 169.4, 170.0, 170.3 and 170.6; mass spectrum (APCI), m/z 727.2453 (M+H)⁺ (C₃₃H₄₃O₁₈ requires 727.2450).

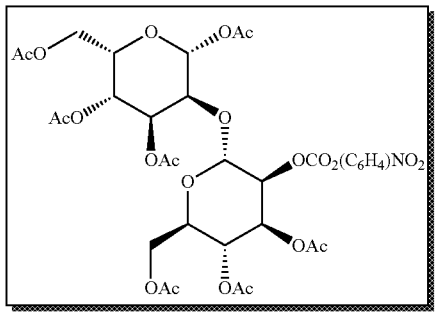

1,3,4,6-Tetra-O-acetyl-2-O-(3,4,6-tri-O-acetyl-2-O-((p-nitrophenyl)carbamoyl)-α-D-mannopyranosyl)-β-L-gulopyranose (34)

To a solution containing 200 mg (0.27 mmol) of disaccharide 33 in 38 mL of ethyl acetate was added a catalytic amount of Pd(OH)₂/C and the reaction mixture was stirred overnight under 1 atm of H₂. The solvent was filtered through a pad of Celite 545® and the filtrate was concentrated under diminished pressure to afford a crude residue. The residue was used for the next reaction; silica gel TLC R$_f$ 0.08 (1:1 ethyl acetate-hexanes).

To a solution containing 198 mg (0.31 mmol) of the crude residue in 1.2 mL of anh pyridine was added 151 mg (1.24 mmol) of DMAP and 276 mg (1.24 mmol) of p-nitrophenyl chloroformate. The reaction mixture was stirred at 40° C. overnight at which time it was poured into a mixture of 30 mL ethyl acetate and 10 mL of H₂O. The organic and aqueous layers were separated and the organic layer was washed with three 10-mL portions of 1 N HCl and 10 mL of satd aq NaHCO₃ and then brine. The solution was dried (MgSO₄) and filtered and the filtrate was concentrated under diminished pressure to afford a crude residue. The residue was applied to a silica gel column (25×3 cm). Elution with 1:1 ethyl acetate-hexanes afforded 34 as a colorless foam: yield 211 mg (96% over two steps); silica gel TLC R$_f$ 0.30 (1:1 ethyl acetate-hexanes); ¹H NMR (CDCl₃) δ 1.98 (m, 3H), 2.03 (s, 6H), 2.10 (s, 3H), 2.12 (s, 3H), 2.14 (s, 3H), 2.17 (s, 3H), 3.96-4.18 (m, 2H), 4.19-4.29 (m, 2H), 4.35 (t, 1H, J=6.5 Hz), 4.96-5.03 (m, 2H), 5.06-5.23 (m, 3H), 5.27-5.40 (m, 2H), 5.44 (t, 1H, J=3.0 Hz), 5.88 (d, 1H, J=8.4 Hz), 7.39 (d, 2H, J=8.0 Hz) and 8.26 (d, 2H, J=9.1 Hz); ¹³C NMR (CDCl₃) δ 20.70, 20.72, 20.75, 20.76, 20.9, 61.3, 62.0, 65.5, 65.7, 67.8, 68.8, 69.4, 70.1, 71.4, 73.5, 90.6, 94.5, 121.7, 125.4, 145.6, 149.8, 151.6, 155.3, 168.7, 169.3, 169.5, 169.7, 169.7, 170.5 and 170.6; HRMS (APCI), m/z 802.2053 (M+H)⁺ (C₃₃H₄₀NO₂₂ requires m/z 802.2042).

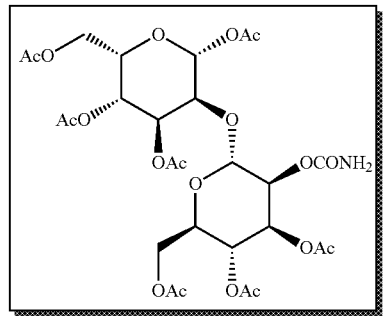

1,3,4,6-Tetra-O-acetyl-2-O-(3,4,6-tri-O-acetyl-2-O-(carbamoyl)-α-D-mannopyranosyl)-β-L-gulopyranose (35)

To a solution containing 94 mg (0.12 mmol) of 34 in 5.0 mL of dichloromethane was added 2.2 mL of THF saturated with NH₃. The reaction mixture was stirred at room temperature for 3 h. The solvent was concentrated under diminished pressure to afford a crude residue. The residue was purified by flash chromatography on a silica gel column (2.5×15 cm). Elution with 3:1 ethyl acetate-hexanes afforded 35 as a white foam: yield 73 mg (92%); silica gel TLC R$_f$ 0.13 (3:1 ethyl acetate-hexanes). ¹H NMR (CDCl₃) δ 1.98 (s, 3H), 2.02 (s, 3H), 2.04 (s, 3H), 2.11 (s, 3H), 2.13 (s, 3H), 2.14 (s, 3H), 2.18 (s, 3H), 3.98 (dd, 1H, J=8.4, 3.3 Hz), 4.06-4.11 (m, 2H), 4.14-4.15 (m, 1H), 4.17-4.19 (m, 1H), 4.22-4.27 (m, 1H), 4.33-4.37 (m, 1H), 4.85 (br s, 2H), 4.95-4.97 (m, 1H), 5.00-5.02 (m, 2H), 5.08-5.14 (m, 1H), 5.22-5.27 (m, 1H), 5.44 (t, 1H, J=3.6 Hz), 5.89 (d, 1H, J=8.4 Hz); ¹³C NMR (CDCl₃) δ 20.62, 20.65, 20.68, 20.71, 20.82, 61.35, 62.11, 65.59, 65.74, 67.59, 68.88, 69.10, 69.43, 69.79, 71.30, 90.67, 95.29, 154.88, 168.68, 169.21, 169.64, 169.87, 170.43, 170.53; mass spectrum (APCI), m/z 680.2026 (M+H)⁺ (C₂₇H₃₈O₁₉ requires m/z 680.2038).

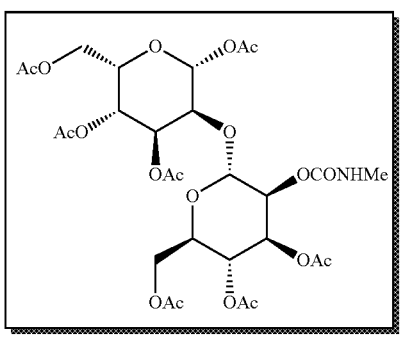

1,3,4,6-Tetra-O-acetyl-2-O-(3,4,6-tri-O-acetyl-2-O-(methylcarbamoyl)-α-D-mannopyranosyl)-β-L-gulopyranose (36)

To a solution containing 201 mg (0.25 mmol) of nitrophenyl ester 34 in 6 mL of anh THF was added dropwise at 0° C. 125 µL (2 M solution in THF, 0.25 mmol) of $CH_3NH_2$. The reaction mixture was stirred at room temperature for 15 h at which time silica gel TLC analysis indicated that the reaction was complete. The solvent was concentrated under diminished pressure to afford a crude residue. The residue was applied to a silica gel column (25×3 cm). Elution with 1:1 ethyl acetate-hexanes afforded disaccharide 36 as a colorless oil: yield 134 mg (77%); silica gel TLC $R_f$ 0.14 (1:1 ethyl acetate-hexanes); $^1$H NMR ($CDCl_3$) δ 1.94 (s, 3H), 1.98-2.15 (m, 18H), 2.75 (d, 3H, J=3.7 Hz), 3.93-4.13 (m, 4H), 4.18-4.22 (m, 2H), 4.30-4.33 (m, 1H), 4.87-5.10 (m, 4H), 5.17-5.21 (m, 2H) and 5.33 (m, 2H); $^{13}$C NMR ($CDCl_3$) δ 20.62, 20.63, 20.68, 20.72, 20.75, 20.77, 20.85, 27.6, 61.4, 62.0, 65.9, 67.6, 68.0, 70.5, 71.4, 90.7, 93.2, 155.38, 155.40, 155.49, 169.24, 169.27, 169.30, 170.50, 170.51, 170.6 and 170.9; HRMS (APCI), m/z 694.2169 $(M+H)^+$ ($C_{28}H_{40}NO_{19}$ requires m/z 694.2195).

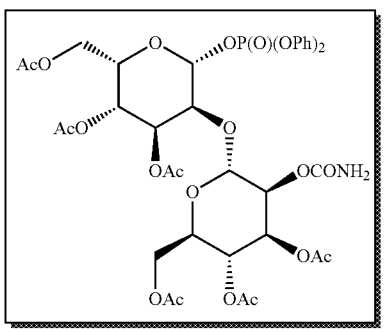

3,4,6-Tri-O-acetyl-2-O-(3,4,6-tri-O-acetyl-2-O-(carbamoyl)-α-D-mannopyranosyl)-β-L-gulopyranosyl Diphenyl Phosphate (37)

To a solution containing 66 mg (0.10 mmol) of disaccharide 35 in 1.0 mL of anh DMF was added 13.0 mg (0.14 mmol) of hydrazine acetate. The reaction mixture was stirred at room temperature for 3 h and quenched by the addition of 14 mL of ethyl acetate. The organic solution was washed with 12 mL of water, 12 mL of satd aq. $NaHCO_3$, 12 mL of brine and then dried ($MgSO_4$). The solvent was concentrated under diminished pressure to afford the crude product as a light yellow oil: yield 56 mg (90%); silica gel TLC $R_f$ 0.23 (1:4 hexanes-ethyl acetate). MALDI, m/z 660.18 for $(M+Na)^+$. The residue was used for next reaction.

To a stirred solution containing 56.0 mg (0.09 mmol) of the crude residue in 3.30 mL of anh dichloromethane was added 13.0 mg (0.11 mmol) of DMAP, 133 µL (96 mg, 0.95 mmol) of $Et_3N$ and 176 µL (229 mg, 0.85 mmol) of diphenyl chlorophosphate. The reaction mixture was stirred at 0° C. for 2 h and poured into a mixture of 5 mL of ethyl acetate and 5 mL of satd aq $NaHCO_3$. The organic layer was washed with three 10-mL portions of water and brine and then dried ($MgSO_4$). The solvent was concentrated under diminished pressure to afford a crude residue. The residue was applied to a silica gel column (20×2 cm). Elution with 2:1 ethyl acetate-hexanes afforded phosphate ester 37 as a colorless oil: yield 36 mg (47% over two steps); silica gel TLC $R_f$ 0.18 (2:1 ethyl acetate-hexanes); $^1$H NMR ($CDCl_3$) δ 1.77 (s, 3H), 2.03 (s, 3H), 2.05 (s, 3H), 2.13 (s, 3H), 2.21 (s, 3H), 2.27 (s, 3H), 4.03-4.10 (m, 2H), 4.14-4.21 (m, 2H), 4.24-4.28 (m, 1H), 4.36-4.42 (m, 2H), 4.87 (br s, 2H), 5.05-5.10 (m, 3H), 5.24-5.27 (m, 1H), 5.29-5.35 (m, 1H), 5.51-5.53 (m, 1H), 5.75-5.79 (m, 1H), 7.22-7.28 (m, 2H), 7.32-7.43 (m, 8H). $^{13}$C NMR ($CDCl_3$) δ 20.3, 20.63, 20.64, 20.68, 20.71, 61.2, 61.8, 65.3, 65.6, 67.4, 69.0, 69.1, 69.5, 71.1, 71.2, 71.6, 95.6, 96.17, 96.22, 120.19, 120.24, 125.57, 125.71, 125.70, 129.6, 129.9, 150.05, 150.10, 154.9, 169.2, 169.6, 169.7, 170.4, 170.6; mass spectrum (APCI), m/z 870.2224 $(M+H)^+$ ($C_{37}H_{45}NO_{21}P$ requires m/z 870.2222).

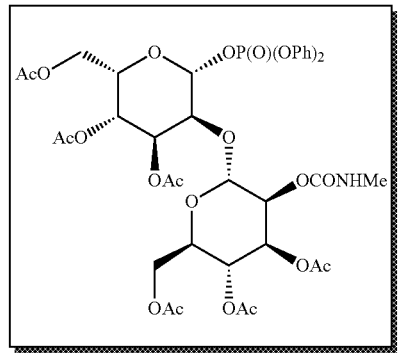

3,4,6-Tri-O-acetyl-2-O-(3,4,6-tri-O-acetyl-2-O-(methylcarbamoyl)-α-D-mannopyranosyl)-β-L-gulopyranosyl Diphenyl Phosphate (38)

To a solution containing 108 mg (0.16 mmol) of disaccharide 36 in 1.2 mL of anh DMF was added 17.0 mg (0.19 mmol) of hydrazine acetate. The reaction mixture was stirred at room temperature for 1.5 h and quenched by the addition of 20 mL of ethyl acetate. The organic solution was washed with three 10-mL portions of brine and dried ($MgSO_4$). The solvent was concentrated under diminished pressure to afford a crude residue. The residue was used for the next reaction.

To a stirred solution containing 90.0 mg (0.14 mmol) of the crude residue in 8.2 mL of anh dichloromethane was added 21.0 mg (0.17 mmol) of DMAP, 210 µL (152 mg, 1.49 mmol) of $Et_3N$ and 270 µL (351 mg, 1.32 mmol) of diphenyl chlorophosphate. The reaction mixture was stirred at 0° C. for 2 h and poured into a mixture of 40 mL of ethyl acetate and 20 mL of satd aq $NaHCO_3$. The organic layer was washed with three 10-mL portions of water and brine and then dried ($MgSO_4$). The solvent was concentrated under diminished pressure to afford a crude residue. The residue was applied to a silica gel column (25×3 cm). Elution with 2:1 ethyl acetate-hexanes afforded phosphate ester 38 as a colorless oil: yield 82 mg (56% over two steps); silica gel TLC R$_f$ 0.18 (2:1 ethyl acetate-hexanes); $^1$H NMR (CDCl$_3$) δ 1.67 (s, 3H), 1.94 (d, 6H, J=7.4 Hz), 2.01 (s, 3H), 2.11 (s, 3H), 2.16 (s, 3H), 2.76 (s, 3H), 3.89-4.39 (m, 7H), 4.75-5.05 (m, 4H), 5.10-5.30 (m, 2H), 5.44 (s, 1H), 5.68 (s, 1H) and 7.11-7.39 (m, 10H); $^{13}$C NMR (CDCl$_3$) δ 20.4, 20.70, 20.76, 20.8, 20.9, 27.7, 61.2, 62.0, 65.5, 65.8, 67.5, 69.1, 69.3, 69.4, 71.4, 71.5, 71.7, 95.9, 96.34, 120.31, 120.33, 125.6, 125.72, 125.78, 125.83, 129.7, 130.0, 155.4, 169.3, 169.7, 169.8, 170.4, 170.67 and 170.68; HRMS (APCI), m/z 884.2371 (M+H)$^+$ (C$_{38}$H$_{47}$NO$_{19}$ requires m/z 884.2378).

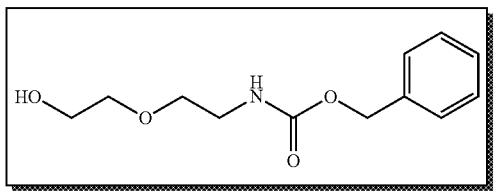

Benzyl 2-(2-Hydroxyethoxy)ethylcarbamate (39)

To a solution containing 1.01 g (9.61 mmol) of 2-(2-aminoethoxy)ethanol in 100 mL of THF at room temperature was added 1.34 mL (9.61 mmol) of Et$_3$N and 1.49 mL (1.78 g, 10.6 mmol) of CBzCl. The reaction mixture was stirred for 1 h and was then diluted with 250 mL of ethyl acetate. The organic layer was washed with two 250-mL portions of H$_2$O, two 250-mL portions of brine, and was then dried (MgSO$_4$) and concentrated under diminished pressure. The residue was purified by flash chromatography on a silica gel column (30×4 cm). Elution with 9:1 ethyl acetate-hexanes afforded alcohol 39 as a colorless oil: yield 2.21 g (96%); silica gel TLC R$_f$ 0.30 (9:1 ethyl acetate-hexanes); $^1$H NMR (CDCl$_3$) 3.30 (m, 2H), 3.45 (m, 4H), 3.52 (s, 1H), 3.62 (m, 2H), 5.03 (s, 2H), 5.86 (m, 1H) and 7.27 (m, 5H); $^{13}$C NMR (CDCl$_3$) 40.5, 61.1, 66.3, 69.7, 72.0, 127.72, 127.75, 128.1, 136.3 and 156.5.

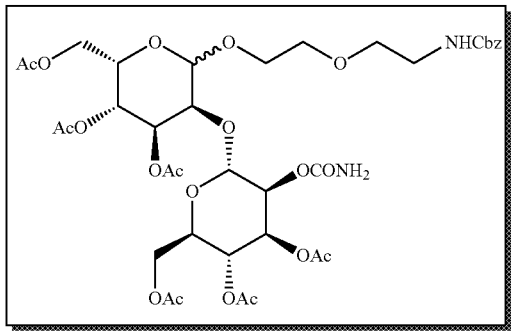

3,4,6-Tri-O-acetyl-2-O-(3,4,6-tri-O-acetyl-2-O-(carbamoyl)-α-D-mannopyranosyl)-α,β-L-gulopyranosyl Benzyl 2-(2-Ethoxy)ethylcarbamate (40)

To a stirred solution containing 31.0 mg (0.04 mmol) of phosphate ester 37 in 3.9 mL of anh dichloromethane was added a solution of 9.40 mg (0.04 mmol) of CBz linker 39 in 4.5 mL of anh dichloromethane at 0° C. To the cooled reaction mixture was then added 41.0 μL (51.0 mg, 0.23 mmol) of TMSOTf and the reaction mixture was stirred at 0° C. for 15 min at which time it was poured into a mixture of 20 mL of ethyl acetate and 20 mL of satd aq NaHCO$_3$. The aqueous and organic layers were separated and the organic layer was washed with three 10-mL portions of water and brine, and then dried (MgSO$_4$). The solvent was concentrated under diminished pressure to afford a crude residue. The residue was applied to a silica gel column (12×2 cm). Elution with 3:1 ethyl acetate-hexanes afforded disaccharide-linker conjugate 40 as a colorless oil: yield 12 mg (39%); silica gel TLC R$_f$ 0.12 (3:1 ethyl acetate-hexanes); $^1$H NMR (CDCl$_3$) δ 1.99 (s, 3H), 2.02 (s, 2H), 2.04 (s, 3H), 2.07 (s, 3H), 2.09 (s, 3H), 2.12 (s, 3H), 3.37-3.42 (m, 2H), 3.55-3.65 (m, 3H), 3.67-3.69 (m, 2H), 3.83-3.88 (m, 1H), 3.97 (t, 1H, J=3.9 Hz), 4.03-4.09 (m, 2H), 4.10-4.15 (m, 1H), 4.28 (dd, 1H, J=11.9, 5.2 Hz), 4.46 (t, 1H, J=6.6 Hz), 4.77-4.90 (br s, 2H), 4.93 (d, J=3.9 Hz, 1H), 5.03-5.06 (m, 3H), 5.09 (s, 2H), 5.23-5.29 (m, 3H), 5.46-5.48 (m, 1H), 7.28-7.37 (m, 5H); $^{13}$C NMR (CDCl$_3$) δ 20.62, 20.65, 20.72, 20.76, 40.9, 62.1, 62.5, 63.8, 65.8, 66.1, 66.6, 67.6, 68.6, 68.7, 69.0, 70.07, 70.16, 70.3, 71.0, 77.2, 97.0, 97.6, 128.10, 128.18, 128.5, 136.5, 155.0, 169.3, 169.72, 169.73, 170.0, 170.56, 170.59; mass spectrum (APCI), m/z 859.2987 (M+H)$^+$ (C$_{37}$H$_{51}$N$_2$O$_{21}$ requires m/z 859.2984).

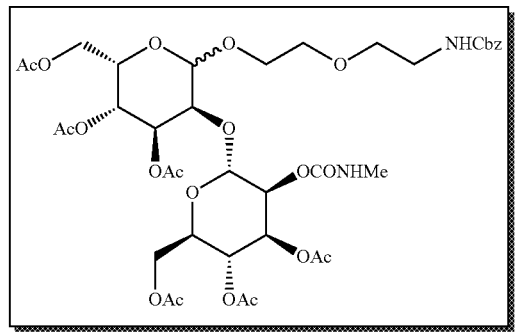

3,4,6-Tri-O-acetyl-2-O-(3,4,6-tri-O-acetyl-2-O-(methylcarbamoyl)-α-D-mannopyranosyl)-α,β-L-gulopyranosyl Benzyl 2-(2-Ethoxy)ethylcarbamate (41)

To a stirred solution containing 90.0 mg (0.10 mmol) of phosphate ester 38 in 1.1 mL of anh dichloromethane was added a solution of 22.0 mg (0.09 mmol) of CBz linker 39 in 1.1 mL of anh dichloromethane at 0° C. To the cooled reaction mixture was then added 33.0 μL (41.0 mg, 0.18 mmol) of TMSOTf and the reaction mixture was stirred at 0° C. for 15 min at which time it was poured into a mixture of 20 mL of ethyl acetate and 20 mL of satd aq NaHCO$_3$. The aqueous and organic layers were separated and the organic layer was washed with three 10-mL portions of water and brine and then dried (MgSO$_4$). The solvent was concentrated under diminished pressure to afford a crude residue. The residue was applied to a silica gel column (25×3 cm). Elution with 12:12:1 ethyl acetate-hexanes-methanol afforded disaccharide-linker conjugate 41 as a colorless oil: yield 56 mg (63%); silica gel TLC R$_f$ 0.20 (12:12:1 ethyl acetate-hexanes-methanol); $^1$H NMR (CDCl$_3$) δ 1.96 (s, 3H), 2.00 (s, 3H), 2.01 (s, 3H), 2.05-2.08 (m, 6H), 2.10 (s, 3H), 2.78 (d, 3H, J=4.6 Hz), 3.38 (d, 2H, J=4.4 Hz), 3.51-3.70 (m, 4H), 3.78-3.87 (m, 1H), 3.95 (d, 1H, J=3.5 Hz), 4.00-4.15 (m, 4H), 4.20-4.30 (m, 2H), 4.45 (t, 1H, J=6.1 Hz), 4.89-5.12 (m, 6H), 5.20-5.30 (m, 3H), 5.42-5.49 (m, 1H), 5.46 (s, 1H) and 7.27-7.38 (m, 5H); $^{13}$C NMR (CDCl$_3$) δ 20.71, 20.73, 20.77, 20.80, 20.84, 20.88, 27.7, 62.3, 62.7, 63.9, 66.0, 66.3, 66.7, 68.7, 68.9, 69.2, 70.1, 70.2, 70.4, 97.2, 97.9, 128.21, 128.23, 128.28, 128.59, 128.61, 136.7, 155.5, 169.4, 169.80, 169.84, 170.0, 170.66 and 170.69; HRMS (APCI), m/z 873.3166 (M+H)$^+$ (C$_{38}$H$_{53}$N$_2$O$_{21}$ requires m/z 873.3141).

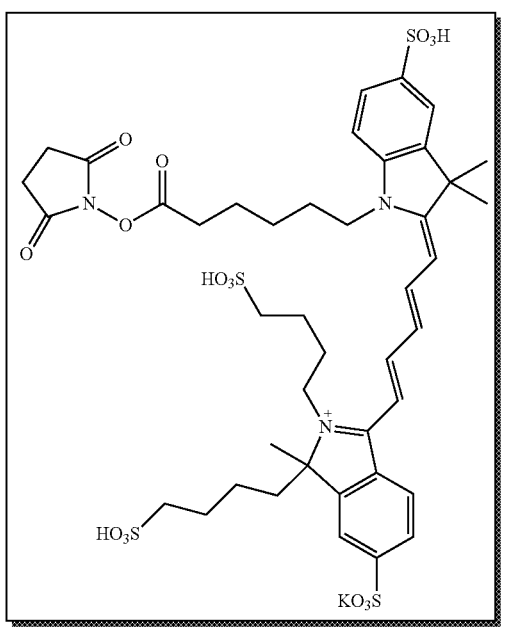

Cy5** Succinimidyl Ester (44)

To a solution containing 0.5 mg (0.6 µmol) of Cy5**COOH was added 5.0 mg (16 µmol) of TSTU dissolved in 100 µL, of anh DMF, followed by 7.5 µL, (5.6 mg, 43 µmol) of anh DIPEA dissolved in 75 µL, of anh DMF. The reaction mixture was stirred at room temperature for 3 h and then diluted with 3 mL of ethyl acetate. The solution was then centrifuged at 12000 rpm for 10 min. The supernatant solution was discarded and the residue was washed with 1 mL of ethyl acetate. The residue was then dried under vacuum in the dark for 30 min to afford the product 44 as a dark blue solid: yield 480 µg (86%); mass spectrum (MALDI-TOF), m/z 1023.5 (M+H)$^+$ (theoretical m/z 1023.2).

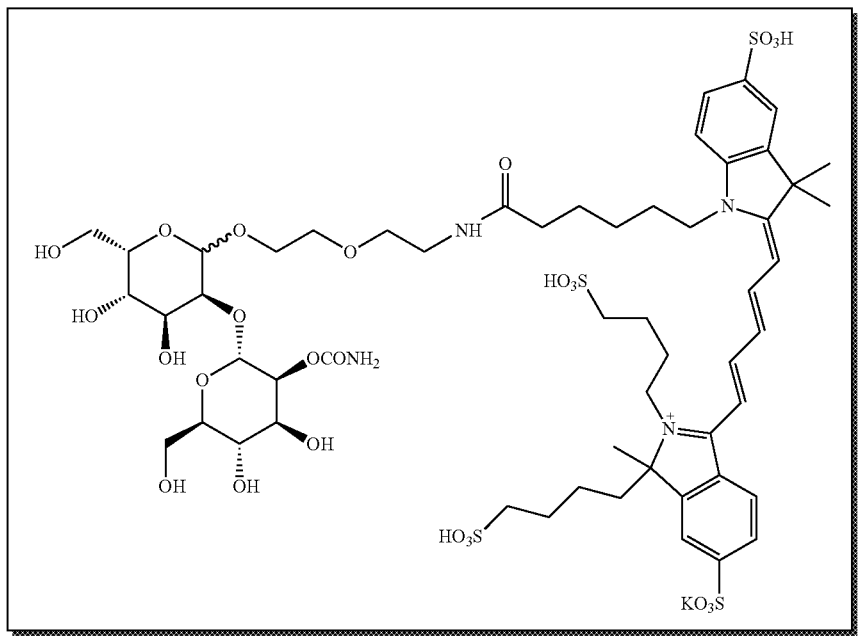

Disaccharide-Dye Conjugate 45

To a solution of 2.20 mg (2.60 µmol) of compound 40 in 1 mL of anh methanol was added a freshly prepared solution of 0.4 M sodium methoxide in methanol. The reaction mixture was allowed to stir at room temperature for 3 h, and the complete consumption of starting material was confirmed by MALDI-TOF mass spectral analysis. The reaction mixture was then quenched by the addition of 500 mg of Dowex 50× resin, shaken for 15 min and filtered. To the solution of the crude product in methanol was added Pd/C and $H_2$ gas was bubbled through for 1 h. The complete consumption of starting material was confirmed by MALDI-TOF mass spectral analysis. The reaction mixture was filtered through Celite 545® and then concentrated under diminished pressure to afford 42, which was used for the next reaction; HRMS (APCI), m/z 473.1986 (M+H)$^+$ ($C_{17}H_{33}N_2O_{13}$ requires m/z 473.1983).

To 101 µg (0.21 µmol) of 42 was added a solution of 106 µg (0.11 µmol) of Cy5**COOSu (44) in 100 µL of 0.2 M phosphate buffer and the reaction mixture was stirred overnight in the dark. The reaction mixture was purified on an Alltech Alltima $C_{18}$ reversed phase semi-preparative (250× 10 mm, 5 µm) HPLC column using aq 0.1% TFA and $CH_3CN$ mobile phases. A linear gradient was employed (99:1 0.1% aq TFA-$CH_3CN$→69:31 0.1% aq TFA-$CH_3CN$) over a period of 35 min at a flow rate of 4 mL/min. The fractions containing the desired product eluted at 23.5 min and were collected, frozen and lyophilized to give 45 as a blue solid: yield 48 µg (35% over two steps); HRMS (APCI), m/z 669.1883 (M−K−2H)$^{2−}$ ($C_{55}H_{78}N_4O_{26}S_4^{2−}$ requires m/z 669.1899).

Disaccharide-Dye Conjugate 46

To a solution of 4.40 mg (5.00 µmol) of compound 41 in 2 mL of anh methanol was added a freshly prepared solution of 0.4 M sodium methoxide in methanol. The reaction mixture was allowed to stir at room temperature for 3 h, and the complete consumption of starting material was confirmed by MALDI-TOF mass spectral analysis. The reaction mixture was then quenched by the addition of 500 mg of Dowex 50× resin, shaken for 15 min and filtered. To the solution of the crude product in methanol was then added Pd/C and $H_2$ gas was bubbled through for 1 h. The complete consumption of starting material was confirmed by MALDI-TOF mass spectral analysis. The reaction mixture was filtered through Celite 545® and concentrated under diminished pressure to afford 43, which was used for the next reaction; HRMS (APCI), m/z 487.2140 (M+H)$^+$ ($C_{18}H_{35}N_2O_{13}$ requires m/z 487.2139).

To 101 µg (0.21 µmol) of 43 was added a solution of 106 µg (0.11 µmol) of Cy5**COOSu (44) in 100 µL of 0.2 M phosphate buffer and the reaction mixture was stirred overnight in the dark. The reaction mixture was purified on an Alltech Alltima $C_{18}$ reversed phase semi-preparative (250× 10 mm, 5 µm) HPLC column using aq 0.1% TFA and $CH_3CN$ mobile phases. A linear gradient was employed (99:1 0.1% aq TFA-$CH_3CN$→69:31 0.1% aq TFA-$CH_3CN$) over a period of 35 min at a flow rate of 4 mL/min. The fractions containing the desired product eluted at 23.5 min and were collected, frozen and lyophilized to give 46 as a blue solid: yield 53 µg (37% over two steps); HRMS (APCI), m/z 676.1996 (M−K−2H)$^{2−}$ ($C_{56}H_{80}N_4O_{26}S_4^{2−}$ requires m/z 676.1977).

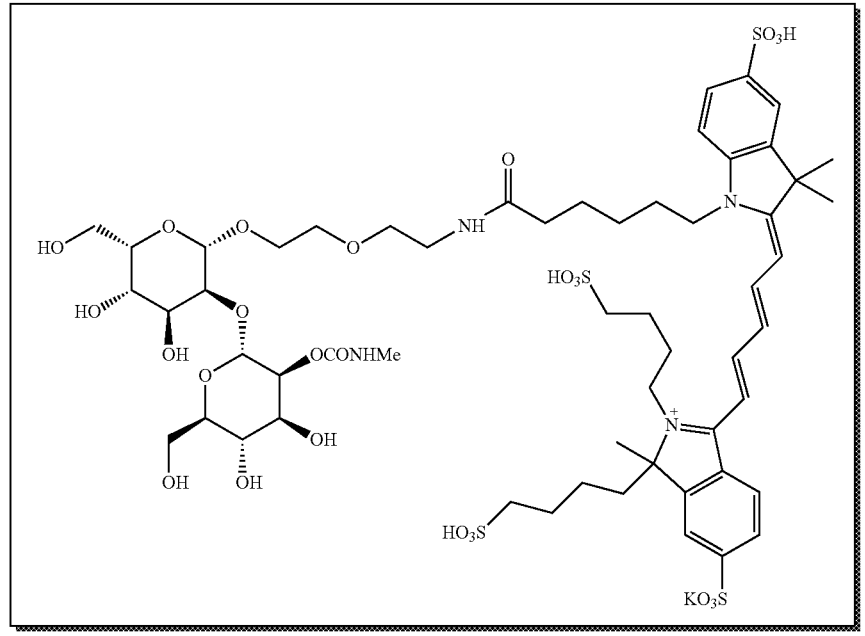

Example 8: Synthesis of C₃ Modified Mannose Disaccharide-Dye Conjugate 53
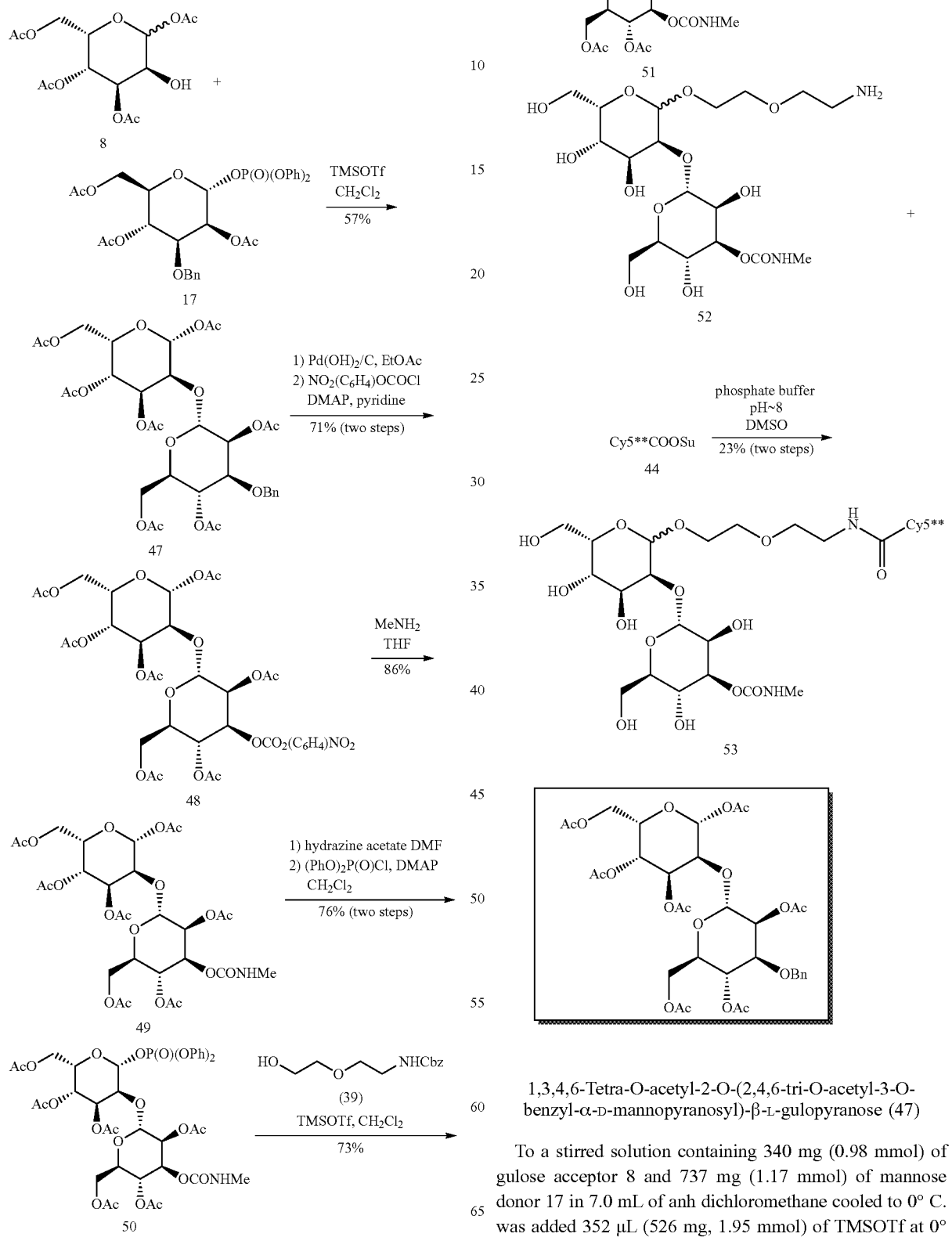
1,3,4,6-Tetra-O-acetyl-2-O-(2,4,6-tri-O-acetyl-3-O-benzyl-α-D-mannopyranosyl)-β-L-gulopyranose (47)
To a stirred solution containing 340 mg (0.98 mmol) of gulose acceptor 8 and 737 mg (1.17 mmol) of mannose donor 17 in 7.0 mL of anh dichloromethane cooled to 0° C. was added 352 μL (526 mg, 1.95 mmol) of TMSOTf at 0° C. The reaction mixture was stirred for 10 min at which time it was poured into a mixture of 30 mL of ethyl acetate and 30 mL of satd aq NaHCO$_3$. The organic and aqueous layers were separated and the organic layer was washed with two 20-mL portions of brine and dried (MgSO$_4$). The solvent was concentrated under diminished pressure to afford a crude residue. The residue was applied to a silica gel column (30×3 cm). Elution with 2:1 ethyl acetate-hexanes afforded disaccharide 47 as a colorless oil: yield 407 mg (57%); silica gel TLC R$_f$ 0.31 (1:1 ethyl acetate-hexanes); $^1$H NMR (CDCl$_3$) δ 1.92 (s, 3H), 2.00-2.01 (m, 6H, J=2.8 Hz,), 2.04 (s, 3H, J=5.3 Hz), 2.08 (d, 6H, J=1.9 Hz), 2.12 (s, 3H), 3.61 (ddd, 1H, J=12.7, 9.6 and 3.3 Hz), 3.84-3.95 (m, 2H), 3.96-4.20 (m, 4H), 4.26-4.37 (m, 2H), 4.59 (t, 1H, J=10.4 Hz,), 4.90-5.18 (m, 4H), 5.39 (dd, 1H, J=11.1 and 3.3 Hz), 5.86 (d, 1H, J=8.3 Hz) and 7.24 (m, 5H); $^{13}$C NMR (CDCl$_3$) δ 20.56, 20.59, 20.61, 20.64, 20.65, 20.75, 20.78, 61.4, 62.3, 65.5, 66.9, 67.2, 67.5, 69.4, 71.3, 73.8, 90.5, 95.1, 127.6, 127.7, 127.9, 128.3, 137.4, 168.7, 168.8, 168.9, 169.1, 169.4, 169.6, 170.3 and 170.4; mass spectrum (APCI), m/z 727.2444 (M+H)$^+$ (C$_{33}$H$_{43}$O$_{18}$ requires 727.2450).

satd aq NaHCO$_3$. The organic layer was then washed with brine and dried (MgSO$_4$). The solvent was concentrated under diminished pressure to afford a crude residue. The residue applied to a silica gel column (25×3 cm). Elution with 1:1 ethyl acetate-hexanes afforded the ester 48 as a colorless foam: yield 320 mg (71% over two steps); silica gel TLC R$_f$ 0.24 (1:1 ethyl acetate-hexanes); $^1$H NMR (CDCl$_3$) δ 1.99 (s, 3H), 2.05 (s, 3H), 2.06-2.14 (m, 15H), 3.95 (dd, 1H, J=8.4 and 3.0 Hz), 3.99-4.16 (m, 4H), 4.16-4.27 (m, 2H), 4.30 (dd, 1H, J=15.0 and 8.7 Hz,), 5.21-5.35 (m, 2H), 5.39 (dd, 1H, J=14.8 and 11.5 Hz), 4.91-5.08 (m, 2H), 5.84 (d, 1H, J=8.4 Hz), 7.33 (d, 2H, J=9.0 Hz) and 8.21 (d, 2H, J=9.0 Hz); $^{13}$C NMR (CDCl$_3$) δ 20.57, 20.63, 20.64, 20.70, 20.71, 20.8, 61.3, 61.9, 65.3, 65.5, 67.6, 67.7, 69.2, 69.8, 71.3, 74.3, 90.5, 94.9, 122.0, 125.3, 145.6, 151.4, 155.2, 168.6, 169.2, 169.37, 169.41, 169.7, 170.36 and 170.43; mass spectrum (APCI), m/z 742.1841 (M-AcOH)$^+$ (C$_{31}$H$_{36}$NO$_{20}$ requires 742.1831).

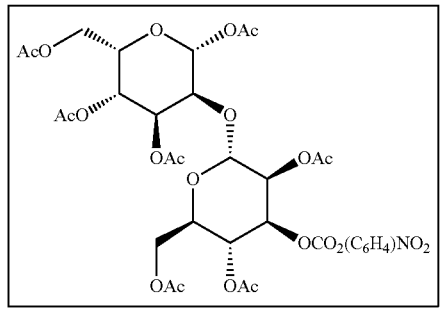

1,3,4,6-Tetra-O-acetyl-2-O-(2,4,6-tri-O-acetyl-3-O-((p-nitrophenyl)carbamoyl)-α-D-mannopyranosyl)-β-L-gulopyranose (48)

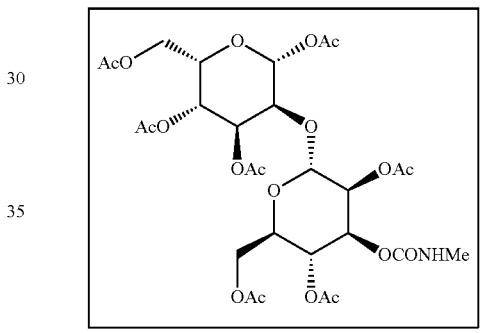

1,3,4,6-Tetra-O-acetyl-2-O-(2,4,6-tri-O-acetyl-3-O-(methylcarbamoyl)-α-D-mannopyranosyl)-β-L-gulopyranose (49)

To a solution containing 470 mg (0.56 mmol) of disaccharide 47 in 40 mL of ethyl acetate was added a catalytic amount of Pd(OH)$_2$/C and the reaction mixture was stirred overnight under 1 atm of H$_2$. The solvent was filtered through a pad of Celite 545® and the filtrate was concentrated under diminished pressure to afford a crude residue. The residue was used for the next reaction; silica gel TLC R$_f$ 0.16 (1:2 ethyl acetate-hexanes); mass spectrum (APCI), m/z 637.1993 (M+H)$^{-1}$ (C$_{26}$H$_{37}$O$_{18}$ requires 637.1980).

To a solution containing 338 mg (0.53 mmol) of the crude residue in 2 mL of pyridine was added 259 mg (2.12 mmol) of DMAP and 471 mg (2.12 mmol) of p-nitrophenyl chloroformate. The reaction mixture was stirred at 40° C. overnight at which time it was poured into a mixture of 30 mL of ethyl acetate and 10 mL of distilled water. The organic and aqueous layers were separated and the organic layer was washed with three 10-mL portions of 1 N HCl and 10 mL of To a solution containing 320 mg (0.40 mmol) of disaccharide 48 in 12 mL of THF was added 200 μL (0.4 mmol) of 2 M methylamine in THF at 0° C. The reaction mixture was stirred at room temperature for 15 h at which time silica gel TLC analysis indicated that the reaction was complete. The solvent was concentrated under diminished pressure to afford a crude residue. The residue was applied to a silica gel column (25×3 cm). Elution with 1:1 ethyl acetate-hexanes afforded disaccharide 49 as a colorless oil: yield 239 mg (86%); silica gel TLC R$_f$ 0.17 (1:1 ethyl acetate-hexanes); $^1$H NMR (CDCl$_3$) δ 1.98 (d, 6H, J=7.5 Hz), 2.03-2.11 (m, 12H), 2.13 (d, 3H, J=8.8 Hz), 2.69 (d, 3H, J=4.2 Hz), 3.88-4.22 (m, 6H), 4.31 (t, 1H, J=6.0 Hz), 4.67 (d, 1H, J=4.1 Hz), 4.89-5.01 (m, 2H), 5.00-5.10 (m, 2H), 5.12-5.20 (m, 1H), 5.38 (s, 1H) and 5.82 (d, 1H, J=8.3 Hz,); $^{13}$C NMR (CDCl$_3$) δ 20.66, 20.69, 20.71, 20.79, 27.6, 61.4, 62.1, 65.4, 66.0, 67.7, 69.17, 69.27, 69.33, 69.38, 71.31, 77.36, 90.6, 94.8, 155.4, 168.6, 169.2, 169.4, 169.8, 170.42 and 170.49; mass spectrum (APCI), m/z 694.2206 (M+H)$^+$ ($C_{28}H_{40}NO_{19}$ requires 694.2195).

169.42, 169.49, 169.9, 170.5 and 170.7; mass spectrum (APCI), m/z 884.2369 (M+H)$^+$ ($C_{38}H_{47}O_{21}PN$ requires 884.2378).

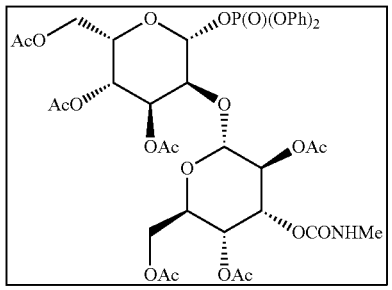

3,4,6-Tri-O-acetyl-2-O-(2,4,6-tri-O-acetyl-3-O-(methylcarbamoyl)-α-D-mannopyranosyl)-β-L-gulopyranosyl Diphenyl Phosphate (50)

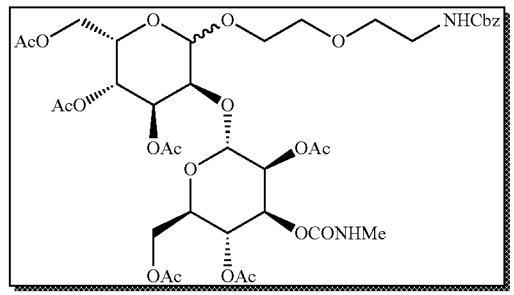

3,4,6-Tri-O-acetyl-2-O-(2,4,6-tri-O-acetyl-3-O-(methylcarbamoyl)-α-D-mannopyranosyl)-α,β-L-gulopyranosyl Benzyl 2-(2-Ethoxy)ethylcarbamate (51)

To a solution containing 65.0 mg (0.09 mmol) of disaccharide 49 in 0.8 mL of anh DMF was added 11.0 mg (0.11 mmol) of hydrazine acetate. The reaction mixture was stirred at room temperature for 1.5 h and quenched by the addition of 20 mL of ethyl acetate. The organic layer was washed with three 10-mL portions of brine and dried (MgSO$_4$). The solvent was concentrated under diminished pressure to afford a crude residue which was used for next reaction; mass spectrum (APCI), m/z 652.2086 (M+H)$^+$ ($C_{26}H_{38}NO_{18}$ requires 652.2089).

To a stirred solution containing 43.0 mg (0.07 mmol) of the crude residue in 4.0 mL of anh dichloromethane was added 10.0 mg (0.08 mmol) of DMAP and 100 μL (72.0 mg, 0.71 mmol) of Et$_3$N and 131 μL (170 mg, 0.06 mmol) of diphenyl chlorophosphate. The reaction mixture was stirred at 0° C. for 2 h and then poured into a mixture of 40 mL of ethyl acetate and 20 mL of satd aq NaHCO$_3$. The organic and aqueous layers were separated and the organic layer was washed with three 10-mL portions of water and brine and then dried (MgSO$_4$). The solvent was concentrated under diminished pressure to afford a crude residue. The residue was applied to a silica gel column (25×3 cm). Elution with 2:1 ethyl acetate-hexanes afforded phosphate ester 50 as a colorless oil: yield 44 mg (76% over two steps); silica gel TLC R$_f$ 0.25 (3:1 ethyl acetate-hexanes); $^1$H NMR (CDCl$_3$) δ 1.70 (s, 3H), 1.98 (s, 3H), 2.06 (s, 3H), 2.12 (d, 6H, J=11.4 Hz), 2.21 (s, 3H), 2.75 (d, 3H, J=4.5 Hz), 3.93-4.22 (m, 5H), 4.25-4.40 (m, 2H), 4.56 (d, 1H, J=4.6 Hz), 4.93-5.05 (m, 2H), 5.12-5.24 (m, 2H), 5.29 (s, 1H), 5.44 (s, 1H), 5.65-5.73 (m, 1H) and 7.13-7.40 (m, 10H); $^{13}$C NMR (CDCl$_3$) δ 20.5, 20.9, 27.7, 36.7, 61.3, 62.0, 65.7, 67.5, 69.2, 69.4, 69.7, 71.2, 71.3, 71.7, 95.6, 96.29, 96.34, 120.36, 120.41, 125.7, 125.8, 129.7, 130.0, 150.2, 150.3, 150.4, 150.5, 155.3, 169.36, To a stirred solution containing 44 mg (50 μmol) of the phosphate ester 50 in 0.6 mL of anh dichloromethane was added a solution of 11 mg (40 μmol) of the CBz-protected linker 39 in 0.6 mL of anh dichloromethane at 0° C. To the cooled reaction mixture was added 16 μL (20 mg, 90 μmol) of TMSOTf and the reaction mixture was stirred at 0° C. for 15 min. The reaction mixture was poured into a mixture of 10 mL ethyl acetate and 10 mL satd aq NaHCO$_3$. The organic and aqueous layers were separated and the organic layer was washed with three 10-mL portions of water and brine and then dried (MgSO$_4$). The organic layer was concentrated under diminished pressure to afford a crude residue. The residue was applied to a silica gel column (25×3 cm). Elution with 12:12:1 ethyl acetate-hexanes-methanol afforded linker conjugate 51 as a colorless oil. The product was isolated as a (5:3) mixture of anomers: yield 32 mg (73%); silica gel TLC R$_f$ 0.11 (12:12:1 ethyl acetate-hexanes-methanol); $^1$H NMR (CDCl$_3$) (major anomer) δ 2.03 (s, 3H), 2.05 (s, 3H), 2.06-2.15 (m, 12H), 2.71 (d, 3H, J=4.8 Hz), 3.40 (s, 1H), 3.51-3.74 (m, 6H), 3.79-3.89 (m, 1H), 3.92-4.01 (m, 1H), 3.99-4.21 (m, 4H), 4.21-4.41 (m, 2H), 4.55-4.63 (m, 2H), 4.89-5.04 (m, 2H), 5.09 (d, 2H, J=5.6 Hz), 5.12-5.30 (m, 3H), 5.32-5.41 (m, 1H), 5.65-5.73 (m, 1H) and 7.27-7.39 (m, 5H); $^{13}$C NMR (CDCl$_3$) δ 20.78, 20.83, 20.87, 20.91, 20.93, 20.98, 21.0, 27.67, 27.69, 40.9, 41.1, 53.6, 61.8, 61.9, 62.3, 62.7, 63.9, 65.6, 65.7, 66.1, 66.4, 66.7, 67.9, 68.0, 68.6, 68.8, 69.0, 69.3, 69.5, 69.72, 69.76, 70.0, 70.1, 70.3, 70.4, 70.52, 70.55, 70.7, 72.3, 97.1, 97.2, 120.38, 120.43, 128.2, 128.3, 128.60, 128.65, 129.8, 130.0, 136.8, 155.7, 156.7, 169.33, 169.37, 169.39, 169.47, 169.54, 169.6, 170.0, 170.5, 170.6, 170.7, 170.8 and 170.9; mass spectrum (APCI), m/z 873.3150 (M+H)$^+$ ($C_{34}H_{53}N_2O_{21}$ requires 873.3141).

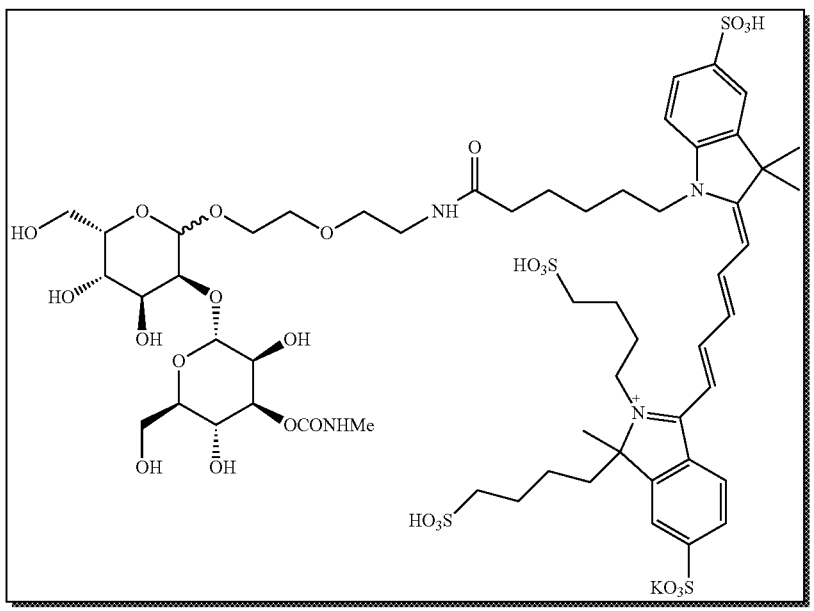

Disaccharide-Dye Conjugate 53

To a solution of 5.80 mg (6.60 μmol) of compound 51 in 2 mL of anh methanol was added a freshly prepared solution of 0.4 M sodium methoxide in methanol. The reaction mixture was allowed to stir at room temperature for 3 h, and the complete consumption of starting material was confirmed by MALDI-TOF mass spectral analysis. The reaction mixture was then quenched by the addition of 500 mg of Dowex 50× resin, shaken for 15 min and filtered. To the solution of the crude product in methanol was added Pd/C and $H_2$ gas was bubbled through for 1 h. The complete consumption of starting material was confirmed by MALDI-TOF mass spectral analysis. The reaction mixture was filtered through Celite 545® and then concentrated under diminished pressure to afford 52, which was used for the next reaction. HRMS (APCI), m/z 487.2133 (M+H)$^+$ ($C_{18}H_{35}N_2O_{13}$ requires m/z 487.2139).

To 87.0 μg (0.18 μmol) of 52 was added a solution of 90.0 μg (0.09 μmol) of Cy5**COOSu (44) in 150 μL of 0.2 M phosphate buffer and the reaction mixture was stirred overnight in the dark. The reaction mixture was purified on an Alltech Alltima $C_{18}$ reversed phase semi-preparative (250× 10 mm, 5 μm) HPLC column using aq 0.1% TFA and $CH_3CN$ mobile phases. A linear gradient was employed (99:1 0.1% aq TFA-$CH_3CN$→69:31 0.1% aq TFA-$CH_3CN$) over a period of 35 min at a flow rate of 4 mL/min. The fractions containing the desired product eluted at 23.9 min and were collected, frozen and lyophilized to give 53 as a blue solid: yield 27 μg (23% over two steps); HRMS (APCI), m/z 676.1984 (M–K–2H)$^{2-}$ ($C_{56}H_{80}N_4O_{26}S_4^{2-}$ requires m/z 676.1977).

Example 9: Synthesis of $C_4$ Modified Mannose Disaccharide-Dye Conjugates 64 and 65

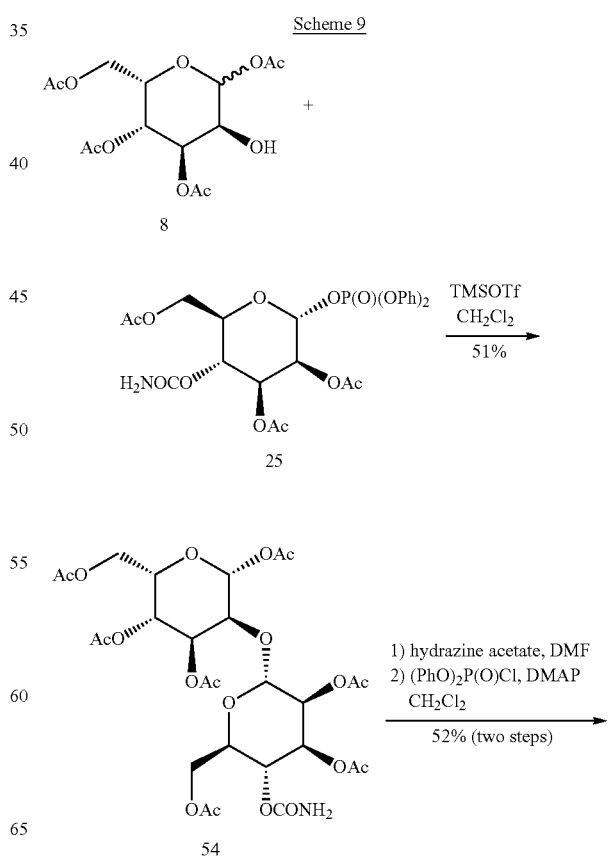

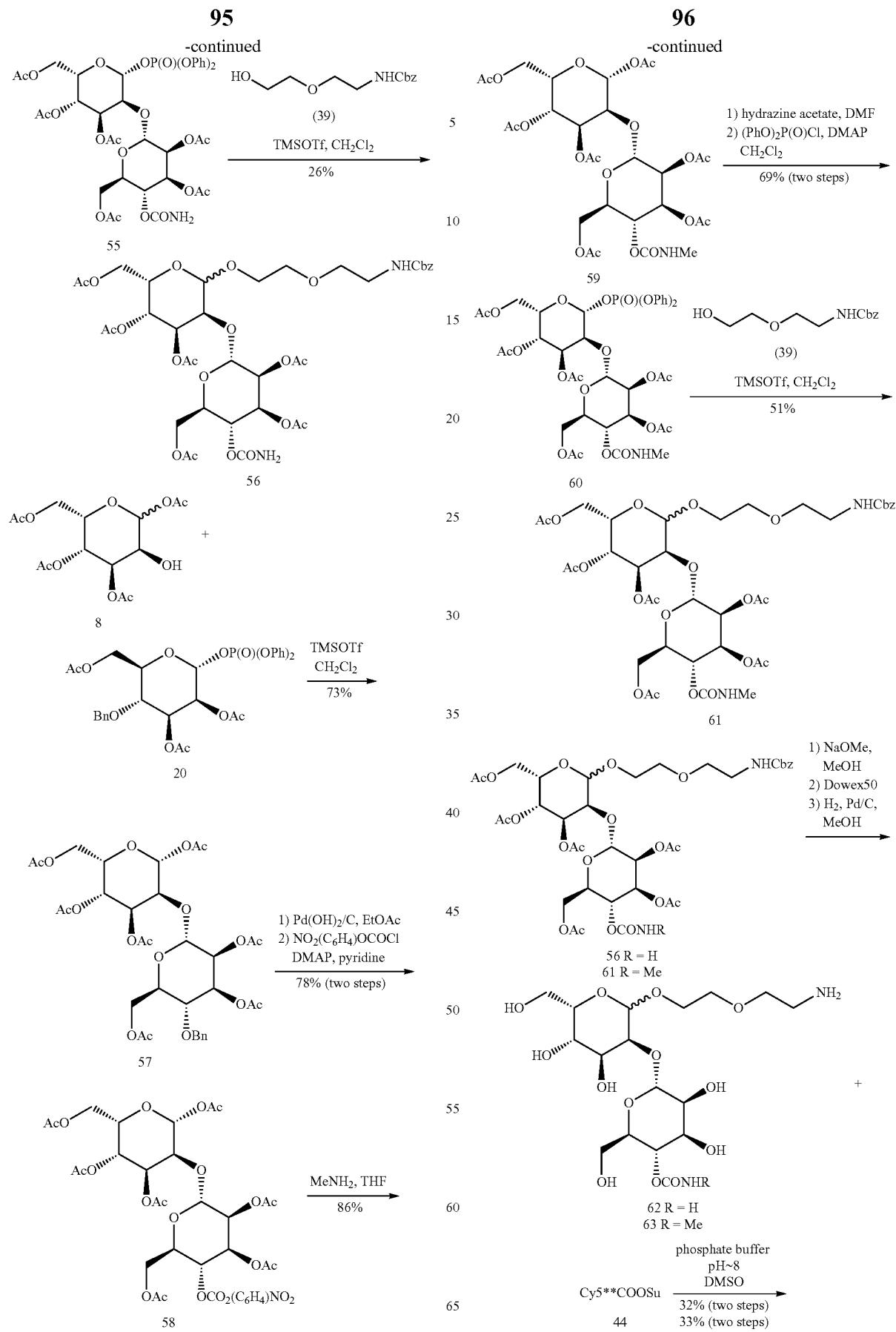

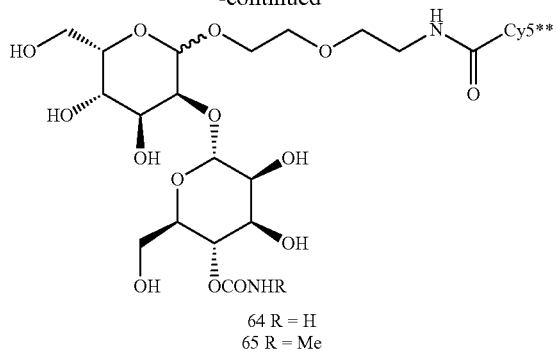

64 R = H
65 R = Me

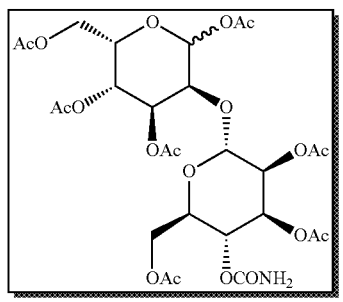

1,3,4,6-Tetra-O-acetyl-2-O-(2,3,6-tri-O-acetyl-4-O-(carbamoyl)-α-D-mannopyranosyl)-β-L-gulopyranose (54)

To activated molecular sieves, a solution of 460 mg (0.79 mmol) of 8 in 5.10 mL of dichloromethane and 191 mg (0.33 mmol) of 25 in 4.80 mL of dichloromethane were added. The solution was cooled to 0° C. and was then treated with 220 μL (1.22 mmol) of TMSOTf. The reaction mixture was stirred for 20 min at which time it was poured into a two phase solution of 70 mL of ethyl acetate and 43 mL of satd aq. NaHCO$_3$. The organic layer was washed with two 50-mL portions of brine, dried (MgSO$_4$) and concentrated under diminished pressure to afford a crude residue. The residue was purified by flash chromatography on a silica gel column (25×3 cm). Elution with 3:1 ethyl acetate-hexanes afforded 54 as a colorless oil: yield 275 mg (51%); silica gel TLC R$_f$ 0.26 (3:1 ethyl acetate-hexanes). $^1$H NMR (CDCl$_3$) δ 1.99 (s, 3H), 2.05 (s, 3H), 2.12 (s, 3H), 2.13 (s, 6H), 2.14 (s, 3H), 2.18 (s, 3H), 3.97-4.00 (m, 1H), 4.03-4.16 (m, 2H), 4.26-4.28 (m, 1H), 4.33-4.37 (m, 1H), 4.73 (br s, 2H), 4.94-4.97 (m, 1H), 4.99-5.01 (m, 1H), 5.06-5.09 (m, 2H), 5.13-5.15 (m, 2H), 5.14-5.15 (m, 1H), 5.43 (t, 1H, J=3.6 Hz), 5.88 (d, 1H, J=8.3 Hz), $^{13}$C NMR (CDCl$_3$) 20.56, 20.63, 20.68, 20.69, 20.7, 20.8, 20.9, 61.3, 62.2, 65.5, 65.89, 66.9, 67.0, 67.57, 67.60, 68.66, 68.71, 69.4, 69.8, 71.3, 90.6, 95.1, 155.0, 155.2, 168.7, 169.24, 169.26, 169.5, 170.0, 170.4, 170.6; mass spectrum (FAB), m/z 680.2045 (M+H)$^+$ (C$_{27}$H$_{38}$NO$_{19}$ requires m/z 680.2038).

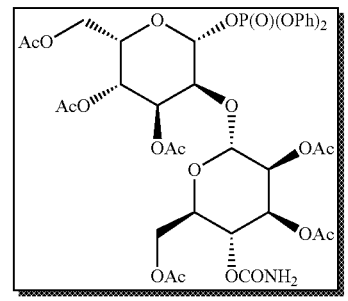

3,4,6-Tri-O-acetyl-2-O-(2,3,6-tri-O-acetyl-4-O-(carbamoyl)-α-D-mannopyranosyl)-β-L-gulopyranosyl Diphenyl Phosphate (55)

To a solution containing 62.0 mg (0.09 mmol) of disaccharide 54 in 1.0 mL of anh DMF was added 12.0 mg (0.13 mmol) of hydrazine acetate. The reaction mixture was stirred at room temperature for 2.5 h and quenched by the addition of 15 mL of ethyl acetate. The organic solution was washed with 10 mL of water, satd aq NaHCO$_3$, brine and dried (MgSO$_4$). The solvent was concentrated under diminished pressure to afford the product as a yellow oil: yield 51 mg (88%); silica gel TLC R$_f$ 0.1 (1:3 hexanes-ethyl acetate). $^1$H NMR (400 MHz, CDCl$_3$) δ 2.00 (s, 3H), 2.07 (s, 3H), 2.12 (s, 3H), 2.13 (s, 3H), 2.14 (s, 3H), 2.17 (s, 3H), 3.74-3.77 (m, 1H), 4.11-4.19 (m, 2H), 4.23-4.26 (m, 2H), 4.33-4.38 (m, 1H), 4.53-4.56 (br s, 2H), 4.94-4.95 (m, 1H), 4.97-5.01 (m, 2H), 5.09-5.15 (m, 3H), 5.26-5.30 (m, 1H), 5.39 (t, 1H, J=3.6 Hz). MALDI, m/z 660.18 for (M+Na)$^+$. The crude residue was used for the next reaction.

To a stirred solution containing 51.0 mg (0.10 mmol) of the crude residue in 3.00 mL of anh dichloromethane was added 15.0 mg (0.12 mmol) of DMAP, 147 μL (106 mg, 1.04 mmol) of Et$_3$N and 194 μL (252 mg, 0.94 mmol) of diphenyl chlorophosphate. The reaction mixture was stirred at 0° C. for 2 h and then poured into a mixture of 40 mL of ethyl acetate and 20 mL of satd aq NaHCO$_3$. The aqueous and organic layers were separated and the organic layer was washed with three 10-mL portions of water and brine and then dried (MgSO$_4$). The solvent was concentrated under diminished pressure to afford a crude residue. The residue was applied to a silica gel column (20×2 cm). Elution with 2:1 ethyl acetate-hexanes afforded the phosphate ester 55 as a colorless oil: yield 41 mg (52% over two steps); silica gel TLC R$_f$ 0.23 (3:1 ethyl acetate-hexanes); $^1$H NMR (CDCl$_3$) δ 1.95 (s, 3H), 1.97 (s, 3H), 2.07 (s, 3H), 2.11 (s, 3H), 2.13 (s, 3H), 2.20 (s, 3H), 3.95-4.06 (m, 2H), 4.08-4.15 (m, 1H), 4.17-4.21 (m, 2H), 4.25-4.35 (m, 2H), 4.94-5.00 (m, 2H), 5.05-5.13 (m, 3H), 5.20-5.23 (m, 1H), 5.40-5.45 (br s, 2H), 5.70 (t, 1H, J=8.0 Hz), 7.15-7.21 (m, 4H), 7.28-7.38 (m, 6H); $^{13}$C NMR (CDCl$_3$) 20.62, 20.68, 20.76, 61.13, 61.98, 65.42, 66.41, 67.39, 68.60, 68.92, 69.21, 71.58, 95.06, 96.19, 120.18, 120.23, 120.44, 120.49, 125.59, 125.66, 129.66, 129.93, 154.86, 169.28, 169.48, 169.80, 170.40, 170.63; mass spectrum (APCI), m/z 870.2230 (M+H)$^+$ (C$_{37}$H$_{45}$NO$_{21}$P requires m/z 870.2222).

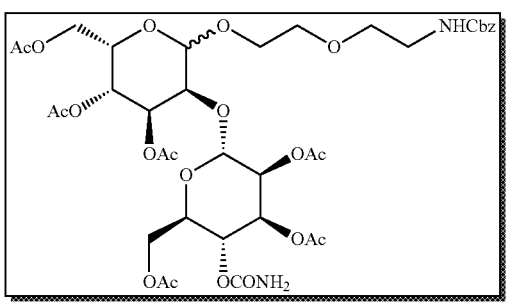

3,4,6-Tri-O-acetyl-2-O-(2,3,6-tri-O-acetyl-4-O-(carbamoyl)-α-D-mannopyranosyl)-α,β-L-gulopyranosyl Benzyl 2-(2-Ethoxy)ethylcarbamate (56)

To a stirred solution containing 27.0 mg (0.03 mmol) of phosphate ester 55 in 3.9 mL of anh dichloromethane was added a solution of 8.20 mg (0.03 mmol) of CBz-protected linker 39 in 3.9 mL of anh dichloromethane at 0° C. To the cooled reaction mixture was then added 8.20 µL (10.1 mg, 0.04 mmol) of TMSOTf. The reaction mixture was stirred at 0° C. for 15 min and then poured into a mixture of 20 mL of ethyl acetate and 4 mL of satd aq NaHCO$_3$. The aqueous and organic layers were separated and the organic layer was washed with three 10-mL portions of water and brine and then dried (MgSO$_4$). The solvent was concentrated under diminished pressure to afford a crude residue. The residue was applied to a silica gel column (12×2 cm). Elution with 3:1 ethyl acetate-hexanes afforded 56 as a colorless oil. The product isolated as a mixture of anomers: yield 7 mg (26%); silica gel TLC R$_f$ 0.11 (4:1 ethyl acetate-hexanes); $^1$H NMR (CDCl$_3$) δ 1.99 (s, 3H), 2.04 (s, 3H), 2.09 (s, 3H), 2.10 (s, 3H), 2.12 (s, 3H), 2.13 (s, 3H), 3.33-3.45 (br s, 2H), 3.56-3.65 (m, 2H), 3.67-3.73 (m, 2H), 3.82-3.88 (m, 1H), 3.96 (t, 1H, J=4.0 Hz), 4.03-4.11 (m, 3H), 4.12-4.19 (m, 2H), 4.30 (dd, 1H, J=12.0, 5.7 Hz), 4.42 (t, 1H, J=6.5 Hz), 4.93-4.98 (m, 3H), 5.00-5.03 (m, 1H), 5.07 (s, 2H), 5.12-5.17 (m, 2H), 5.24-5.30 (m, 3H), 7.30-7.36 (m, 5H); $^{13}$C NMR (CDCl$_3$) 20.81, 20.89, 20.90, 20.93, 21.0, 29.8, 41.2, 62.3, 62.9, 63.8, 65.7, 67.0, 67.1, 68.1, 68.69, 68.72, 69.6, 70.1, 71.1, 77.5, 97.2, 97.6, 128.32, 128.38, 128.7, 136.5, 155.5, 156.9, 169.5, 169.8, 169.9, 170.2, 170.7, 170.8; mass spectrum (APCI), m/z 859.2975 (M+H)$^+$ (C$_{37}$H$_{51}$N$_2$O$_{21}$ requires m/z 859.2984).

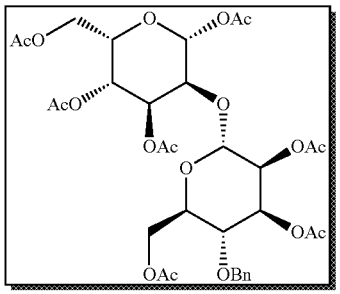

1,3,4,6-Tetra-O-acetyl-2-O-(2,3,6-tri-O-acetyl-4-O-benzyl-α-D-mannopyranosyl)-β-L-gulopyranose (57)

To a stirred solution containing 217 mg (0.62 mmol) of gulose acceptor 8 and 471 mg (0.75 mmol) of mannose donor 20 in 4.50 mL of anh dichloromethane cooled to 0° C. was added 230 µL (283 mg, 1.25 mmol) of TMSOTf. The reaction mixture was stirred at 0° C. for 10 min and then poured into a mixture of 30 mL of ethyl acetate and 30 mL of satd aq NaHCO$_3$. The aqueous and organic layers were separated and the organic layer was washed with two 20-mL portions of brine and dried (MgSO$_4$). The solvent was concentrated under diminished pressure to afford a crude residue. The residue was applied to a silica gel column (30×3 cm). Elution with 2:1 ethyl acetate-hexanes afforded 57 as a colorless oil: yield 330 mg (73%); silica gel TLC R$_f$ 0.25 (1:1 ethyl acetate-hexanes); $^1$H NMR (CDCl$_3$) δ 1.92 (s, 3H), 2.02 (s, 3H), 2.07 (t, 6H, J=3.2 Hz), 2.08-2.11 (m, 6H), 2.15 (d, 3H, J=3.7 Hz), 3.70-3.83 (m, 1H), 3.92-4.18 (m, 4H), 4.23-4.40 (m, 2H), 4.50-4.71 (m, 2H), 4.89 (dd, 1H, J=7.2 and 1.7 Hz), 4.96-4.99 (m, 1H), 5.01-5.10 (m, 2H), 5.10-5.16 (m, 1H), 5.35-5.45 (m, 1H), 5.85 (d, 1H, J=8.4 Hz) and 7.18-7.34 (m, 5H); $^{13}$C NMR (CDCl$_3$) δ 20.68, 20.71, 20.73, 20.79, 20.84, 20.88, 20.9, 61.4, 65.6, 67.7, 69.1, 69.5, 70.3, 71.3, 71.7, 72.4, 74.8, 90.7, 95.0, 127.6, 127.89, 127.99, 128.46, 128.49, 137.6, 168.8, 169.32, 169.36, 169.4, 169.7, 170.5 and 170.6; HRMS (APCI), m/z 727.2439 (M+H)$^+$ (C$_{33}$H$_{43}$O$_{18}$ requires m/z 727.2450).

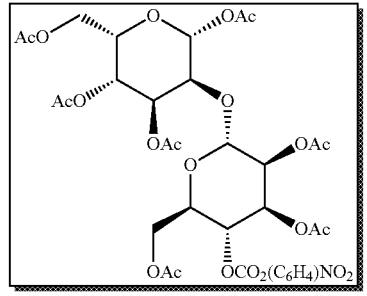

1,3,4,6-Tetra-O-acetyl-2-O-(2,3,6-tri-O-acetyl-4-O-((p-nitrophenyl)carbamoyl)-α-D-mannopyranosyl)-β-L-gulopyranose (58)

To a solution containing 140 mg (0.19 mmol) of disaccharide 57 in 13 mL of ethyl acetate was added a catalytic amount of Pd(OH)$_2$/C and the reaction mixture was stirred overnight under 1 atm of H$_2$. The solvent was filtered through a pad of Celite 545® and the filtrate was concentrated under diminished pressure to afford a crude residue. The residue was used for the next reaction; silica gel TLC R$_f$ 0.08 (1:1 ethyl acetate-hexanes).

To a solution containing 120 mg (0.19 mmol) of the crude residue in 2.0 mL of anh pyridine was added 92.0 mg (0.76 mmol) of DMAP and 168 mg (0.76 mmol) of p-nitrophenyl chloroformate. The reaction mixture was stirred at 40° C. overnight and then poured into a mixture of 30 mL of ethyl acetate and 10 mL of H$_2$O. The aqueous and organic layers were separated and the organic layer was washed with three 10-mL portions of 1 N HCl and 10 mL of satd aq NaHCO$_3$ and brine. The organic solution was dried (MgSO$_4$) and concentrated under diminished pressure to afford a crude residue. The residue was applied to a silica gel column (25×3 cm). Elution with 1:1 ethyl acetate-hexanes afforded ester 58 as a colorless foam: yield 121 mg (78% over two steps); silica gel TLC R$_f$ 0.30 (1:1 ethyl acetate-hexanes); $^1$H NMR (CDCl$_3$) δ 1.98 (s, 3H), 2.03 (s, 3H), 2.11 (d, 6H, J=5.0 Hz), 2.14 (s, 3H), 2.19 (d, 3H, J=5.4 Hz), 3.99 (dd, 1H, J=8.4 and 3.3 Hz), 4.02-4.25 (m, 4H), 4.27 (d, 1H, J=2.4 Hz), 4.35 (t, 1H, J=6.0 Hz), 4.46-4.55 (m, 2H), 4.93-5.01 (m, 2H), 5.11-5.18 (m, 2H), 5.24 (dd, 1H, J=10.1 and 3.3 Hz), 5.32 (dd, 1H, J=7.7 and 4.3 Hz), 5.43 (t, 1H, J=3.5 Hz), 5.89 (d, 1H, J=8.5 Hz), 7.29-7.39 (m, 2H) and 8.25 (t, 2H, J=6.0 Hz); $^{13}$C NMR (CDCl$_3$) δ 20.69, 20.71, 21.0, 61.3, 61.7, 65.6, 67.7, 68.6, 68.8, 70.0, 71.3, 71.4, 90.6, 95.1, 121.7, 125.4, 145.7, 151.8, 155.2, 168.7, 169.29, 169.33, 169.38, 169.58, 169.65, 169.7, 169.8, 170.44, 170.46 and 170.58; HRMS (APCI), m/z 802.2035 (M+H)$^+$ (C$_{33}$H$_{40}$NO$_{22}$ requires m/z 802.2042).

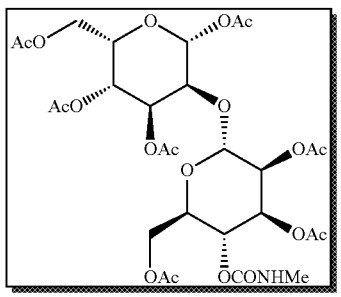

1,3,4,6-Tetra-O-acetyl-2-O-(2,3,6-tri-O-acetyl-4-O-(methylcarbamoyl)-α-D-mannopyranosyl)-β-L-gulopyranose (59)

To a solution containing 121 mg (0.15 mmol) of 58 in 3.2 mL of anh THF was added 76.0 μL, (0.15 mmol) of a 2 M solution of CH$_3$NH$_2$ in THF at 0° C. The reaction mixture was stirred at room temperature for 15 h at which time silica gel TLC analysis indicated that the reaction was complete. The solvent was concentrated under diminished pressure to afford a crude residue. The residue was applied to a silica gel column (25×3 cm). Elution with 1:1 ethyl acetate-hexanes afforded disaccharide 59 as a colorless oil: yield 90 mg (86%); silica gel TLC R$_f$ 0.14 (1:1 ethyl acetate-hexanes); $^1$H NMR (CDCl$_3$) δ 1.96 (t, 3H, J=3.4 Hz), 2.04 (d, 3H, J=6.4 Hz), 2.11 (dd, 12H, J=5.4 and 2.8 Hz), 2.17 (d, 3H, J=2.5 Hz), 2.76 (d, 3H, J=4.8 Hz), 3.97 (dd, 1H, J=8.4 and 3.2 Hz), 4.00-4.39 (m, 3H), 4.48-4.80 (m, 1H), 4.93 (d, 1H, J=7.2 Hz), 4.99 (dd, 1H, J=7.0 and 4.4 Hz), 5.04-5.10 (m, 2H), 5.08-5.17 (m, 2H), 5.29 (dd, 1H, J=13.2 and 9.8 Hz), 5.42 (t, 1H, J=3.5 Hz), 5.87 (d, 1H, J=8.4 Hz) and 6.28 (d, 1H, J=4.2 Hz); $^{13}$C NMR (CDCl$_3$) δ 20.68, 20.75, 20.76, 20.80, 20.82, 20.84, 27.8, 61.5, 61.8, 62.5, 62.7, 65.6, 66.0, 66.3, 66.8, 67.8, 68.9, 69.75, 69.79, 71.4, 90.7, 169.3, 169.59, 169.61, 169.65, 170.53, 170.55 and 170.7; HRMS (APCI), m/z 694.2199 (M+H)$^+$ (C$_{28}$H$_{40}$NO$_{19}$ requires m/z 694.2195).

3,4,6-Tri-O-acetyl-2-O-(2,3,6-tri-O-acetyl-4-O-(methylcarbamoyl)-α-D-mannopyranosyl)-δ-L-gulopyranosyl Diphenyl Phosphate (60)

To a solution containing 44.0 mg (0.06 mmol) of disaccharide 59 in 0.50 mL of anh DMF was added 7.00 mg (0.08 mmol) of hydrazine acetate. The reaction mixture was stirred at room temperature for 1.5 h and quenched by the addition of 20 mL of ethyl acetate. The organic solution was washed with three 10-mL portions of brine and dried (MgSO$_4$). The solvent was concentrated under diminished pressure to afford a crude residue. The crude residue was used for the next reaction.

To a stirred solution containing 43.0 mg (0.07 mmol) of the crude residue in 4.00 mL of anh dichloromethane was added 10.0 mg (0.08 mmol) of DMAP, 100 μL (72.0 mg, 0.71 mmol) of Et$_3$N and 130 μL (160 mg, 0.63 mmol) of diphenyl chlorophosphate. The reaction mixture was stirred at 0° C. for 2 h and then poured into a mixture of 40 mL of ethyl acetate and 20 mL of satd aq NaHCO$_3$. The aqueous and organic layers were separated and the organic layer was washed with three 10-mL portions of water and brine and then dried (MgSO$_4$). The solvent was concentrated under diminished pressure to afford a crude residue. The residue was applied to a silica gel column (25×3 cm). Elution with 2:1 ethyl acetate-hexanes afforded the phosphate ester 60 as a colorless oil: yield 38 mg (69% over two steps); silica gel TLC R$_f$ 0.48 (2:1 ethyl acetate-hexanes); $^1$H NMR (CDCl$_3$) δ 1.95 (s, 3H), 2.00 (s, 3H), 2.09 (s, 3H), 2.12 (s, 3H), 2.15 (s, 3H), 2.21 (s, 3H), 2.57 (d, 3H, J=4.0 Hz), 3.70 (s, 1H), 4.03 (s, 2H), 4.15 (d, 2H, J=9.6 Hz), 4.24 (d, 2H, J=12.2 Hz), 4.32-4.38 (m, 1H), 4.99 (d, 2H, J=12.6 Hz), 5.05-5.25 (m, 2H), 5.30 (s, 1H), 5.45 (s, 1H), 5.71 (d, 1H, J=7.4 Hz) and 7.19-7.41 (m, 10H); $^{13}$C NMR (CDCl$_3$) δ 20.77, 20.83, 20.89, 20.93, 27.6, 61.3, 62.3, 65.6, 66.3, 67.5, 68.8, 69.2, 69.5, 70.7, 70.8, 71.7, 95.1, 96.4, 120.4, 125.7, 129.8, 130.0, 150.4, 155.4, 169.37, 169.39, 169.6, 169.9, 170.5 and 170.73, 170.76; HRMS (APCI), m/z 884.2381 (M+H)$^+$ (C$_{38}$H$_{47}$NO$_{21}$P requires m/z 884.2378).

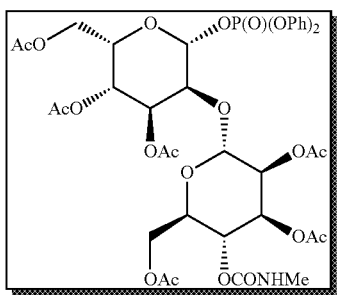

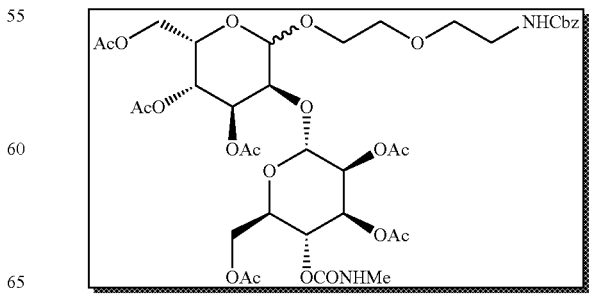

3,4,6-Tri-O-acetyl-2-O-(2,3,6-tri-O-acetyl-4-O-(methylcarbamoyl)-α-D-mannopyranosyl)-α,β-L-gulopyranosyl Benzyl 2-(2-Ethoxy)ethylcarbamate (61)

To a stirred solution containing 38.0 mg (0.04 mmol) of phosphate ester 60 in 0.5 mL of anh dichloromethane was added a solution of 10.0 mg (0.04 mmol) of CBz-protected linker 39 in 0.5 mL of anh dichloromethane at 0° C. To the cooled reaction mixture was then added 14.0 µL (17.0 mg, 0.08 mmol) of TMSOTf. The reaction mixture was stirred at 0° C. for 15 min and then poured into a mixture of 20 mL of ethyl acetate and 20 mL of satd aq $NaHCO_3$. The aqueous and organic layers were separated and the organic layer was washed with three 10-mL portions of water and brine and then dried ($MgSO_4$). The solvent was concentrated under diminished pressure to afford a crude residue. The residue was applied to a silica gel column (25×3 cm). Elution with 12:12:1 ethyl acetate-hexanes-methanol afforded 61 as a colorless oil. The product isolated as a mixture of anomers: yield 19 mg (51%); silica gel TLC $R_f$ 0.14 (12:12:1 ethyl acetate-hexanes-methanol); $^1$H NMR ($CDCl_3$) δ 1.92-2.14 (m, 18H), 2.71 (t, 3H, J=4.1 Hz), 3.40 (d, 3H, J=4.9 Hz), 3.52-3.77 (m, 8H), 3.85 (dd, 1H, J=8.4 and 3.2 Hz), 3.95 (t, 1H, J=3.9 Hz), 4.27 (dd, 2H, J=13.4 and 7.3 Hz), 4.40 (t, 1H, J=6.4 Hz), 4.88-5.04 (m, 3H), 5.05-5.22 (m, 6H), 5.25 (dd, 1H, J=7.3 and 3.6 Hz) and 7.28-7.40 (m, 5H); $^{13}$C NMR ($CDCl_3$) δ 20.78, 20.83 20.85, 20.87, 20.92, 20.95, 27.7, 61.9, 62.3, 63.1, 63.8, 65.7, 66.8, 66.9, 68.1, 68.7, 68.8, 69.6, 69.8, 70.2, 71.0, 72.3, 97.2, 97.5, 128.27, 128.33, 128.65, 128.67, 169.5, 169.7, 169.8, 169.9, 170.57, 170.63 and 170.7; HRMS (APCI), m/z 873.3142 (M+H)$^+$ ($C_{38}H_{53}N_2O_{21}$ requires m/z 873.3141).

Disaccharide-Dye Conjugate 64

To a solution containing 2.20 mg (2.56 µmol) of compound 56 in 1 mL of anh methanol was added a freshly prepared solution of 0.4 M sodium methoxide in methanol. The reaction mixture was allowed to stir at room temperature for 3 h, and the complete consumption of starting material was confirmed by MALDI-TOF mass spectral analysis. The reaction mixture was then quenched by the addition of 500 mg of Dowex 50× resin, shaken for 15 min and filtered. To the solution of the crude product in methanol was then added Pd/C and $H_2$ gas was bubbled through for 1 h. The complete consumption of starting material was confirmed by MALDI-TOF mass spectral analysis. The reaction mixture was filtered through Celite 545® and then concentrated under diminished pressure to afford 62, which was used for the next reaction; HRMS (APCI), m/z 473.1972 (M+H)$^+$ ($C_{17}H_{33}N_2O_{13}$ requires m/z 473.1983).

To 101 µg (0.21 µmol) of 62 was added a solution of 106 µg (0.11 µmol) of Cy5**COOSu (44) in 100 µL of 0.2 M phosphate buffer and the reaction mixture was stirred overnight in the dark. The reaction mixture was purified on an Alltech Alltima $C_{18}$ reversed phase semi-preparative (250× 10 mm, 5 µm) HPLC column using aq 0.1% TFA and $CH_3CN$ mobile phases. A linear gradient was employed (99:1 0.1% aq TFA-$CH_3CN$→69:31 0.1% aq TFA-$CH_3CN$) over a period of 35 min at a flow rate of 4 mL/min. The fractions containing the desired product eluted at 23.5 min and were collected, frozen and lyophilized to give 64 as a blue solid: yield 44 µg (32% over two steps); HRMS (APCI), m/z 669.1880 (M−K−2H)$^{2−}$ ($C_{55}H_{78}N_4O_{26}S_4^{2−}$ requires m/z 669.1899).

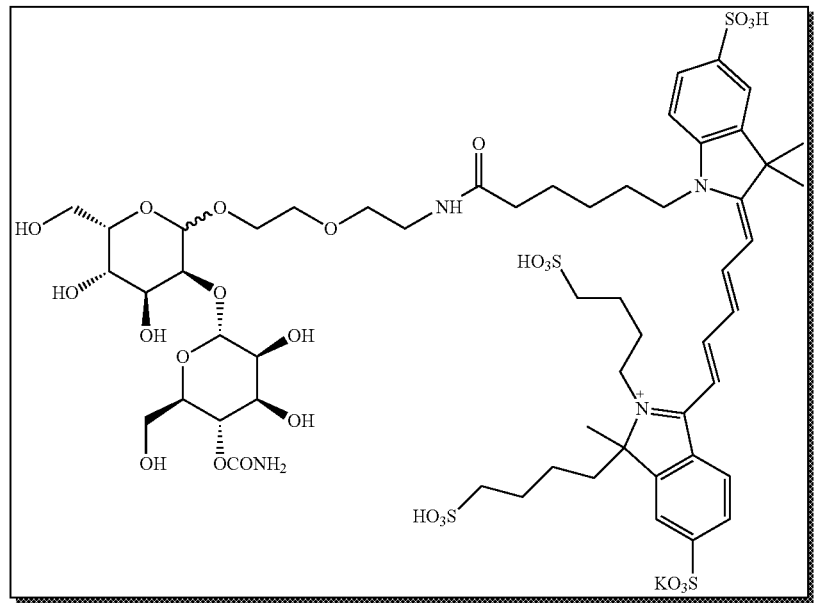

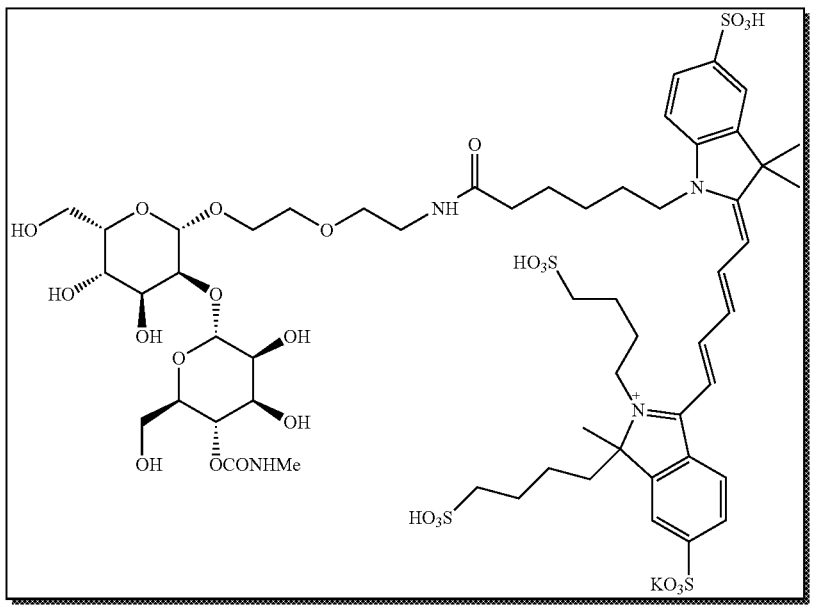

Disaccharide-Dye Conjugate 65

To a solution containing 2.70 mg (3.10 μmol) of 61 in 2 mL of anh methanol was added a freshly prepared solution of 0.4 M sodium methoxide in methanol. The reaction mixture was allowed to stir at room temperature for 3 h, and the complete consumption of starting material was confirmed by MALDI-TOF mass spectral analysis. The reaction mixture was then quenched by the addition of 500 mg of Dowex 50× resin, shaken for 15 min and filtered. To the solution of the crude product in methanol was added Pd/C and $H_2$ gas was bubbled through for 1 h. The complete consumption of starting material was confirmed by MALDI-TOF mass spectral analysis. The reaction mixture was filtered through Celite 545® and concentrated under diminished pressure to afford 63, which was used for the next reaction; HRMS (APCI), m/z 487.2153 (M+H)$^+$ ($C_{18}H_{35}N_2O_{13}$ requires m/z 487.2139).

To 134 μg (0.27 μmol) of 63 was added a solution of 90.0 μg (0.09 μmol) of Cy5**COOSu (44) in 150 μL of 0.2 M phosphate buffer and the reaction mixture was stirred overnight in the dark. The reaction mixture was purified on an Alltech Alltima $C_{18}$ reversed phase semi-preparative (250× 10 mm, 5 μm) HPLC column using aq 0.1% TFA and $CH_3CN$ mobile phases. A linear gradient was employed (99:1 0.1% aq TFA-$CH_3CN$→69:31 0.1% aq TFA-$CH_3CN$) over a period of 35 min at a flow rate of 4 mL/min. The fractions containing the desired product eluted at 24.8 min and were collected, frozen and lyophilized to give 65 as a blue solid: yield 60 μg (33% over two steps); HRMS (APCI), m/z 676.1995 (M–K–2H)$^{2-}$ ($C_{56}H_{80}N_4O_{26}S_4^{2-}$ requires m/z 676.1977).

Example 10: Synthesis of $C_3$ Modified Altrose Disaccharide-Dye Conjugates 76 and 77

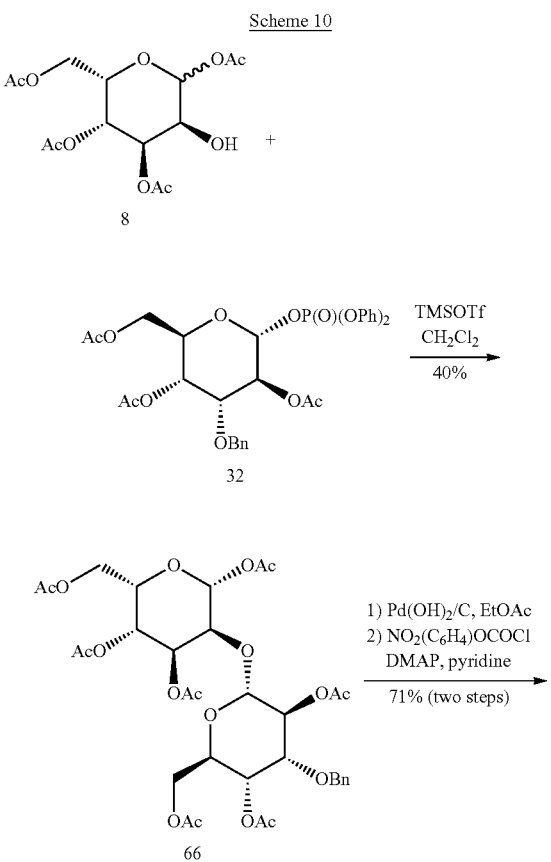

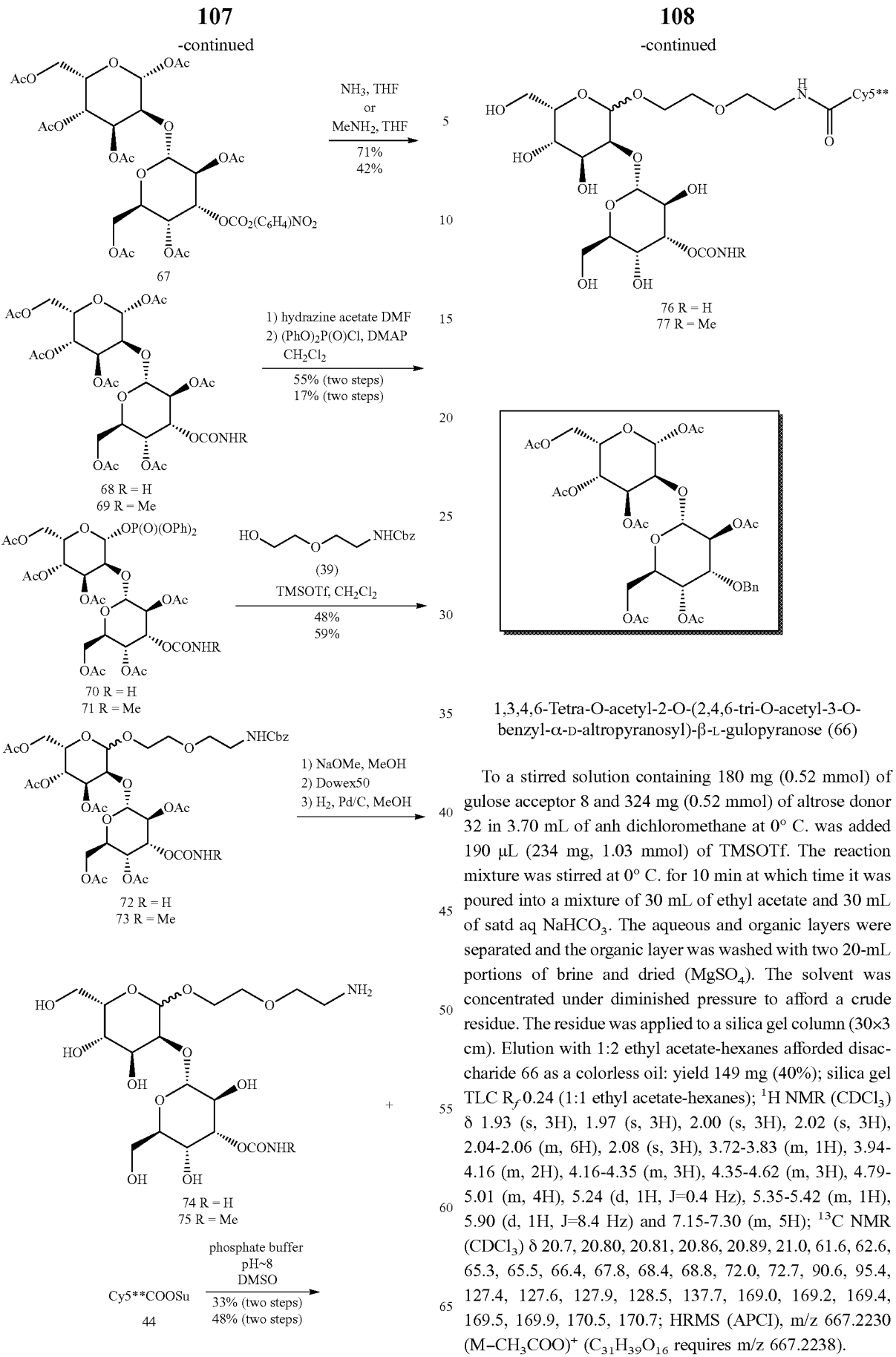

1,3,4,6-Tetra-O-acetyl-2-O-(2,4,6-tri-O-acetyl-3-O-benzyl-α-D-altropyranosyl)-β-L-gulopyranose (66)

To a stirred solution containing 180 mg (0.52 mmol) of gulose acceptor 8 and 324 mg (0.52 mmol) of altrose donor 32 in 3.70 mL of anh dichloromethane at 0° C. was added 190 μL (234 mg, 1.03 mmol) of TMSOTf. The reaction mixture was stirred at 0° C. for 10 min at which time it was poured into a mixture of 30 mL of ethyl acetate and 30 mL of satd aq NaHCO$_3$. The aqueous and organic layers were separated and the organic layer was washed with two 20-mL portions of brine and dried (MgSO$_4$). The solvent was concentrated under diminished pressure to afford a crude residue. The residue was applied to a silica gel column (30×3 cm). Elution with 1:2 ethyl acetate-hexanes afforded disaccharide 66 as a colorless oil: yield 149 mg (40%); silica gel TLC R$_f$ 0.24 (1:1 ethyl acetate-hexanes); $^1$H NMR (CDCl$_3$) δ 1.93 (s, 3H), 1.97 (s, 3H), 2.00 (s, 3H), 2.02 (s, 3H), 2.04-2.06 (m, 6H), 2.08 (s, 3H), 3.72-3.83 (m, 1H), 3.94-4.16 (m, 2H), 4.16-4.35 (m, 3H), 4.35-4.62 (m, 3H), 4.79-5.01 (m, 4H), 5.24 (d, 1H, J=0.4 Hz), 5.35-5.42 (m, 1H), 5.90 (d, 1H, J=8.4 Hz) and 7.15-7.30 (m, 5H); $^{13}$C NMR (CDCl$_3$) δ 20.7, 20.80, 20.81, 20.86, 20.89, 21.0, 61.6, 62.6, 65.3, 65.5, 66.4, 67.8, 68.4, 68.8, 72.0, 72.7, 90.6, 95.4, 127.4, 127.6, 127.9, 128.5, 137.7, 169.0, 169.2, 169.4, 169.5, 169.9, 170.5, 170.7; HRMS (APCI), m/z 667.2230 (M–CH$_3$COO)$^+$ (C$_{31}$H$_{39}$O$_{16}$ requires m/z 667.2238).

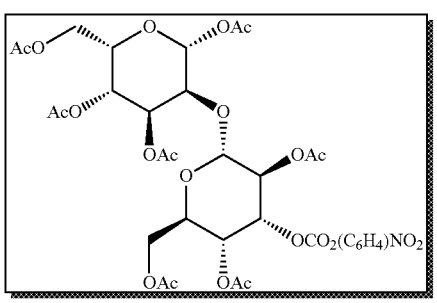

1,3,4,6-Tetra-O-acetyl-2-O-(2,4,6-tri-O-acetyl-3-O-((p-nitrophenyl)carbamoyl)-α-D-altropyranosyl)-β-L-gulopyranose (67)

To a solution containing 190 mg (0.26 mmol) of disaccharide 66 in 18 mL of ethyl acetate was added a catalytic amount of Pd(OH)$_2$/C and the reaction mixture was stirred overnight under 1 atm of H$_2$. The solvent was filtered through a pad of Celite 545® and the filtrate was concentrated under diminished pressure to afford a crude residue. The crude product was used for the next reaction; silica gel TLC $R_f$ 0.12 (1:1 ethyl acetate-hexanes).

To a solution containing 198 mg (0.31 mmol) of the crude residue in 1.1 mL of anh pyridine was added 151 mg (1.24 mmol) of DMAP and 280 mg (1.24 mmol) of p-nitrophenyl chloroformate. The reaction mixture was stirred at 40° C. overnight and then poured into a mixture of 30 mL ethyl acetate and 10 mL of H$_2$O. The aqueous and organic layers were separated and the organic layer was washed with three 10-mL portions of 1 N HCl and 10 mL of satd aq NaHCO$_3$ and brine. The solvent was dried (MgSO$_4$) and then concentrated under diminished pressure to afford a crude residue. The residue was applied to a silica gel column (25×3 cm). Elution with 1:1 ethyl acetate-hexanes afforded ester 67 as a colorless foam: yield 177 mg (71% over two steps); silica gel TLC $R_f$ 0.28 (1:1 ethyl acetate-hexanes); $^1$H NMR (CDCl$_3$) δ 2.02 (s, 3H), 2.04 (s, 3H), 2.09 (s, 3H), 2.10 (s, 3H), 2.12 (s, 3H), 2.13 (s, 3H), 2.14 (s, 3H), 3.99-4.17 (m, 3H), 4.23-4.38 (m, 2H), 4.41-4.50 (m, 1H), 4.89-5.02 (m, 2H), 5.02-5.13 (m, 2H), 5.20 (dt, 1H, J=10.4 and 5.2 Hz), 5.25-5.34 (m, 1H), 5.43 (t, 1H, J=3.5 Hz), 5.94 (d, 1H, J=8.4 Hz), 7.42 (t, 2H, J=7.1 Hz) and 8.22-8.30 (m, 2H); $^{13}$C NMR (CDCl$_3$) δ 20.66, 20.71, 20.72, 20.76, 20.9, 61.5, 62.2, 64.7, 65.1, 65.4, 67.6, 68.1, 68.6, 71.3, 72.1, 90.5, 94.5, 121.4, 125.4, 136.0, 145.6, 149.8, 151.6, 155.2, 168.8, 168.9, 169.1, 169.3, 169.5, 170.4 and 170.6; HRMS (APCI), m/z 742.1851 (M–CH$_3$COO)$^+$ (C$_{31}$H$_{36}$NO$_{20}$ requires m/z 742.1831).

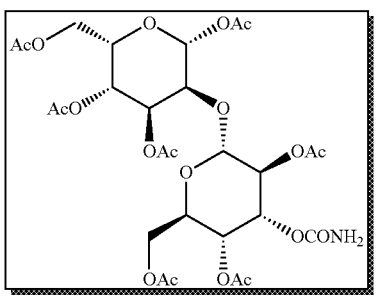

1,3,4,6-Tetra-O-acetyl-2-O-(2,4,6-tri-O-acetyl-3-O-carbamoyl-α-D-altropyranosyl)-β-L-gulopyranoside (68)

To a solution containing 73.0 mg (0.09 mmol) of ester 67 in 2 mL of anh THF was added a solution of 0.7 mL of anh THF saturated with NH$_3$ at 0° C. The reaction mixture was allowed to warm to room temperature and then stirred for 2.5 h at which time silica gel TLC analysis indicated that the reaction was complete. The solvent was concentrated under diminished pressure to afford a crude residue. The residue was applied to a silica gel column (20×3 cm). Elution with 3:1 ethyl acetate-hexanes afforded disaccharide 68 as a colorless oil: yield 44 mg (71%); silica gel TLC $R_f$ 0.38 (ethyl acetate); $^1$H NMR (CDCl$_3$) δ 2.00 (s, 3H), 2.05 (s, 3H), 2.11 (s, 6H), 2.13 (s, 3H), 2.16 (s, 3H), 2.17 (s, 3H), 3.98 (dd, 1H, J=8.1 and 3.3 Hz), 4.02-4.38 (m, 7H), 4.75 (d, 1H, J=3.3 Hz), 4.82-4.96 (m, 2H), 4.99-5.12 (m, 2H), 5.13 (dd, 1H, J=7.8 and 4.4 Hz), 5.44 (t, 1H, J=3.7 Hz) and 6.11 (d, 1H, J=8.1 Hz); $^{13}$C NMR (CDCl$_3$) δ 20.72, 20.75, 20.79, 20.82, 20.83, 20.87, 21.2, 61.8, 62.4, 64.6, 64.9, 65.5, 66.8, 67.6, 69.0, 69.5, 71.7, 91.0, 94.4, 155.6, 168.9, 169.3, 169.4, 169.6, 170.2, 170.5 and 170.7; HRMS (APCI), m/z 680.2039 (M+H)$^+$ (C$_{27}$H$_{38}$NO$_{19}$ requires m/z 680.2038).

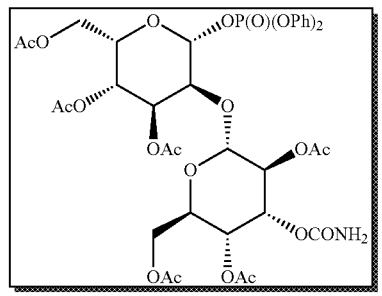

3,4,6-Tri-O-acetyl-2-O-(2,4,6-Tri-O-acetyl-3-O-carbamoyl-α-D-altropyranosyl)-β-L-gulopyranosyl Diphenyl Phosphate (70)

To a solution containing 44.0 mg (60.0 μmol) of disaccharide 68 in 0.50 mL of anh DMF was added 7.00 mg (80.0 μmol) of hydrazine acetate. The reaction mixture was stirred at room temperature for 1.5 h and then quenched by the addition of 20 mL of ethyl acetate. The organic layer was washed with three 10-mL portions of brine and dried (MgSO$_4$). The solvent was concentrated under diminished pressure to afford a crude residue. The residue was used for the next reaction.

To a stirred solution containing 41.0 mg (60.0 μmol) of the crude residue in 4.00 mL of anh dichloromethane was added 10.0 mg (80.0 μmol) of DMAP, 100 μL (72.0 mg, 0.68 mmol) of Et$_3$N and 125 μL (162 mg, 0.61 mmol) of diphenyl chlorophosphate at 0° C. The reaction mixture was stirred at 0° C. for 2 h and then poured into a mixture of 40 mL of ethyl acetate and 20 mL of satd aq NaHCO₃. The aqueous and organic layers were separated and the organic layer was washed with three 10-mL portions of distilled water and brine and then dried (MgSO₄). The solvent was concentrated under diminished pressure to afford a crude residue. The residue was applied to a silica gel column (25×2 cm). Elution with 2:1 ethyl acetate-hexanes afforded phosphate ester 70 as a colorless oil: yield 31 mg (55% over two steps); silica gel TLC $R_f$ 0.30 (2:1 ethyl acetate-hexanes); ¹H NMR (CDCl₃) δ 1.83 (s, 3H), 1.98 (s, 3H), 2.04 (s, 3H), 2.12 (d, 3H, J=2.8 Hz), 2.15 (d, 6H, J=3.9 Hz), 3.98-4.09 (m, 2H), 4.09-4.25 (m, 4H), 4.26-4.36 (m, 2H), 4.66 (d, 1H, J=9.8 Hz), 4.83 (d, 1H, J=2.1 Hz), 4.91 (d, 1H, J=6.4 Hz), 5.03 (t, 1H, J=5.7 Hz), 5.09-5.19 (m, 2H), 5.45 (d, 1H, J=3.2 Hz), 5.74 (t, 1H, J=8.0 Hz) and 7.09-7.41 (m, 10H); ¹³C NMR (CDCl₃) δ 20.62, 20.66, 20.77, 20.83, 20.88, 61.6, 62.2, 64.5, 64.7, 65.1, 67.1, 67.3, 68.9, 71.7, 94.1, 120.28, 120.32, 120.37, 125.98, 125.99, 126.23, 126.24, 129.93, 129.94, 130.1, 155.9, 168.8, 169.0, 169.3, 169.5, 170.4, and 170.8; HRMS (APCI), m/z 870.2230 $(M+H)^+$ $(C_{37}H_{45}NO_{21}P$ requires m/z 870.2222).

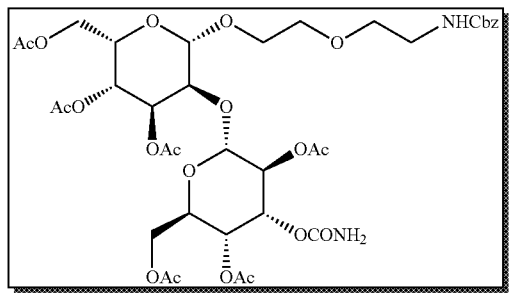

3,4,6-Tri-O-acetyl-2-O-(2,4,6-Tri-O-acetyl-3-O-carbamoyl-α-D-altropyranosyl)-β-L-gulopyranosyl Benzyl 2-(2-Ethoxy)ethylcarbamate (72)

To a stirred solution containing 31 mg (40 μmol) of phosphate ester 70 in 0.45 mL of anh dichloromethane was added a solution of 8.0 mg (30 μmol) of CBz-protected linker 44 in 0.45 mL of anh dichloromethane at 0° C. To the reaction mixture was added 12 μL (15 mg, 80 μmol) of TMSOTf and the reaction mixture was stirred at 0° C. for 15 min. The reaction mixture was poured into a mixture of 10 mL of ethyl acetate and 10 mL satd aq NaHCO₃. The aqueous and organic layers were separated and the organic layer was washed with three 10-mL portions of water and brine and then dried (MgSO₄). The solvent was concentrated under diminished pressure to afford a crude residue. The residue was applied to a silica gel column (25×2 cm). Elution with 12:12:1 ethyl acetate-hexanes-methanol afforded 72 as a colorless oil: yield 15 mg (48%); silica gel TLC $R_f$ 0.17 (11:11:1 ethyl acetate-hexanes-methanol); ¹H NMR (CDCl₃) δ ¹H NMR (CDCl₃) δ 1.95-2.07 (m, 6H), 2.07-2.15 (m, 12H), 3.41 (t, 2H, J=9.5 Hz), 3.59 (d, 2H, J=5.0 Hz), 3.61-3.71 (m, 3H), 3.87 (dt, 1H, J=12.8 and 6.5 Hz), 3.94-4.04 (m, 1H), 4.04-4.20 (m, 3H), 4.21-4.26 (m, 1H), 4.36-4.48 (m, 1H), 4.49-4.60 (m, 1H), 4.75 (d, 1H, J=7.5 Hz), 4.84-5.05 (m, 4H), 5.05-5.20 (m, 4H), 5.21-5.29 (m, 1H), 5.32-5.49 (m, 2H) and 7.27-7.38 (m, 5H); ¹³C NMR (CDCl₃) δ 20.75, 20.77, 20.82, 20.85, 20.88, 20.92, 40.9, 62.1, 62.3, 62.6, 65.1, 65.2, 66.9, 67.8, 68.1, 68.5, 68.6, 69.2, 70.37, 70.45, 99.5, 128.3, 128.4, 128.5, 128.7, 136.6, 155.7, 169.0, 169.4, 169.61, 169.65, 170.6, 170.82 and 170.89; HRMS (APCI), m/z 859.2973 $(M+H)^+$ $(C_{37}H_{51}N_2O_{21}$ requires m/z 859.2984).

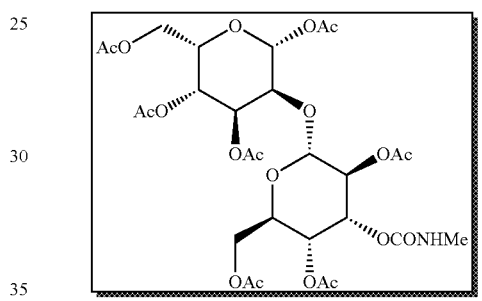

1,3,4,6-Tetra-O-acetyl-2-O-(2,4,6-tri-O-acetyl-3-O-(methylcarbamoyl)-α-D-altropyranosyl)-β-L-gulopyranose (69)

To a solution containing 86.0 mg (0.11 mmol) of ester 67 in 2.4 mL of anh THF was added 54.0 μL (0.11 mmol) of a 2 M solution of CH₃NH₂ in THF at 0° C. The reaction mixture was stirred at room temperature for 15 h at which time analysis by silica gel TLC indicated that the reaction was complete. The solvent was concentrated under diminished pressure to afford a crude residue. The residue was applied to a silica gel column (35×2 cm). Elution with 2:1 ethyl acetate-hexanes afforded disaccharide 69 as a colorless oil: yield 31 mg (42%); silica gel TLC $R_f$ 0.13 (3:1 ethyl acetate-hexanes); ¹H NMR (CDCl₃) δ 2.01 (s, 3H), 2.05 (s, 3H), 2.11 (s, 6H), 2.13 (s, 3H), 2.15 (s, 3H), 2.16 (s, 3H), 2.79 (d, 3H, J=4.7 Hz), 3.98 (dd, 1H, J=8.0 and 3.3 Hz), 4.04-4.30 (m, 4H), 4.33 (dt, 1H, J=12.1 and 6.1 Hz), 4.71-4.77 (m, 1H), 4.84-4.95 (m, 1H), 5.06 (dd, 2H, J=10.1 and 6.6 Hz), 5.11-5.19 (m, 1H), 5.21-5.41 (m, 2H), 5.43 (dd, 1H, J=10.0 and 6.3 Hz) and 6.10 (d, 1H, J=8.0 Hz); ¹³C NMR (CDCl₃) δ 20.77, 20.81, 20.82, 20.85, 20.88, 20.9, 21.3, 27.8, 61.8, 62.5, 64.8, 65.0, 65.5, 66.4, 66.7, 67.6, 69.2, 71.6, 91.1, 94.7, 155.9, 169.0, 169.3, 169.4, 169.6, 170.1, 170.5 and 170.8; HRMS (APCI), m/z 694.2204 $(M+H)^+$ $(C_{28}H_{40}NO_{19}$ requires m/z 694.2195).

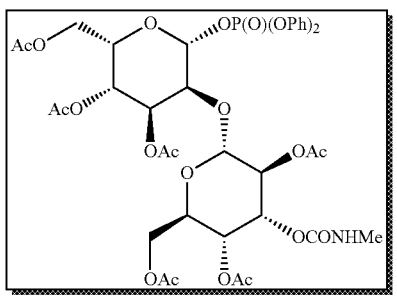

3,4,6-Tri-O-acetyl-2-O-(2,4,6-tri-O-acetyl-3-O-(methylcarbamoyl)-α-D-altropyranosyl)-β-L-gulopyranosyl Diphenyl Phosphate (71)

To a solution containing 31.0 mg (40.0 µmol) of disaccharide 69 in 0.5 mL of anh DMF was added 5.00 mg (50.0 µmol) of hydrazine acetate. The reaction mixture was stirred at room temperature for 1.5 h and then quenched by the addition of 20 mL of ethyl acetate. The organic solution was washed with three 10-mL portions of brine and dried (MgSO$_4$). The solvent was concentrated under diminished pressure to afford a crude residue. The residue was used for the next reaction.

To a stirred solution containing 22.0 mg (30.0 µmol) of the residue in 2 mL of anh dichloromethane was added 6.00 mg (40.0 µmol) of DMAP, 52.0 µL (38.0 mg, 370 µmol) of Et$_3$N and 70.0 µL (91.0 mg, 330 µmol) of diphenyl chlorophosphate at 0° C. The reaction mixture was stirred at 0° C. for 2 h and then poured into a mixture of 40 mL of ethyl acetate and 20 mL of satd aq NaHCO$_3$. The aqueous and organic layers were separated and the organic layer was washed with three 10-mL portions of distilled water and brine and then dried (MgSO$_4$). The solvent was concentrated under diminished pressure to afford a crude residue. The residue was applied to a silica gel column (25×2 cm). Elution with 2:1 ethyl acetate-hexanes afforded phosphate ester 71 as a colorless oil: yield 7.0 mg (17% over two steps); silica gel TLC R$_f$ 0.28 (3:1 ethyl acetate-hexanes); $^1$H NMR (CDCl$_3$) δ 1.85 (s, 3H), 1.98 (s, 3H), 2.04 (s, 3H), 2.12 (s, 3H), 2.15 (d, 6H, J=2.5 Hz), 2.63 (d, 3H, J=4.7 Hz), 3.98-4.08 (m, 2H), 4.09-4.26 (m, 3H), 4.30 (t, 1H, J=6.1 Hz), 4.63 (d, 1H, J=10.5 Hz), 4.80 (d, 1H, J=3.0 Hz), 4.89 (s, 1H), 5.00-5.06 (m, 1H), 5.13 (dd, 1H, J=10.5 and 3.1 Hz), 5.18 (d, 1H, J=3.0 Hz), 5.45 (d, 1H, J=2.9 Hz), 5.73 (t, 1H, J=8.0 Hz), 6.46 (d, 1H, J=4.8 Hz) and 7.12-7.40 (m, 10H); $^{13}$C NMR (CDCl$_3$) δ 20.67, 20.72, 20.77, 20.8, 20.9, 27.4, 61.6, 62.3, 64.67, 64.72, 65.1, 66.7, 67.2, 69.1, 71.7, 94.2, 96.52, 96.56, 120.1, 120.2, 120.32, 120.37, 126.0, 126.1, 129.9, 130.1, 156.1, 168.8, 169.0, 169.4, 169.5, 170.5 and 170.8; HRMS (APCI), m/z 884.2403 (M+H)$^+$ (C$_{38}$H$_{47}$NO$_{21}$P requires m/z 884.2378).

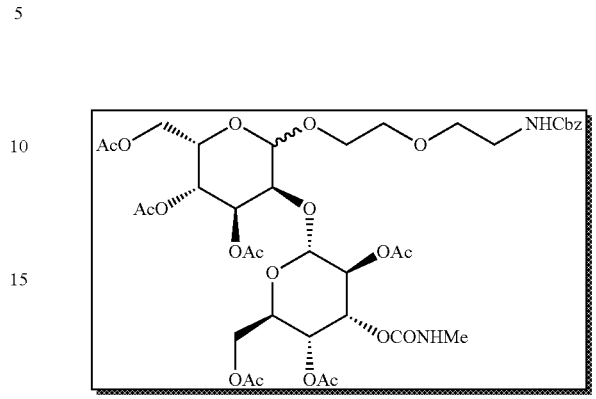

3,4,6-Tri-O-acetyl-2-O-(2,4,6-tri-O-acetyl-3-O-(methylcarbamoyl)-α-D-altropyranosyl)-α,β-L-gulopyranosyl Benzyl 2-(2-Ethoxy)ethylcarbamate (73)

To a stirred solution containing 17 mg (19 µmol) of phosphate ester 71 in 0.25 mL of anh dichloromethane was added a solution of 5.0 mg (17 µmol) of CBz-protected linker 44 in 0.25 mL of anh dichloromethane at 0° C. To the reaction mixture was added 7.0 µL (8.6 mg, 34 µmol) of TMSOTf. The reaction mixture was stirred at 0° C. for 15 min and then poured into a mixture of 10 mL ethyl acetate and 10 mL satd aq NaHCO$_3$. The aqueous and organic layers were separated and the organic layer was washed with three 10-mL portions of distilled water and brine and then dried (MgSO$_4$). The solvent was concentrated under diminished pressure to afford a crude residue. The residue was applied to a silica gel column (25×2 cm). Elution with 12:12:1 ethyl acetate-hexanes-methanol afforded 73 as a colorless oil: yield 10 mg (59%); silica gel TLC R$_f$ 0.14 (11:11:1 ethyl acetate-hexanes-methanol); $^1$H NMR (CDCl$_3$) δ 1.97 (d, 3H, J=8.6 Hz), 2.04 (d, 3H, J=4.2 Hz), 2.07-2.15 (m, 12H), 2.75 (d, 3H, J=4.7 Hz), 3.34-3.44 (m, 2H), 3.51-3.70 (m, 8H), 3.72 (dd, 1H, J=10.3 and 5.6 Hz), 3.82-3.93 (m, 1H), 3.95-4.25 (m, 3H), 4.26-4.56 (m, 1H), 4.63 (d, 1H, J=7.2 Hz), 4.86-5.02 (m, 1H), 4.96-5.28 (m, 6H), 5.33-5.51 (m, 1H), 5.83 (d, 1H, J=4.7 Hz) and 7.27-7.39 (m, 5H); $^{13}$C NMR (CDCl$_3$) δ 20.79, 20.84, 20.86, 20.89, 20.93, 21.0, 29.8, 41.0, 61.9, 62.2, 62.3, 62.7, 62.9, 65.26, 65.33, 66.9, 67.1, 70.2, 70.4, 70.5, 72.3, 128.3, 128.4, 128.66, 128.67, 136.6, 169.61, 169.65, 169.68, 170.6, 170.7, 170.8 and 170.9; HRMS (APCI), m/z 873.3150 (M+H)$^+$ (C$_{38}$H$_{53}$N$_2$O$_{21}$ requires m/z 873.3141).

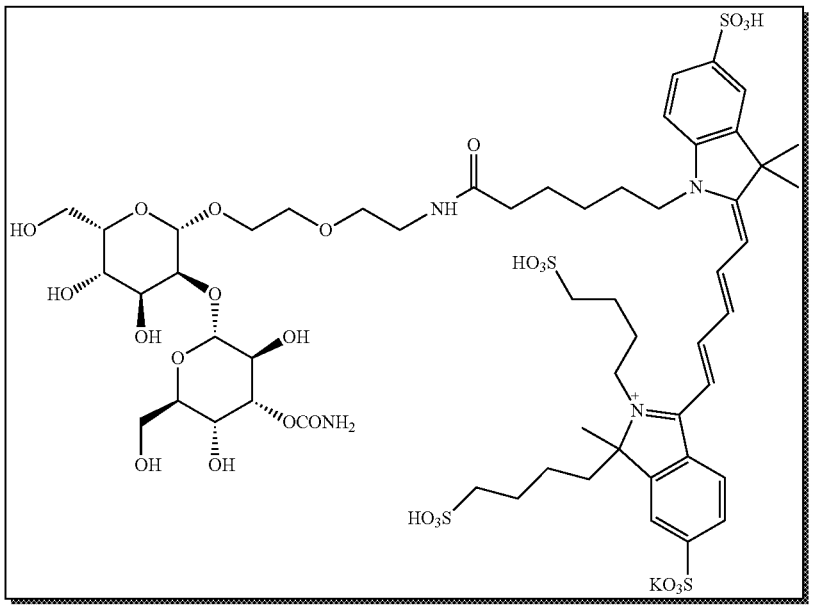

Disaccharide-Dye Conjugate 76

To a solution containing 2.40 mg (2.80 μmol) of compound 72 in 2 mL of anh methanol was added a freshly prepared solution of 0.4 M sodium methoxide in methanol. The reaction mixture was allowed to stir at room temperature for 3 h, and the complete consumption of starting material was confirmed by MALDI-TOF mass spectral analysis. The reaction mixture was then quenched by the addition of 500 mg of Dowex 50× resin, shaken for 15 min and filtered. To the solution of the crude product in methanol was then added Pd/C and $H_2$ gas was bubbled through for 1 h. The complete consumption of starting material was confirmed by MALDI-TOF mass spectral analysis. The reaction was filtered through Celite 545® and then concentrated under diminished pressure to afford 74, which was used for the next reaction. HRMS (APCI), m/z 473.1978 (M+H)$^+$ ($C_{17}H_{33}N_2O_{13}$ requires m/z 473.1983).

To 87.0 μg (0.18 μmol) of 74 was added a solution of 90.0 μg (0.09 μmol) of Cy5\*\*COOSu (44) in 150 μL of 0.2 M phosphate buffer and the reaction mixture was stirred overnight in the dark. The reaction mixture was purified on an Alltech Alltima $C_{18}$ reversed phase semi-preparative (250× 10 mm, 5 μm) HPLC column using aq 0.1% TFA and $CH_3CN$ mobile phases. A linear gradient was employed (99:1 0.1% aq TFA-$CH_3CN$→69:31 0.1% aq TFA-$CH_3CN$) over a period of 35 min at a flow rate of 4 mL/min. The fractions containing the desired product eluted at 23.5 min and were collected, frozen and lyophilized to give 76 as a blue solid: yield 39 μg (33% over two steps); HRMS (APCI), m/z 669.1916 (M−K−2H)$^{2-}$ ($C_{55}H_{78}N_4O_{26}S_4^{2-}$ requires m/z 669.1899).

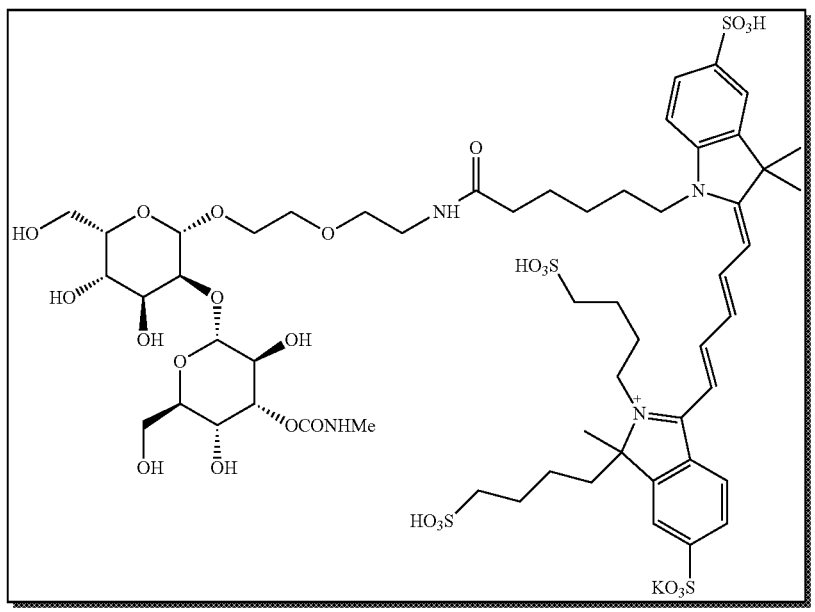

117
Disaccharide-Dye Conjugate 77

To a solution containing 1.00 mg (1.10 µmol) of compound 73 in 2 mL of anh methanol was added a freshly prepared solution of 0.4 M sodium methoxide in methanol. The reaction mixture was allowed to stir at room temperature for 3 h, and the complete consumption of starting material was confirmed by MALDI-TOF mass spectral analysis. The reaction mixture was then quenched by the addition of 300 mg of Dowex 50× resin, shaken for 15 min and filtered. To the solution of the crude product in methanol was added Pd/C and H₂ gas was bubbled through for 1 h. The complete consumption of starting material was confirmed by MALDI-TOF mass spectral analysis. The reaction mixture was filtered through Celite 545® and then concentrated under diminished pressure to afford 75, which was used for the next reaction. HRMS (APCI), m/z 487.2143 (M+H)⁺ ($C_{18}H_{35}N_2O_{13}$ requires m/z 487.2139).

To 87.0 µg (0.18 µmol) of 75 was added a solution of 90.0 µg (0.09 µmol) of Cy5**COOSu (44) in 150 µL of 0.2 M phosphate buffer and the reaction mixture was stirred overnight in the dark. The reaction mixture was purified on an Alltech Alltima $C_{18}$ reversed phase semi-preparative (250× 10 mm, 5 µm) HPLC column using aq 0.1% TFA and $CH_3CN$ mobile phases. A linear gradient was employed (99:1 0.1% aq TFA-$CH_3CN$→69:31 0.1% aq TFA-$CH_3CN$) over a period of 35 min at a flow rate of 4 mL/min. The fractions containing the desired product eluted at 24.7 and were collected, frozen and lyophilized to give 77 as a blue solid: yield 57 µg (48% over two steps); HRMS (APCI), m/z 676.1967 $(M-K-2H)^{2-}$ ($C_{56}H_{80}N_4O_{26}S_4^{2-}$ requires m/z 676.1977).

Example 11: Synthesis of Bleomycin Disaccharide Trimer-Dye Conjugate 96

Scheme 11

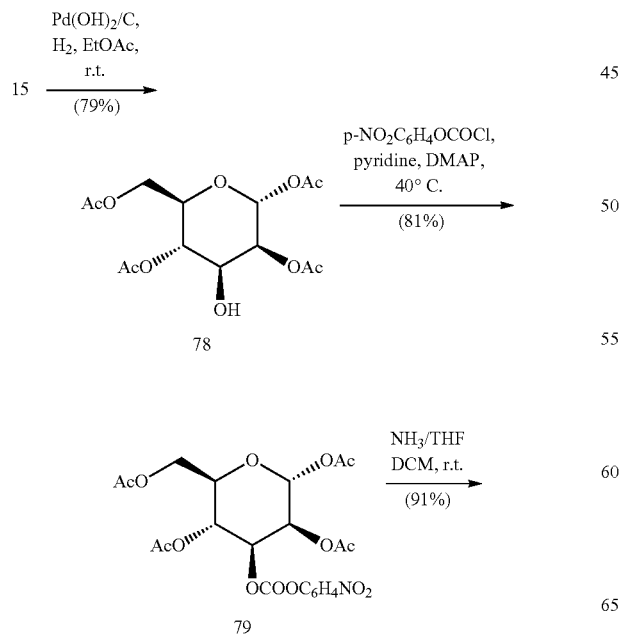

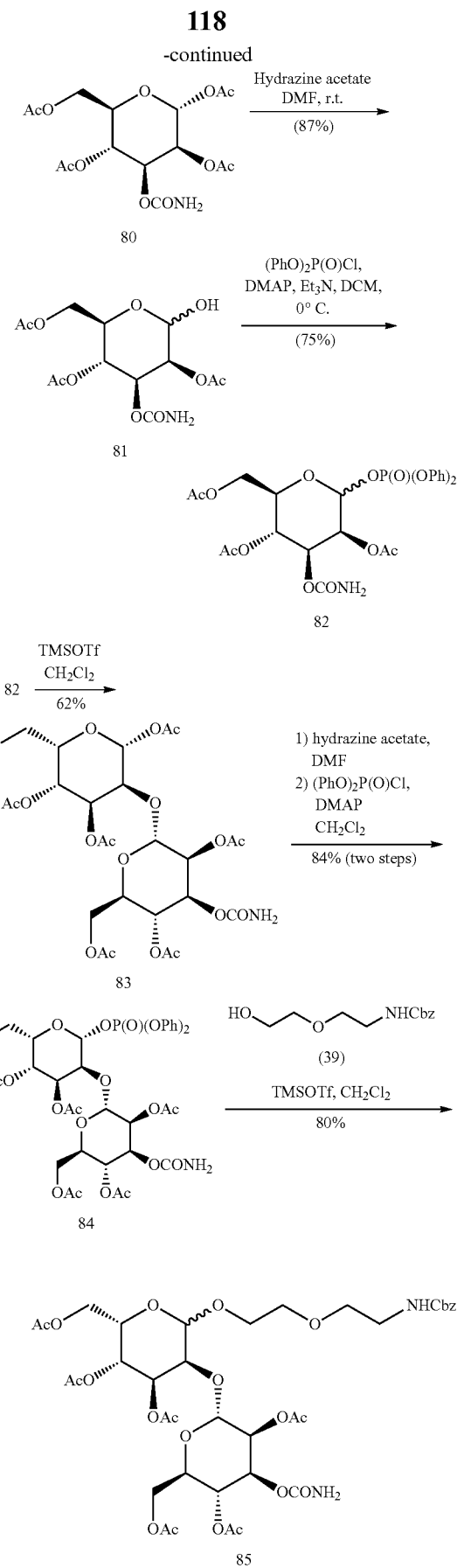

119
-continued
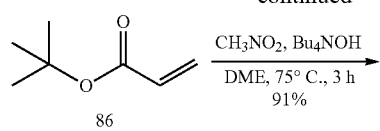
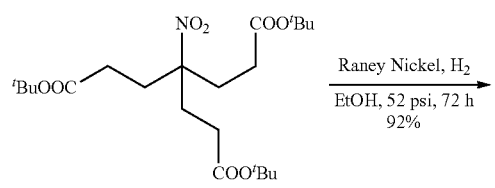
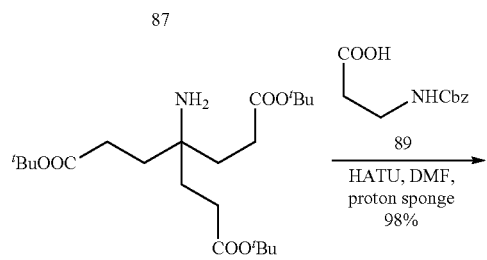
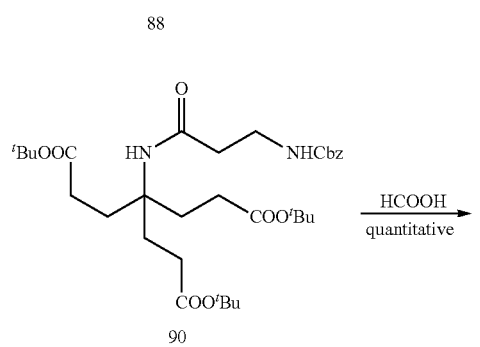
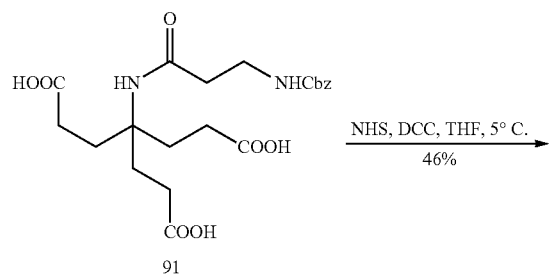
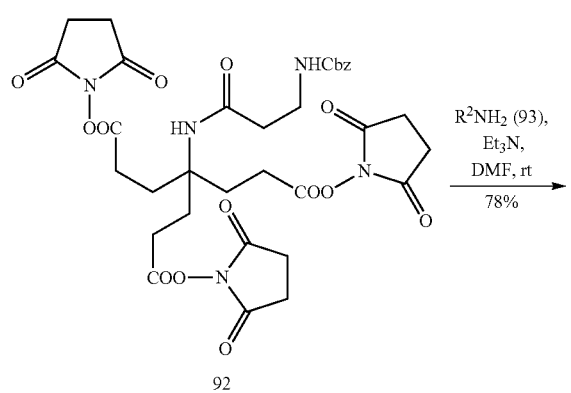
120
-continued
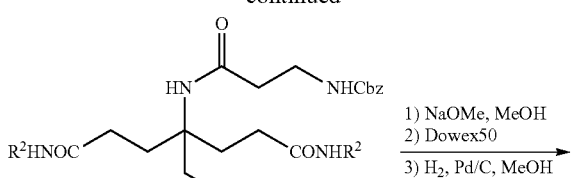
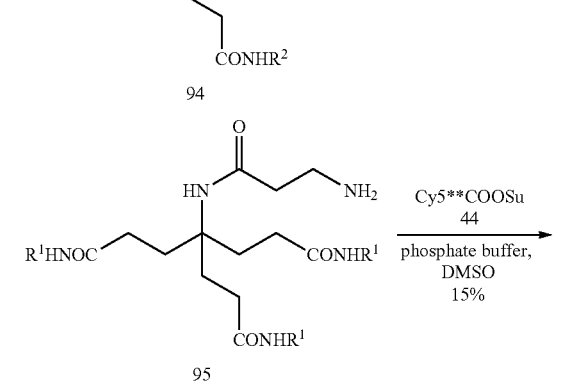
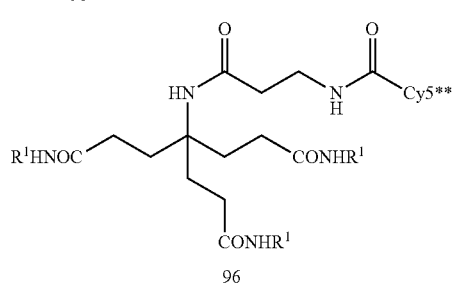
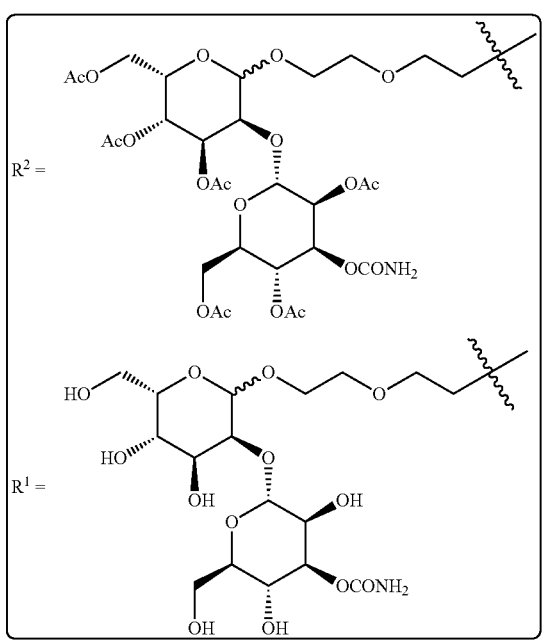
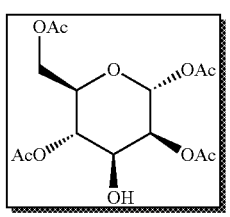

1,2,4,6-Tetra-O-acetyl-α-D-mannopyranose (78)

To a solution containing 0.88 g (2.00 mmol) of compound 15 in 24 mL of ethyl acetate was added a catalytic amount of Pd(OH)$_2$/C and the reaction was maintained under 1 atm of H$_2$(g) overnight. The catalyst was removed by filtration through a pad of Celite and the filtrate was concentrated under diminished pressure. The residue was purified by flash chromatography on a silica gel column (20×3 cm). Elution with 75% ethyl acetate in hexanes afforded compound 78 as a colorless oil: yield 550 mg (79%); silica gel TLC R$_f$ 0.11 (1:1 ethyl acetate-hexanes); $^1$H NMR (CDCl$_3$) δ 2.04 (s, 3H), 2.09 (s, 3H), 2.13 (s, 3H), 2.15 (s, 3H), 2.97 (s, 1H), 3.95 (m, 1H), 4.04 (m, 1H), 4.09 (m, 1H), 4.19 (dd, 1H, J=12.3 and 4.8 Hz), 5.07 (m, 1H), 5.13 (m, 1H) and 5.99 (m, 1H); $^{13}$C NMR (CDCl$_3$) δ 20.7, 20.8, 62.3, 68.0, 68.6, 70.3, 70.9, 90.4, 168.2, 170.3, 170.8 and 170.9.

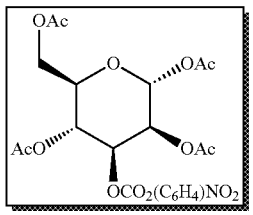

1,2,4,6-Tetra-O-acetyl-3-O-((p-nitrophenyl)carbamoyl)-α-D-mannopyranose (79)

To a solution containing 0.55 g (1.60 mmol) of 78 in 5.6 mL of pyridine were added 0.77 g (6.30 mmol) of DMAP and 1.30 g (6.30 mmol) of p-nitrophenyl chloroformate. The reaction mixture was stirred at 40° C. for 2 h at which time it was poured into a two-phase solution of 40 mL of ethyl acetate and 10 mL of H$_2$O. The organic layer was washed successively with three 10-mL portions of 1 N HCl, 10 mL of satd aq NaHCO$_3$ and 10 mL of brine. The solution was dried (Na$_2$SO$_4$) and concentrated under diminished pressure. The residue was purified by flash chromatography on a silica gel column (20×3 cm). Elution with 50% ethyl acetate in hexanes afforded compound 79 as a yellow oil: yield 0.66 g (81%); silica gel TLC R$_f$ 0.58 (1:1 ethyl acetate-hexanes); $^1$H NMR (CDCl$_3$) δ 2.07 (s, 3H), 2.09 (s, 3H), 2.14 (s, 3H), 2.17 (s, 3H), 4.08 (m, 2H), 4.25 (m, 1H), 5.15 (dd, 1H), 5.41 (m, 2H), 6.11 (s, 1H), 7.34 (d, 2H) and 8.23 (d, 2H); $^{13}$C NMR (CDCl$_3$) δ 20.6, 20.9, 61.8, 64.9, 67.4, 70.5, 74.1, 90.5, 121.8, 125.2, 145.5, 151.6, 155.1, 167.8, 169.3, 169.9 and 170.5.

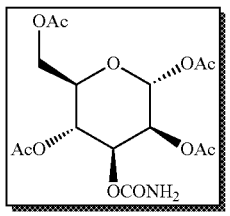

1,2,4,6-Tetra-O-acetyl-3-O-carbamoyl-α-D-mannopyranose (80)

To a solution of 0.51 g (1.31 mmol) of carbonate 79 in 27 mL of anh CH$_2$Cl$_2$ was added 15 mL of THF that had been saturated with NH$_3$ (g). The solution was stirred at room temperature for 1.5 h (at which time silica gel TLC analysis indicated that the reaction was complete). The solution was concentrated under diminished pressure. The residue was purified by flash chromatography on a silica gel column (14×3 cm). Elution with 3:1→1:2 hexanes-ethyl acetate afforded compound 80 as a colorless oil: yield 355 mg (91%); silica gel TLC R$_f$ 0.10 (1:1 hexanes-ethyl acetate). $^1$H NMR (CDCl$_3$) δ 2.02 (s, 3H), 2.04 (s, 3H), 2.11 (s, 3H), 2.12 (s, 3H), 4.04 (m, 2H), 4.22 (dd, 1H, J=12.6 and 5.0 Hz), 5.03 (br s, 2H), 5.24 (m, 3H) and 6.03 (d, 1H, J=1.7 Hz); $^{13}$C NMR (CDCl$_3$) δ 20.6, 20.6, 20.7, 61.9, 65.4, 68.6, 69.4, 70.4, 90.3, 155.2, 168.0, 169.6, 169.6 and 170.5.

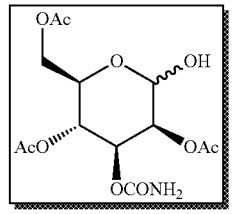

2,4,6-Tri-O-carbamoyl-α,β-D-mannopyranose (81)

To a solution of 365 mg (0.93 mmol) of compound 80 in 10.5 mL of dry DMF was added 120 mg (1.31 mmol) of acetate salt of hydrazine. The reaction mixture was stirred at room temperature for 1 h (at which time silica gel TLC analysis indicated that 80 had been consumed) and diluted with 80 mL of ethyl acetate. The solution was washed with three 25-mL portions of brine and concentrated under diminished pressure. The residue was purified by flash chromatography on a silica gel column (15×3 cm). Elution with 1:1 hexanes-ethyl acetate afforded compound 81 as a colorless oil: yield 285 mg (87%); silica gel TLC R$_f$ 0.24 (1:1 hexanes-ethyl acetate). $^1$H NMR (CDCl$_3$) δ 2.06 (s, 3H), 2.09 (s, 3H), 2.15 (s, 3H), 4.15 (m, 1H), 4.23 (m, 2H), 4.83 (s, 2H) and 5.25 (m, 4H).

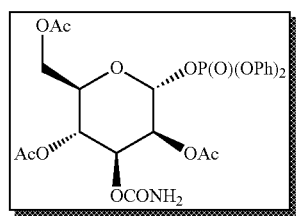

2,4,6-Tri-O-acetyl-3-O-carbamoyl-α-D-mannopyranosyl Diphenyl Phosphate (82)

To a solution of 160 mg (0.46 mmol) of intermediate 81, 64.0 mg (0.57 mmol) of DMAP and 640 µL (468 mg; 4.63 mmol) of Et$_3$N in 12.0 mL of CH$_2$Cl$_2$ at 0° C. was added dropwise 0.95 mL (1.23 g; 4.6 mmol) of diphenyl chlorophosphate. The solution was stirred at 0° C. for 1.5 h and was poured into a two-phase solution of EtOAc (100 mL) and satd aq NaHCO$_3$ (40 mL). The organic layer was washed with two 30-mL portions of brine, dried over Na$_2$SO$_4$, filtered and concentrated under diminished pressure. The residue was purified by flash chromatography on a silica gel column (15×3 cm). Elution with 2:1→1:2 hexanes-ethyl acetate afforded the phosphate ester 82 as a colorless oil: yield 201 mg (75%); silica gel TLC $R_f$ 0.41 (2:3 hexanes-ethyl acetate). $^1$H NMR (CDCl$_3$) δ 1.95 (s, 3H), 2.03 (s, 3H), 2.12 (s, 3H), 3.91 (d, 1H, J=12.4 and 2.2 Hz), 4.08 (m, 1H), 4.17 (dd, 1H, J=12.4 and 4.7 Hz), 4.66 (br s, 2H), 5.30 (m, 3H), 5.87 (dd, 1H, J=6.5 and 1.6 Hz) and 7.28 (m, 10H); $^{13}$C NMR (CDCl$_3$) δ 20.6, 20.7, 20.7, 61.7, 65.3, 69.0, 69.1, 69.2, 70.7, 96.0, 96.1, 120.1, 120.1, 120.2, 120.3, 125.8, 125.9, 130.0, 129.0, 150.0, 150.1, 150.2, 150.3, 155.2, 169.5, 169.8 and 170.6.

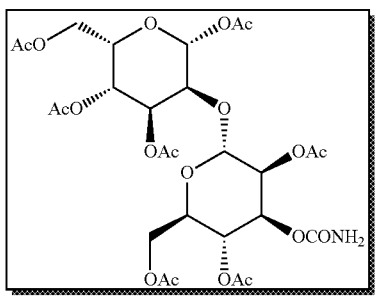

1,3,4,6-Tetra-O-acetyl-2-O-(2,4,6-tri-O-acetyl-3-O-carbamoyl-α-D-mannopyranosyl)-α-L-gulopyranoside (83)

To a round bottom flask containing 200 mg (0.34 mmol) of 82 was added a solution of 95.0 mg (0.27 mmol) of 8 in 3.80 mL of anhydrous CH$_2$Cl$_2$. The solution was cooled to 0° C. and to it was added 98.0 μL (120 mg; 0.55 mmol) of TMSOTf dropwise. The reaction mixture was stirred at 0° C. for 17 min at which time it was poured into a two-phase solution of EtOAc (60 mL) and satd aq NaHCO$_3$ (25 mL). The organic layer was washed with two 20-mL portions of brine, dried (Na$_2$SO$_4$), filtered and concentrated under diminished pressure. The residue was purified by flash chromatography on a silica gel column (25×2 cm). Elution with 3:2→1:3 hexanes-ethyl acetate afforded the disaccharide 83 as a colorless oil: yield 115 mg (62%); silica gel TLC $R_f$ 0.38 (1:4 hexanes-ethyl acetate); $^1$H NMR (CDCl$_3$) δ 2.05 (s, 3H), 2.06 (s, 3H), 2.07 (s, 3H), 2.14 (s, 6H), 2.16 (s, 3H), 2.20 (s, 3H), 3.98 (dd, 1H, J=8.4 and 3.3 Hz), 4.19 (m, 2H), 4.38 (m, 1H), 4.85 (s, 2H), 5.13 (m, 7H), 5.45 (m, 1H) and 5.88 (d, 1H, J=8.4 Hz); $^{13}$C NMR (CDCl$_3$) δ 14.4, 20.9, 21.0, 21.0, 21.2, 21.3, 60.6, 61.6, 62.3, 65.7, 66.1, 67.9, 69.3, 69.4, 69.9, 71.5, 90.8, 95.2, 155.4, 168.9, 169.5, 169.6, 170.0, 170.7 and 170.8.

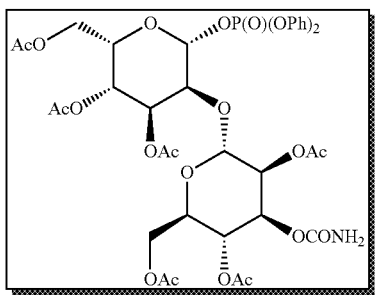

3,4,6-Tri-O-acetyl-2-O-(2,4,6-tri-O-acetyl-3-O-carbamoyl-α-D-mannopyranosyl)-α-L-gulopyranosyl Diphenyl Phosphate (84)

To a solution containing 112 mg (0.165 mmol) of 83 in 0.80 mL of anhydrous DMF was added 21 mg (0.23 mmol) of the acetate salt of hydrazine. The reaction mixture was stirred at room temperature for 1 h and quenched by the addition of 60 mL of ethyl acetate. The organic layer was washed with three 10-mL portions of brine and dried (Na$_2$SO$_4$). The solvent was filtered and then concentrated under diminished pressure to afford the deacetylated intermediate as a crude residue which was used for next reaction without further purification.

To a solution of 115 mg of the crude residue, 26.0 mg (0.21 mmol) of DMAP and 242 μL (177 mg, 1.75 mmol) of Et$_3$N in 16.5 mL of anhydrous CH$_2$Cl$_2$ at 0° C. was added 0.33 mL (428 mg, 1.59 mmol) of diphenyl chlorophosphate dropwise. The solution was stirred at 0° C. for 1.5 h and was then poured into a two-phase solution of EtOAc (80 mL) and satd aq NaHCO$_3$ soln (30 mL). The organic layer was washed with three 25-mL portions of H$_2$O, two 25-mL portions of brine, then dried over Na$_2$SO$_4$, filtered, and concentrated under diminished pressure. The residue was purified by flash chromatography on a silica gel column (22×2 cm). Elution with 1:1→1:3 hexanes-ethyl acetate afforded compound 84 a colorless oil: yield 121 mg (84%); $^1$H NMR (CDCl$_3$) δ 1.70 (s, 3H), 1.97 (s, 3H), 2.05 (s, 3H), 2.11 (s, 3H), 2.13 (s, 3H), 2.19 (s, 3H), 4.13 (m, 5H), 4.31 (m, 2H), 4.76 (s, 2H), 4.96 (m, 1H), 4.98 (m, 1H), 5.18 (m, 3H), 5.43 (m, 1H), 5.69 (m, 1H) and 7.25 (m, 10H); $^{13}$C NMR (CDCl$_3$) δ 20.2, 20.6, 20.7, 61.1, 61.7, 65.3, 65.4, 67.3, 69.0, 69.8, 71.5, 95.3, 96.1, 120.1, 120.2, 125.5, 129.6, 129.8, 129.9, 155.0, 169.2, 169.3, 169.7, 170.3 and 170.5.

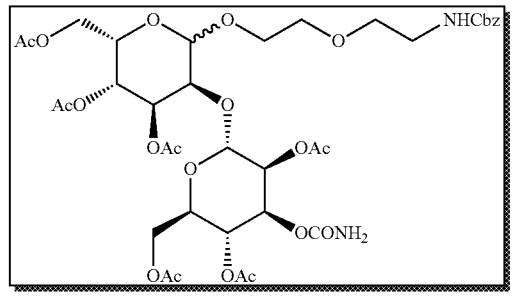

3,4,6-Tri-O-acetyl-2-O-(2,4,6-tri-O-acetyl-3-O-carbamoyl-α-D-mannopyranosyl)-α-L-gulopyranosyl benzyl 2-(2-ethoxy)ethylcarbamate (85)

To a solution of 78 mg (91 μmol) of 84 and 19 mg (79 μmol) of 39 in 2.4 mL of anhydrous CH$_2$Cl$_2$ was added 28 μL (34 mg, 0.16 mmol) of TMSOTf at 0° C. The reaction mixture was stirred at 0° C. for 17 min, at which time it was poured into a two-phase solution of EtOAc (50 mL) and satd aq NaHCO$_3$ (20 mL). The organic layer was washed with two 20-mL portions of brine, dried (Na$_2$SO$_4$), filtered and concentrated under diminished pressure. The residue was purified by flash chromatography on a silica gel column (25×2 cm). Elution with 15:32:1→11:36:1 hexanes-ethyl acetate-methanol afforded compound 85 as a colorless oil: yield 62 mg (80%); silica gel TLC R$_f$ 0.30 (1:4 hexanes-ethyl acetate); $^1$H NMR (CDCl$_3$) δ 2.03 (s, 6H), 2.07 (s, 3H), 2.09 (s, 3H), 2.11 (s, 3H), 2.12 (s, 3H), 3.54 (m, 8H), 3.83 (m, 1H), 3.96 (m, 1H), 4.05 (m, 4H), 4.25 (m, 1H), 4.46 (m, 1H), 4.69 (s, 1H), 4.91 (m, 1H), 5.12 (m, 8H), 5.61 (m, 1H) and 7.34 (m, 5H); $^{13}$C NMR (CDCl$_3$) δ 20.6, 20.7, 20.8, 29.6, 40.9, 62.1, 62.5, 63.7, 65.5, 66.1, 66.6, 67.6, 68.5, 69.1, 69.6, 69.7, 70.0, 70.3, 70.6, 97.0, 97.1, 128.1, 128.2, 128.4, 136.5, 156.5, 169.3, 169.5, 169.8 and 170.5.

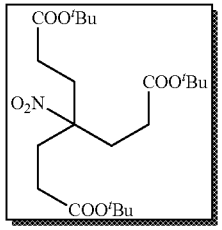

4-(2-tert-Butoxycarbonyl-ethyl)-4-nitro-heptanedioic Acid Di-tert-butyl Ester (87)

To a solution of 2.14 mL (2.43 g; 39.8 mmol) of nitromethane in 10 mL of dimethoxyethane at 65° C. was added 0.4 mL of 40% aq tetrabutylammonium hydroxide soln and the reaction mixture was heated to 75° C. To the reaction mixture was added dropwise 18.2 mL (125 mmol) of tert-butyl acrylate (86). To this mixture was added 0.8 mL of 40% aq tetrabutylammonium hydroxide soln in portions over a period of 1 h. The reaction mixture was stirred at 75° C. for 2 h. The reaction mixture was concentrated under diminished pressure and the residue was diluted in 100 mL of diethyl ether. The ether layer was washed with two 30-mL portions of 10% aq citric acid soln, two 30-mL portions of sat aq NaHCO$_3$ soln, 20 mL of brine, then dried over anhydrous Na$_2$SO$_4$, filtered and concentrated under diminished pressure. The residue was crystallized from absolute ethanol to afford compound 87 as colorless needles: yield 16.1 g (91%); mp 92-94° C., $^1$H NMR (CDCl$_3$) δ 1.43 (s, 27H) and 2.19 (m, 12H); $^{13}$C NMR (CDCl$_3$) δ 28.2, 29.9, 30.5, 81.3, 92.3 and 171.2.

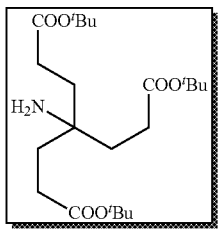

4-Amino-4-(2-tert-butoxycarbonylethyl)heptanedioic Acid Di-tert-butyl Ester (88)

A mixture of 1.02 g (2.29 mmol) of compound 87, ~6 mL of T1-Raney Ni (suspension in ethanol) and 18 mL of absolute ethanol was shaken in a Parr shaker at room temperature and 52 psi H$_2$ for 72 h. The reaction mixture was filtered through a pad of Celite and the filtrate was concentrated under diminished pressure to afford the amine 88 as a waxy solid which was used directly in the next step: yield 0.88 g (92%); silica gel TLC R$_f$ 0.14 (1:3 hexanes-ethyl acetate); $^1$H NMR (CDCl$_3$) δ 1.42 (s, 27H), 1.58 (t, 6H, J=8.4 Hz) and 2.22 (t, 6H, J=8.4 Hz); $^{13}$C NMR (CDCl$_3$) δ 28.0, 29.9, 34.4, 52.3, 80.3 and 173.0.

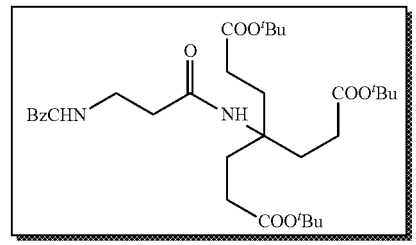

4-(3-Benzyloxycarbonylaminopropionylamino)-4-(2-tert-butoxycarbonyl-ethyl)-heptanedioic Acid Di-tert-butyl Ester (90)

To a solution of 0.84 g (2.02 mmol) of compound 88 and 0.43 g (1.91 mmol) of CBz-fl-alanine (89) in 15 mL of dry DMF were added 0.74 g (1.95 mmol) of HATU and 0.82 g (3.82 mmol) of proton sponge. The resulting yellow mixture was stirred at room temperature for 16 h. The reaction mixture was concentrated under diminished pressure and the residue was dissolved in 80 mL of ethyl acetate. The ethyl acetate layer was washed with two 40-mL portions of 2 M aq HCl, two 30-mL portions of H$_2$O, and 20 mL of brine, then dried over anhydrous Na$_2$SO$_4$, filtered and concentrated under diminished pressure. The residue was purified by flash chromatography on a silica gel column (12×3 cm). Elution with 1:1 hexanes-ethyl acetate gave compound 90 as a colorless solid: yield 1.17 g (98%); silica gel TLC R$_f$ 0.40 (1:1 hexanes-ethyl acetate); $^1$H NMR (CDCl$_3$) δ 1.42 (s, 27H), 1.94 (t, 6H, J=8.0 Hz), 2.19 (t, 6H, J=8.4 Hz), 2.34 (m, 2H), 3.44 (m, 2H), 5.09 (s, 2H), 5.57 (brs, 1H), 5.99 (brs, 1H) and 7.32 (m, 5H); $^{13}$C NMR (CDCl$_3$) δ 28.1, 29.8, 30.0, 36.8, 37.3, 57.8, 66.6, 80.8, 128.0, 128.5, 136.7, 156.6, 170.9 and 172.9; mass spectrum (ESI), m/z 621.3753 (M+H)$^+$ (C$_{33}$H$_{53}$N$_2$O$_9$ requires m/z 621.3746).

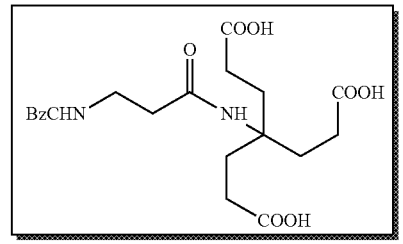

4-(3-Benzyloxycarbonylaminopropionylamino)-4-(2-carboxyethyl)-heptanedioic Acid (91)

A solution of 1.21 g (1.93 mmol) of 90 in 25 mL of formic acid was stirred at room temperature for 12 h. The reaction mixture was concentrated under diminished pressure. The residue was co-evaporated with six 10-mL portions of toluene to afford the tri-acid 91 as colorless oil: yield 0.91 g (100%); $^1$H NMR (CD$_3$OD) δ 2.01 (m, 6H), 2.26 (m, 6H), 2.40 (m, 2H), 3.36 (m, 2H), 5.07 (s, 2H) and 7.31 (m, 5H); $^{13}$C NMR (DMSO-d$_6$) δ 28.1, 29.0, 36.2, 37.3, 56.4, 65.2, 127.71, 127.75, 137.2, 156.0, 170.0 and 174.5; mass spectrum (ESI), m/z 453.1886 (M+H)$^+$ (C$_{21}$H$_{29}$N$_2$O$_9$ requires m/z 453.1868).

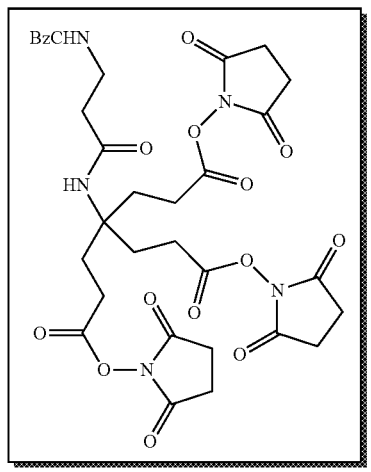

4-(3-Benzyloxycarbonylaminopropionylamino)-4-[2-(2,5-dioxo-pyrrolidin-1-yloxycarbonyl)ethyl]heptanedioic Acid Bis-(N-hydroxysuccinimide) Ester (92)

To a solution of 0.48 g (1.06 mmol) of compound 91 and 0.44 g (3.82 mmol) of N-hydroxysuccinimide in 9.00 mL of dry THF at 0° C. was added dropwise a solution of 0.83 g (4.03 mmol) of DCC in 2.00 mL of dry THF. The reaction mixture was stirred at 5° C. for 16 h. The reaction mixture was concentrated under diminished pressure and the residue was suspended in 10 mL of acetonitrile. The suspension was filtered and the filtrate was concentrated under diminished pressure. The residue was the purified by crystallization from absolute ethanol to afford 92 as colorless crystals: yield 366 mg (46%); $^1$H NMR (CD$_3$CN) δ 2.08 (m, 6H), 2.31 (m, 2H), 2.58 (m, 6H), 2.74 (s, 12H), 3.28 (m, 2H), 5.02 (s, 2H), 5.73 (brs, 1H), 6.10 (brs, 1H) and 7.32 (m, 5H); $^{13}$C NMR (CD$_3$CN) δ 25.9, 26.3, 29.5, 37.0, 37.9, 58.0, 66.7, 128.6, 128.7, 129.3, 138.3, 157.2, 169.8, 171.0 and 172.1; mass spectrum (ESI), m/z 744.2342 (M+H)$^+$ (C$_{33}$H$_{38}$N$_5$O$_{15}$ requires m/z 744.2359).

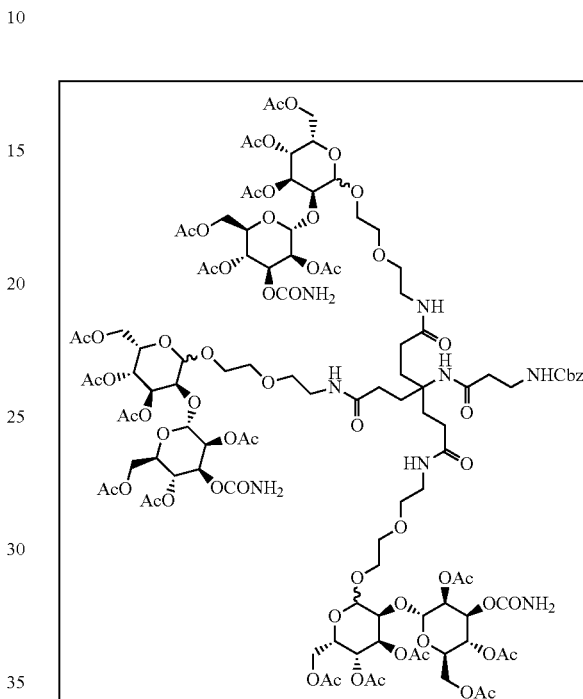

TrimerBLM-Disaccharide (94)

H$_2$ gas was bubbled through a mixture containing 18 mg (21 μmol) of 85 and a catalytic amount of Pd/C in 5.0 mL of dry THF for 45 min. The reaction mixture was filtered through a pad of Celite and the filtrate was concentrated under diminished pressure to obtain crude 93 as a colorless oil, which was used immediately in the next step: crude yield 14 mg; mass spectrum (MALDI) m/z 725.28 (M+H)$^+$ (theoretical m/z 725.26).

To a solution containing 14 mg (19 μmol) of 93 and 20 μL (15 mg, 0.14 mmol) of triethylamine in 1.5 mL of dry DMF was added 1.6 mg (2.2 μmol) of 92 and the mixture was stirred at room temperature for 20 h. The reaction mixture was concentrated under diminished pressure. The residue was purified by flash chromatography on a silica gel column (14×1 cm). Elution with 32:15:1→11:10:1 chloroform-acetone-methanol afforded trimerBLM-disaccharide 94 as a colorless oil: yield 4.5 mg (81%); silica gel TLC R$_f$ 0.60 (4:4:1 chloroform-acetone-methanol); mass spectrum (MALDI), m/z 2595.11 (M+Na)$^+$ (theoretical m/z 2594.90); mass spectrum (ESI), m/z 1297.4575 (M+H+Na)$^{2+}$ (C$_{10}$H$_{155}$N$_8$O$_{63}$Na requires m/z 1297.4529).

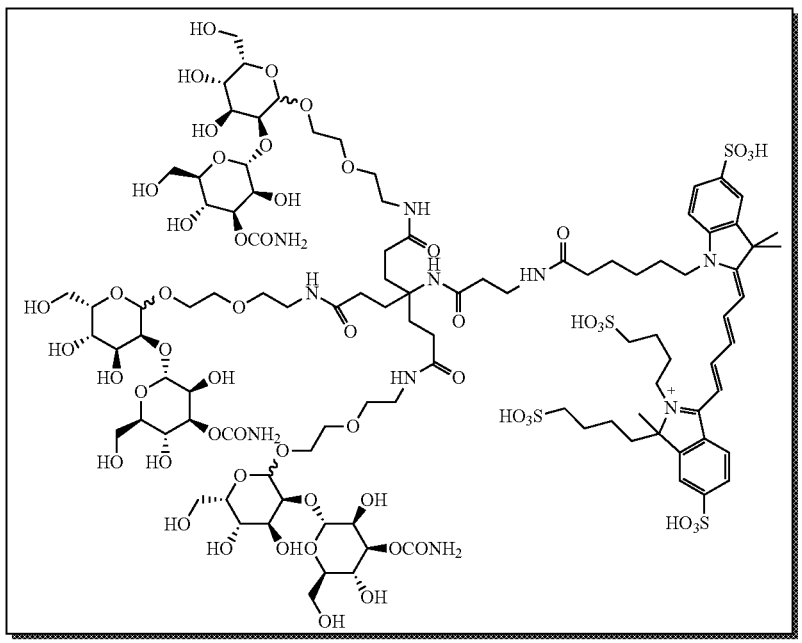

TrimerBLM-Disaccharide-Cy5** (96)

To a solution of 5.0 mg (1.94 μmol) of 94 in 2 mL of dry MeOH was added 0.3 mL of a 25% w/w solution of NaOMe in MeOH. The reaction mixture was shaken at room temperature for 2 h. One hundred mg of Dowex 50 W resin was added and the mixture was shaken at room temperature for 30 min. The mixture was filtered, diluted to 5 mL with methanol and a catalytic amount of Pd/C was added. $H_2$ gas was bubbled through the mixture for 30 min and the mixture was filtered. The filtrate was concentrated to obtain compound 95 as colorless solid: crude yield 2.6 mg (80%). To 110 μg (0.11 μmol) of Cy5COOSu (44) was added 100 μL of 0.2 M aq sodium phosphate buffer (pH ~8). This solution was added to a vial containing 0.56 mg (0.34 μmol) of 95 in 40 μL of DMSO and the mixture was shaken at room temperature overnight in the dark. The crude reaction mixture was purified on an Econosil $C_{18}$ reversed phase semi-preparative (250×10 mm, 10 μm) HPLC column using 0.1% aq TFA and $CH_3CN$ mobile phases. A linear gradient was employed (99:1 0.1% aq TFA-$CH_3CN$→45:55 0.1% aq TFA-$CH_3CN$) over a period of 30 min at a flow rate of 3 mL/min. Fractions containing the desired product eluted at 14.8 min (monitoring at 651 nm) and were collected, frozen, and lyophilized to give the trimerBLM-disaccharide-Cy5 96 as a blue solid: yield 43 μg (15%); mass spectrum (MALDI), m/z 2588.4 (M)+ (theoretical m/z 2587.8); mass spectrum (ESI), m/z 848.6223 (M–4H)$^{3-}$ ($C_{10}H_{167}N_{10}O_{56}S_4$ requires m/z 848.6215).

Example 12: Synthesis of Decarbamoyl Disaccharide-Dye Conjugates 97

Scheme 12

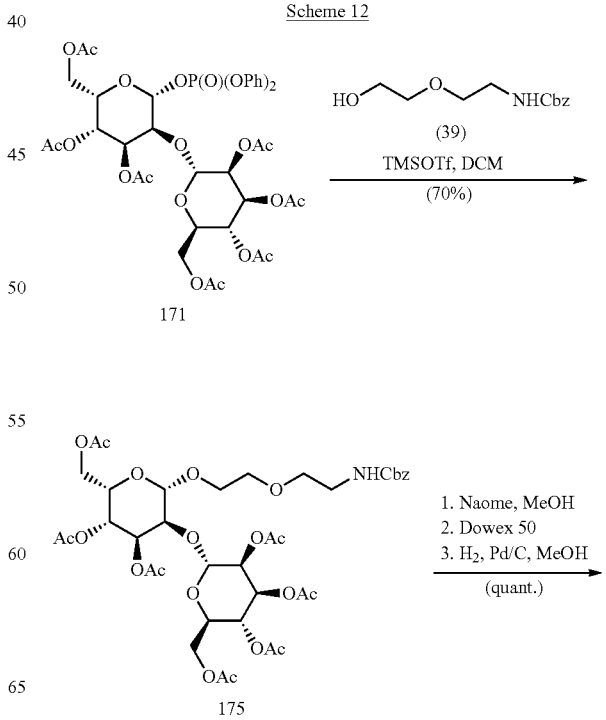

131

-continued

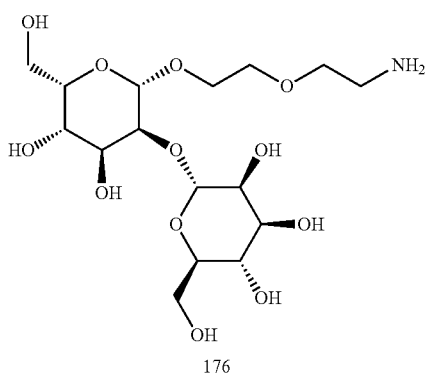

176

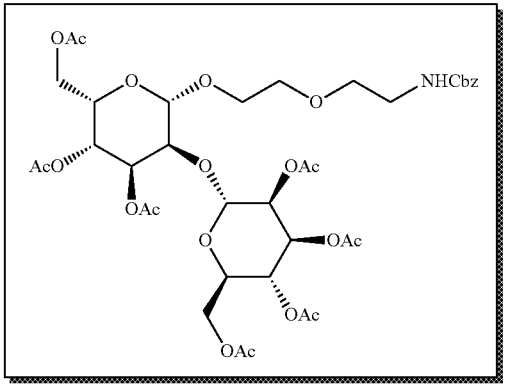

132

3,4,6-Tri-O-acetyl-2-O-(2,3,4,6-tetra-O-acetyl-α-D-mannopyranosyl)-α,β-L-gulopyranosyl benzyl 2-(2-ethoxy)ethylcarbamate (175).

To a solution of 26 mg (30 μmol) of phosphate ester 171 and 6.5 mg (27 μmol) of the alcohol 39 in 1.0 mL of anhydrous $CH_2Cl_2$ was added 10 μL (12.3 mg; 54 μmol) of TMSOTf at 0° C. The reaction was stirred at 0° C. for 17 min and was then poured into a two-phase solution of EtOAc (50 mL) and satd aq $NaHCO_3$ (20 mL). The organic layer was washed with two 20-mL portions of brine, dried ($Na_2SO_4$), filtered and concentrated under diminished pressure. The residue was purified by flash chromatography on a silica gel column (25×2 cm). Elution with 32:16:1→12:12:1 hexanes-ethyl acetate-methanol afforded compound 175 as a colorless oil: yield 18 mg (70%); silica gel TLC $R_f$ 0.80 (12:12:1 hexanes-ethyl acetate-methanol); $^1H$ NMR ($CDCl_3$) δ 1.97 (s, 3H), 2.02 (s, 3H), 2.04 (s, 3H), 2.08 (s, 3H), 2.10 (s, 3H), 2.12 (s, 3H), 2.14 (s, 3H), 3.40 (m, 2H), 3.61 (m, 3H), 3.68 (m, 2H), 3.85 (m, 1H), 3.97 (m, 1H), 4.18 (m, 5H), 4.27 (m, 4H), 4.47 (t, 1H, J=6.4 and 6.4 Hz), 4.92 (d, 1H, J=3.7 Hz), 5.01 (m, 2H), 5.09 (s, 2H), 5.15 (s, 1H), 5.28 (m, 3H), 5.45 (s, 1H) and 7.33 (m, 5H); $^{13}C$ NMR ($CDCl_3$) δ 20.61, 20.62, 20.70, 20.75, 20.8, 29.7, 40.9, 62.1, 62.5, 63.7, 65.5, 6.0, 66.6, 68.6, 68.6, 69.1, 69.2, 70.1, 70.3, 70.6, 97.0, 97.1, 128.05, 128.15, 128.5, 136.5, 156.4, 169.3, 169.5, 169.6, 169.8, 169.9, 170.52 and 170.53; mass spectrum (ESI), m/z 858.3036 $(M+H)^+$ ($C_{38}H_{52}NO_{21}$ requires m/z 858.3026).

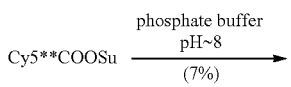

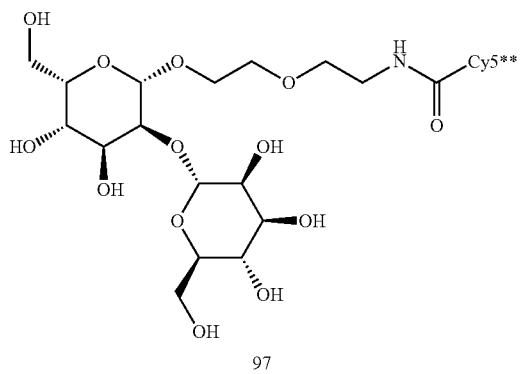

97

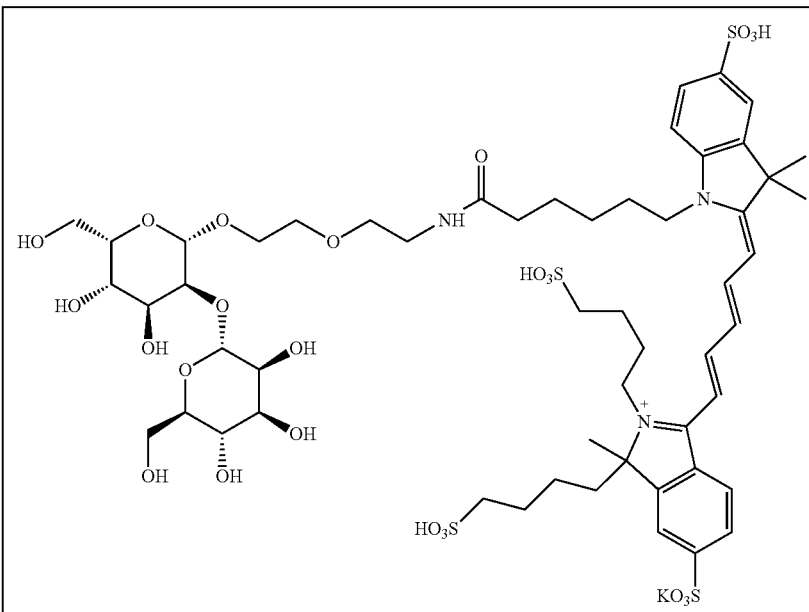

Decarbamoyl BLM-Disaccharide-Cy5** (97)

To a solution containing 5.0 mg (5.8 μmol) of compound 175 in 2 mL of anh methanol was added a freshly prepared solution of 0.4 M sodium methoxide in methanol. The reaction mixture was allowed to stir at room temperature for 2 h, and the complete consumption of starting material was confirmed by MALDI-TOF mass spectral analysis. The reaction mixture was then quenched by the addition of 500 mg of Dowex 50× resin, shaken for 15 min and filtered. To the solution of the crude product in methanol was then added Pd/C and $H_2$ gas was bubbled through for 30 mins. The complete consumption of starting material was confirmed by MALDI-TOF mass spectral analysis. The reaction mixture was filtered through Celite 545® and then concentrated under diminished pressure to afford 176, which was used for the next reaction.

To 200 μg (0.47 μmol) of 176 was added a solution of 110 μg (0.11 μmol) of Cy5**COOSu (44) in 100 μL of 0.2 M phosphate buffer and the reaction mixture was stirred overnight in the dark. The reaction mixture was purified on an Alltech Alltima $C_{18}$ reversed phase semi-preparative (250× 10 mm, 5 μm) HPLC column using aq 0.1% TFA and $CH_3CN$ mobile phases. A linear gradient was employed (99:1 0.1% aq TFA-$CH_3CN$→45:55 0.1% aq TFA-$CH_3CN$) over a period of 30 min at a flow rate of 3 mL/min. The fractions containing the desired product eluted at 16.0 min and were collected, frozen and lyophilized to give 97 as a blue solid: yield 34 μg (7%); mass spectrum (MALDI), m/z 1336.99 $(M)^+$ (theoretical 1336.35); mass spectrum (ESI), m/z 647.6858 $(M-K-2H)^2$ ($C_{54}H_{77}N_3O_{25}S_4$ requires m/z 647.6870).

Example 13: Synthesis of BLM Disaccharide-Dye Conjugates 98

Scheme 13

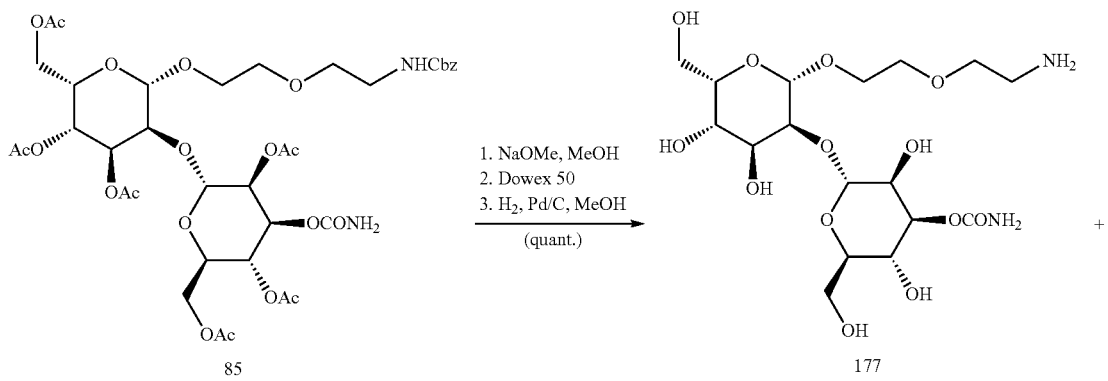

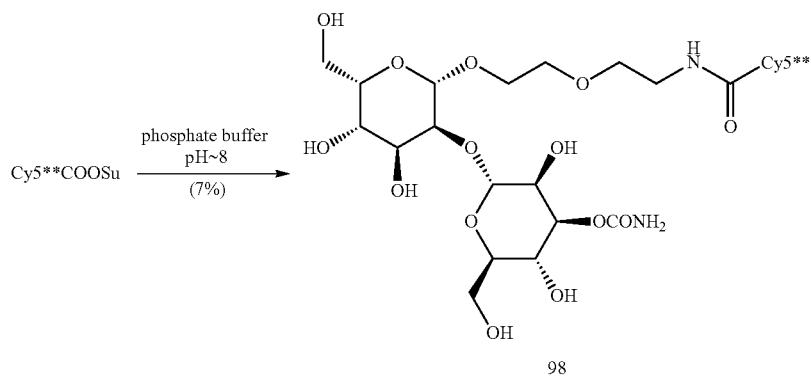

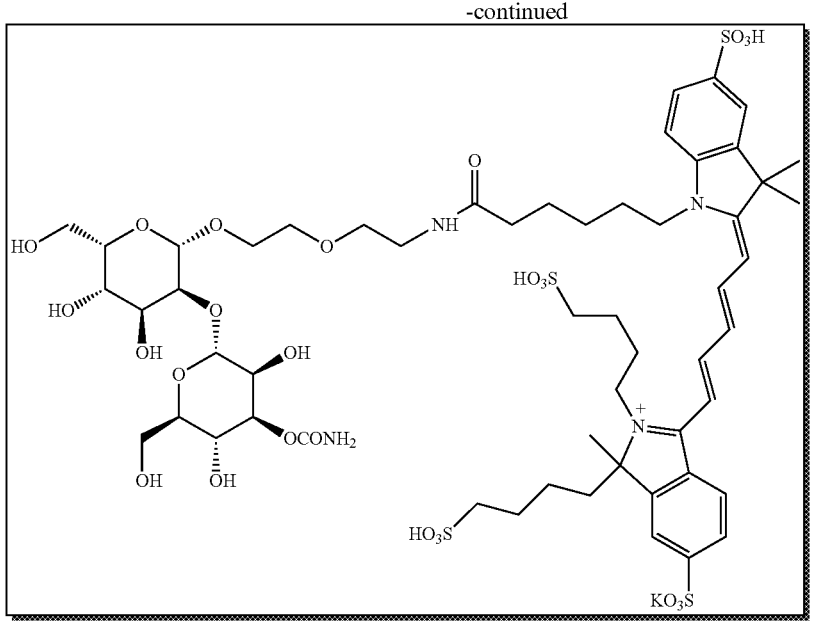

BLM-Disaccharide-Cy5** (98)

To a solution of 8.0 mg (9.30 μmol) of compound 85 in 2 mL of anh methanol, was added 0.2 mL of 25% w/w freshly prepared solution of sodium methoxide in methanol. The reaction mixture was allowed to stir at room temperature for 2.5 h, and the complete consumption of starting material was confirmed by MALDI-TOF mass spectral analysis. The reaction mixture was then quenched by the addition of 500 mg of Dowex 50× resin, shaken for 15 min and filtered. To the solution of the crude product in methanol was added Pd/C and $H_2$ gas was bubbled through for 45 min. The complete consumption of starting material was confirmed by MALDI-TOF mass spectral analysis. The reaction mixture was filtered through Celite 545® and then concentrated under diminished pressure to afford 177, which was used for the next reaction.

To 175 μg (0.37 μmol) of 177 was added a solution of 110 μg (0.11 μmol) of Cy5**COOSu (44) in 100 μL of 0.2 M phosphate buffer and the reaction mixture was stirred overnight in the dark. The reaction mixture was purified on an Econosil $C_{18}$ reversed phase semi-preparative (250×10 mm, 10 μm) HPLC column using aq 0.1% TFA and $CH_3CN$ mobile phases. A linear gradient was employed (99:1 0.1% aq TFA-$CH_3CN$→45:55 0.1% aq TFA-$CH_3CN$) over a period of 30 min at a flow rate of 3 mL/min. The fractions containing the desired product eluted at 16.1 min and were collected, frozen and lyophilized to give 98 as a blue solid: yield 62 μg (42%); mass spectrum (MALDI), m/z 1379.59 (M)$^+$ (theoretical m/z 1379.36).

Example 14: Synthesis of Bleomycin Monosaccharide-Dye Conjugate 117

Scheme 14

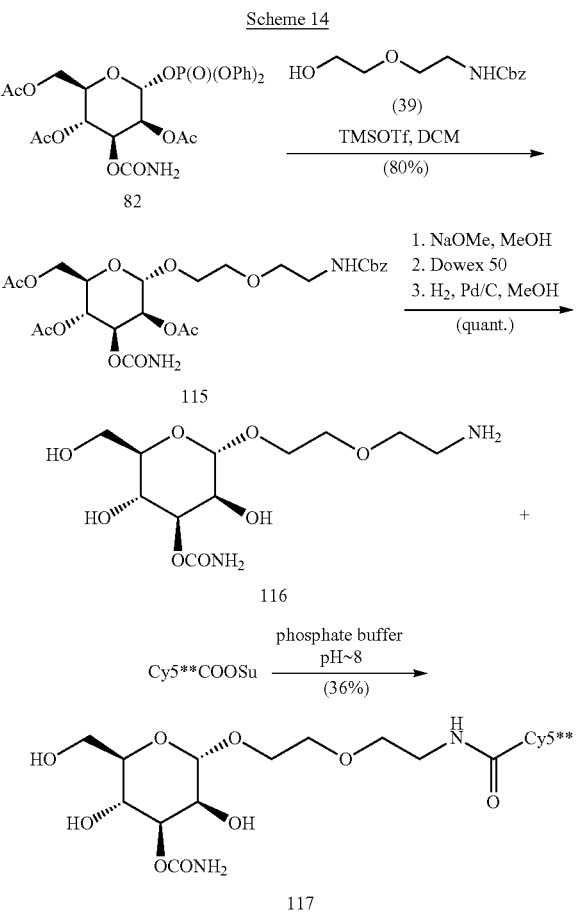

-continued

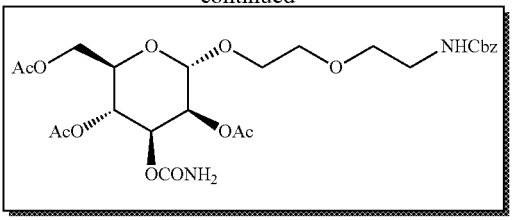

2,4,6-tri-O-acetyl-3-O-(carbamoyl)-α-D-mannopyranosyl Benzyl 2-(Ethoxy)ethylcarbamate (115)

To a solution of 121 mg (0.21 mmol) of 82 and 45 mg (0.19 mmol) of 39 in 3.5 mL of anhydrous $CH_2Cl_2$ was added 68 μL (83 mg, 0.38 mmol) of TMSOTf at 0° C. The reaction mixture was stirred at 0° C. for 20 min, at which time it was poured into a two-phase solution of EtOAc (70 mL) and satd aq $NaHCO_3$ (28 mL). The organic layer was washed with two 28-mL portions of brine, dried ($Na_2SO_4$), filtered and concentrated under diminished pressure. The residue was purified by flash chromatography on a silica gel column (25×2.5 cm). Elution with 1:1→1:2→1:3 hexanes-ethyl acetate afforded compound 115 as a colorless oil: yield 95 mg (80%); silica gel TLC $R_f$ 0.26 (1:3 hexanes-ethyl acetate); $^1$H NMR (CDCl$_3$) δ 2.02 (s, 3H), 2.08 (s, 3H), 2.12 (s, 3H), 3.39 (m, 2H), 3.54 (m, 2H), 3.64 (m, 3H), 3.79 (m, 1H), 4.08 (m, 2H), 4.26 (m, 1H), 4.71 (br s, 2H), 4.91 (s, 1H), 5.10 (s, 2H), 5.25 (m, 3H), 5.37 (br s, 1H) and 7.35 (m, 5H); $^{13}$C NMR (CDCl$_3$) δ 20.8, 20.9, 21.0, 41.1, 62.7, 66.5, 66.8, 67.3, 68.5, 70.0, 70.1, 70.3, 70.4, 77.4, 97.6, 128.1, 128.2, 128.6, 136.8, 155.3, 170.1, 170.2, 170.8; mass spectrum (APCI), m/z 571.2141 (M+H)$^+$ ($C_{25}H_{35}N_2O_{13}$ requires m/z 571.2139).

BLM Monosaccharide-Dye Conjugate 117

To a solution of 4.60 mg (8.06 μmol) of compound 115 in 2 mL of anh methanol, was added 0.2 mL of 25% w/w freshly prepared solution of sodium methoxide in methanol. The reaction mixture was allowed to stir at room temperature for 2.5 h, and the complete consumption of starting material was confirmed by MALDI-TOF mass spectral analysis. The reaction mixture was then quenched by the addition of 500 mg of Dowex 50× resin, shaken for 15 min and filtered; mass spectrum MALDI), m/z 467.27 (M+Na)$^+$; mass spectrum (APCI), m/z 445.1815 (M+H)$^+$ ($C_{19}H_{29}N_2O_{10}$ requires m/z 445.1822). To the solution of the crude product in methanol was added Pd/C and $H_2$ gas was bubbled through for 45 min. The complete consumption of starting material was confirmed by MALDI-TOF mass spectral analysis. The reaction mixture was filtered through Celite 545® and then concentrated under diminished pressure to afford 116, which was used for the next reaction; mass spectrum (MALDI), m/z 333.22 (M+Na)$^+$; mass spectrum (APCI), m/z 311.1455 (M+H)$^+$ ($C_{11}H_{23}N_2O_8$ requires m/z 311.1454).

To 122 μg (0.39 μmol) of 116 was added a solution of 110 μg (0.11 μmol) of Cy5**COOSu (44) in 100 μL of 0.2 M phosphate buffer and the reaction mixture was stirred overnight in the dark. The reaction mixture was purified on an Econosil $C_{18}$ reversed phase semi-preparative (250×10 mm, 10 μm) HPLC column using aq 0.1% TFA and $CH_3CN$ mobile phases. A linear gradient was employed (99:1 0.1% aq TFA-$CH_3CN$→69:31 0.1% aq TFA-$CH_3CN$) over a period of 35 min at a flow rate of 4.5 mL/min. The fractions containing the desired product eluted at 22.5 min and were collected, frozen and lyophilized to give 117 as a blue solid: yield 50 μg (36%); mass spectrum (MALDI), m/z 1201.47 (M–H+Na)$^+$, 1223.47 (M–2H+2Na)$^+$, 1245.45 (M–3H+3Na)$^+$, 1267.43 (M–4H+4Na)$^+$, ($C_{49}H_{71}N_4O_{21}S_4$ requires m/z 1179.35); mass spectrum (TOF), m/z 588.1614 (M–3H)$^{2-}$ ($C_{49}H_{68}N_4O_{21}S_4^{2-}$ requires m/z 588.1629).

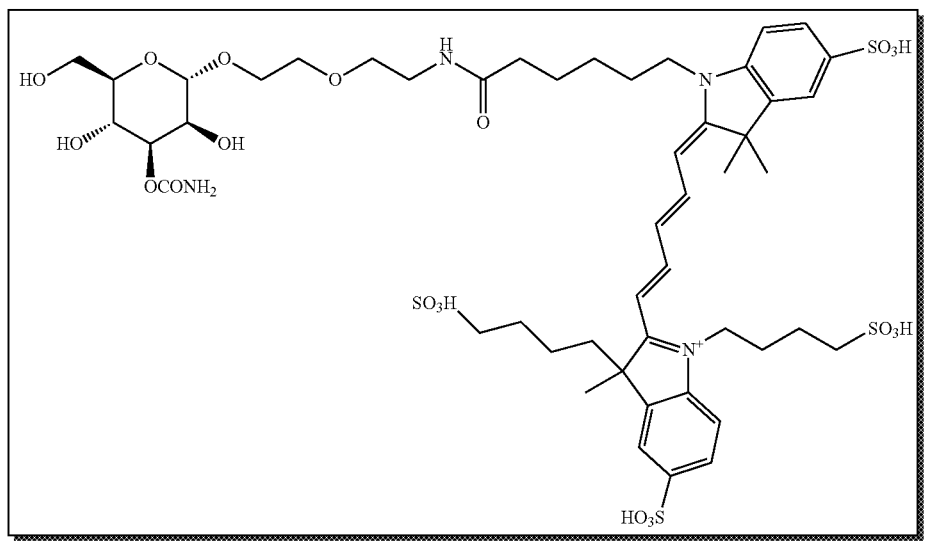

Example 15: Synthesis of Decarbamoyl Bleomycin Monosaccharide-Dye Conjugates 123

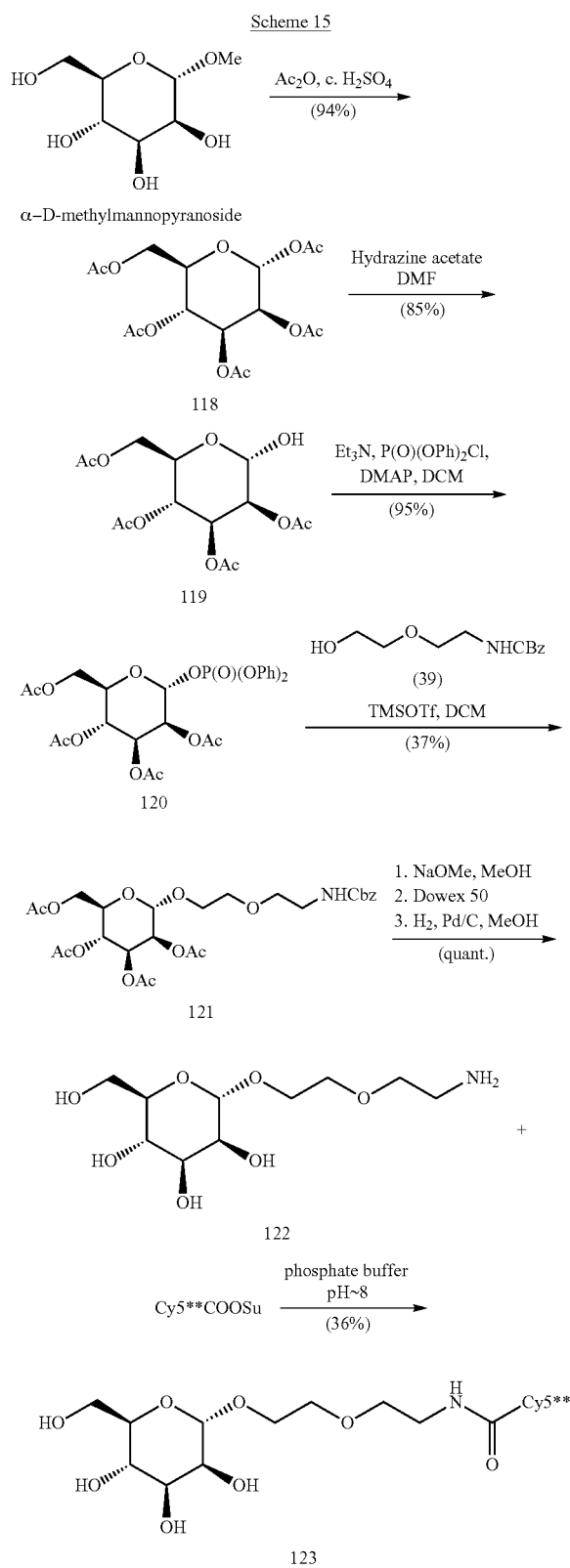

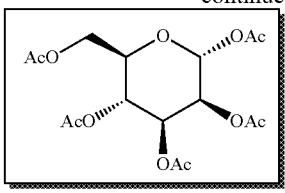

Penta-O-acetyl-α-D-mannopyranose (118)

To a solution containing 1.00 g (5.15 mmol) of O-methyl-α-D-mannopyranose in 18.9 mL of Ac$_2$O, was added a catalytic amount of H$_2$SO$_4$, and the solution was stirred at room temperature for 12 h. The reaction mixture was poured into a stirred mixture of 150 mL of ethyl acetate and 80 mL of satd aq NaHCO$_3$. The organic phase was separated and washed with 40 mL of satd aq NaHCO$_3$, 30 mL of brine, then dried (Na$_2$SO$_4$) and concentrated under diminished pressure. The residue was purified by flash chromatography on a silica gel column (5×18 cm). Elution with 5:1→3:1 hexanes-ethyl acetate afforded 118 as a colorless oil: yield 1.97 g (98%); silica gel TLC R$_f$ 0.60 (1:2 hexanes-ethyl acetate); $^1$H NMR (CDCl$_3$) δ 1.86 (s, 3H), 1.91 (s, 3H), 1.95 (m, 3H), 2.04 (m, 6H), 3.94 (m, 2H), 4.13 (m, 1H), 5.12 (s, 1H), 5.20 (m, 2H) and 5.94 (s, 1H); $^{13}$C NMR (CDCl$_3$) δ 20.40, 20.43, 20.47, 20.53, 20.6, 61.9, 65.3, 68.1, 68.6, 70.4, 76.8, 77.2, 77.5, 167.8, 169.3, 169.5, 169.7 and 170.3.

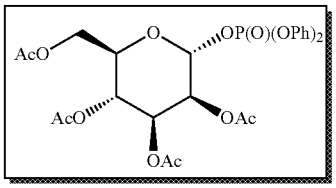

2,3,4,6-Tetra-O-acetyl-α-D-mannopyranosyl Diphenyl Phosphate (120)

To a solution of 525 mg (1.34 mmol) 118 in 8.1 mL of dry DMF, was added 170 mg (1.88 mmol) of hydrazine acetate. The reaction was stirred at room temperature for 2 h until analysis by silica gel TLC indicated it was complete. The reaction mixture was diluted with 50 mL of ethyl acetate and washed with three 20-mL portions of brine. The aq layer was re-extracted with three 30-mL portions of ethyl acetate. The combined organic layer was dried (Na$_2$SO$_4$) and concentrated under diminished pressure and dried to afford compound 119 as a colorless oil: yield 397 mg (85%); silica gel TLC R$_f$ 0.39 (3:1 hexanes-ethyl acetate).

To a solution of 397 mg (1.14 mmol) of 119 in 16.5 mL of dry CH$_2$Cl$_2$, 180 mg (1.47 mmol) of DMAP and 1.6 mL (11.4 mmol) of Et$_3$N. The reaction mixture was stirred for 10 min, followed by the addition of 2.3 mL (10.9 mmol) of diphenyl chlorophosphate dropwise at 0° C. The solution was stirred at 0° C. for 1.5 h and was poured into a two-phase solution of EtOAc (200 mL) and satd aq NaHCO$_3$ soln (80 mL). The organic layer was washed with two 50-mL portions of brine, dried over Na$_2$SO$_4$, filtered, and concentrated under diminished pressure. The residue was purified by flash chromatography on a silica gel column (18×5 cm). Elution with 3:12:1 hexanes-ethyl acetate afforded compound 120 as a colorless oil: yield 424 mg (54% over two steps); silica gel TLC $R_f$ 0.54 (3:1 hexanes-ethyl acetate); $^1$H NMR (CDCl$_3$) δ 2.04 (s, 3H), 2.06 (s, 3H), 2.10 (s, 3H), 2.22 (s, 3H), 3.98 (dd, 1H, J=12.4 and 2.0 Hz), 4.14 (m, 1H), 4.25 (dd, 1H, J=12.4 and 4.8 Hz), 5.40 (m, 3H), 5.92 (dd, 1H, J=6.8 and 1.6 Hz), 7.28-7.33 (m, 6H) and 7.40-7.45 (m, 4H); $^{13}$C NMR (CDCl$_3$) δ 20.70, 20.72, 20.78, 20.84, 61.8, 65.2, 68.3, 68.7, 68.8, 70.9, 96.17, 96.22, 120.18, 120.22, 120.3, 120.4, 125.90, 125.91, 126.0, 130.1, 130.2, 169.6, 169.9 and 170.7.

δ 20.80, 20.82, 20.9, 21.0, 39.4, 41.1, 62.7, 66.4, 66.8, 67.2, 68.6, 69.1, 69.8, 70.1, 70.4, 97.7, 128.2, 128.6, 136.8, 169.9, 170.0, 170.3, 170.8 and 170.9; mass spectrum (MALDI), m/z 592.34 (M+Na)$^+$; mass spectrum (APCI), m/z 570.2182 (M+H)$^+$ (C$_{26}$H$_{36}$NO$_{13}$ requires m/z 570.2187).

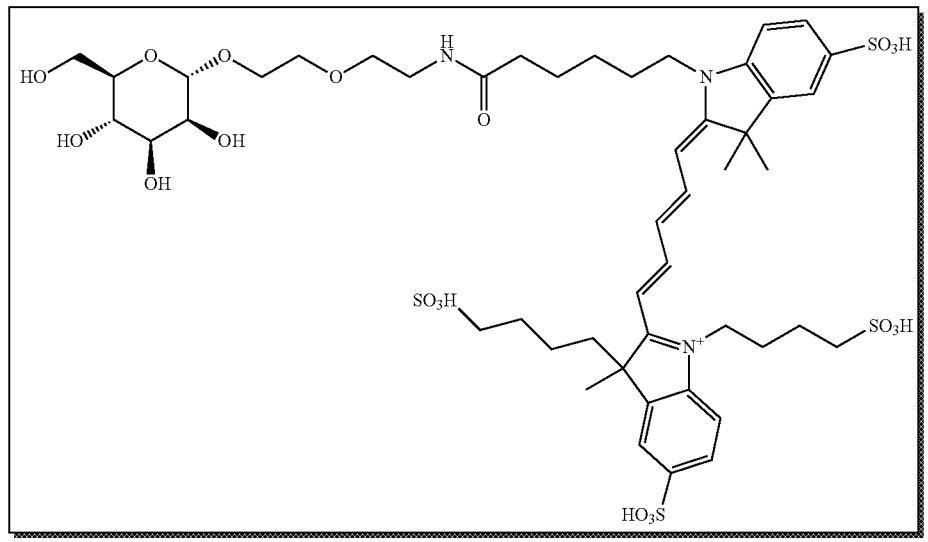

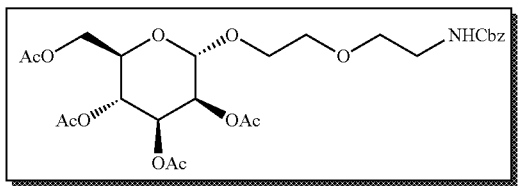

2,3,4,6-Tetra-O-acetyl-α-D-mannopyranosyl benzyl 2-(2-ethoxy)ethylcarbamate (121)

To a solution of 300 mg (0.52 mmol) of phosphate ester 120 and 111 mg (0.46 mmol) of the alcohol 39 in 5.5 mL of anhydrous CH$_2$Cl$_2$, was added 168 μL (207 mg, 0.93 mmol) of TMSOTf at 0° C. The reaction was stirred at 0° C. for 18 min and was then poured into a two-phase solution of EtOAc (100 mL) and satd aq NaHCO$_3$ (40 mL). The organic layer was washed with two 40-mL portions of brine, dried (Na$_2$SO$_4$), filtered and concentrated under diminished pressure. The residue was purified by flash chromatography on a silica gel column (2.5×25 cm). Elution with 2:1→1:2 hexanes-ethyl acetate afforded compound 121 as a colorless oil: yield 110 mg (37%); silica gel TLC $R_f$ 0.35 (1:3 hexanes-ethyl acetate); $^1$H NMR (CDCl$_3$) δ 1.61 (s, 1H), 1.96 (s, 3H), 1.98 (s, 3H), 2.06 (s, 3H), 2.11 (s, 3H), 3.38 (m, 2H), 3.53 (m, 2H), 3.63 (m, 3H), 3.77 (m, 1H), 4.05 (m, 1H), 4.09 (m, 1H), 4.24 (dd, 1H, J=12.4 and 5.2 Hz), 4.87 (d, 1H, J=1.2 Hz), 5.08 (s, 2H), 5.22 (m, 1H), 5.26 (m, 1H), 5.31 (br s, 1H), 5.34 (m, 5H), 7.26-7.34 (m, 5H); $^{13}$C NMR (CDCl$_3$)

Decarbamoyl BLM Monosaccharide-Dye Conjugate 123

To a solution of 8.9 mg (15.6 μmol) of compound 115 in 2 mL of anh methanol was added, 0.2 mL of 25% w/w freshly prepared solution of sodium methoxide in methanol. The reaction mixture was allowed to stir at room temperature for 2.5 h, and the complete consumption of starting material was confirmed by MALDI-TOF mass spectral analysis. The reaction mixture was then quenched by the addition of 500 mg of Dowex 50× resin, shaken for 15 min and filtered; mass spectrum (MALDI), m/z 424.24 (M+Na)$^+$; Mass spectrum (APCI), m/z 402.1759 (M+H)$^+$ (C$_{18}$H$_{28}$NO$_9$ requires m/z 402.1764). To the solution of the crude product in 5 mL methanol was added Pd/C and H$_2$ gas was bubbled through for 45 min. The complete consumption of starting material was confirmed by MALDI-TOF mass spectral analysis. The reaction mixture was filtered through Celite 545® and then concentrated under diminished pressure to afford 122, which was used for the next reaction; mass spectrum (MALDI), m/z 268.25 (M+H)$^+$, 290.25 (M+Na)$^+$; mass spectrum (APCI), m/z 268.1391 (M+H)$^+$ (C$_{10}$H$_{22}$NO$_7$ requires m/z 268.1396).

To 152 μg (0.57 μmol) of 122 was added a solution of 110 μg (0.11 μmol) of Cy5**COOSu (44) in 100 μL of 0.2 M phosphate buffer and the reaction mixture was stirred overnight in the dark. The reaction mixture was purified on an Econosil C$_{18}$ reversed phase semi-preparative (250×10 mm, 10 μm) HPLC column using aq 0.1% TFA and CH$_3$CN mobile phases. A linear gradient was employed (99:1 0.1% aq TFA-CH$_3$CN→69:31 0.1% aq TFA-CH$_3$CN) over a period of 35 min at a flow rate of 4.5 mL/min. The fractions containing the desired product eluted at 19.5 min and were collected, frozen and lyophilized to give 123 as a blue solid: yield 39 μg (30%); mass spectrum (MALDI), m/z 1158.40 (M−H+Na)$^+$, 1180.47 (M−2H+2Na)$^+$.

Example 16: Synthesis of Bleomycin Monosaccharide Trimer-Dye Conjugate 127
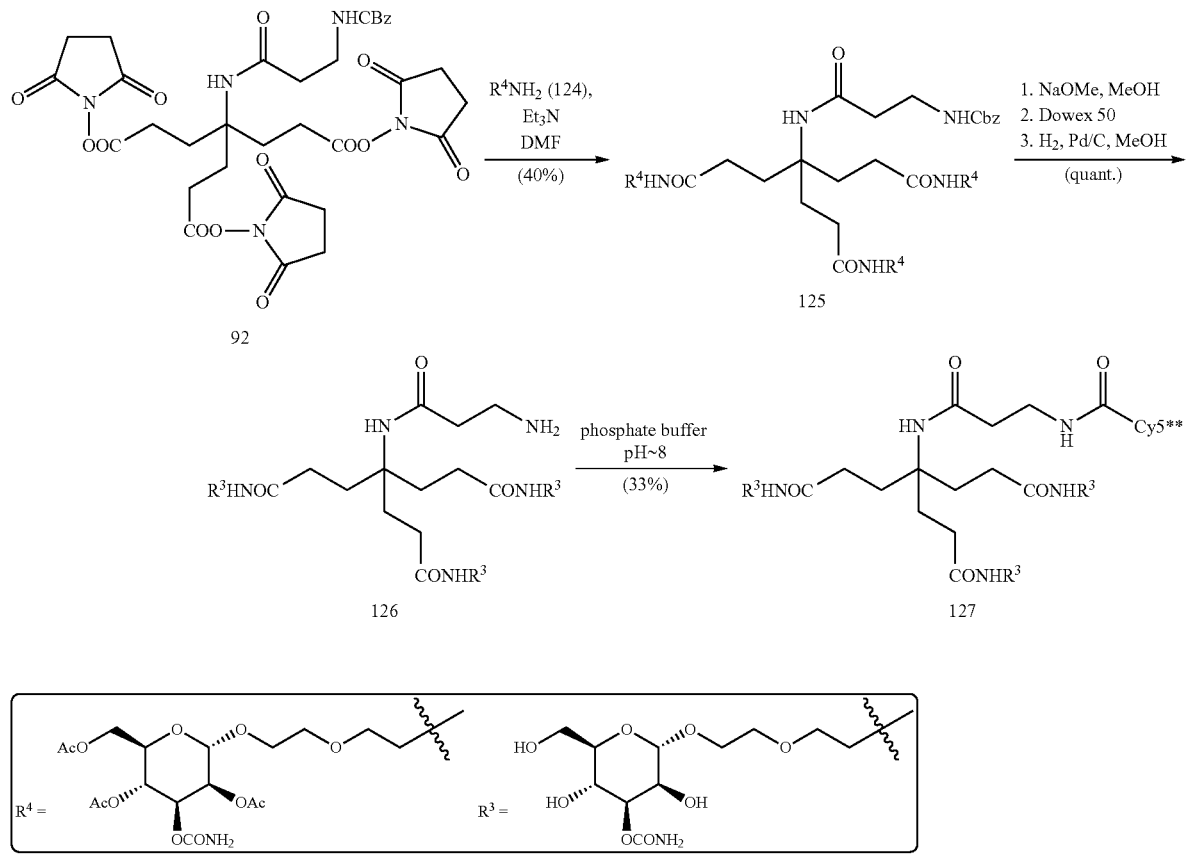
Scheme 16
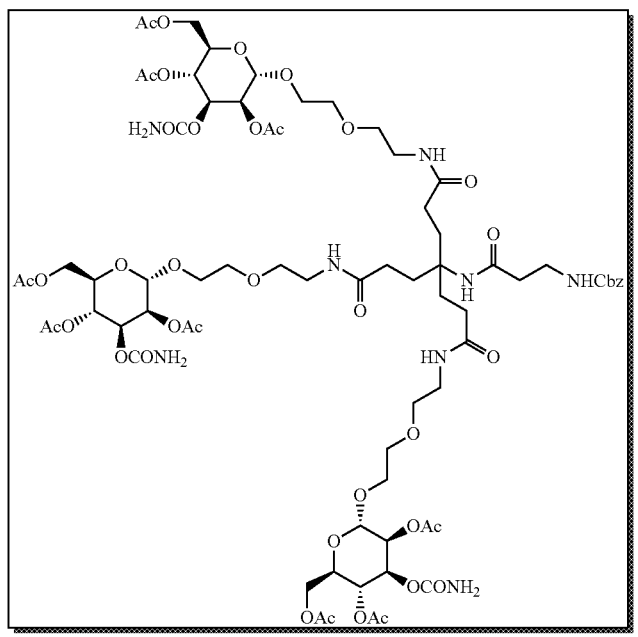

Trimer BLM-Monosaccharide (125)

$H_2$ gas was bubbled through a mixture containing 36 mg (21 µmol) of 115 and a catalytic amount of Pd/C in 6 mL of dry THF for 45 min. The reaction mixture was filtered through a pad of Celite and the filtrate was concentrated under diminished pressure to obtain crude 124 as a colorless oil, which was used immediately in the next step: crude yield 27 mg (99%); silica gel TLC $R_f$ 0.29 (1:3 hexanes-ethyl acetate); mass spectrum (MALDI), m/z 459.26 $(M+Na)^+$; mass spectrum (APCI), m/z 437.1768 $(M+H)^+$ ($C_{17}H_{29}N_2O_{11}$ requires m/z 437.1772).

To a solution containing 27 mg (61.8 µmol) of 124 in 0.53 mL of dry DMF, 13 µL (0.09 mmol) of triethylamine was added 15.2 mg (204 µmol) of 92 were added and stirred at room temperature for 24 h. The reaction mixture was concentrated under diminished pressure. The residue was purified by flash chromatography on a silica gel column (1.5×15 cm). Elution with 16:12:1→11:12:1 chloroform-acetone-methanol afforded trimer BLM monosaccharide 125 as a colorless oil: yield 15 mg (43%); silica gel TLC $R_f$ 0.56 (4:4:1 chloroform-acetone-methanol); mass spectrum (MALDI), m/z 1730.76 $(M+Na)^+$; mass spectrum (TOF), m/z 854.3351 $(M+2H)^{2+}$ ($C_{72}H_{108}N_8O_{39}$ requires m/z 854.3357).

Trimer BLM Monosaccharide-Cy5** (127)

To a solution of 4.2 mg (2.46 µmol) of 125 in 2 mL of anh methanol was added 0.2 mL of 25% w/w freshly prepared solution of sodium methoxide in methanol. The reaction mixture was allowed to stir at room temperature for 2.5 h, and the complete consumption of starting material was confirmed by MALDI-TOF mass spectral analysis. The reaction mixture was then quenched by the addition of 500 mg of Dowex 50× resin, shaken for 15 min and filtered; mass spectrum (MALDI), m/z 1351.40 $(M+Na)^+$ (theoretical m/z 1328.56). To the solution of the crude product in methanol was added Pd/C and $H_2$ gas was bubbled through for 45 min. The complete consumption of starting material was confirmed by MALDI-TOF mass spectral analysis. The reaction mixture was filtered through Celite 545® and then concentrated under diminished pressure to afford 2.9 mg of 126 (quant.), which was used for the next reaction; mass spectrum (MALDI), m/z 1217.62 $(M+Na)^+$; mass spectrum (TOF), m/z 1229.4961 $(M+C_1)^-$ ($C_{46}H_{82}N_8O_{28}Cl$ requires m/z 1229.4927).

To 540 µg (0.448 µmol) of 126 was added a solution of 110 µg (0.11 µmol) of Cy5**COOSu (44) in 100 µL of 0.2 M phosphate buffer and the reaction mixture was stirred overnight in the dark. The reaction mixture was purified on an Econosil $C_{18}$ reversed phase semi-preparative (250×10 mm, 10 µm) HPLC column using aq 0.1% TFA and $CH_3CN$ mobile phases. A linear gradient was employed (99:1 0.1% aq TFA-$CH_3CN$→69:31 0.1% aq TFA-$CH_3CN$) over a period of 28 min at a flow rate of 4.5 mL/min. The fractions containing the desired product eluted at 21.0 min (monitor-

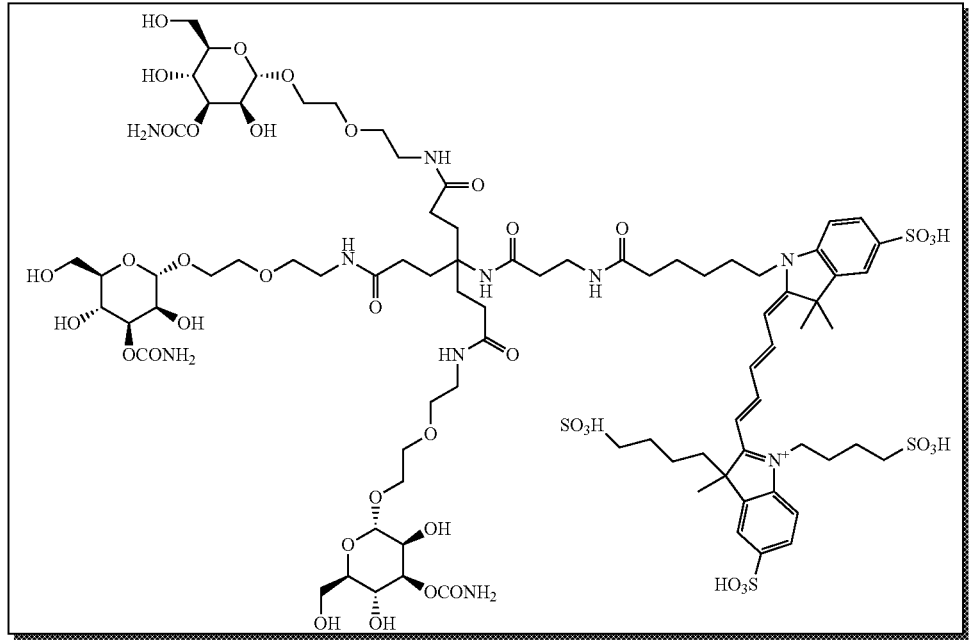

ing at 651 nm) and were collected, frozen and lyophilized to give 127 as a blue solid: yield 77 µg (33%); mass spectrum (MALDI), m/z 2085.85 $(M+Na-H)^+$, 2107.85 $(M+2Na-2H)^+$; mass spectrum (TOF), m/z 686.6584 $(M-4H)^{3-}$ ($C_{84}H_{127}N_{10}O_{41}S_4$ requires m/z 686.5679).

Example 17: Synthesis of $C_2$ Modified Mannose Monosaccharide-Dye Conjugates 140, 141, 142 and 143
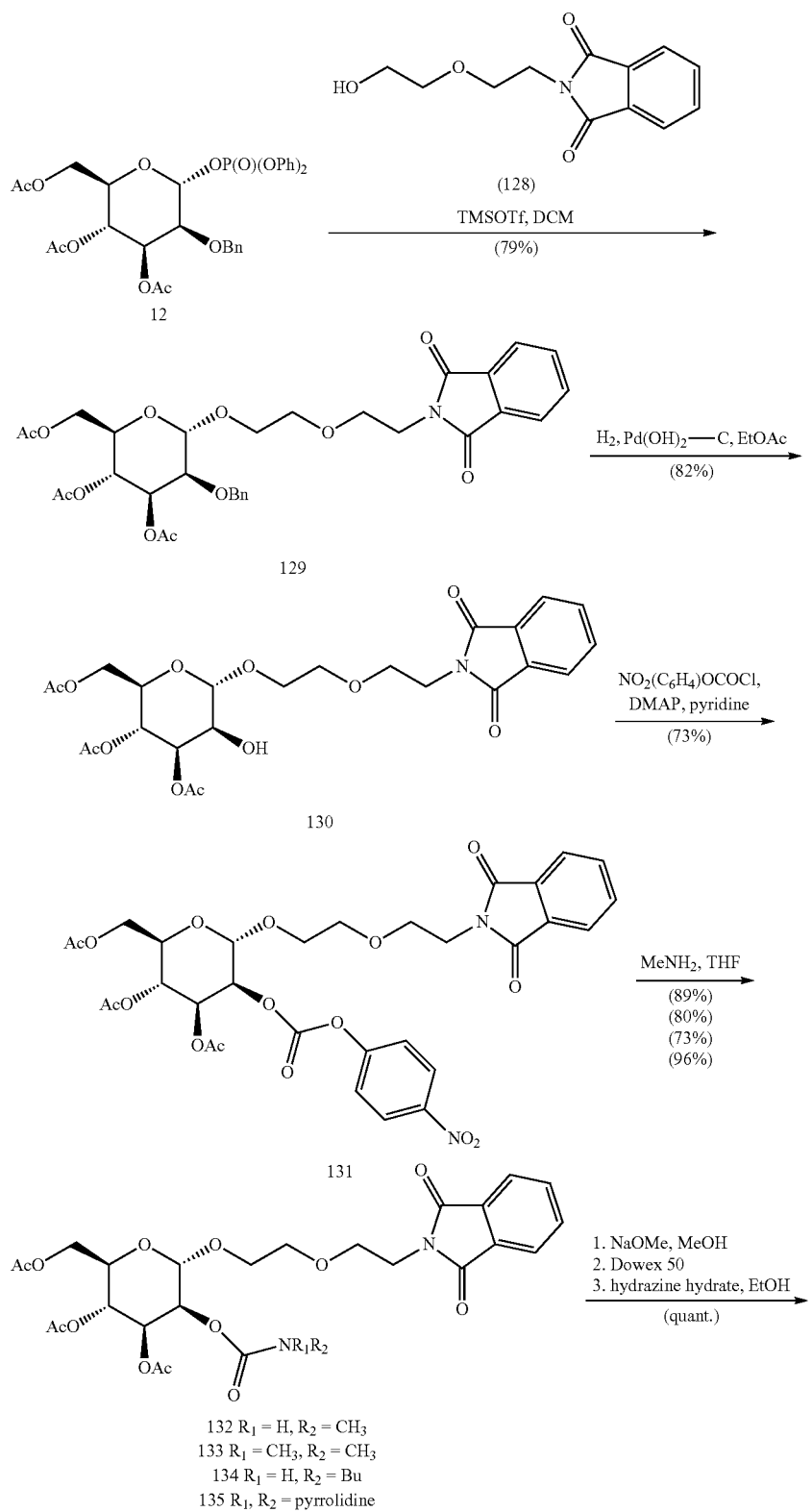
Scheme 17

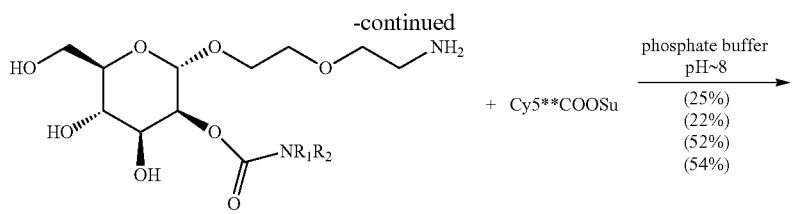

136 R₁ = H, R₂ = CH₃
137 R₁ = CH₃, R₂ = CH₃
138 R₁ = H, R₂ = Bu
139 R₁, R₂ = pyrrolidine

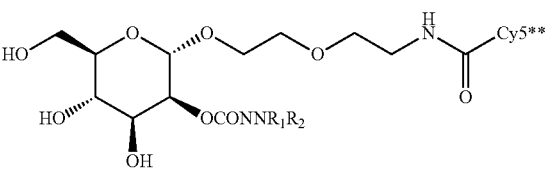

140 R₁ = H, R₂ = CH₃
141 R₁ = CH₃, R₂ = CH₃
142 R₁ = H, R₂ = Bu
143 R₁, R₂ = pyrrolidine

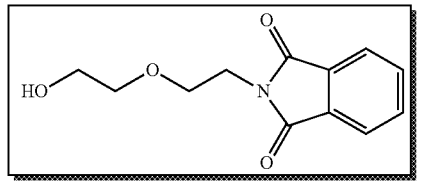

2-(2-(2-hydroxyethoxy)ethyl)isoindoline-1,3-dione (128)

2-(2-aminoethyl)-ethanol (2.10 g, 19.94 mmol) and phthalic anhydride (2.95 g, 19.94 mmol) were dissolved in 90 mL toluene and the resulting solution was then heated under reflux for 6 h with Dean-Stark apparatus. The reaction mixture was allowed to cool, dried over MgSO₄, filtered, and concentrated under diminished pressure afforded compound 128 as a white solid: yield 4.67 g (99%); silica gel TLC $R_f$ 0.35 (1:2 hexanes-ethyl acetate); $^1$H NMR (CDCl₃) δ 3.61 (m, 2H), 3.69 (m, 2H), 3.75 (t, 2H, J=5.3 Hz), 3.91 (t, 2H, J=5.3 Hz), 7.73 (m, 2H), 7.85 (m, 2H, m).

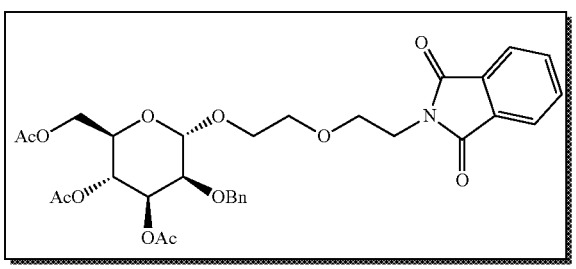

3,4,6-Tri-O-acetyl-2-O-benzyl-α-D-mannopyranosyl 2-(2-(ethoxy)ethyl)isoindoline-1,3-dione (129)

To a solution of 1.11 g (1.77 mmol) of phosphate ester 12 and 374 mg (1.59 mmol) of the alcohol 128 in 30 mL of anhydrous CH₂Cl₂, was added 0.58 mL (707 mg, 3.18 mmol) of TMSOTf at 0° C. The reaction was stirred at 0° C.

for 20 min and was then poured into a two-phase solution of EtOAc (150 mL) and satd aq NaHCO₃ (60 mL). The organic layer was washed with two 40-mL portions of brine, dried (MgSO₄), filtered and concentrated under diminished pressure. The residue was purified by flash chromatography on a silica gel column (5×22 cm). Elution with 4:1→1:1 hexanes-ethyl acetate afforded compound 129 as a colorless oil: yield 860 mg (79%); silica gel TLC $R_f$ 0.41 (1:1 hexanes-ethyl acetate); $^1$H NMR (CDCl₃) δ 1.91 (s, 3H), 1.96 (s, 3H), 2.00 (s, 3H), 3.54 (m, 3H), 3.67 (m, 3H), 3.78 (m, 1H), 3.82 (m, 1H), 3.88 (m, 1H), 4.00 (m, 1H), 4.16 (m, 1H), 4.57 (q, 2H, J=12.0 Hz), 4.82 (d, 1H, J=1.2 Hz), 5.16 (m, 1H), 5.32 (t, 1H, J=10.0 Hz), 7.22-7.30 (m, 5H), 7.63 (m, 2H) and 7.76 (m, 2H); $^{13}$C NMR (CDCl₃) δ 20.83, 20.85, 20.93, 37.29, 62.76, 66.71, 67.01, 68.13, 68.63, 69.55, 71.33, 73.09, 75.47, 97.98, 123.34, 127.86, 127.89, 128.41, 132.16, 133.02, 137.90, 168.27, 169.79, 170.18, 170.87; mass spectrum (ESI), m/z 636.2040 (M+Na)⁺ (C₃₁H₃₅NO₁₂Na requires m/z 636.2057).

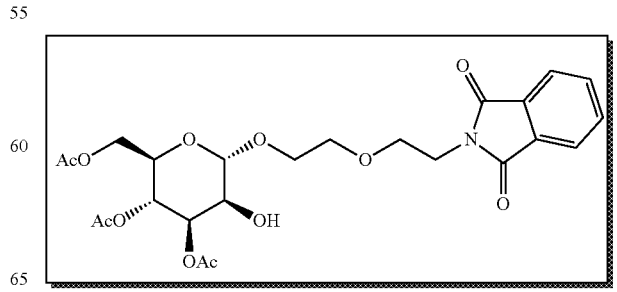

3,4,6-Tri-O-acetyl-α-D-mannopyranosyl 2-(2-(ethoxy)ethyl)isoindoline-1,3-dione (130)

To a solution of 860 mg (1.40 mmol) of 129 in 23 mL of EtOAc was added a catalytic amount of Pd(OH)$_2$—C and the reaction was placed under 1 atm of H$_{2(g)}$ overnight. The catalyst was removed by filtration through a pad of Celite 545® and concentrated under diminished pressure. The residue was purified by flash chromatography on a silica gel column (3.5×18 cm). Elution with 3:1→1:1 hexanes-ethyl acetate afforded 130 as a colorless foam: yield 601 mg (82%); silica gel TLC R$_f$ 0.13 (1:1 hexanes-ethyl acetate). $^1$H NMR (CDCl$_3$) δ 1.97 (s, 3H), 2.01 (s, 3H), 2.011 (s, 3H), 2.94 (br s, 1H), 3.60 (m, 3H), 3.69 (m, 3H), 3.84 (m, 2H), 3.94 (m, 1H), 4.00 (m, 2H), 4.20 (m, 1H), 4.84 (d, 1H, J=2.0 Hz), 5.17 (m, 1H), 5.28 (t, 1H, J=10.0 Hz), 7.67 (m, 2H) and 7.80 (m, 2H); $^{13}$C NMR (CDCl$_3$) δ 20.73, 20.77, 20.90, 37.40, 62.57, 66.30, 66.96, 68.09, 68.33, 69.06, 69.74, 71.62, 99.87, 123.34, 132.00, 134.05, 168.34, 169.90, 170.01, 170.86; mass spectrum (ESI), m/z 546.1596 (M+Na)$^+$ (C$_{24}$H$_{29}$NO$_{12}$Na requires m/z 546.1588).

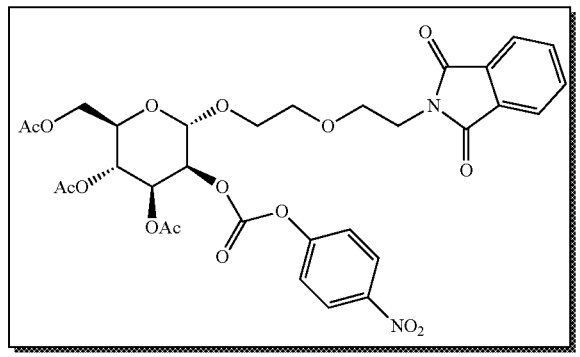

3,4,6-Tri-O-acetyl-2-O-((p-nitrophenyl)carbamoyl)-α-D-mannopyranosyl 2-(2-(ethoxy)ethyl)isoindoline-1,3-dione (131)

To a solution of 461 mg (0.88 mmol) of 130 in 4.8 mL of pyridine was added 430 mg (3.52 mmol) of DMAP and 710 mg (3.52 mmol) of p-nitrophenyl chloroformate and was stirred at 40° C. overnight. The solution was cooled and poured into a two-phase solution of 20 mL EtOAc and 5 mL of H$_2$O. The organic layer was washed with three 10 mL portions of 1N HCl, 5 mL of satd aq. NaHCO$_3$ and 5 mL of brine. The solution was dried over MgSO$_4$, filtered, and concentrated under diminished pressure. The residue was purified by flash chromatography on a silica gel column (2.5×30 cm). Elution with 4:1→1:1 hexanes-ethyl acetate afforded 131 as a white foam: yield 730 mg (73%); silica gel TLC R$_f$ 0.55 (1:1 hexanes-ethyl acetate). $^1$H NMR (CDCl$_3$) δ 2.02 (s, 3H), 2.05 (s, 3H), 2.07 (s, 3H), 3.66 (m, 2H), 3.72 (m, 3H), 3.79 (m, 1H), 3.89 (m, 2H), 4.06 (m, 2H), 4.17 (m, 1H), 5.08 (m, 1H), 5.18 (m, 1H), 5.30 (t, 1H, J=10.0 Hz), 5.41 (m, 1H), 7.44 (d, 2H, J=9.2 Hz), 7.70 (m, 2H) and 7.84 (m, 2H), 8.29 (d, 2H, J=9.2 Hz); $^{13}$C NMR (CDCl$_3$) δ 20.83, 20.85, 20.86, 37.46, 62.45, 66.03, 67.31, 68.37, 68.57, 69.14, 69.84, 74.54, 97.18, 121.89, 123.45, 125.51, 132.23, 134.12, 145.68, 152.06, 155.53, 168.39, 169.85, 170.80; mass spectrum (APCI), m/z 689.1817 (M+H)$^+$ (C$_{31}$H$_{33}$N$_2$O$_{16}$ requires m/z 689.1830).

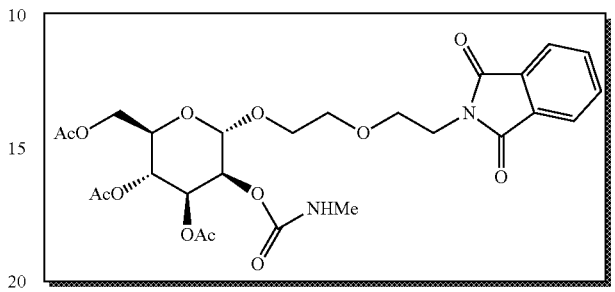

3,4,6-Tri-O-acetyl-2-O-(methylcarbamoyl)-α-D-mannopyranosyl 2-(2-(ethoxy)ethyl)isoindoline-1,3-dione (132)

To a solution containing 166 mg (0.24 mmol) of carbamate 131 in 7.6 mL of anh THF, was added dropwise 0.12 mL (2 M solution in THF, 0.24 mmol) of methylamine at 0° C. The reaction mixture was allowed to warm to room temperature and then stirred overnight at which time silica gel TLC analysis indicated that the reaction was complete. The solvent was concentrated under diminished pressure to afford a crude residue, which was purified by flash chromatography on a silica gel column (2.5×18 cm). Elution with 3:1→1:2 hexanes-ethyl acetate afforded disaccharide 132 as a colorless foam: yield 125 mg (89%); silica gel TLC R$_f$ 0.11 (1:1 hexanes-ethyl acetate). $^1$H NMR (CDCl$_3$) δ 1.96 (s, 3H), 2.01 (s, 3H), 2.04 (s, 3H), 2.77 (d, 3H, J=4.8 Hz), 3.62 (m, 3H), 3.71 (m, 3H), 3.89 (m, 2H), 4.01 (m, 2H), 4.27 (m, 1H), 4.85 (s, 1H), 4.89 (q, 1H, J=4.8 Hz), 5.11 (m, 1H), 5.21 (m, 1H), 5.28 (m, 1H), 7.68 (m, 2H) and 7.82 (m, 2H); $^{13}$C NMR (CDCl$_3$) δ 20.80, 20.85, 27.64, 37.27, 62.59, 64.40, 66.24, 67.22, 68.13, 68.30, 69.40, 70.11, 77.36, 98.08, 123.36, 132.17, 134.00, 155.82, 168.25, 169.90, 169.94, 170.75; mass spectrum (ESI), m/z 603.1797 (M+Na)$^+$ (C$_{26}$H$_{32}$N$_2$O$_3$Na requires m/z 603.1802).

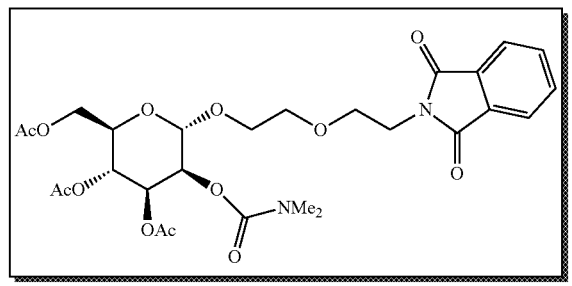

3,4,6-Tri-O-acetyl-2-O-(dimethylcarbamoyl)-α-D-mannopyranosyl 2-(2-(ethoxy)ethyl)isoindoline-1,3-dione (133)

To a solution containing 180 mg (0.26 mmol) of carbamate 131 in 8.2 mL of anh THF, was added dropwise 0.13 mL (2 M solution in THF, 0.26 mmol) of dimethylamine at 0° C. The reaction mixture was allowed to warm to room temperature and then stirred overnight at which time silica gel TLC analysis indicated that the reaction was complete. The solvent was concentrated under diminished pressure to afford a crude residue, which was purified by flash chromatography on a silica gel column (2.5×18 cm). Elution with 3:1→1:2 hexanes-ethyl acetate afforded disaccharide 133 as a colorless foam: yield 125 mg (80%); silica gel TLC $R_f$ 0.15 (1:1 hexanes-ethyl acetate). $^1$H NMR (CDCl$_3$) δ 1.95 (s, 3H), 2.01 (s, 3H), 2.014 (s, 3H), 2.88 (s, 3H), 2.96 (s, 3H), 3.61 (m, 3H), 3.72 (m, 3H), 3.86 (m, 2H), 4.02 (m, 2H), 4.25 (m, 1H), 4.85 (d, 1H, J=1.6 Hz), 5.08 (m, 1H), 5.28 (m, 2H), 7.68 (m, 2H) and 7.81 (m, 2H); $^{13}$C NMR (CDCl$_3$) δ 20.71, 20.80, 20.84, 36.04, 36.57, 37.26, 62.49, 66.20, 67.26, 68.11, 68.36, 69.39, 69.41, 70.59, 97.92, 123.33, 132.15, 133.97, 155.19, 168.22, 169.87, 169.92, 170.62; mass spectrum (ESI), m/z 617.1963 (M+Na)$^+$ (C$_{27}$H$_{34}$N$_2$O$_{13}$Na requires m/z 617.1959).

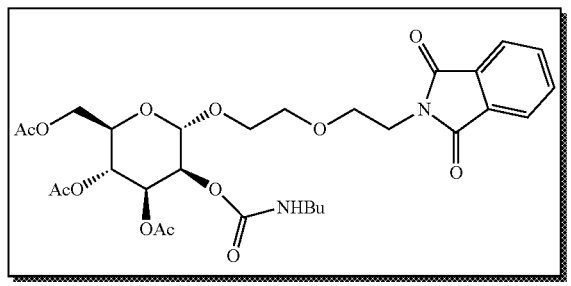

3,4,6-Tri-O-acetyl-2-O-(butylcarbamoyl)-α-D-mannopyranosyl 2-(2-(ethoxy)ethyl)isoindoline-1,3-dione (134)

To a solution containing 41 mg (0.06 mmol) of carbamate 131 in 1.9 mL of anh THF, was added dropwise 30 μL (2 M solution in THF, 0.06 mmol) of butylamine at 0° C. The reaction mixture was allowed to warm to room temperature and then stirred overnight at which time silica gel TLC analysis indicated that the reaction was complete. The solvent was concentrated under diminished pressure to afford a crude residue, which was purified by flash chromatography on a silica gel column (2.5×18 cm). Elution with 3:1→1:2 hexanes-ethyl acetate afforded disaccharide 134 as a colorless foam: yield 27 mg (73%); silica gel TLC $R_f$ 0.17 (1:1 hexanes-ethyl acetate). $^1$H $^1$H NMR (CDCl$_3$) δ 0.91 (t, 3H, J=7.2 Hz), 1.35 (m, 2H), 1.48 (m, 2H), 1.98 (s, 3H), 2.03 (s, 3H), 2.06 (s, 3H), 3.16 (q, 2H, J=6.8 Hz), 3.63 (m, 3H), 3.75 (m, 3H), 3.89 (m, 2H), 4.04 (m, 2H), 4.30 (m, 1H), 4.87 (s, 2H), 5.13 (br s, 1H), 5.27 (m, 2H), 7.70 (m, 2H) and 7.84 (m, 2H); $^{13}$C NMR (CDCl$_3$) δ 13.81, 19.98, 20.85, 20.87, 20.92, 29.81, 31.96, 37.33, 41.03, 62.68, 66.36, 67.31, 68.19, 68.36, 69.44, 69.49, 69.99, 98.22, 123.42, 132.24, 134.04, 155.26, 168.32, 169.95, 170.83; mass spectrum (ESI), m/z 645.2278 (M+Na)$^+$ (C$_{29}$H$_{38}$N$_2$O$_3$Na requires m/z 645.2272).

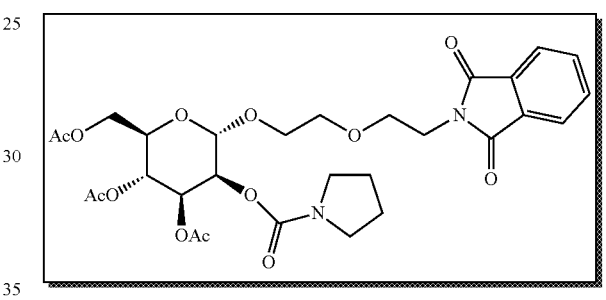

3,4,6-Tri-O-acetyl-2-O-(pyrrolidinylcarbamoyl)-α-D-mannopyranosyl 2-(2-(ethoxy)ethyl)isoindoline-1,3-dione (135)

To a solution containing 80 mg (0.12 mmol) of carbamate 131 in 3.7 mL of anh THF, was added dropwise 10 μL (0.12 mmol) of pyrrolidine at 0° C. The reaction mixture was allowed to warm to room temperature and then stirred overnight at which time silica gel TLC analysis indicated that the reaction was complete. The solvent was concentrated under diminished pressure to afford a crude residue, which was purified by flash chromatography on a silica gel column (2.5×18 cm). Elution with 3:1-hexanes-ethyl acetate afforded disaccharide 135 as a colorless foam: yield 69 mg (96%); silica gel TLC $R_f$ 0.19 (1:1 hexanes-ethyl acetate). $^1$H NMR (CDCl$_3$) δ 1.88 (m, 4H), 1.96 (s, 3H), 2.01 (s, 3H), 2.03 (s, 3H), 3.35 (m, 2H), 3.45 (s, 2H), 3.62 (m, 3H), 3.71 (m, 3H), 3.89 (m, 2H), 4.04 (m, 2H), 4.26 (m, 1H), 4.87 (s, 1H), 5.11 (m, 1H), 5.31 (m, 2H), 7.68 (m, 2H) and 7.82 (m, 2H); $^{13}$C NMR (CDCl$_3$) δ 20.75, 20.83, 20.89, 25.02, 25.68, 37.28, 45.95, 46.31, 62.60, 66.33, 67.28, 68.14, 68.42, 69.41, 69.45, 70.25, 98.02, 123.36, 132.19, 134.00, 153.58, 168.27, 169.95, 169.98, 170.67; mass spectrum (ESI), m/z 643.2123 (M+Na)$^+$ (C$_{29}$H$_{36}$N$_2$O$_{13}$Na requires m/z 643.2115).

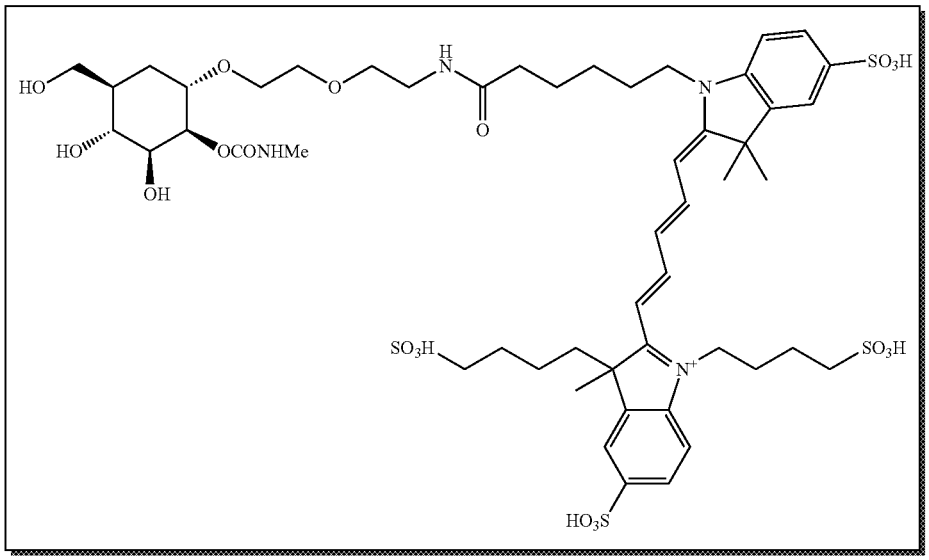

Monosaccharide-Dye Conjugate 140

To a solution of 9.0 mg (15.5 µmol) of compound 132 in 2 mL of anh methanol, was added 0.2 mL of 25% w/w freshly prepared solution of sodium methoxide in methanol. The reaction mixture was allowed to stir at room temperature for 2.5 h, and the complete consumption of starting material was confirmed by MALDI-TOF mass spectral analysis. The reaction mixture was then quenched by the addition of 500 mg of Dowex 50× resin, shaken for 15 min and filtered; mass spectrum MALDI), m/z 477.33 (M+Na)$^+$; mass spectrum (APCI), m/z 445.1661 (M+H)$^+$ ($C_{20}H_{27}N_2O_{10}$ requires m/z 445.1665). To the solution of the crude product in methanol was added Pd/C and $H_2$ gas was bubbled through for 45 min. The complete consumption of starting material was confirmed by MALDI-TOF mass spectral analysis. The reaction mixture was filtered through Celite 545® and then concentrated under diminished pressure to afford 136, which was used for the next reaction; mass spectrum (MALDI), m/z 347.12 (M+Na)$^+$.

To 191 µg (0.59 µmol) of 136 was added a solution of 110 µg (0.11 µmol) of Cy5**COOSu (44) in 100 µL of 0.2 M phosphate buffer and the reaction mixture was stirred overnight in the dark. The reaction mixture was purified on an Econosil $C_{18}$ reversed phase semi-preparative (250×10 mm, 10 µm) HPLC column using aq 0.1% TFA and $CH_3CN$ mobile phases. A linear gradient was employed (99:1 0.1% aq TFA-$CH_3CN$→69:31 0.1% aq TFA-$CH_3CN$) over a period of 28 min at a flow rate of 4.5 mL/min. The fractions containing the desired product eluted at 19.4 min and were collected, frozen and lyophilized to give 140 as a blue solid: yield 34 µg (25%); mass spectrum (MALDI), m/z 1193.34 (M)$^+$, 1215.33 (M−H+Na)$^+$.

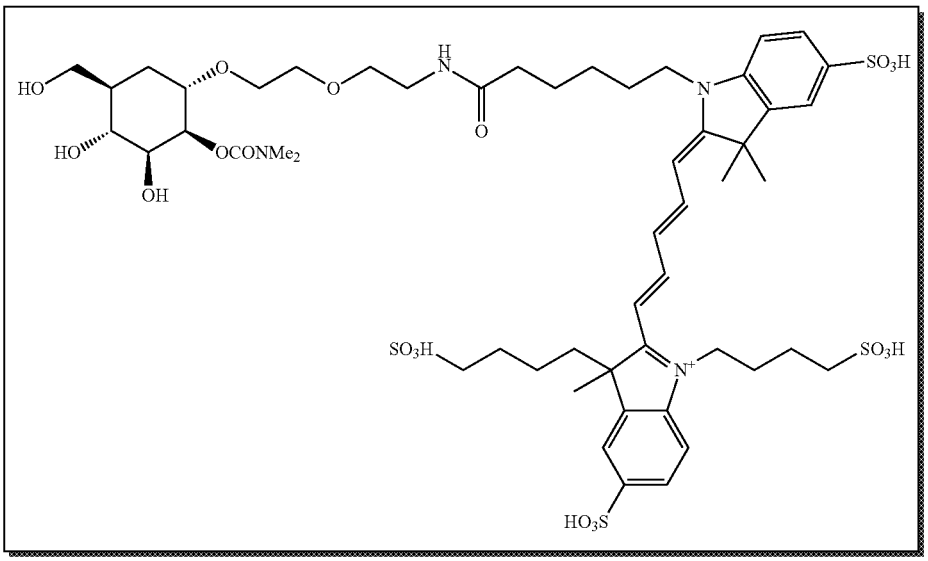

Monosaccharide-Dye Conjugate 141

To a solution of 9.0 mg (15.1 µmol) of compound 133 in 2 mL of anh methanol, was added 0.2 mL of 25% w/w freshly prepared solution of sodium methoxide in methanol. The reaction mixture was allowed to stir at room temperature for 2.5 h, and the complete consumption of starting material was confirmed by MALDI-TOF mass spectral analysis. The reaction mixture was then quenched by the addition of 500 mg of Dowex 50× resin, shaken for 15 min and filtered; mass spectrum (MALDI), m/z 491.32 (M+Na)$^+$; mass spectrum (APCI), m/z 491.1639 (M+Na)$^+$ ($C_{21}H_{28}N_2O_{10}Na$ requires m/z 491.1642). To the solution of the crude product in methanol was added Pd/C and $H_2$ gas was bubbled through for 45 min. The complete consumption of starting material was confirmed by MALDI-TOF mass spectral analysis. The reaction mixture was filtered through Celite 545® and then concentrated under diminished pressure to afford 137, which was used for the next reaction; mass spectrum (MALDI), m/z 339.22 (M+H)$^+$; mass spectrum (APCI), m/z 339.1773 (M+H)$^+$ ($C_{13}H_{27}N_2O_8$ requires m/z 339.1767).

To 192 µg (0.57 µmol) of 137 was added a solution of 110 µg (0.11 µmol) of Cy5**COOSu (44) in 100 µL of 0.2 M phosphate buffer and the reaction mixture was stirred overnight in the dark. The reaction mixture was purified on an Econosil $C_{18}$ reversed phase semi-preparative (250×10 mm, 10 µm) HPLC column using aq 0.1% TFA and $CH_3CN$ mobile phases. A linear gradient was employed (99:1 0.1% aq TFA-$CH_3CN$→69:31 0.1% aq TFA-$CH_3CN$) over a period of 28 min at a flow rate of 4.5 mL/min. The fractions containing the desired product eluted at 21.0 min and were collected, frozen and lyophilized to give 141 as a blue solid: yield 30 µg (22%); mass spectrum (MALDI), m/z 1208.36 (M)$^+$, 1246.34 (M−H+K)$^+$.

Monosaccharide-Dye Conjugate 142

To a solution of 10.0 mg (16.1 µmol) of compound 134 in 2 mL of anh methanol, was added 0.2 mL of 25% w/w freshly prepared solution of sodium methoxide in methanol. The reaction mixture was allowed to stir at room temperature for 2.5 h, and the complete consumption of starting material was confirmed by MALDI-TOF mass spectral analysis. The reaction mixture was then quenched by the addition of 500 mg of Dowex 50× resin, shaken for 15 min and filtered; mass spectrum (MALDI), m/z 519.40 (M+Na)$^+$; mass spectrum (ESI), m/z 519.1958 (M+Na)$^+$ ($C_{23}H_{32}N_2O_{10}Na$ requires m/z 519.1954). To the solution of the crude product in methanol was added Pd/C and $H_2$ gas was bubbled through for 45 min. The complete consumption of starting material was confirmed by MALDI-TOF mass spectral analysis. The reaction mixture was filtered through Celite 545® and then concentrated under diminished pressure to afford 138, which was used for the next reaction; mass spectrum (APCI), m/z 367.2078 (M+H)$^+$ ($C_{15}H_{31}N_2O_8$ requires m/z 367.2080).

To 221 µg (0.60 µmol) of 138 was added a solution of 110 µg (0.11 µmol) of Cy5**COOSu (44) in 100 µL of 0.2 M phosphate buffer and the reaction mixture was stirred overnight in the dark. The reaction mixture was purified on an Econosil $C_{18}$ reversed phase semi-preparative (250×10 mm, 10 µm) HPLC column using aq 0.1% TFA and $CH_3CN$ mobile phases. A linear gradient was employed (99:1 0.1% aq TFA-$CH_3CN$→69:31 0.1% aq TFA-$CH_3CN$) over a 19.3 min and were collected, frozen and lyophilized to give 142 as a blue solid: yield 73 µg (52%); mass spectrum (MALDI), m/z 1235.41 (M)$^+$.

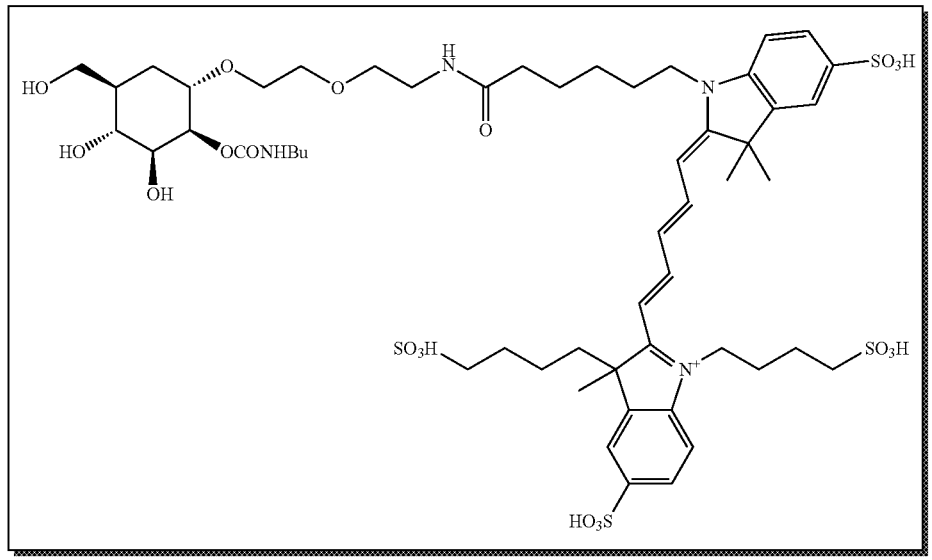

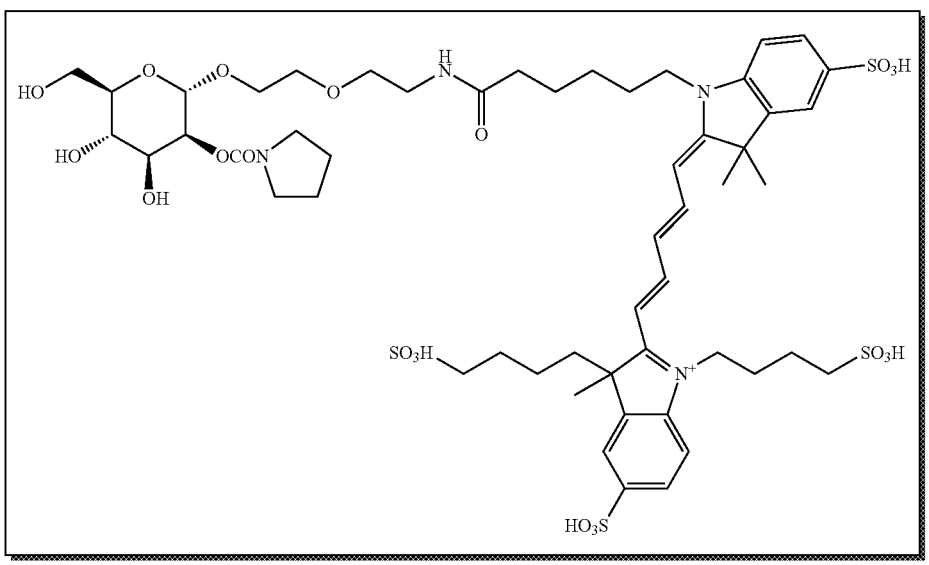

Monosaccharide-Dye Conjugate 143

To a solution of 18.0 mg (29.0 μmol) of compound 135 in 4 mL of anh methanol, was added 0.4 mL of 25% w/w freshly prepared solution of sodium methoxide in methanol. The reaction mixture was allowed to stir at room temperature for 2.5 h, and the complete consumption of starting material was confirmed by MALDI-TOF mass spectral analysis. The reaction mixture was then quenched by the addition of 500 mg of Dowex 50x resin, shaken for 15 min and filtered; mass spectrum (ESI), m/z 517.1808 (M+Na)$^+$ ($C_{23}H_{30}N_2O_{10}Na$ requires m/z 517.1798). To the solution of the crude product in methanol was added Pd/C and $H_2$ gas was bubbled through for 45 min. The complete consumption of starting material was confirmed by MALDI-TOF mass spectral analysis. The reaction mixture was filtered through Celite 545® and then concentrated under diminished pressure to afford 139, which was used for the next reaction; mass spectrum (APCI), m/z 365.1926 (M+H)$^+$ ($C_{15}H_{29}N_2O_8$ requires m/z 365.1924).

To 220 μg (0.60 μmol) of 139 was added a solution of 110 μg (0.11 μmol) of Cy5**COOSu (44) in 100 μL of 0.2 M phosphate buffer and the reaction mixture was stirred overnight in the dark. The reaction mixture was purified on an Econosil $C_{18}$ reversed phase semi-preparative (250×10 mm, 10 μm) HPLC column using aq 0.1% TFA and $CH_3CN$ mobile phases. A linear gradient was employed (99:1 0.1% aq TFA-$CH_3CN$→69:31 0.1% aq TFA-$CH_3CN$) over a period of 35 min at a flow rate of 4.5 mL/min. The fractions containing the desired product eluted at 20.7 min and were collected, frozen and lyophilized to give 143 as a blue solid: yield 75 μg (54%); mass spectrum (MALDI), m/z 1255.47 (M−H+Na)$^+$, 1277.55 (M−2H+2Na)$^+$, 1299.49 (M−3H+3Na)$^+$; mass spectrum (APCI), m/z 1233.4021 (M)$^+$ ($C_{53}H_{77}N_4O_{21}S_4$ requires m/z 1233.3958).

Example 18: Synthesis of Peracetylated Fluoro BLM Disaccharide 169

Scheme 18

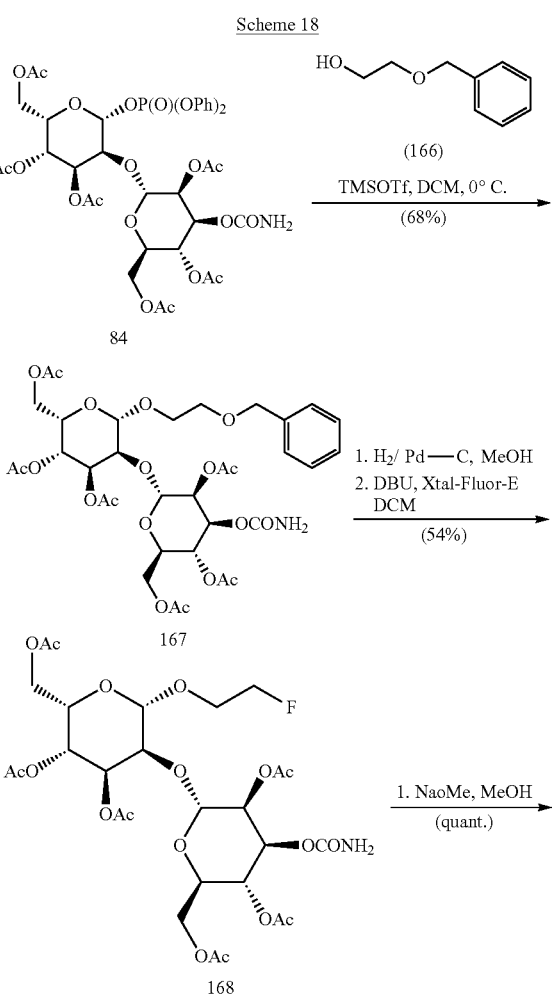

-continued

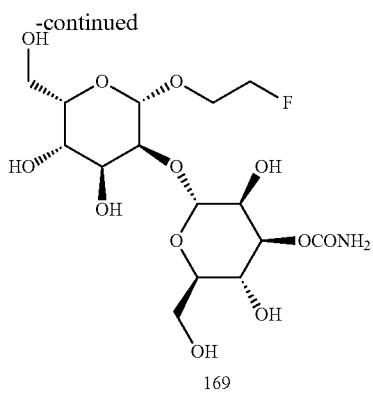

169

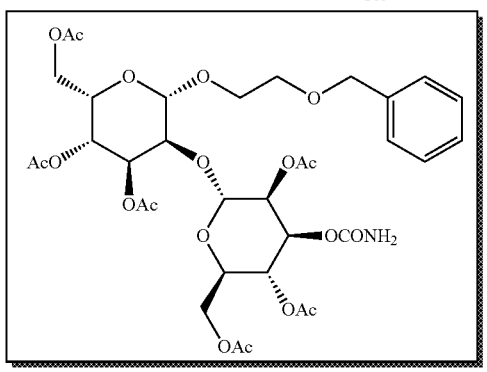

3,4,6-Tri-acetyl-2-O-(2,4,6-tri-O-acetyl-3-O-carbamoyl-α-D-mannopyranosyl)-α-L-gulopyranosyl 2-(benzyloxy)ethane (167)

To a solution of 63 mg (0.07 mmol) of 84 and 9.2 µL (0.06 mmol) of 2-(benzyloxy)ethanol (166) in 1.8 mL of anhydrous CH$_2$Cl$_2$ was added 24 µL (29 mg, 0.13 mmol) of TMSOTf at 0° C. The reaction mixture was stirred at 0° C. for 18 min, at which time it was poured into a two-phase solution of EtOAc (30 mL) and satd aq NaHCO$_3$ (15 mL). The organic layer was washed with two 15 mL portions of brine, dried (Na$_2$SO$_4$), filtered and concentrated under diminished pressure. The residue was purified by flash chromatography on a silica gel column (1.5×25 cm). Elution with 1:1 hexanes-ethyl acetate afforded compound 167 as a colorless oil: yield 34 mg (68%); silica gel TLC R$_f$ 0.41 (1:3 hexanes-ethyl acetate). $^1$H NMR (CDCl$_3$) δ 1.98-2.14 (m, 18H), 3.69 (m, 3H), 3.81 (m, 2H), 4.19 (m, 4H), 4.26 (m, 2H), 4.57 (m, 3H), 4.75 (m, 1H), 4.91 (m, 2H), 5.35 (m, 3H), 7.27-7.31 (m, 5H); mass spectrum (APCI), m/z 772.2665 (M+H)$^+$ (C$_{34}$H$_{46}$NO$_{91}$ requires m/z 772.2664).

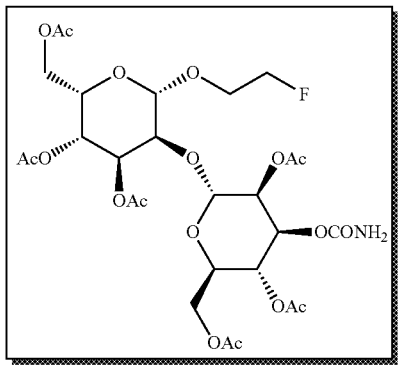

3,4,6-Tri-acetyl-2-O-(2,4,6-tri-O-acetyl-3-O-carbamoyl-α-D-mannopyranosyl)-α-L-gulopyranosyl 2-(fluoro)ethane (168)

To a solution of 20 mg (0.03 mmol) of 167 in 3 mL of MeOH was added a catalytic amount of Pd—C and the reaction was placed under 1 atm of H$_{2(g)}$ overnight. The catalyst was removed by filtration through a pad of Celite 545® and concentrated under diminished pressure to give a colorless oil: yield 19 mg (quant.); silica gel TLC R$_f$ 0.08 (1:3 hexanes-ethyl acetate).

To the solution of 19 mg (0.3 mmol) of the residue in 0.3 mL of anhydrous CH$_2$Cl$_2$ at −78° C., 6.2 mL (0.04 mmol) of DBU and 10 mg (0.04 mmol) of Xtal-Fluor-E were added and stirred for 30 min. The reaction mixture was then allowed to warm to rt and stirred for 24 h. The solution was poured into a two-phase solution of EtOAc (10 mL) and satd aq NaHCO$_3$ (5 mL). The organic layer was washed with 5 mL portions of brine, dried (Na$_2$SO$_4$), filtered and concentrated under diminished pressure. The residue was purified by flash chromatography on a silica gel column (1.5×25 cm). Elution with 1:1→1:3 hexanes-ethyl acetate afforded compound 168 as a colorless oil: yield 9 mg (54% over two steps); silica gel TLC R$_f$ 0.34 (1:3 hexanes-ethyl acetate). $^1$H NMR (CDCl$_3$) δ 1.99-2.17 (m, 21H), 3.41 (m, 3H), 4.17 (m, 3H), 4.28 (m, 2H), 4.52 (m, 2H), 4.64 (br s, 2H), 4.71 (m, 2H), 4.91 (m, 1H), 5.08 (m, 2H), 5.29 (m, 3H); $^{19}$F NMR (CDCl$_3$) δ −223.1 (m), −223.9 (m); m/z 722.43 (M+K)$^+$; mass spectrum (APCI), m/z 684.2151 (M+H)$^+$ (C$_{27}$H$_{39}$FNaO$_{18}$ requires m/z 684.2151).

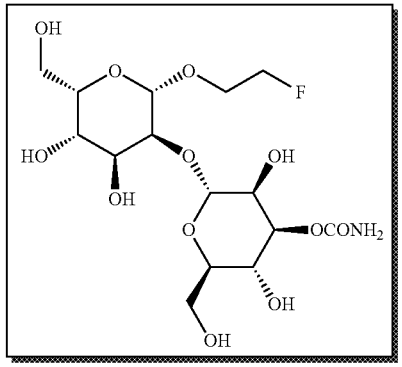

Fluoro-BLM-Disaccharide (169)

To a solution of 1.0 mg (1.5 µmol) of 168 in 1 mL of anh methanol, was added 0.1 mL of 25% w/w freshly prepared solution of sodium methoxide in methanol. The reaction mixture was allowed to stir at room temperature for 2.5 h, and the complete consumption of starting material was confirmed by MALDI-TOF mass spectral analysis. The reaction mixture was then quenched by the addition of 500 mg of Dowex 50× resin, shaken for 15 min, filtered, concentrated, and lyophilized to afford 169 as a white solid: mass spectrum MALDI), m/z 454.33 (M+Na)$^+$.

Example 19: Synthesis of Peracetylated Fluoro BLM Disaccharide 174

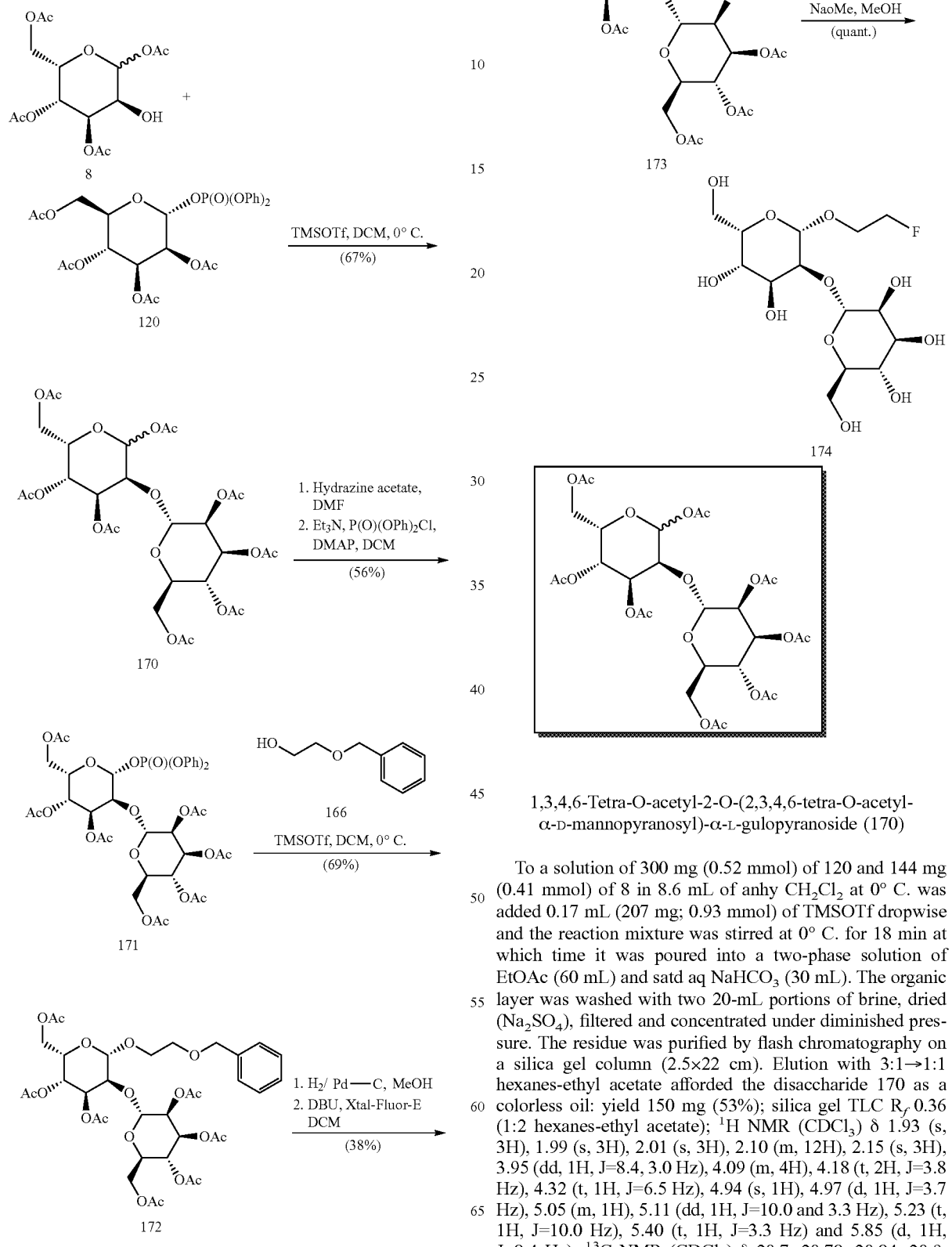

1,3,4,6-Tetra-O-acetyl-2-O-(2,3,4,6-tetra-O-acetyl-α-D-mannopyranosyl)-α-L-gulopyranoside (170)

To a solution of 300 mg (0.52 mmol) of 120 and 144 mg (0.41 mmol) of 8 in 8.6 mL of anhy CH$_2$Cl$_2$ at 0° C. was added 0.17 mL (207 mg; 0.93 mmol) of TMSOTf dropwise and the reaction mixture was stirred at 0° C. for 18 min at which time it was poured into a two-phase solution of EtOAc (60 mL) and satd aq NaHCO$_3$ (30 mL). The organic layer was washed with two 20-mL portions of brine, dried (Na$_2$SO$_4$), filtered and concentrated under diminished pressure. The residue was purified by flash chromatography on a silica gel column (2.5×22 cm). Elution with 3:1→1:1 hexanes-ethyl acetate afforded the disaccharide 170 as a colorless oil: yield 150 mg (53%); silica gel TLC R$_f$ 0.36 (1:2 hexanes-ethyl acetate); $^1$H NMR (CDCl$_3$) δ 1.93 (s, 3H), 1.99 (s, 3H), 2.01 (s, 3H), 2.10 (m, 12H), 2.15 (s, 3H), 3.95 (dd, 1H, J=8.4, 3.0 Hz), 4.09 (m, 4H), 4.18 (t, 2H, J=3.8 Hz), 4.32 (t, 1H, J=6.5 Hz), 4.94 (s, 1H), 4.97 (d, 1H, J=3.7 Hz), 5.05 (m, 1H), 5.11 (dd, 1H, J=10.0 and 3.3 Hz), 5.23 (t, 1H, J=10.0 Hz), 5.40 (t, 1H, J=3.3 Hz) and 5.85 (d, 1H, J=8.4 Hz); $^{13}$C NMR (CDCl$_3$) δ 20.7, 20.78, 20.84, 20.9, 61.4, 62.2, 65.6, 65.8, 67.7, 68.7, 68.9, 69.3, 69.7, 71.4, 90.7, 95.1, 168.7, 169.32, 169.35, 169.5, 169.6, 169.9, 170.5 and 170.6.

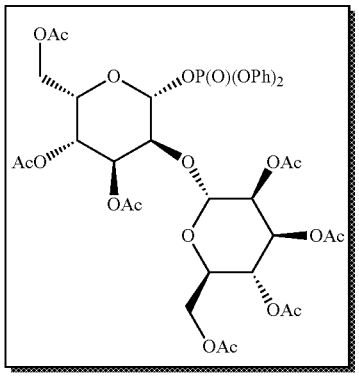

3,4,6-Tri-O-acetyl-2-O-(2,3,4,6-tetra-O-acetyl-α-D-mannopyranosyl)-α-L-gulopyranosyl Diphenyl Phosphate (171)

To a solution of 150 mg (0.22 mmol) of compound 170 in 1.9 mL of anhy DMF was added 28 mg (0.31 mmol) of hydrazine acetate salt and the reaction mixture was stirred for 2.5 h at which time analysis by silica gel TLC indicated complete consumption of the disaccharide. The solution was diluted with 50 mL of EtOAc and washed with three 20-mL portions of brine, dried over $Na_2SO_4$, filtered and concentrated under diminished pressure. The residue was co-evaporated with toluene, dried under diminished pressure to give a colorless oil: yield 140 mg (99%); silica gel TLC $R_f$ 0.25 (1:2 hexanes-ethyl acetate).

To the solution of 140 mg of the residue in 5.5 mL of anhydrous $CH_2Cl_2$ were added 35 mg (0.28 mmol) of DMAP and 0.31 mL (222 mg; 2.20 mmol) of $Et_3N$; the mixture was stirred for 10 min, followed by addition of 0.44 mL (564 mg; 2.10 mmol) of diphenyl chlorophosphate dropwise at 0° C. The solution was stirred at 0° C. for 1.5 h and was then poured into a two-phase solution of EtOAc (50 mL) and satd aq $NaHCO_3$ soln (20 mL). The organic layer was washed with 15 mL portions of brine, dried ($Na_2SO_4$), filtered and concentrated under diminished pressure. The residue was purified by flash chromatography on a silica gel column (2.5×25 cm). Elution with 2:1→1:1 hexanes-ethyl acetate afforded compound 171 as a colorless oil: yield 108 mg (56% over two steps); silica gel TLC $R_f$ 0.28 (1:2 hexanes-ethyl acetate). $^1H$ NMR ($CDCl_3$) δ 1.70 (s, 3H), 1.94 (s, 3H), 1.99 (s, 3H), 2.08 (s, 3H), 2.13 (s, 3H), 2.15 (s, 3H), 2.21 (s, 3H), 4.00 (m, 3H), 4.13 (m, 2H), 4.33 (dd, 2H, J=15.5 and 8.8 Hz), 4.99 (m, 2H), 5.14 (m, 1H), 5.24 (m, 2H), 5.44 (s, 1H), 5.71 (t, 1H, J=7.3 Hz) and 7.28 (m, 10H); $^{13}C$ NMR ($CDCl_3$) δ 20.2, 20.60, 20.61, 20.65, 20.7, 61.1, 61.8, 65.3, 65.5, 67.4, 68.6, 69.0, 69.1, 71.0, 71.6, 95.4, 96.1, 120.2, 120.2, 125.6, 125.7, 129.6, 129.9, 150.0, 150.3, 169.2, 169.3, 169.4, 169.5, 169.6, 170.3 and 170.5.

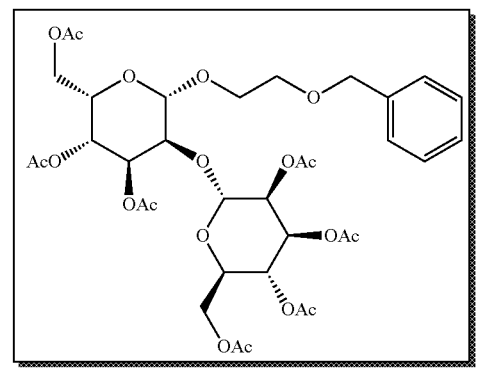

3,4,6-Tri-acetyl-2-O-(2,3,4,6-tri-O-acetyl-α-D-mannopyranosyl)-α-L-gulopyranosyl 2-(benzyloxy)ethane (172)

To a solution of 108 mg (0.12 mmol) of 171 and 16 μL (0.12 mmol) of 2-(benzyloxy)ethanol (166) in 3.5 mL of anhydrous $CH_2Cl_2$ was added 40 μL (0.22 mmol) of TMSOTf at 0° C. The reaction mixture was stirred at 0° C. for 20 min, at which time it was poured into a two-phase solution of EtOAc (30 mL) and satd aq $NaHCO_3$ (15 mL). The organic layer was washed with two 15 mL portions of brine, dried ($Na_2SO_4$), filtered and concentrated under diminished pressure. The residue was purified by flash chromatography on a silica gel column (2.5×25 cm). Elution with 3:1→1:1 hexanes-ethyl acetate afforded compound 172 as a colorless oil: yield 60 mg (69%); silica gel TLC $R_f$ 0.51 (1:1 hexanes-ethyl acetate). $^1H$ NMR ($CDCl_3$) δ 1.97-2.15 (m, 21H), 3.67 (m, 3H), 3.84 (m, 2H), 4.09 (m, 4H), 4.25 (m, 2H), 4.55 (m, 3H), 4.76 (m, 1H), 4.95 (m, 2H), 5.32 (m, 3H), 7.33 (m, 5H); $^{13}C$ NMR ($CDCl_3$) δ 20.77, 20.83, 20.90, 20.92, 20.99, 21.11, 62.55, 66.17, 66.43, 67.49, 67.99, 68.54, 68.88, 69.00, 69.30, 69.44, 70.18, 70.20, 71.51, 73.36, 73.40, 97.76, 127.61, 127.81, 127.84, 128.59, 138.19, 155.34, 169.79, 170.11, 170.80.

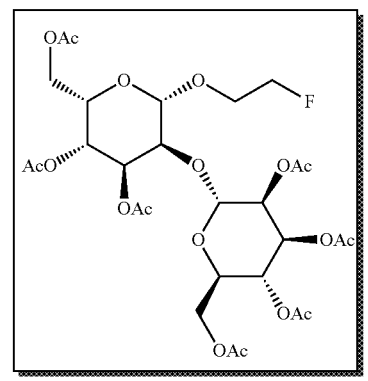

3,4,6-Tri-acetyl-2-O-(2,3,4,6-tri-O-acetyl-α-D-mannopyranosyl)-α-L-gulopyranosyl 2-(fluoro)ethane (173)

To a solution of 60 mg (0.08 mmol) of 172 in 8 mL of MeOH was added a catalytic amount of Pd—C and the reaction was placed under 1 atm of $H_{2(g)}$ overnight. The catalyst was removed by filtration through a pad of Celite 545® and concentrated under diminished pressure to give a colorless oil: yield 45 mg (85%); silica gel TLC $R_f$ 0.08 (1:1 hexanes-ethyl acetate).

To the solution of 45 mg (0.06 mmol) of the residue in 0.3 mL of anhydrous $CH_2Cl_2$ at −78° C., 15 µL (0.10 mmol) of DBU and 23 mg (0.10 mmol) of Xtal-Fluor-E were added and stirred for 30 min. The reaction mixture was then allowed to warm to rt and stirred for 24 h. The solution was poured into a two-phase solution of EtOAc (15 mL) and satd aq $NaHCO_3$ (7.5 mL). The organic layer was washed with 7.5 mL portions of brine, dried ($Na_2SO_4$), filtered and concentrated under diminished pressure. The residue was purified by flash chromatography on a silica gel column (1.5×25 cm). Elution with 3:1→1:2 hexanes-ethyl acetate afforded compound 173 as a colorless oil: yield 20 mg (34% over two steps); silica gel TLC $R_f$ 0.37 (1:1 hexanes-ethyl acetate). $^1$H NMR ($CDCl_3$) δ 1.98-2.18 (m, 21H), 3.40 (m, 1H), 4.07 (m, 2H), 4.14 (m, 3H), 4.27 (m, 2H), 4.52 (m, 1H), 4.64 (m, 1H), 4.71 (m, 2H), 4.89 (m, 1H), 5.01 (m, 2H), 5.29 (m, 3H); $^{13}$C NMR ($CDCl_3$) δ 11.19, 20.77, 20.82, 20.88, 20.91, 20.96, 20.98, 21.09, 62.57, 62.68, 66.18, 66.33, 67.41, 67.61, 68.74, 68.77, 68.83, 70.03, 70.07, 70.13, 81.47, 83.16, 97.86, 98.70, 155.27, 170.11, 170.77; $^{19}$F NMR ($CDCl_3$) δ −224.43 (m); mass spectrum (MALDI), m/z 705.46 $(M+Na)^+$; mass spectrum (ESI), m/z 705.2027 $(M+Na)^+$ ($C_{28}H_{39}FNaO_{18}$ requires m/z 705.2018).

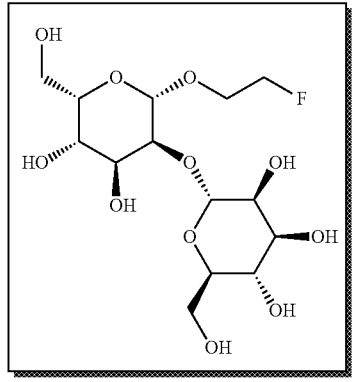

Decarbamoyl Fluoro-BLM-Disaccharide (174)

To a solution of 7.0 mg (10.2 µmol) of 173 in 2 mL of anh methanol, was added 0.2 mL of 25% w/w freshly prepared solution of sodium methoxide in methanol. The reaction mixture was allowed to stir at room temperature for 2.5 h, and the complete consumption of starting material was confirmed by MALDI-TOF mass spectral analysis. The reaction mixture was then quenched by the addition of 500 mg of Dowex 50× resin, shaken for 15 min, filtered, concentrated, and lyophilized to afford 174 as a light yellowish solid: mass spectrum (MALDI), m/z 411.31 $(M+Na)^+$; mass spectrum (ESI), m/z 411.1280 $(M+Na)^+$ ($C_{14}H_{25}FNaO_{11}$ requires m/z 411.1279).

Example 20

Evaluation of Carbohydrate Analogues by Fluorescence Microscopy.

Cell Growth Conditions.

A549 cells (ATCC CCL-185), A498 cells (ATCC HTB-44), BxPC-3 (ATCC CRL-1687), SW 1088 (ATCC HTB-12) and, SW-480 (ATCC CCL-228) were grown in RPMI 1640 (Gibco, Grand Island, N.Y.) supplemented with 10% fetal bovine serum (HyClone, South Logan, Utah) and 1% penicillin-streptomycin mix antibiotic supplement (Cellgro, Manassas, Va.). DU-145 (ATCC HTB-81), PZ-HPV-7 (ATCC CRL-2221) prostate cells, WI-38 (ATCC CCL-75), CCD-1105 KITDr (CCL-2305), SVR A221a (ATTC CLR-2386), Hs 895.T (ATCC CRL-7637), Hs 895.Sk (ATCC CRL-7636), CCD-16Lu (ATCC CCL-204) and CCD-112CoN (ATCC CRL-1541) were grown in MEM (Gibco, Grand Island, N.Y.) supplemented with 10% fetal bovine serum (HyClone) and 1% penicillin-streptomycin mix antibiotic supplement. Cell lines were maintained at 37° C. under a humidified atmosphere of 5% $CO_2$ and 95% air.

Fluorescence Microscopy.

Fluorescence images were obtained using a Zeiss Axiovert 200M inverted fluorescence microscope fitted with an AxioCam MRm camera equipped with a 300-w xenon lamp (Sutter, Novato, Calif.) and a Cy5 cyanine filter (Chroma, Bellows Falls, Vt.). Adherent cancer cells were grown on 16-well Lab-Tek glass chamber slides at a cell density of 5000 cells/well (Thermo Scientific, Waltham, Mass.) at 37° C. for 48 h. Cells were rinsed twice with phosphate buffered saline (PBS), when the cell confluence was about 70% the medium was replaced with RPMI 1640 (no phenol red). The dye-labeled conjugates were subsequently added to the final desired concentrations. The cells were incubated at 37° C. for 1 h, washed with PBS, then fixed with 4% paraformaldehyde at 37° C. for 5 min. Finally the slide was mounted with Prolong Antifade Gold reagent with DAPI (Invitrogen), then covered with a glass coverslip and dried for 24 h before fluorescence microscope analysis. Cells were imaged using a Zeiss EC Plan-Neofluor 40×/1,3 DIC M27 oil objective. For comparative studies, the exposure time and source intensity were kept identical for accurate measurements. Three different viewing fields containing at least 10 individual cells from each experiment were analyzed. The mean pixel intensities [per unit area of the cells] in the viewing fields were measured to give the normalized fluorescence. Quantification values were generated by using AxioVision 4 v 4.7.1.0 software in conjunction with the interactive measurement tool.

Although the disclosure has been described and illustrated in the foregoing illustrative embodiments, it is understood that the present disclosure has been made only by way of example, and that numerous changes in the details of implementation of the disclosure can be made without departing from the spirit and scope of the disclosure. Features of the disclosed embodiments can be combined and rearranged in various ways. All publications, patents and other documents mentioned herein are incorporated by reference in their entirety.

What is claimed is:

1. A compound of formula (I):

$$[A-R_6]_n-R_7-R_8 \quad (I)$$

or a pharmaceutically acceptable salt thereof, wherein A is:

[structure with HO, HO, OH, O, R1, R2, R3, R' groups]

or

[structure with O, R1, R2, R3, R' groups]

$R_1$ is selected from the group consisting of H, OH, SH, $NH_2$, $OR_4$, $OC(O)R_4$, $OC(O)NHR_4$, $OC(O)NR_4R_5$, $OC(S)NHR_4$, $OC(S)NR_4R_5$, $SC(O)NHR_4$, $SC(O)NR_4R_5$, $NHC(O)NHR_4$, $NHC(O)NR_4R_5$, $NHC(S)NHR_4$, $NHC(S)NR_4R_5$, $NHC(N)NHR_4$, $NHC(N)NR_4R_5$, $OCH_2C(O)NHR_4$, $OCH_2C(O)NR_4R_5$, $OCH_2C(S)NHR_4$, $OCH_2C(S)NR_4R_5$, $SCH_2C(O)NHR_4$, $SCH_2C(O)NR_4R_5$, $NHCH_2C(O)NHR_4$, $NHCH_2C(O)NR_4R_5$, $NHCH_2C(S)NHR_4$ and $NHCH_2C(S)NR_4R_5$;

each $R_4$ is selected from the group consisting of H, $C_1$-$C_6$ alkyl, $C_2$-$C_6$ alkenyl and $C_2$-$C_6$ alkynyl;

each $R_5$ is selected from the group consisting of $C_1$-$C_6$ alkyl, $C_2$-$C_6$ alkenyl and $C_2$-$C_6$ alkynyl;

$R_2$ is selected from the group consisting of H, OH, SH, $NH_2$, $OR_4$, $OC(O)R_4$, $OC(O)NHR_4$, $OC(O)NR_4R_5$, $OC(S)NHR_4$, $OC(S)NR_4R_5$, $SC(O)NHR_4$, $SC(O)NR_4R_5$, $NHC(O)NHR_4$, $NHC(O)NR_4R_5$, $NHC(S)NHR_4$, $NHC(S)NR_4R_5$, $NHC(N)NHR_4$, $NHC(N)NR_4R_5$, $OCH_2C(O)NHR_4$, $OCH_2C(O)NR_4R_5$, $OCH_2C(S)NHR_4$, $OCH_2C(S)NR_4R_5$, $SCH_2C(O)NHR_4$, $SCH_2C(O)NR_4R_5$, $NHCH_2C(O)NHR_4$, $NHCH_2C(O)NR_4R_5$, $NHCH_2C(S)NHR_4$ and $NHCH_2C(S)NR_4R_5$;

$R_3$ is selected from the group consisting of H, OH, SH, $NH_2$, $OR_4$, $OC(O)R_4$, $OC(O)NHR_4$, $OC(O)NR_4R_5$, $OC(S)NHR_4$, $OC(S)NR_4R_5$, $SC(O)NHR_4$, $SC(O)NR_4R_5$, $NHC(O)NHR_4$, $NHC(O)NR_4R_5$, $NHC(S)NHR_4$, $NHC(S)NR_4R_5$, $NHC(N)NHR_4$, $NHC(N)NR_4R_5$, $OCH_2C(O)NHR_4$, $OCH_2C(O)NR_4R_5$, $OCH_2C(S)NHR_4$, $OCH_2C(S)NR_4R_5$, $SCH_2C(O)NHR_4$, $SCH_2C(O)NR_4R_5$, $NHCH_2C(O)NHR_4$, $NHCH_2C(O)NR_4R_5$, $NHCH_2C(S)NHR_4$ and $NHCH_2C(S)NR_4R_5$;

R' is selected from the group consisting of H, OH and $NHR_4$;

$R_6$ is a first linker;

n is an integer selected from 1 to 3;

$R_7$ is absent or a second linker, provided that when n is 1, $R_7$ is absent; and $R_8$ is Cy5**.

2. The compound according to claim 1, wherein A is selected from the group consisting of:

[four structures shown]

3. The compound according to claim 1, wherein the first linker is X-($L^1$-Y)$_m$-$L^2$-Z, wherein X is $CH_2$ or O;

$L^1$ is $C_2$-$C_6$ alkyl;

Y is O, S, or $NR^y$, wherein $R^y$ is hydrogen or $C_1$-$C_6$ alkyl;

m is an integer selected from 1 to 10;

$L^2$ is $C_1$-$C_{20}$ alkyl, $C_2$-$C_{20}$ alkenyl, $C_2$-$C_{20}$ alkynyl, aryl, heteroaryl, heterocyclyl, $C_3$-$C_5$ cycloalkyl; and Z is absent, O, $NR^x$, S, C(O), S(O), $S(O)_2$, OC(O), $N(R^x)C(O)$, $N(R^x)S(O)$, $N(R^x)S(O)_2$, C(O)O, C(O)N($R^x$), $S(O)N(R^x)$, $S(O)_2N(R^x)$, OC(O)O, OC(O)N($R^x$), $N(R^x)C(O)O$, $N(R^x)C(O)N(R^x)$, or $N(R^x)S(O)_2N(R^x)$, wherein each $R^x$ is independently hydrogen or $C_1$-$C_6$ alkyl.

4. The compound of claim 3, wherein the first linker is O—($CH_2CH_2$—O)$_m$—$CH_2CH_2$—Z, wherein Z is O, N(H), or S and m is an integer selected from 1 to 20 or the first linker is O—($CH_2CH_2$—O)$_m$—$CH_2CH_2$—Z, wherein Z is C(O) or $S(O)_2$ and m is an integer selected from 1 to 20.

5. The compound according to claim 1, wherein the second linker is (B-$L^3$)$_p$-D-E-$L^4$-F, wherein B is bond, O, $NR^x$, S, C(O), S(O), $S(O)_2$, OC(O), $N(R^x)C(O)$, $N(R^x)S(O)$, $N(R^x)S(O)_2$, C(O)O, C(O)N($R^x$), $S(O)N(R^x)$, $S(O)_2N(R^x)$, OC(O)O, OC(O)N($R^x$), $N(R^x)C(O)O$, $N(R^x)C(O)N(R^x)$, or $N(R^x)S(O)_2N(R^x)$;

L³ is C₂-C₆ alkyl;
p is 2 or 3;
D is CH when p is 2 and D is C when p is 3;
E is a bond, O, NR$^x$, S, C(O), S(O), S(O)$_2$, OC(O), N(R$^x$)C(O), N(R$^x$)S(O), N(R$^x$)S(O)$_2$, C(O)O, C(O)N(R$^x$), S(O)N(R$^x$), S(O)²N(R$^x$), OC(O)O, OC(O)N(R$^x$), N(R$^x$)C(O)O, N(R$^x$)C(O)N(R$^x$), or N(R$^x$)S(O)$_2$N(R$^x$);
L⁴ is C₂-C₆ alkyl; and
F is a bond, O, NR$^x$, S, C(O), S(O), S(O)$_2$, OC(O), N(R$^x$)C(O), N(R$^x$)S(O), N(R$^x$)S(O)$_2$, C(O)O, C(O)N(R$^x$), S(O)N(R$^x$), S(O)$_2$N(R$^x$), OC(O)O, OC(O)N(R$^X$), N(R$^X$)C(O)O, N(R$^x$)C(O)N(R$^x$), or N(R$^x$)S(O)$_2$N(R$^x$), wherein each R$^x$ is independently hydrogen or C₁-C₆ alkyl.

6. The compound according to claim 1, wherein R₁ is selected from the group consisting of H, OH, OR₄, OC(O)R₄, NHC(N)NHR₄, NHC(N)NR₄R₅, OCONHR₄, and OCONR₄R₅.

7. The compound according to claim 1, wherein R₂ is selected from the group consisting of H, OH, OR₄, OC(O)R₄, NHC(N)NHR₄, NHC(N)NR₄R₅, OCONHR₄, OCONR₄R₅, OCSNHR₄, NHCONHR₄, OCH₂CONHR₄, and OCH₂CONR₄R₅.

8. The compound according to claim 1, wherein R₃ is selected from the group consisting of OH, OR₄, OC(O)R₄, NHC(N)NHR₄, NHC(N)NR₄R₅, and OCONHR₄.

9. The compound according to claim 1, wherein R' is H or OH.

10. The compound according to claim 1, wherein each R₄ is selected from the group consisting of H, methyl and ethyl.

11. The compound according to claim 1, wherein each R₅ is selected from the group consisting of methyl, ethyl, and isobutyl.

12. A compound selected from the group consisting of:

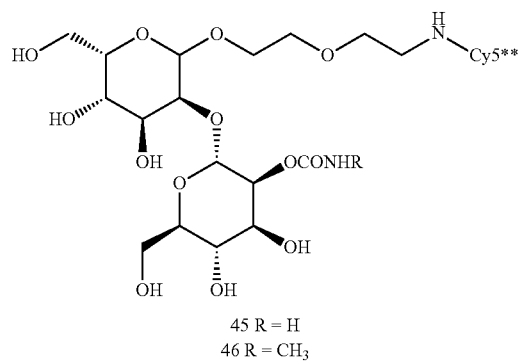

45 R = H
46 R = CH₃

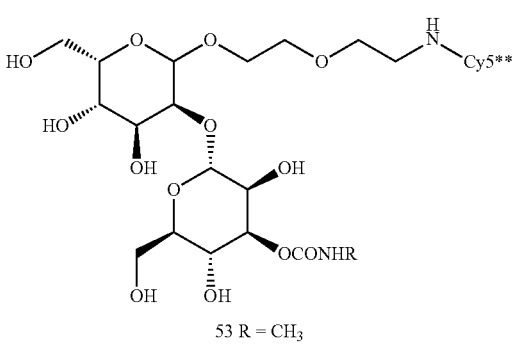

53 R = CH₃

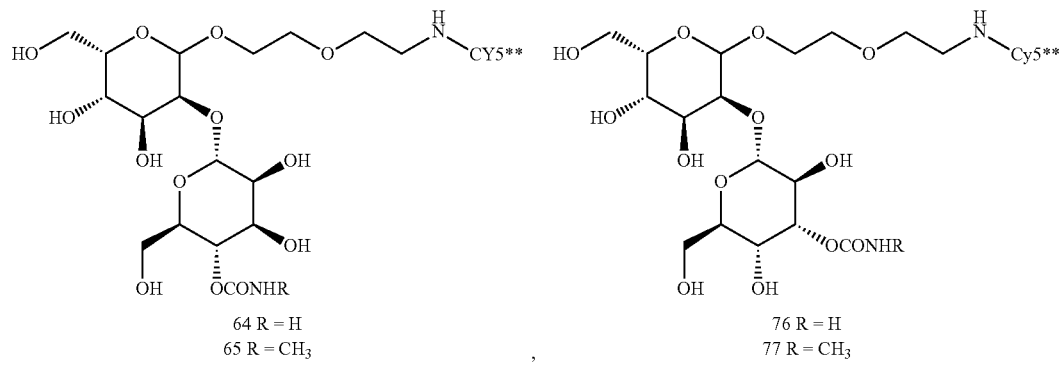

64 R = H
65 R = CH₃

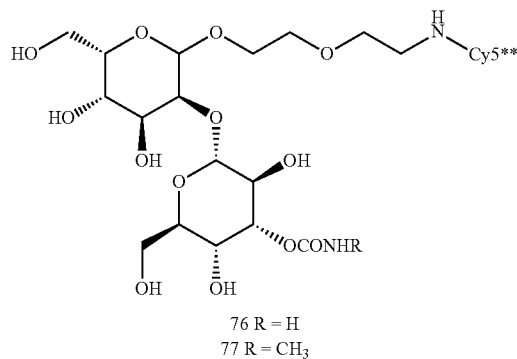

76 R = H
77 R = CH₃

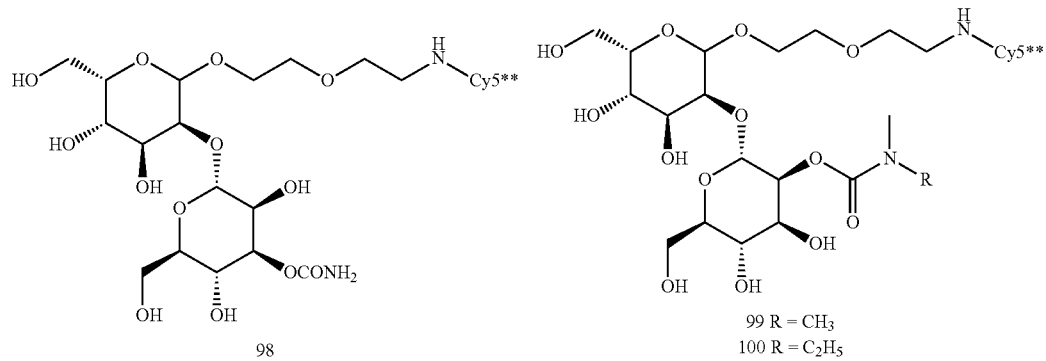

98

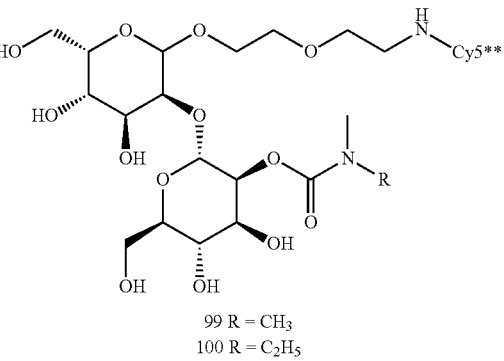

99 R = CH₃
100 R = C₂H₅

-continued
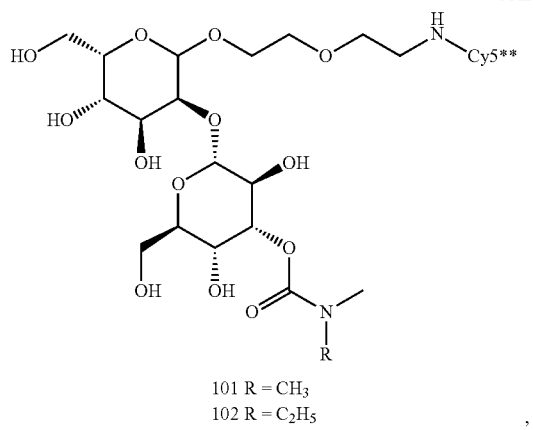
101 R = CH₃
102 R = C₂H₅
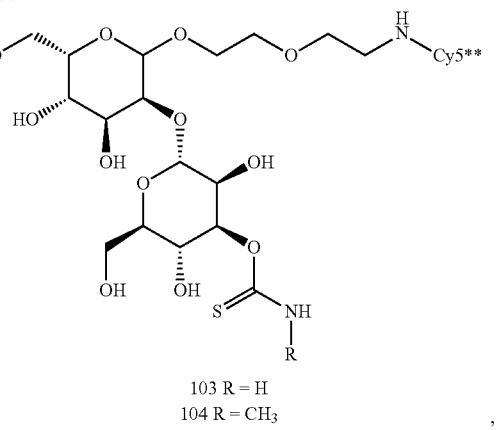
103 R = H
104 R = CH₃
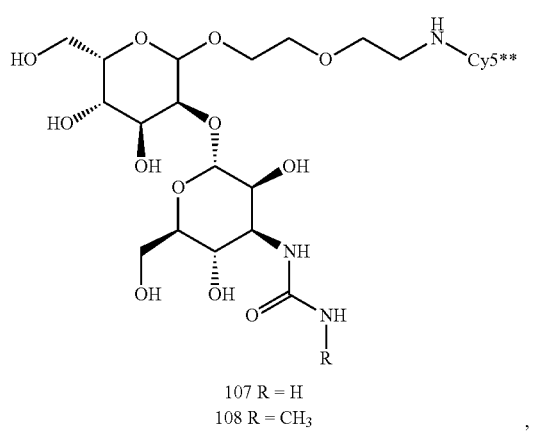
107 R = H
108 R = CH₃
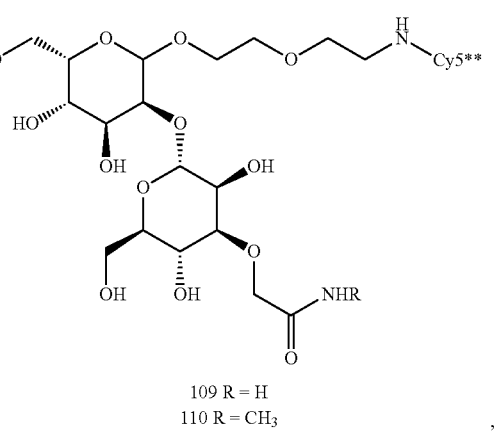
109 R = H
110 R = CH₃
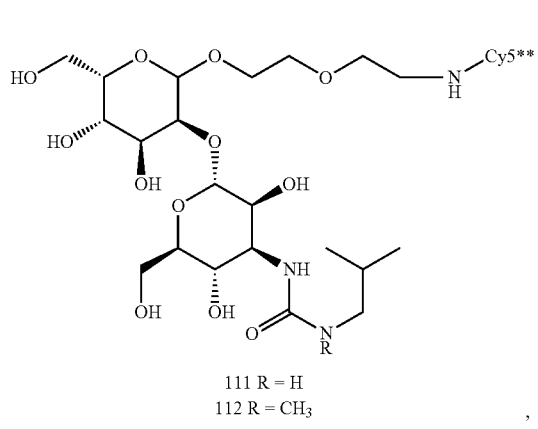
111 R = H
112 R = CH₃
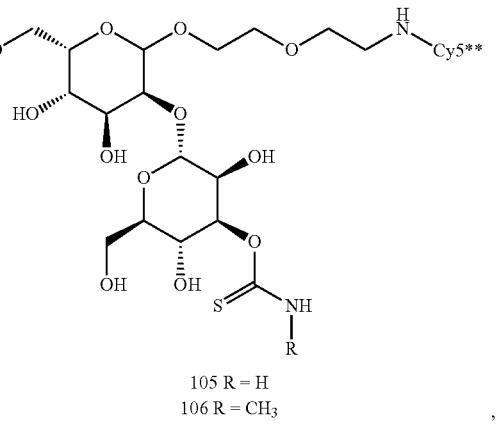
105 R = H
106 R = CH₃
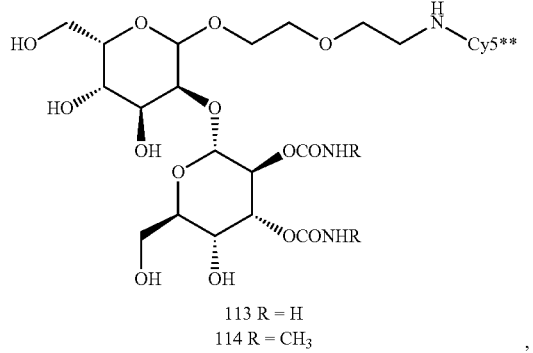
113 R = H
114 R = CH₃
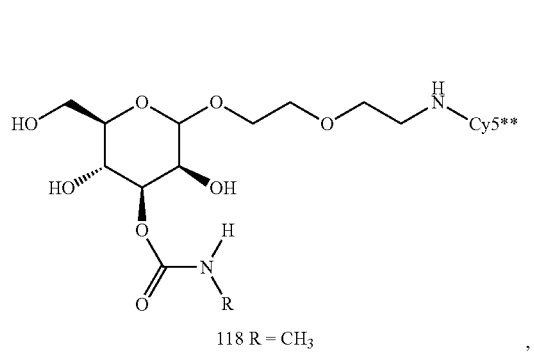
118 R = CH₃

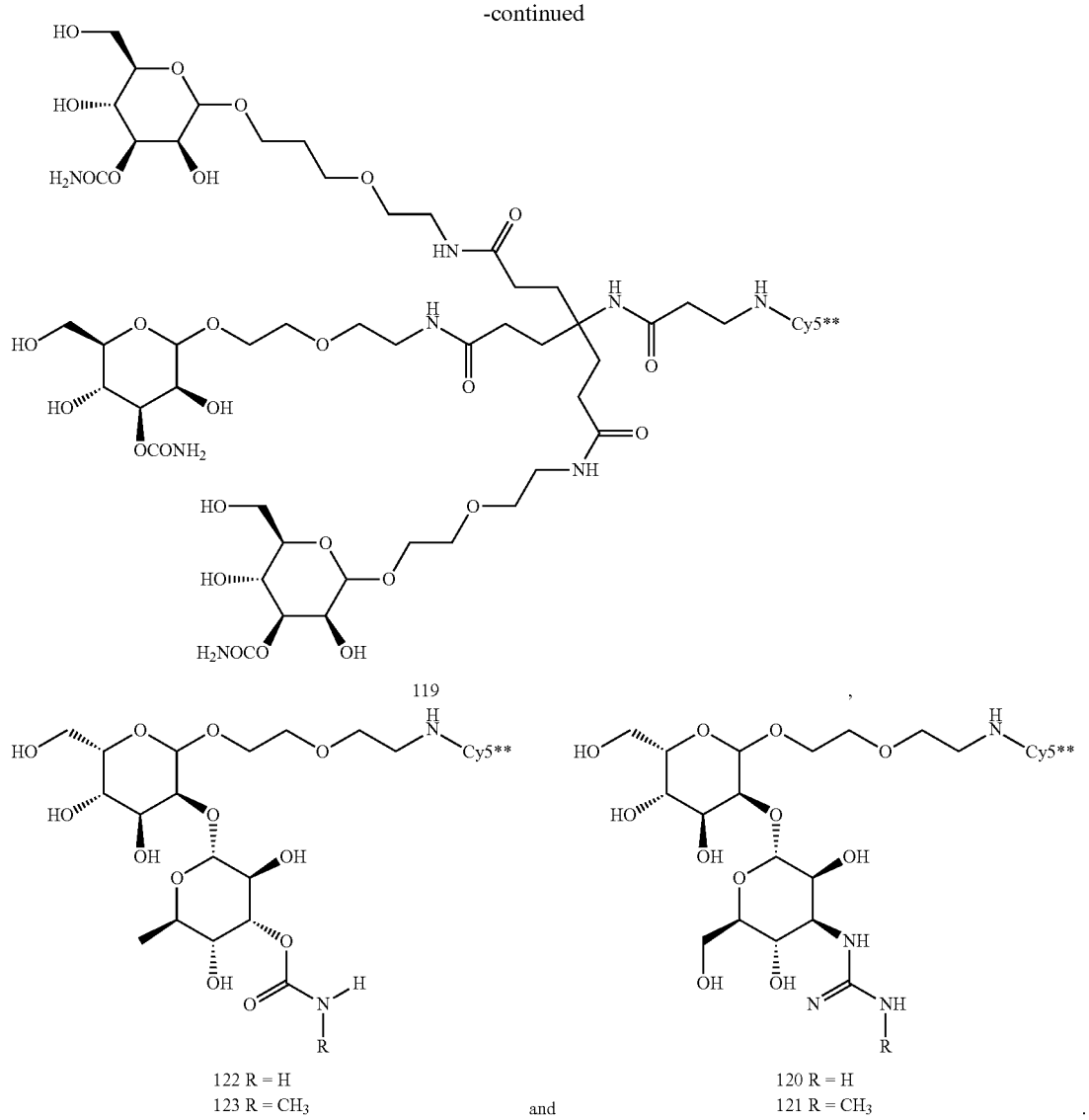
* * * * *